(12) United States Patent
Mkrtichyan et al.

(10) Patent No.: US 12,168,687 B2
(45) Date of Patent: Dec. 17, 2024

(54) ANTIBODIES TO PROGRAMMED CELL DEATH PROTEIN 1 THAT ARE PD-1 AGONISTS

(71) Applicant: Georgiamune Inc., Gaithersburg, MD (US)

(72) Inventors: Mikayel Mkrtichyan, Tujunga, CA (US); Samir Khleif, Bethesda, MD (US)

(73) Assignee: Georgiamune Inc., Gaithersburg, MD (US)

( * ) Notice: Subject to any disclaimer, the term of this patent is extended or adjusted under 35 U.S.C. 154(b) by 0 days.

(21) Appl. No.: 18/423,752

(22) Filed: Jan. 26, 2024

(65) Prior Publication Data

US 2024/0182574 A1   Jun. 6, 2024

Related U.S. Application Data

(63) Continuation of application No. PCT/US2023/061449, filed on Jan. 27, 2023.

(60) Provisional application No. 63/304,365, filed on Jan. 28, 2022.

(51) Int. Cl.
| | |
|---|---|
| *C07K 16/28* | (2006.01) |
| *A61K 9/00* | (2006.01) |
| *A61K 39/00* | (2006.01) |
| *A61P 35/00* | (2006.01) |

(52) U.S. Cl.
CPC ........ *C07K 16/2818* (2013.01); *A61K 9/0019* (2013.01); *A61P 35/00* (2018.01); *A61K 2039/505* (2013.01); *C07K 2317/565* (2013.01); *C07K 2317/70* (2013.01); *C07K 2317/75* (2013.01)

(58) Field of Classification Search
CPC .......... C07K 16/2818; C07K 2317/565; C07K 2317/70; A61K 9/0019; A61K 2039/505; A61P 35/00
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,816,397 A | 3/1989 | Boss et al. |
| 4,816,567 A | 3/1989 | Cabilly et al. |
| 5,225,539 A | 7/1993 | Winter |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,766,886 A | 6/1998 | Studnicka et al. |
| 5,807,715 A | 9/1998 | Morrison et al. |
| 5,814,318 A | 9/1998 | Lonberg et al. |
| 5,916,771 A | 6/1999 | Hori et al. |
| 5,939,598 A | 8/1999 | Kucherlapati et al. |
| 6,005,079 A | 12/1999 | Casterman et al. |
| 6,180,370 B1 | 1/2001 | Queen et al. |
| 6,194,551 B1 | 2/2001 | Idusogie et al. |
| 6,350,861 B1 | 2/2002 | Co et al. |
| 6,407,213 B1 | 6/2002 | Carter et al. |
| 7,052,694 B2 | 5/2006 | Pease et al. |
| 7,332,582 B2 | 2/2008 | Hardy et al. |
| 7,390,888 B2 | 6/2008 | Pease et al. |
| 7,411,051 B2 | 8/2008 | Rosen et al. |
| 7,488,802 B2 | 2/2009 | Collins et al. |

(Continued)

FOREIGN PATENT DOCUMENTS

| | | |
|---|---|---|
| BR | 112020004458 A2 | 10/2020 |
| CN | 101213297 A | 7/2008 |

(Continued)

OTHER PUBLICATIONS

International Search Report mailed Aug. 23, 2023 in PCT/US2023/061449

Abuchowski, et al., Soluble Polymer-Enzyme Adducts, "Enzymes as Drugs" by Hocenberg and Roberts, Chapter 13, Published by Wiley-Interscience, 1981, pp. 367-383.

Angal, et al., A single amino acid substitution abolishes the heterogeneity of chimeric mouse/human (IgG4) antibody, Mol Immunol., vol. 30, No. 1, Jan. 1993, pp. 105-108.

Ausubel, et al., Mutagenesis of Cloned DNA, Short Protocols in Molecular Biology, Chapter 8, Published by Green Publishing Associates and John Wiley & Sons, 1992, pp. 8-Jan. 8, 25. .

(Continued)

*Primary Examiner* — Julie Wu
*Assistant Examiner* — Carol Ann Chase
(74) *Attorney, Agent, or Firm* — Hogan Lovells US LLP

(57) ABSTRACT

Antibodies and antigen-binding fragments thereof that immunospecifically bind to PD-1, such as human or mouse PD-1, and are agonists of PD-1 and can induce or promote an immune response that activates immune cell proliferation or activity. Unlike the majority of known anti-PD-1 and anti-PD-L1 antibodies, which reduce the suppression of PD-1 function by e.g., PD-L1 by physically blocking the interaction between PD-1 and an inactivating ligand, although not to be bound by theory, the disclosed antibodies and antigen-binding fragments thereof are currently best understood to immunospecifically bind to an epitope of PD-1 whereby PD-1 is activated directly. Methods for the treatment of cancer comprising administration of the antibodies or antigen-binding fragments to a subject in need thereof. Polynucleotides encoding the antibodies or antigen-binding fragments. Host cells comprising the polynucleotides.

30 Claims, 15 Drawing Sheets

Specification includes a Sequence Listing.

(56) References Cited

U.S. PATENT DOCUMENTS

| | | | |
|---|---|---|---|
| 7,521,051 | B2 | 4/2009 | Collins et al. |
| 7,524,498 | B2 | 4/2009 | Hardy et al. |
| 7,563,869 | B2 | 7/2009 | Honjo et al. |
| 7,795,494 | B2 | 9/2010 | Ghayur |
| 7,981,416 | B2 | 7/2011 | Hardy et al. |
| 8,043,620 | B2 | 10/2011 | Qian et al. |
| 8,088,905 | B2 | 1/2012 | Collins et al. |
| 8,114,845 | B2 | 2/2012 | Langermann et al. |
| 8,188,238 | B2 | 5/2012 | Pease et al. |
| 8,232,449 | B2 | 7/2012 | Tanamachi et al. |
| 8,287,856 | B2 | 10/2012 | Li et al. |
| 8,383,796 | B2 | 2/2013 | Korman et al. |
| 8,481,687 | B2 | 7/2013 | Mncent et al. |
| 8,552,154 | B2 | 10/2013 | Freeman et al. |
| 8,580,247 | B2 | 11/2013 | Li et al. |
| 8,609,089 | B2 | 12/2013 | Langermann et al. |
| 8,703,485 | B2 | 4/2014 | Buelow |
| 8,709,416 | B2 | 4/2014 | Langermann et al. |
| 8,728,474 | B2 | 5/2014 | Honjo et al. |
| 8,779,105 | B2 | 7/2014 | Korman et al. |
| 8,835,712 | B2 | 9/2014 | Tomizuka et al. |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,102,725 | B2 | 8/2015 | Korman et al. |
| 9,109,025 | B2 | 8/2015 | Gurney et al. |
| 9,127,071 | B2 | 9/2015 | Yoshida et al. |
| 9,205,148 | B2 | 12/2015 | Langermann et al. |
| 9,255,147 | B2 | 2/2016 | Pease et al. |
| 9,273,135 | B2 | 3/2016 | Korman et al. |
| 9,358,289 | B2 | 6/2016 | Korman et al. |
| 9,387,247 | B2 | 7/2016 | Korman et al. |
| 9,388,446 | B2 | 7/2016 | Murphy et al. |
| 9,393,301 | B2 | 7/2016 | Honjo et al. |
| 9,445,581 | B2 | 9/2016 | Bradley et al. |
| 9,492,539 | B2 | 11/2016 | Korman et al. |
| 9,492,540 | B2 | 11/2016 | Korman et al. |
| 9,499,838 | B2 | 11/2016 | Kuroiwa et al. |
| 9,580,507 | B2 | 2/2017 | Korman et al. |
| 9,686,970 | B2 | 6/2017 | Macdonald et al. |
| 9,708,635 | B2 | 7/2017 | Murphy et al. |
| 9,987,500 | B2 | 6/2018 | Papadopoulos et al. |
| 10,155,037 | B2 | 12/2018 | Abdiche et al. |
| 10,428,146 | B2 | 10/2019 | Qiu et al. |
| 11,021,540 | B2 * | 6/2021 | Khleif ............... A61P 35/00 |
| 11,780,921 | B2 | 10/2023 | Khleif et al. |
| 2003/0229208 | A1 | 12/2003 | Queen et al. |
| 2004/0049014 | A1 | 3/2004 | Queen et al. |
| 2005/0037000 | A1 | 2/2005 | Stavenhagen et al. |
| 2005/0064514 | A1 | 3/2005 | Stavenhagen et al. |
| 2006/0088883 | A1 | 4/2006 | Smider et al. |
| 2009/0130114 | A1 | 5/2009 | Qian et al. |
| 2009/0217401 | A1 | 8/2009 | Korman et al. |
| 2010/0074916 | A1 | 3/2010 | Nabel et al. |
| 2011/0256154 | A1 | 10/2011 | Mncent et al. |
| 2012/0251556 | A1 | 10/2012 | Allison et al. |
| 2013/0273089 | A1 | 10/2013 | Getts et al. |
| 2013/0309250 | A1 | 11/2013 | Cogswell et al. |
| 2014/0271629 | A1 | 9/2014 | Corbit et al. |
| 2015/0203579 | A1 | 7/2015 | Papadopoulos et al. |
| 2015/0210769 | A1 | 7/2015 | Freeman et al. |
| 2016/0032019 | A1 | 2/2016 | Xiao et al. |
| 2016/0159905 | A1 | 6/2016 | Abdiche et al. |
| 2017/0210821 | A1 | 7/2017 | Zimring |
| 2017/0239351 | A1 | 8/2017 | Hamdy et al. |
| 2017/0240644 | A1 | 8/2017 | Zhou et al. |
| 2020/0317808 | A1 | 10/2020 | Afar et al. |
| 2021/0032341 | A1 | 2/2021 | Khleif et al. |

FOREIGN PATENT DOCUMENTS

| | | |
|---|---|---|
| EP | 0239400 A2 | 9/1987 |
| EP | 0519596 A1 | 12/1992 |
| EP | 0592106 A1 | 4/1994 |
| EP | 2530091 A1 | 12/2012 |
| WO | 9109967 A1 | 7/1991 |
| WO | 9110741 A1 | 7/1991 |
| WO | 9317105 A1 | 9/1993 |
| WO | 9404678 A1 | 3/1994 |
| WO | 9425591 A1 | 11/1994 |
| WO | 9633735 A1 | 10/1996 |
| WO | 9634096 A1 | 10/1996 |
| WO | 9816654 A1 | 4/1998 |
| WO | 9824893 A2 | 6/1998 |
| WO | 9846645 A2 | 10/1998 |
| WO | 9850433 A2 | 11/1998 |
| WO | 9958572 A1 | 11/1999 |
| WO | 2007056539 A2 | 5/2007 |
| WO | 2008112017 A2 | 9/2008 |
| WO | 2010036959 A2 | 4/2010 |
| WO | 2011110621 A1 | 9/2011 |
| WO | 2013012747 A1 | 1/2013 |
| WO | 2015112800 A1 | 7/2015 |
| WO | 2015112900 A1 | 7/2015 |
| WO | 2016014688 A2 | 1/2016 |
| WO | 2016020856 A2 | 2/2016 |
| WO | 2016168716 A1 | 10/2016 |
| WO | 2019051164 A1 | 3/2019 |
| WO | 2023147470 A2 | 8/2023 |

OTHER PUBLICATIONS

Baca, et al., Antibody humanization using monovalent phage display, J Biol Chem., vol. 272, No. 16, Apr. 18, 1997, pp. 10678-10684.

Berger, et al., Phase I safety and pharmacokinetic study of CT-011, a humanized antibody interacting with PD-1, in patients with advanced hematologic malignancies, Clin Cancer Res., vol. 14, No. 10, May 15, 2008, pp. 3044-3051.

Bruggemann, et al., Human antibody production in transgenic animals, Arch Immunol Ther Exp (Warsz)., vol. 63, No. 2, Apr. 2015, pp. 101-108.

Butte, et al., Programmed death-1 ligand 1 interacts specifically with the B7-1 costimulatory molecule to inhibit T cell responses, Immunity., vol. 27, No. 1, Jul. 2007, pp. 111-122.

Caldas, et al., Design and synthesis of germline-based hemi-humanized single-chain Fv against the CD18 surface antigen, Protein Eng., vol. 13, No. 5, May 2000, pp. 353-360.

Chothia, et al., Canonical structures for the hypervariable regions of immunoglobulins, J Mol Biol., vol. 196, No. 4, Aug. 20, 1987, pp. 901-917.

Chothia, et al., Structural determinants in the sequences of immunoglobulin variable domain, J Mol Biol., vol. 278, No. 2, May 1, 1988, pp. 457-479.

Chilean Examiner's Report, received in CL 2020-000576, received on Dec. 11, 2021, 15 pages (1 page of English Translation and 14 Pages Official Copy).

Couto, et al., Anti-BA46 monoclonal antibody Mc3: humanization using a novel positional consensus and in vivo and in vitro characterization, Cancer Res., vol. 55, No. 8, Apr. 15, 1995, pp. 1717-1722.

Couto, et al., Designing human consensus antibodies with minimal positional templates, Cancer Res., vol. 55, No. 23 Suppl, Dec. 1, 1995, pp. 5973s-5977s.

Cubillos-Ruiz, et al., Polyethylenimine-based siRNA nanocomplexes reprogram tumor-associated dendritic cells via TLR5 to elicit therapeutic antitumor immunity, J Clin Invest., vol. 119, No. 8, Aug. 2009, pp. 2231-2244.

Erbe, et al., Small molecule ligands define a binding site on the immune regulatory protein B7.1, J Biol Chem., vol. 277, No. 9, Mar. 1, 2002, pp. 7363-7368.

Freeman, Gordon J., Structures of PD-1 with its ligands: sideways and dancing cheek to cheek, Proc Natl Acad Sci U S A., vol. 105, No. 30, Jul. 29, 2008, pp. 10275-10276.

Gillies, et al., High-level expression of chimeric antibodies using adapted cDNA variable region cassettes, J Immunol Methods., vol. 125, No. 1-2, Dec. 20, 1989, pp. 191-202.

(56) References Cited

OTHER PUBLICATIONS

Grimaldi, et al., Nivolumab plus interferon-y in the treatment of intractable mucormycosis, Lancet Infect Dis., vol. 17, No. 1, Jan. 2017, p. 18.

Guatelli, et al., Isothermal, in vitro amplification of nucleic acids by a multienzyme reaction modeled after retroviral replication, Proc Natl Acad Sci U S A., vol. 87, No. 5, Mar. 1990, pp. 1874-1878.

He, et al., Development of PD-1/PD-L1 Pathway in Tumor Immune Microenvironment and Treatment for Non-Small Cell Lung Cancer, Sci Rep., vol. 5, No. 13110, Aug. 17, 2015, 9 pages.

International Preliminary Report on Patentability received for PCT Patent Application No. PCT/US18/049854, mailed on Mar. 19, 2020, 10 pages.

International Search Report received for PCT Patent Application No. PCT/US2018/049854, mailed on Dec. 10, 2018, 9 pages.

Iwai, et al., Cancer immunotherapies targeting the PD-1 signaling pathway, J Biomed Sci., vol. 24, No. 1, Apr. 4, 2017, 11 pages.

Jakobovits, AYA, Production of fully human antibodies by transgenic mice, Curr Opin Biotechnol., vol. 6, No. 5, Oct. 1995, pp. 561-566.

Jakobovits, et al., From XenoMouse technology to panitumumab, the first fully human antibody product from transgenic mice, Nat Biotechnol., vol. 25, No. 10, Oct. 2007, pp. 1134-1143.

Jasion, et al., Survival and digestibility of orally-administered immunoglobulin preparations containing IgG through the gastrointestinal tract in humans, Nutr J., vol. 14, No. 22, Mar. 7, 2015, 8 pages.

Jones, et al., Replacing the complementarity-determining regions in a human antibody with those from a mouse, Nature., vol. 321, No. 6069, 1986, pp. 522-525.

Lazar-Molnar, et al., Crystal structure of the complex between programmed death-1 (PD-1) and its ligand PD-L2, Proc Natl Acad Sci U S A., vol. 105, No. 30, Jul. 29, 2008, pp. 10483-10488.

Li, et al., Vascular endothelial growth factor blockade reduces intratumoral regulatory T cells and enhances the efficacy of a GM-CSF-secreting cancer immunotherapy, Clin Cancer Res., vol. 12, No. 22, Nov. 15, 2006, pp. 6808-6816.

Lonberg, et al., Human antibodies from transgenic mice, Int Rev Immunol., vol. 13, No. 1, 1995, pp. 65-93.

Lonberg, Nils, Human antibodies from transgenic animals, Nat Biotechnol., vol. 23, No. 9, Sep. 2005, pp. 1117-1125.

Morea, et al., Antibody modeling: implications for engineering and design, Methods., vol. 20, No. 3, Mar. 2000, pp. 267-279.

Morrison, S L., Transfectomas provide novel chimeric antibodies, Science, vol. 229, No. 4719, Sep. 20, 1985, pp. 1202-1207.

Muyldermans, et al., Recognition of antigens by single-domain antibody fragments: the superfluous luxury of paired domains, Trends Biochem Sci., vol. 26, No. 4, Apr. 2001, pp. 230-235.

Notice of Allowance received for U.S. Appl. No. 16/645,289, mailed on Dec. 22, 2020.

Office Action received for European Patent Application No. 18779878.0, mailed on Aug. 20, 2021, 5 pages.

Padlan, Eduardo A., A possible procedure for reducing the immunogenicity of antibody variable domains while preserving their ligand-binding properties, Mol Immunol., vol. 28, No. 4-5, 1991, pp. 489-498.

Pedersen, et al., Comparison of surface accessible residues in human and murine immunoglobulin Fv domains. Implication for humanization of murine antibodies, J Mol Biol., vol. 235, No. 3, Jan. 21, 1994, pp. 959-973.

Philippart, et al., Oral Delivery of Therapeutic Proteins and Peptides: An Overview of Current Technologies and Recommendations for Bridging from Approved Intravenous or Subcutaneous Administration to Novel Oral Regimens, Drug Res (Stuttg)., vol. 66, No. 3, Mar. 2016, pp. 113-120.

Pluckthun, A., Antibodies from Escherichia coli, "The Pharmacology of Monoclonal Antibodies" by Rosenburg and Moore, vol. 113, Chapter 11, Published by Springer-Verlag, 1994, pp. 269-315.

Sammartino, et al., Anti-GBM disease following CTLA4 blockade in a patient with metastatic melanoma, NDT Plus, vol. 3, No. 2, Apr. 2010, pp. 135-137.

Sandhu, Jasbir Singh, A rapid procedure for the humanization of monoclonal antibodies, Gene., vol. 150, No. 2, Dec. 15, 1994, pp. 409-410.

Studnicka, et al., Human-engineered monoclonal antibodies retain full specific binding activity by preserving non-CDR complementarity-modulating residues, Protein Eng., vol. 7, No. 6, Jun. 1994, pp. 805-814.

Tan, et al., "Superhumanized" antibodies: reduction of immunogenic potential by complementarity-determining region grafting with human germline sequences: application to an anti-CD28, J Immunol., vol. 169, No. 2, Jul. 15, 2002, pp. 1119-1125.

Wang, et al., In vitro characterization of the anti-PD-1 antibody nivolumab, BMS-936558, and in vivo toxicology in non-human primates, Cancer Immunol Res., vol. 2, No. 9, Sep. 2014, pp. 846-856.

Weiss, R, Hot prospect for new gene amplifier, Science, vol. 254, No. 5036, Nov. 29, 1991, pp. 1292-1293.

* cited by examiner

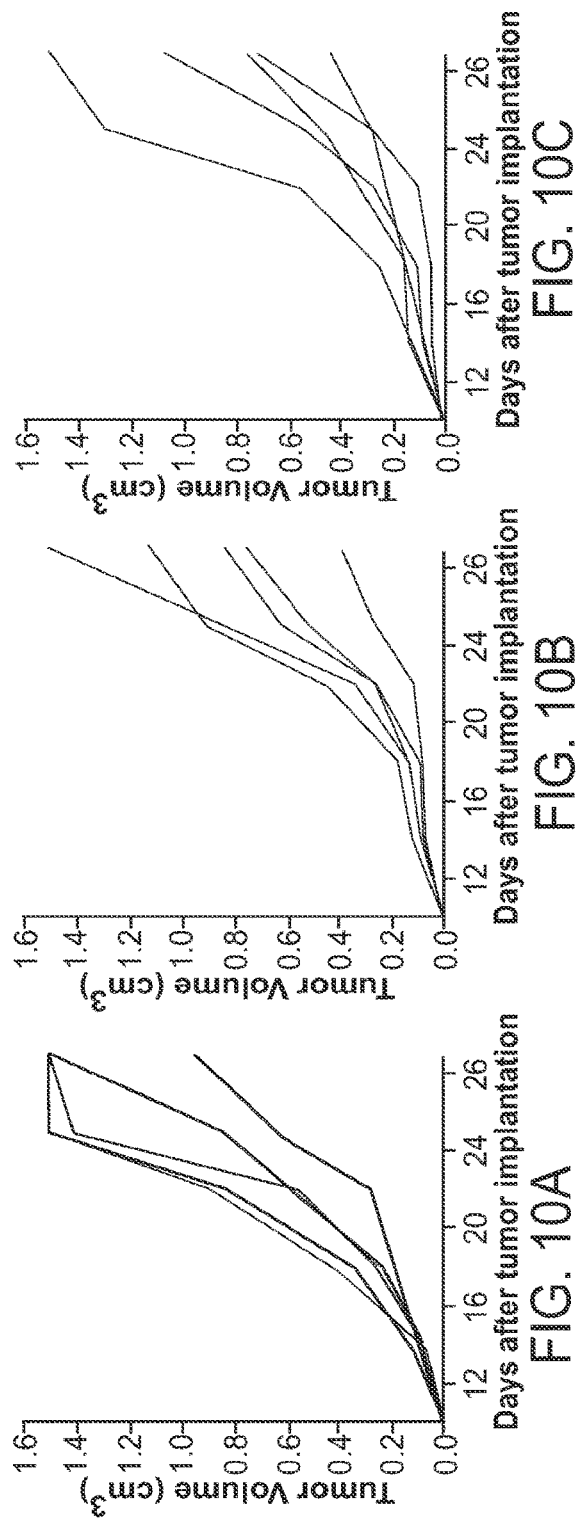
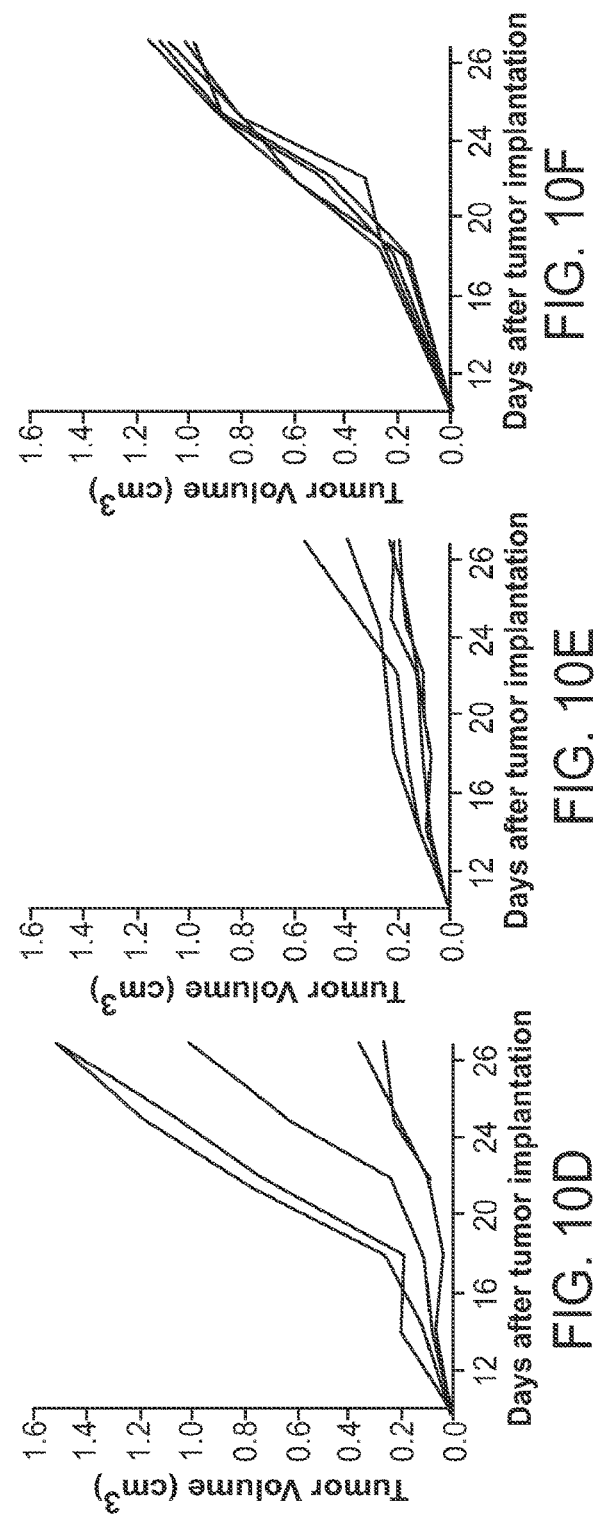

ANTIBODIES TO PROGRAMMED CELL DEATH PROTEIN 1 THAT ARE PD-1 AGONISTS

CROSS-REFERENCE TO RELATED APPLICATIONS

The present application is a continuation of International Patent Application No. PCT/US2023/061449, filed on Jan. 27, 2023, which claims the benefit of U.S. Provisional Application No. 63/304,365, filed on Jan. 28, 2022, the entire contents of each of which are incorporated herein by reference.

REFERENCE TO A SEQUENCE LISTING XML

This application contains a Sequence Listing which has been submitted electronically in XML format. The Sequence Listing XML is incorporated herein by reference. Said XML file, created on Jan. 24, 2023, is named 775935.000022_SL.xml and is 421,073 bytes in size.

TECHNICAL FIELD OF THE INVENTION

The invention is generally related to antibodies that specifically bind to PD-1, and methods of their use.

BACKGROUND OF THE INVENTION

The programmed cell death receptor protein 1 (PD-1)/programmed cell death receptor protein ligand 1 (PD-L1) pathway has shown promising clinical success as a cancer immunotherapy target. Antibodies that disrupt this pathway by physically inhibiting the interaction between PD-1 and PD-L1 can boost patient immune responses against cancer cells. For example, pembrolizumab (Keytruda®, Merck & Co., Inc., Kenilworth, NJ) binds to amino acids in the range of 64-89 in human PD-1, which overlaps with the portion of PD-1 bound by PD-L1. (Zak et al., Cell Structure 25(8): 1163-1174 (2017)). Successful clinical trials with PD-1 monoclonal antibodies and other immune-checkpoint inhibitors have opened new avenues in cancer immunology. However, the failure of a large subset of cancer patients to respond to new immunotherapies including to blocking anti-PD1 therapy has led to intensified research on combination therapies and predictive biomarkers (Iwai, Y. et al Journal of Biomedical Science, 24:26 (2017)).

Thus, it would be desirable to provide compositions and methods for modulating PD-1 signal transduction. It would be particularly desirable to provide compositions and methods that are PD-1 agonists, i.e., activate PD-1 independently of disrupting the PD-1/PD-L1 interaction.

It would also be desirable to provide antibodies and antigen binding fragments thereof that specifically bind to PD-1 and modulate PD-1 signal transduction. It would be particularly desirable to provide antibodies and antigen-binding fragments that are PD-1 agonists, i.e., activate PD-1 independently of disrupting the PD-1/PD-L1 interaction.

It would also be desirable to provide compositions and methods for treating cancer.

It would also be desirable to provide compositions and methods for treating infections.

SUMMARY OF THE INVENTION

This disclosure relates to antibodies and antigen binding fragments thereof that immunospecifically bind to PD-1, desirably human or mouse PD-1, and are PD-1 agonists. Such antibodies can be used to induce or promote an immune response that activates immune cell proliferation or activity. In embodiments, the disclosed antibodies and antigen binding fragments thereof specifically bind to PD-1 expressed on immune cells. In a particular embodiment, the disclosed antibodies and antigen-binding fragments thereof specifically bind to a PD-1 epitope distant from the site of the interaction between PD-1 and PD-L1, e.g., not at amino acid residues in the range of 64-89 in human PD-1. In a particular embodiment, the antibody or antigen-binding fragment does not compete with PD-L1 for binding to PD-1. The binding of the disclosed antibodies and antigen binding fragments thereof to PD-1 on immune cells can cause an activating signal to be transmitted into the immune cell, for example a signal that enhances or promotes cytokine production and/or activation of immune cell proliferation. Immune cells that express PD-1 include, but are not limited to, B and T cells as well as myeloid-derived cells (Riley, J., Immunol Rev. 229(i); 114-125-(2009)). In embodiments, the immune cell is a T cell, desirably a $CD8^+$ T cell.

This disclosure also relates to a method of stimulating, promoting, or enhancing an immune response (e.g., an adaptive immune response) in a subject in need thereof by administering to the subject an effective amount of an anti-PD-1 antibody or an antigen binding fragment thereof as disclosed herein to induce, enhance, or promote an immune response (e.g., an adaptive immune response) in the subject.

The antibody or antigen-binding fragment thereof having binding specificity for programmed cell death receptor protein 1 (PD-1) can comprise a light chain variable region and a heavy chain variable region, wherein the light chain variable region contains a CDR L1, a CDR L2, and a CDR L3 from Table 2 or Table 4, and the heavy chain variable region contains a CDR H1, a CDR H2, and a CDR H3 from Table 1 or Table 3.

In embodiments, the antibody or antigen-binding fragment thereof having binding specificity for programmed cell death receptor protein 1 (PD-1) may comprise a light chain variable region and a heavy chain variable region, wherein a) the light chain variable region contains CDR L1 comprising $QX^8X^9X^{10}X^{11}X^{12}$, CDR L2 comprising $X^{13}X^{14}S$, and CDR L3 comprising $X^{15}QX^{16}X^{17}X^{18}X^{19}PX^{20}X^{21}$, and the heavy chain variable region contains CDR H1 comprising GYTFTTYG (SEQ ID NO: 394), CDR H2 comprising INTYSGVP (SEQ ID NO: 395), and CDR H3 comprising $ARX^1X^2X^3X^4X^5X^6X^7$, wherein $X^1$ is selected from the group consisting of G and V; $X^2$ is selected from the group consisting of G, S, L, V, I, and E; $X^3$ is selected from the group consisting of and R, G, P, W, S, H, and K; $X^4$ is selected from the group consisting of G, E, S, V, W, and K; $X^5$ is selected from the group consisting of I, F, S, G, D, and V; $X^6$ is selected from the group consisting of A, G, Y, and S; $X^7$ is selected from the group consisting of Y, H, and D; $X^8$ is selected from the group consisting of G, S, and D; $X^9$ is selected from the group consisting of I and L; $X^{10}$ is selected from the group consisting of S, V, G, and R; $X^{11}$ is selected from the group consisting of N, Y, T, S, and R; $X^{12}$ is selected from the group consisting of S, Y, D, and W; $X^{13}$ is selected from the group consisting of A, K, Y, and D; $X^{14}$ is selected from the group consisting of A and V; $X^{15}$ is selected from the group consisting of Q, M, and L; $X^{16}$ is selected from the group consisting of S, G, and D; $X^{17}$ is selected from the group consisting of Y, T, N, and S; $X^{18}$ is selected from the group consisting of S, H, and D; $X^{19}$ is selected from the group consisting of T, W, and F; $X^{20}$ is selected from the group consisting of Y, P, R, and W; and $X^{21}$ is selected from the group consisting of T and F; or b) the light chain variable region contains CDR L1 comprising $QX^{42}X^{43}X^{44}X^{45}X^{46}$, CDR L2 comprising $X^{47}AS$, and CDR L3 comprising $X^{48}X^{49}X^{50}X^{51}X^{52}X^{53}X^{54}$, and the heavy chain variable region contains CDR H1 comprising $GX^{22}TFX^{23}X^{24}YX^{25}$ (SEQ ID NO: 163), CDR H2 comprising $IX^{26}X^{27}X^{28}X^{29}X^{30}X^{31}T$, and CDR H3 comprising $AX^{32}X^{33}X^{34}X^{35}X^{36}X^{37}X^{38}X^{39}FX^{40}X^{41}$, wherein $X^{22}$ is selected from the group consisting of Y and Q; $X^{23}$ is selected from the group consisting of N, T, and G; $X^{24}$ is selected from the group consisting of S, I, and N; $X^{25}$ is selected from the group consisting of W and L; $X^{26}$ is selected from the group consisting of H, L, R, and P; $X^{27}$ is selected from the group consisting of P and L; $X^{28}$ is selected from the group consisting of R, S, I, and N; $X^{29}$ is selected from the group consisting of G, D, N, and Y; $X^{30}$ is selected from the group consisting of I, S, G, and R; $X^{31}$ is selected from the group consisting of H, D, and Y; $X^{32}$ is selected from the group consisting of P and S; $X^{33}$ is selected from the group consisting of S, R, N, and Y; $X^{34}$ is selected from the group consisting of S, D, G, V, and F; $X^{35}$ is selected from the group consisting of S, N, G, I, D, and R; $X^{36}$ is selected from the group consisting of Y, N, C, L, S, and H; $X^{37}$ is selected from the group consisting of A, G, T, and E; $X^{38}$ is selected from the group consisting of W, C, S, R, D, and G; $X^{39}$ is selected from the group consisting of A, S, G, and D; $X^{40}$ is selected from the group consisting of A, S, and L; $X^{41}$ is selected from the group consisting of H, Y, and S; $X^{42}$ is selected from the group consisting of D, S, and G; $X^{43}$ is selected from the group consisting of V and I; $X^{44}$ is selected from the group consisting of S and G; $X^{45}$ is selected from the group consisting of T and S; $X^{46}$ is selected from the group consisting of A, S, D, and W; $X^{47}$ is selected from the group consisting of W, G, and D; $X^{48}$ is selected from the group consisting of Q and H; $X^{49}$ is selected from the group consisting of Q, K, and H; $X^{50}$ is selected from the group consisting of H, Y, F, R, D, and G; $X^{51}$ is selected from the group consisting of Y, N, Y, D, S, and G; $X^{52}$ is selected from the group consisting of R, S, V, T, and I; $X^{53}$ is selected from the group consisting of S, A, F, T, Y, and W; and $X^{54}$ is selected from the group consisting of P, L, S, and T.

In embodiments, the antibody or antigen-binding fragment thereof comprises CDR L1, CDR L2, CDR L3, CDR H1, CDR H2, and CDR H3 of 4G9-12; CDR L1, CDR L2, CDR L3, CDR H1, CDR H2, and CDR H3 of 4G9-1; CDR L1, CDR L2, CDR L3, CDR H1, CDR H2, and CDR H3 of 4G9-2; CDR L1, CDR L2, CDR L3, CDR H1, CDR H2, and CDR H3 of 4G9-3; CDR L1, CDR L2, CDR L3, CDR H1, CDR H2, and CDR H3 of 4G9-4; CDR L1, CDR L2, CDR L3, CDR H1, CDR H2, and CDR H3 of 4G9-5; CDR L1, CDR L2, CDR L3, CDR H1, CDR H2, and CDR H3 of 4G9-6; CDR L1, CDR L2, CDR L3, CDR H1, CDR H2, and CDR H3 of 4G9-7; CDR L1, CDR L2, CDR L3, CDR H1, CDR H2, and CDR H3 of 4G9-8; CDR L1, CDR L2, CDR L3, CDR H1, CDR H2, and CDR H3 of 4G9-9; CDR L1, CDR L2, CDR L3, CDR H1, CDR H2, and CDR H3 of 4G9-10; CDR L1, CDR L2, CDR L3, CDR H1, CDR H2, and CDR H3 of 4G9-11; CDR L1, CDR L2, CDR L3, CDR H1, CDR H2, and CDR H3 of 4G9-13; CDR L1, CDR L2, CDR L3, CDR H1, CDR H2, and CDR H3 of 4G9-14; CDR L1, CDR L2, CDR L3, CDR H1, CDR H2, and CDR H3 of 4G9-15; CDR L1, CDR L2, CDR L3, CDR H1, CDR H2, and CDR H3 of 4G9-16; CDR L1, CDR L2, CDR L3, CDR H1, CDR H2, and CDR H3 of 4G9-17; CDR L1, CDR L2, CDR L3, CDR H1, CDR H2, and CDR H3 of 4G9-18; CDR L1, CDR L2, CDR L3, CDR H1, CDR H2, and CDR H3 of 4G9-19; CDR L1, CDR L2, CDR L3, CDR H1, CDR H2, and CDR H3 of 4G9-20; CDR L1, CDR L2, CDR L3, CDR H1, CDR H2, and CDR H3 of 5C2-1; CDR L1, CDR L2, CDR L3, CDR H1, CDR H2, and CDR H3 of 5C2-2; CDR L1, CDR L2, CDR L3, CDR H1, CDR H2, and CDR H3 of 5C2-3; CDR L1, CDR L2, CDR L3, CDR H1, CDR H2, and CDR H3 of 5C2-4; CDR L1, CDR L2, CDR L3, CDR H1, CDR H2, and CDR H3 of 5C2-5; CDR L1, CDR L2, CDR L3, CDR H1, CDR H2, and CDR H3 of 5C2-6; CDR L1, CDR L2, CDR L3, CDR H1, CDR H2, and CDR H3 of 5C2-7; CDR L1, CDR L2, CDR L3, CDR H1, CDR H2, and CDR H3 of 5C2-8; CDR L1, CDR L2, CDR L3, CDR H1, CDR H2, and CDR H3 of 5C2-9; or CDR L1, CDRL2, CDR L3, CDRH1, CDRH2, and CDRH3 of 5C2-10. In a particular embodiment, the antibody or antigen-binding fragment comprises CDR L1, CDR L2, CDR L3, CDR H1, CDR H2, and CDR H3 of 4G9-12; or CDR L1, CDR L2, CDR L3, CDR H1, CDR H2, and CDR H3 of 4G9-2. Antibodies 4G9-1 to 4G9-20 and 5C2-1 to 5C2-10 are described herein. In a preferred embodiment, the antibody or antigen-binding fragment thereof comprises CDR L1, CDR L2, CDR L3, CDR H1, CDR H2, and CDR H3 of 4G9-12.

In embodiments, the antibody or antigen-binding fragment comprises the light chain variable region and the heavy chain variable region of 4G9-12; the light chain variable region and the heavy chain variable region of 4G9-1; the light chain variable region and the heavy chain variable region of 4G9-2; the light chain variable region and the heavy chain variable region of 4G9-3; the light chain variable region and the heavy chain variable region of 4G9-4; the light chain variable region and the heavy chain variable region of 4G9-5; the light chain variable region and the heavy chain variable region of 4G9-6; the light chain variable region and the heavy chain variable region of 4G9-7; the light chain variable region and the heavy chain variable region of 4G9-8; the light chain variable region and the heavy chain variable region of 4G9-9; the light chain variable region and the heavy chain variable region of 4G9-10; the light chain variable region and the heavy chain variable region of 4G9-11; the light chain variable region and the heavy chain variable region of 4G9-13; the light chain variable region and the heavy chain variable region of 4G9-14; the light chain variable region and the heavy chain variable region of 4G9-15; the light chain variable region and the heavy chain variable region of 4G9-16; the light chain variable region and the heavy chain variable region of 4G9-17; the light chain variable region and the heavy chain variable region of 4G9-18; the light chain variable region and the heavy chain variable region of 4G9-19; the light chain variable region and the heavy chain variable region of 4G9-20; the light chain variable region and the heavy chain variable region of 5C2-1; the light chain variable region and the heavy chain variable region of 5C2-2; the light chain variable region and the heavy chain variable region of 5C2-3; the light chain variable region and the heavy chain variable region of 5C2-4; the light chain variable region and the heavy chain variable region of 5C2-5; the light chain variable region and the heavy chain variable region of 5C2-6; the light chain variable region and the heavy chain variable region of 5C2-7; the light chain variable region and the heavy chain variable region of 5C2-8; the light chain variable region and the heavy chain variable region of 5C2-9; or the light chain variable region and the heavy chain variable region of 5C2-10. In a particular embodiment, the antibody or antigen-binding fragment thereof comprises the light chain variable region and the heavy chain variable region of 4G9-12. In a particular embodiment, the antibody or antigen-binding fragment thereof comprises the light chain variable region and the heavy chain variable region of 4G9-2.

One embodiment provides an antibody or antigen binding fragment thereof wherein CDR L1, CDR L2, CDR L3, CDR H1, CDR H2, and CDR H3 each independently have at least 75% identity, such as at least 85% identity or at least 90% identity, with the corresponding CDR L1, CDR L2, CDR L3, CDR H1, CDR H2, and CDR H3 of any one of the antibodies 4G9-1 to 4G9-20 and 5C2-1 to 5C2-10. In a preferred embodiment, the antibody or antigen binding fragment thereof contains CDR L1, CDR L2, CDR L3, CDR H1, CDR H2, and CDR H3 which each independently have at least 75% identity, such as at least 85% identity or at least 90% identity, with the corresponding CDR L1, CDR L2, CDR L3, CDR H1, CDR H2, and CDR H3 of 4G9-12.

One embodiment provides an antibody or antigen binding fragment thereof comprising a light chain variable region and a heavy chain variable region each independently having at least 75% identity, such as at least 85% identity, at least 90% identity, or at least 95% identity, with the corresponding light chain variable region and the heavy chain variable region of any one of the antibodies 4G9-1 to 4G9-20 and 5C2-1 to 5C2-10. In a preferred embodiment, the antibody or antigen binding fragment thereof comprises a light chain variable region and a heavy chain variable region that each independently having at least 75% identity, such as at least 85% identity, at least 90% identity, or at least 95% identity, with the corresponding light chain variable region and the heavy chain variable region of 4G9-12.

One embodiment provides an antibody or antigen binding fragment thereof wherein CDR L1, CDR L2, CDR L3, CDR H1, CDR H2, and CDR H3 each independently has three or fewer amino acid substitutions, such as two amino acid substitutions or one amino acid substitution, relative to the corresponding CDR L1, CDR L2, CDR L3, CDR H1, CDR H2, and CDR H3 of any one of the antibodies 4G9-1 to 4G9-20 and 5C2-1 to 5C2-10.

An antibody or antigen-binding fragment thereof of the present disclosure may further comprise a light chain constant region or portion thereof and/or a heavy chain constant region or portion thereof, e.g., the heavy chain constant region may be an IgG constant region.

An antibody or antigen-binding fragment thereof of the present disclosure can enhance phosphorylated interleukin-2-inducible T cell kinase (pITK) level, ITK/SHP2 ratio or both pITK level and ITK/SHP2 ratio in cells upon binding to PD-1 on cells. By activating T cells, an antibody or antigen-binding fragments thereof disclosed herein can induce T cell memory and/or inhibit T cell exhaustion. In an embodiment, an antibody or antigen-binding fragment thereof induces central memory T cells (Tcm). In an embodiment, an antibody or antigen-binding fragment thereof inhibits T cell exhaustion.

The present disclosure also relates to polynucleotide(s) encoding a heavy chain, a light chain, or both of an antibody or antigen-binding fragment thereof set forth above.

This disclosure relates to a host cell comprising the polynucleotide(s). In embodiments, the host cell is a mammalian cell (e.g., a human cell, a CHO cell, an immortalized human cell, a NSO cell). In a particular embodiment, the host cell may be a cell of a transgenic animal. In embodiments, the transgenic animal is a mouse.

The present disclosure also relates to a pharmaceutical composition comprising an antibody or antigen-binding fragment thereof set forth above and a pharmaceutically acceptable carrier.

One embodiment provides an antibody or epitope binding fragment thereof or a fusion protein that immunospecifically binds to a PD-1 epitope comprising amino acids 96-110 of human PD-1 (hPD-1). In certain preferred embodiments, the antibody or antigen-binding fragment binds to a PD-1 epitope comprising amino acids 96-110 of hPD-1 expressed on the surface of an immune cell. Without being bound by any particular theory or mechanism, it is believed that binding by the antibody or antigen-binding fragment to this epitope of PD-1 induces or promotes a signal through PD-1 that activates or stimulates the immune cell without disrupting the PD-1/PD-L1 interaction. In embodiments the immune cell that is activated or stimulated is a T cell, for example a CD4 T cell.

In embodiments, the antibody or antigen binding fragment thereof may be human, mouse, chimeric, humanized, monoclonal, bispecific, trispecific, or multispecific.

This disclosure also relates to a pharmaceutical composition including one or more of the disclosed antibodies or antigen binding fragments thereof. The pharmaceutical compositions can include a second therapeutic agent and/or a pharmaceutically acceptable excipient. In embodiments, the second therapeutic agent may be a second antibody or antigen binding fragment thereof that reduces suppression of PD-1 by PD-L1.

This disclosure also relates to a method for treating cancer, comprising administering to a subject in need thereof an effective amount of an antibody, antigen-binding fragment, or a pharmaceutical composition, as described herein. This disclosure also relates to the antibody, antigen-binding fragment, or pharmaceutical compositions disclosed herein for use as a medicament (e.g., particularly cancer therapy) and for use in treating cancer and/or for use in the manufacture of a medicament for treating cancer.

The disclosed therapeutic methods may further comprise administering to the subject one or more additional therapeutic agents. The one or more additional therapeutic agent can be an immunomodulator. The immunomodulator can be a checkpoint inhibitor (e.g., a checkpoint inhibitor with the proviso that the checkpoint inhibitor does not inhibit the interaction of PD-1 with PD-L1 or PD-L2). For example, the checkpoint inhibitor can be an anti-LAG-3 antibody or antigen-binding fragment thereof. As another example, the check point inhibitor can be an anti-CTLA4 antibody or antigen-binding fragment thereof. The immunomodulator can be a T cell engager, including bispecific T cell engagers (BiTEs), bifunctional checkpoint-inhibitory T cell engagers (CiTEs), simultaneous multiple interaction T cell engagers (SMITEs), trispecific killer engagers (TriKEs), BiTE-expressing chimeric antigen receptor (CAR) T cells (CART-.BiTE cells), and combinations thereof.

The one or more additional therapeutic can be a cell therapy. For example, the cell therapy can be a T cell therapy. The cell therapy can be tumor-infiltrating lymphocytes (TILs). The cell therapy can be an engineered cell therapy such as an engineered TCR therapy, a chimeric antigen receptor (CAR) therapy, or a combination thereof. In an embodiment, the cell therapy is chimeric antigen receptor T cells (CAR-T cells). In an embodiment, the cell therapy is engineered TCR T cells (TCR-T cells). For example, the method may comprise administering to the subject an effective combination comprising a therapeutically effect amount of (i) an antibody or antigen-binding fragment that is a PD-1 agonist as described herein and (ii) a second antibody or antigen-binding fragment thereof that reduces suppression of PD-1 by PD-L1. Though not to be bound by theory, the second antibody or antigen-binding fragment may bind to PD-1 or PD-L1 at a location that physically interferes with the interaction between PD-1 and PD-L1. In another example, the method may comprise administering to the subject an effective combination comprising a therapeutically effect amount of (i) an antibody or antigen-binding fragment that is a PD-1 agonist as described herein and (ii) an immune check point inhibitor that does not bind to PD-1 or PD-L1, for example anti-CTLA4 or anti-LAG-3.

This disclosure further relates to a method for inducing or enhancing central memory T cells, comprising administering to a subject in need thereof a therapeutically effective amount of an antibody or antigen-binding fragment disclosed herein.

This disclosure further relates a method for inhibiting T cell exhaustion, comprising administering to a subject in need thereof a therapeutically effective amount of an antibody or antigen-binding fragment disclosed herein.

BRIEF DESCRIPTION OF THE DRAWINGS

FIG. 1A is a graph showing IFNγ levels after human T cell activation from Donor 1 without agonist anti-PD-1 antibody ('Control'), with 4G9-2, or with 4G9-12 at concentrations of 0 and 10 µg/mL of antibody. FIG. 1B is a graph showing IFNγ levels after human T cell activation from Donor 2 without agonist anti-PD-1 antibody ('Control'), with 4G9-2 antibody, or with 4G9-12 antibody at concentrations of 0, 10, 20, and 50 µg/mL of antibody. The level of IFNγ without agonist anti-PD-1 antibody treatment is shown as a dashed line for comparison.

FIG. 3A is a schematic of the experiment described in Example 5. FIG. 3B is a graph showing the central memory T cells ($CD45RO^{high}/CD62L^{high}/CD45RA^{low}$) as a percentage of CD4+ T cells following 4G9-12 treatment. FIG. 3C is a graph showing the terminal effector T cells ($CD45RO^{low}/CD62L^{low}/CD45RA^{high}$) as a percentage of CD4+ T cells following 4G9-12 treatment.

FIG. 4A is a graph showing that treatment of donor CD4+ T cells with increasing concentrations of 4G9-2 antibody or 4G9-12 antibody, but not a blocking anti-PD-1 antibody (PROMEGA Co., clone J1201, "Block-1"), activated T cells and induced production of IFNγ. FIG. 4B is a graph showing that treatment of a second donor CD4+ T cells with increasing concentrations of 4G9-2 antibody or 4G9-12 antibody, but not a blocking anti-PD-1 antibody (PROMEGA Co., clone J1201, "Block-1"), activated T cells and induced production of IFNγ. FIG. 4C is a graph showing that treatment of a third donor CD4+ T cells with increasing concentrations of 4G9-12 antibody, but not an isotype control antibody ("Iso Ctrl"), a blocking anti-PD-1 antibody (PROMEGA Co., clone J1201, "Block-1"), or pembrolizumab (a blocking anti-PD-1 antibody, "Block-2") activated T cells and induced production of IFNγ.

FIG. 6A shows dose-dependent binding of PD-L1 to PD-1 (PD-L1 fluorescence channel) on the cell surface at 1 µg/mL, 2 µg/mL, and 5 µg/mL PD-L1. FIG. 6B shows binding of 4G9-12 (at 5 µg/ml) to the cell PD-1 is unaffected by varying PD-L1 concentrations. FIG. 6C shows dose-dependent binding of PD-L1 to PD1 on the cell surface is unaffected by the presence of 4G9-12 (5 µg/mL).

FIG. 8A is a graph showing the tumor volume of each mouse in the untreated group. FIG. 8B is a graph showing the tumor volume of each mouse in the 4G9-12 antibody (1 mg/kg) group. FIG. 8C is a graph showing the tumor volume of each mouse in the 4G9-12 antibody (0.5 mg/kg) group. FIG. 8D is a graph showing the tumor volume of each mouse in the blocking anti-PD-1 antibody (1 mg/kg, RMP1-14 clone) group.

FIGS. 10A-10F are graphs showing tumor volume of each mouse in the CT26 mouse model of colorectal carcinoma in FIG. 9 and as further described in Example 10. FIG. 10A is a graph showing the tumor volume of each mouse in the untreated group. FIG. 10B is a graph showing the tumor volume of each mouse in the 4G9-12 antibody (0.01 mg/kg) group.

FIG. 10C is a graph showing the tumor volume of each mouse in the 4G9-12 antibody (0.05 mg/kg) group. FIG. 10D is a graph showing the tumor volume of each mouse in the 4G9-12 antibody (0.1 mg/kg) group. FIG. 10E is a graph showing the tumor volume of each mouse in the 4G9-12 antibody (0.25 mg/kg) group. FIG. 10F is a graph showing the tumor volume of each mouse in the blocking anti-PD-1 antibody (1 mg/kg, RMP1-14 clone) group.

FIG. 11A is a graph showing that treatment with 4G9-12 (anti-PD1 agonist antibody), but not blocking anti-PD-1 antibody (RMP1-14), significantly increases CD4$^+$ T cell activation state using CD40L as a marker for activation state. FIG. 11B is a graph showing that treatment with 4G9-12 (anti-PD1 agonist antibody), but not blocking anti-PD-1 antibody (RMP1-14), significantly increases CD8$^+$ T cell activation state using CD25 as a marker for activation state. Statistical analysis consists of one-way ANOVA, with multiple comparison post-test.

FIG. 12A is an image of a Western blot for SHP2 and PD-1. FIG. 12B is a an image of a Western blot staining for PD-1 and ITK (interleukin-2-inducible T cell kinase). FIG. 12C is a bar graph of quantified ITK/SHP2 protein ratios. Values were normalized to PD-1 protein levels.

DETAILED DESCRIPTION OF THE INVENTION

I. Definitions

Figures 1A, 1B:
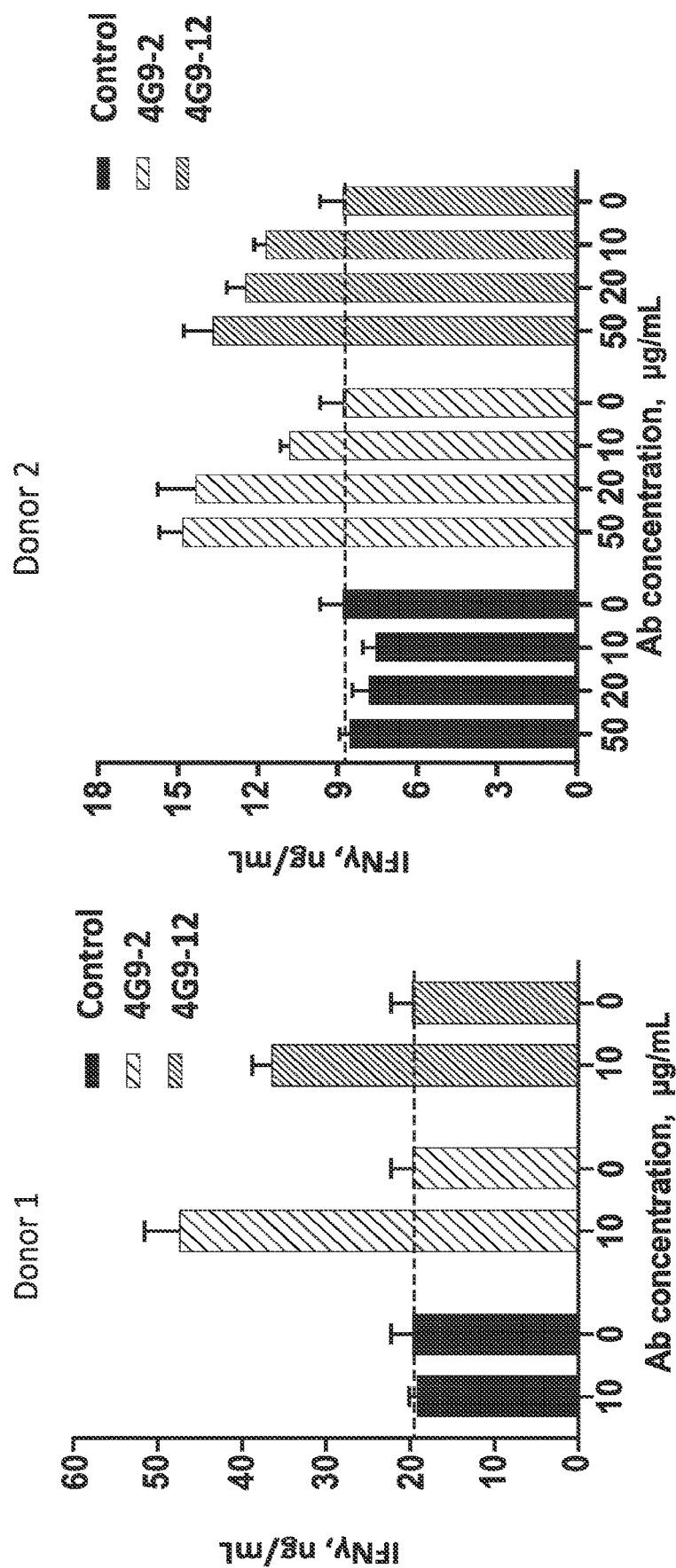
FIGS. 1A and 1B are graphs showing human T cell activation from two donors, as determined by interferon gamma (IFNγ) levels, by antibodies 4G9-2 and 4G9-12 according to Example 3.

As used herein, an antibody or an antigen-binding fragment thereof are said to "immunospecifically bind" to a target region or conformation ("epitope") of an antigen if such binding involves the antigen recognition site of the antibody or the antigen-binding fragment. An antibody that immunospecifically binds to a particular epitope of a particular antigen may bind to other epitopes and/or antigens with lower affinity if the other antigen has some sequence or conformational similarity that is recognized by the antigen recognition site as determined by, e.g., immunoassays, BIA-CORE® assays, or other assays known in the art, but would not bind to a totally unrelated antigen. Desirably, however, antibodies (and their antigen binding fragments) will not cross-react with other antigens and/or epitopes. Antibodies and antigen-binding fragments may also bind to other molecules in a way that is not immunospecific, such as to FcR receptors, by virtue of binding domains in other regions/domains of the molecule that do not involve the antigen recognition site, such as the Fc region.

As used herein, the term "antibody" is intended to denote an immunoglobulin molecule that possesses at least one "variable region" antigen recognition site comprising heavy and light chain variable regions. An antibody also possesses at least one constant domain not including an antigen recognition site.

The variable region includes a "hypervariable region" whose residues are responsible for antigen binding. The hypervariable region includes amino acid residues from a "Complementarity Determining Region" or "CDR" (i.e., typically at approximately residues 24-34 (CDR L1), 50-56 (CDR L2), and 89-97 (CDR L3) in the light chain variable region and at approximately residues 27-35 (CDR H1), 50-65 (CDR H2), and 95-102 (CDR H3) in the heavy chain variable region; Kabat et al., *Sequences of Proteins of Immunological Interest*, 5th. Ed. Public Health Service, National Institutes of Health, Bethesda, MD (1991)) and/or those residues from a "hypervariable loop" (i.e., residues 26-32 (L1), 50-52 (L2), and 91-96 (L3) in the light chain variable region and 26-32 (H1), 53-55 (H2), and 96-101 (H3) in the heavy chain variable region; Chothia and Lesk; 1987, *J. Mol. Biol.* 196:901-917). "Framework Region" or "FR" residues are those variable region residues other than the hypervariable region residues as herein defined. Other well-known amino acid numbering conventions can be used to define CDRs and FR regions, such as the AHo scheme and the Chothia scheme.

The term antibody includes all types or antibodies from any desired species, such as monoclonal antibodies, multispecific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000; *Cur. Plum, Biotech.* 1:253; Reichmann and Muyldermans, 1999, *J. Immunol. Meth*, 231:25; International Publication Nos. WO 94/04678 and WO 94/25591; U.S. Pat. No. 0,305,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies. disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., lgG$_1$, IgG$_2$, IgG$_3$, IgG$_4$, IgA$_1$ and lgA$_2$) or subclass.

As used herein, the term "antigen-binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind an antigen. Such fragments include Fab', F(ab')$_2$, Fv, single chain (ScFv), single variable domains (dAbs) and the like, and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, such as at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 1.25 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g., signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. Desirably, such modulation will provide at least a 10% change in a measurable immune system activity; more desirably, at least a 50% change in such activity, or at least a 2-fold, 5-fold, 10 fold, or still more desirably, at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete. Similarly, a molecule has substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, greater than 97% identical, greater than 98% identical, or greater than 99% identical.

As used herein, the term "derivative" refers to an antibody or antigen-binding fragment thereof that immunospecifically binds to the same target of a parent or reference antibody but which differs in amino acid sequence from the parent or reference antibody or antigen binding fragment thereof by including one, two, three, four, five or more amino acid substitutions, additions, deletions, or modifications relative to the parent or reference antibody or antigen binding fragment thereof. Desirably, such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, so as to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules, such as antibodies having a variable region derived from a non-human antibody and a human immunoglobulin constant region.

As used herein, the "term "humanized antibody" refers to an immunoglobulin including a human framework region and one or more CDRs from a non-human (for example, a mouse or rat) immunoglobulin. The non-human immunoglobulin providing the CDRs is called the "donor" and the human immunoglobulin providing the framework is called the "acceptor." Constant regions need not be present, but if they are, they should be substantially identical to human immunoglobulin constant regions, i.e., at least about 85-99%, desirably about 95% or more, identical. Hence, all parts of a humanized immunoglobulin, except possibly the CDRs, are substantially identical to the corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

As used herein, a "therapeutically effective amount" refers to that amount of a therapeutic agent sufficient to mediate a clinically relevant elimination, reduction, or amelioration of such symptoms under the conditions of administration. An effect is clinically relevant if its magnitude is sufficient to impact the health or prognosis of a recipient subject. A therapeutically effective amount may refer to the amount of therapeutic agent sufficient to delay or minimize the progression or onset of disease, e.g., delay or minimize the spread or progression of cancer. A therapeutically effective amount may also refer to the amount of the therapeutic agent that provides a therapeutic benefit in the treatment or management of a disease.

As used herein, an "immune cell" refers to any cell of hemopoietic origin including, but not limited to, T cells, B-cells, monocytes, dendritic cells, and macrophages.

The terms "subject" and "patient" are used interchangeably herein, and refer to a mammal, including, but not limited to, humans, pets (e.g., cats, dogs), livestock and sporting animals (e.g., cattle, sheep, horses, camels), rodents such as mice and rats, and other laboratory animals, among others.

As used herein, the term "variant" refers to a polypeptide or polynucleotide that differs from a reference polypeptide or polynucleotide but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive. capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid. index in conferring interactive biologic function on a polypeptide is generally understood in the art. it is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8.); glycine (−0.4); threonine (−0.7); serine (−0.8); tryptophan (−0.9); tyrosine (1.3); praline (−1.6); histidine (−3,2); glutamate (−3.5); glutamine (−3.5); aspartate (−3,5); asparagine (−3.5); lysine (−3.9); and arginine (4.5).

Though not to be bound by theory, the relative hydropathic character of the amino acids determines the secondary structure of the resultant polypeptide, which in turn defines the interaction of the polypeptide with other molecules, such as enzymes, substrates, receptors, antibodies, antigens, and cofactors. It is known in the art that an amino acid can generally be substituted by another amino acid having a similar hydropathic index and still obtain a functionally equivalent polypeptide. In such changes, the substitution of amino acids whose hydropathic indices are within +2 is desired, those within ±1 are particularly desired, and those within ±0.5 are even more particularly desired.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate-(+3.0±1); glutamate (+3.0±1); serine (+0.3); asparagine (+0.2); glutamine (+0.2); glycine (0); proline (−0.5.±1); threonine (−0.4); alanine (−0.5); histidine (−0.5); cysteine (−1.0); methionine (−1.3); valine (4.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is desired, those within +1 are particularly desired, and those within +0.5 are even more particularly desired.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue→exemplary substitution): (Ala→Gly, Ser), (Arg→Lys), (Asn→Gln, His), (Asp→Gln, Cys, Ser), (Gln→Asn), (Glu→Asp), (Gly→Ala), (His→Asn, Gln), (Ile→Leu, Val), (Leu→Ile, Val), (Lys→Arg), (Met→Leu, Tyr), (Ser→Thr), (Thr→Ser), (Trp→Tyr); (Tyr→Trp, Phe), and (Val→Ile, Leu). Embodiments of this disclosure thus contemplate functional or biological equivalents of a polypeptide as set forth above. In particular, embodiments of the polypeptides can include variants having about 75% or more, such as 80%, 90%, or 95% or more, sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2, SIM, or Megalign (DNASTAR) software. Appropriate parameters for measuring alignment, including any algorithms walled to achieve maximal alignment over the full length of the sequences being compared can be determined by known methods.

For purposes herein, the percent sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100*W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

II. Compositions

Antibodies and antigen binding fragments thereof that immunospecifically bind to PD-1 are provided. Contrary to the predominant paradigm as of this writing, that anti-PD-1 antibodies act as "checkpoint inhibitors" that reduce suppression of PD-1 activity by PD-L1 (Riley, J., Immunol Rev. 229(1):114-125 (2009)), the disclosed antibodies and antigen binding fragments thereof immunospecifically bind to an epitope of PD-1 distant from the PD-L1 interaction site and are PD-1 agonists, and cause an activating signal to be delivered to the immune cell. The anti-PD-1 agonist antibodies and antigen binding fragments disclosed herein not only inhibit T cell suppression, but also activate T cells. As shown and exemplified herein, PD-1 agonists of this disclosure, in addition to inhibiting T cell suppression, can activate T cells, inhibit T cell exhaustion and enhance T cell memory. In contrast, anti-PD-1 antibodies that block PD-L1 binding (e.g., non-agonist PD-1 antibodies) act as checkpoint inhibitors, and a recognized shortcoming of checkpoint inhibitors is that they can lead to T cell exhaustion and can decrease T cell memory.

A. Programmed Death Receptor Protein 1 (PD-1)

The disclosed antibodies and antigen binding fragments thereof immunospecifically bind to PD-1. The antibodies and antigen binding fragments thereof can bind to PD-1 having, for example, the amino acid sequences provide below.

```
human PD-1 (UniProtKB Q15116)
                                      (SEQ ID NO: 396)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL
```

-continued

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL mouse PD-1 (UniProtKB Q02242)
(SEQ ID NO: 397)
MWVRQVPWSFTWAVLQLSWQSGWLLEVPNGPWRSLTFYPAWLTVSEGANA

TFTCSLSNWSEDLMLNWNRLSPSNQTEKQAAFCNGLSQPVQDARFQIIQL

PNRHDFHMNILDTRRNDSGIYLCGAISLHPKAKIEESPGAELVVTERILE

TSTRYPSPSPKPEGRFQGMVIGIMSALVGIPVLLLLAWALAVFCSTSMSE

ARGAGSKDDTLKEEPSAAPVPSVAYEELDFQGREKTPELPTACVHTEYAT

IVFTEGLGASAMGRRGSADGLQGPRPPRHEDGHCSWPL

Preferably, the antibody or antigen-binding fragment thereof binds PD-1 and is an agonist of PD-1. In a particular embodiment, the antibodies and antigen-binding fragments of the present disclosure bind to an epitope of PD-1 that is not part of the PD-1 structure that interacts with PD-L1. In a particular embodiment, the antibodies and antigen-binding fragments immunospecifically bind to a PD-1 epitope comprising amino acids 96-110 of hPD-1, which have an amino acid sequence TYLCGAISLAPKAQI (SEQ ID NO: 398). This epitope is described in more detail in U.S. Pat. No. 11,021,540, which is hereby incorporated by reference in its entirety. Though not to be bound by theory, immunospecific binding of an antibody or antigen-binding fragment of the present disclosure to PD-1 epitope comprising amino acids 96-110 of hPD-1 is believed to activate PD-1 mediated signal transduction.

B. Antibody Compositions

The disclosed anti-PD-1 antibodies or antigen binding fragments thereof include whole immunoglobulins (i.e., antibodies comprising two heavy and two light chains) of any class, fragments thereof, and proteins containing at least an antigen binding variable region of an antibody. In some embodiments, the disclosed antibody contains both an antibody light chain variable region and an antibody heavy chain variable region. In other embodiments, such molecules can further include one or more of the CH1, hinge, CH2, CH3, and CH4 regions of the heavy chain. The antibody can be selected from any class of immunoglobulins, including IgM, IgG, IgD, IgA, and IgE, and any isotype, including IgG1, IgG2, IgG3 and IgG4. In some embodiments, the constant domain is a complement fixing constant domain where it is desired that the antibody exhibit cytotoxic activity, and the class is typically IgG1. In other embodiments, where such cytotoxic activity is not desirable, the constant domain can be of the IgG2 or IgG4 class. The antibody can include sequences from more than one class or isotype, and selecting particular constant domains to optimize desired effector functions is within the ordinary skill in. the art.

The variable region of native heavy and light chains each comprise four FW regions, largely adopting a beta-sheet configuration, connected by three CDRs, which form loops connecting, and in some cases forming part of, the beta-sheet structure. The CDRs in each chain are held together in close proximity by the FW regions and, with the CDRs from the other chain, contribute to the formation of the antigen binding site of antibodies.

Some embodiments provide antigen-binding fragments of the anti-PD-1 antibodies. The fragments, whether attached to other sequences or not, may include insertions, deletions, substitutions, or other selected modifications of particular regions or specific amino acids residues, provided the activity of the fragment is not significantly altered or impaired compared to the nonmodified antibody or antibody fragment (e.g., an antigen-binding fragment).

Another embodiment provides single-chain antibodies specific to PD-1. Methods for the production of single-chain antibodies are well known to those of skill in the art. A single chain antibody can be created by fusing together the variable regions of the heavy and light chains using a short peptide linker, thereby reconstituting an antigen binding site on a single molecule. Single-chain antibody variable fragments (scFvs) in which the C-terminus of one variable region is tethered to the N-terminus of the other variable regions via a 15 to 25 amino acid peptide or linker have been developed without significantly disrupting antigen binding or specificity of the binding. The linker is chosen to permit the heavy chain and light chain to bind together in their proper conformational orientation.

Another embodiment provides divalent single-chain variable fragments (di-scFvs) that can be engineered by linking two scFvs. This can be done by producing a single peptide chain with two VH and two VL, regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Another embodiment provides a monoclonal antibody specific to PD-1 that induces an activating signal to immune cells. The monoclonal antibody can be obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species. or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired activity.

C. Chimeric and Humanized Antibodies

Another embodiment provides chimeric anti-PD-1 antibodies and antigen binding fragments thereof including one or more of the disclosed sequences and functional variants thereof are also provided that bind to PD-1 and preferably cause an activating signal to be transmitted into an immune cell expressing PD-1.

Methods for producing chimeric antibodies are known in the art. See e.g., Morrison, 1985, *Science* 229:1202; Oi et al., 1986, *BioTechniques* 4:214; Gillies et al., 1989, *J Immunol. Methods* 125:191-202; and U.S. Pat. Nos. 6,311,415, 5,807, 715, 4,816,567, and 4,816,397. Chimeric antibodies including one or more CDRs from a non-human species and framework regions from a human immunoglobulin molecule can be produced using a variety of techniques known in the art including, for example, CDR-grafting (EP 239,400; International Publication No. WO 91109967; and U.S. Pat. Nos. 5,225,539, 5,530,101, and 5,585,089), veneering or resurfacing (EP 592,106; EP 519,596; Padlan, 1991, *Molecular Immunology* 28(4/5):489-498; Studnicka et al., 1.994, *Protein Engineering* 7; 805; and Roguska et al., 1994, *Proc. Natl. Acad. Sci. USA* 91:969), and chain shuffling (U.S. Pat. No. 5,565,332).

The disclosed anti-PD-1 antibodies or antigen binding fragments thereof can be human or humanized antibodies, or antigen binding fragments thereof. Many non-human antibodies (e.g., those derived from mice, rats, or rabbits) are naturally antigenic in humans, and thus can give rise to undesirable immune responses when administered to humans. Therefore, the use of human or humanized antibodies in the methods reduces the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge. Such antibodies can also be produced using a suitable expression or display library, such as phage display.

Optionally, the antibodies are generated in other species and "humanized" for administration in humans. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) which contain minimal sequences derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat, or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable regions, in which all or substantially all of the CDR regions correspond to those of a non-human immunoglobulin and all or substantially all of the FW regions are those of a human immunoglobulin consensus sequence. The humanized antibody optimally also may contain at least a portion of an immunoglobulin constant region (Fc), typically that of a human immunoglobulin.

Methods for humanizing non-human antibodies are well known in art, see, for example, European Patent Nos: EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular immunology* 28(4/5):489-498: Studnicka et al., 1994, *Protein Engineering* 7(6):805-8.1:4; Roguska et al., 1994, *PNAS* 91:969'973; Tan et al., 2002, *J Immunol.* 169:1119-1125; Caldas et al., 2000, *Protein Eng.* 13:353-360; Motet et al., 2000, *Methods* 20:267-79; Baca et al., 1997, *J Mot Chem.* 272:1067840684; Roguska et al., 1996, *Protein Eng.* 9:895-904; Couto et al., 1995, *Cancer Res.* 55 (23 Supp):5973s-5977s; Couto Oat, 1995, *Cancer. Res.* 55:1717-22; Sandhu, 1994, *Gene* 150: 409-10; Pedersen et al., 1994, 1 *Mat Riot* 235:959-973; Jones et. al., 0.1986, *Nature* 321:522'525; Reichmann et al., 1988, *Nature* 332:323.329; and Presta, 1992 (*Curr. Op. Struct. Biol.* 2:593-596).

Generally, a humanized antibody has one or more amino acid residues introduced into it from a source that is non-human. These non-human amino acid residues are often referred to as "import" residues, which are typically taken from an "import" variable region. Antibody humanization techniques generally involve the use of recombinant DNA technology to manipulate the DNA sequence encoding one or more polypeptide chains of an antibody molecule. Humanization can be essentially performed by substituting. rodent CDRs or CDR sequences for the corresponding sequences of a human antibody. Accordingly, a humanized form of a non-human antibody (or a fragment thereof) is a chimeric antibody or fragment wherein substantially less than an intact human variable region has been substituted by the corresponding sequence from a non-human species. In practice, humanized antibodies are typically human antibodies in. which some CDR residues and possibly some FW residues are substituted by residues from analogous sites in rodent antibodies.

The choice of human variable region, both light and heavy, to be used in making the humanized antibodies can be very important in order to reduce antigenicity. According to the "best-fit" method, the sequence of the variable region of a rodent antibody is screened against the entire library of known human variable region sequences. The human sequence which is closest to that of the rodent is then accepted as the human framework (FW) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FW residues can be selected and combined from the consensus and import sequence so that the desired antibody characteristic, such as increased affinity for the target antigen(s), is achieved.

The disclosure also relates to a chimeric antigen receptor (CAR) comprising the light chain variable region and the heavy chain variable region of any of the antibodies or antigen-binding fragments disclosed herein. CARs are well-known transmembrane receptors that can be expressed on T cells to provide T cell activation by a desired antigen in an MHC independent manner. Typically, CARs include an scFv of desired binding specificity that is fused to a hinge region hinge (e.g., and IgG hinge from IgG1, IgG2 or IgG4 with or without CH domains, CD28 hinge, CD8alpha hinge), a transmembrane domain (e.g., CD28 transmembrane domain and cytoplasmic tail), CD3zeta cytosolic domain, and optionally one or more co-stimulatory domain (e.g., 4-1BB, OX40, CD28). In embodiments, the CAR comprises the light chain variable region of any of the antibodies 4G9-1 to 4G9-20 and 5C2-1 to 5C2-10 and the heavy chain variable region of any of the antibodies 4G9-1 to 4G9-20 and 5C2-1 to 5C2-10.

A human, humanized, or chimeric antibody derivative can include substantially all of at least one, and typically two, variable regions in which all or substantially all of the CDR regions correspond to those of a non-human immunoglobulin (i.e., donor antibody) and all or substantially all of the framework regions are those of a human immunoglobulin consensus sequence. Such antibodies can also include at least a portion of an immunoglobulin constant region (Fc), typically that of a human immunoglobulin. The constant domains of such antibodies can be selected with respect to the proposed function of the antibody, in particular the effector function which may be. required. In some embodiments, the constant domains of such antibodies are or can include human IgA, IgD, IgE, IgG or IgM domains. In a specific embodiment, human IgG constant domains, especially of the IgG1 and IgG3 isotypes are used, when the humanized antibody derivative is intended for a therapeutic use and antibody effector functions such as antibody-dependent cell-mediated cytotoxicity (ADCC) and complement-dependent cytotoxicity (CDC) activity are needed. In alternative embodiments, IgG2 and IgG4 isotypes are used when the antibody is intended for therapeutic purposes and antibody effector function is. not required. Fc constant domains including one or more amino acid modifications which alter antibody effector functions such as those disclosed in U.S. Patent Application Publication Nos. 2005/0037000 and 200510004514.

The framework and CDR regions of a humanized antibody need not correspond precisely to the parental sequences, e.g., the donor CDR or the consensus framework can be mutagenized by substitution, insertion, or deletion of at least one residue (e.g., at least two residues, at least three residues, at least four residues, at least five residues, at least six residues, at least seven residues, at least eight residues) so that the CDR or framework residue at that site does not correspond to either the consensus or the donor antibody. In some embodiments, the CDR differs from the parental sequence by substitution, insertion, or deletion of one residue, two residues, three residues, or four residues. In some embodiments, the framework region differs from the parental sequence by substitution, insertion, or deletion of one residue, two residues, three residues, four residues, five residues, six residues, seven residues, or eight residues. In some embodiments, such mutations are not extensive. Usually, at least 75% of the humanized antibody residues will correspond to those of the parental framework region (FW) and CDR sequences, such as at least 80%, at least 90%, or at least 95%. Often, framework residues in the framework regions will be substituted with the corresponding residue from the CDR donor antibody to alter, for example, improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann. et al., 1988, *Nature* 332:323).

In embodiments, the antibodies or antigen-binding fragments are human antibodies or fragments, i.e., contain only human-derived sequences. Such human antibodies or antigen-binding fragments may be particularly desirable for therapeutic treatment of human subjects. Human antibodies can be made by a variety of methods known in the art, including phage display methods using antibody libraries derived from human immunoglobulin sequences (see U.S. Pat. Nos. 4,444,887 and 4,716,111; and International Publication Nos. WO 98/46645, WO 94/50433, WO 98/24893, WO 98/16654, WO 96/34096, WO 96/33735, and WO 91/10741). Such human antibodies can be produced using transgenic mice which are incapable of expressing functional endogenous immunoglobulins, but which can express human immunoglobulin genes.

For example, the human heavy and light chain immunoglobulin gene complexes can be introduced randomly or by homologous recombination into mouse embryonic stem cells. Alternatively, the human variable region, constant region, and diversity region can be introduced into mouse embryonic stein cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice may be immunized using conventional methodologies with a selected antigen, e.g., all or a portion of a polypeptide. Monoclonal antibodies directed against the antigen can be obtained from the immunized, transgenic mice using conventional hybridoma technology. The human immunoglobulin transgenes harbored by the transgenic mice rearrange during B cell differentiation; and sulue4yettly undergo class switching and somatic mutation. Thus, using such a technique, it is possible to produce therapeutically useful IgG, IgA, IgM and IgE antibodies. For an overview of this technology for producing human antibodies, see Lonberg and Huszar 1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893; WO 96/34096, and WO 96433735; and U.S. Pat. Nos. 5,413,923, 5,625,126, 5,633,425, 5,569,825, 5,661,016, 5,545,806, 5,814,318, and 5,939,598, which are incorporated by reference herein in their entirety.

DNA sequences coding for human acceptor framework sequences include but are not limited to FW segments from the human germline VH segment VH1-18 and JH6 and the human germline VL segment VK-A26 and JK4. In a specific embodiment, one or more of the CDRs may be inserted within framework regions using routine recombinant DNA techniques. The framework regions can be naturally occurring or consensus framework regions, and human framework regions. See, e.g., Chothia et al., 1998, *"Structural*

*Determinants In The Sequences Of Immunoglobulin Variable Domain,*" J. Mol. Biol. 278: 457-479 for a listing of human framework regions.

D. Fusion Protein

In embodiments, the antibody or antigen-binding fragment may be component of a fusion protein or fusion polypeptide, in which the antibody or antigen-binding fragment can be coupled to another polypeptide, such as a chimeric antigen receptor (CAR). Fusion polypeptides have a first fusion partner including all or a part of one or more of the disclosed antibodies or antigen-binding fragments, covalently bonded to a second polypeptide directly or via a linker peptide sequence that is covalently bonded to the second polypeptide. The fusion proteins may, but need not, contain a domain that functions to dimerize or multimerize two or more fusion proteins. The peptide/polypeptide linker domain can either be a separate domain, or alternatively can be contained within one of the other domains (antibody/antigen-binding fragment or second polypeptide) of the fusion protein. Similarly, the domain, if any, that functions to dimerize or multimerize the fusion protein can either be a separate domain, or alternatively can be contained within one of the other domains (antibody/antigen-binding fragment, second polypeptide, or linker domain) of the fusion protein. In embodiments, the dimerization/multimerization domain and the peptide/polypeptide linker domain are the same.

Fusion proteins disclosed herein can, for example, be of formula I.

$$N\text{-}R_1\text{-}R_2\text{-}R_3\text{---}C \quad (I)$$

wherein N represents the N-terminus of the fusion protein, C represents the C-terminus of the fusion protein, $R_1$ may be all or part of one of the disclosed antibodies, antigen-binding fragments, or functional variants or fragments thereof, $R_2$ is an optional peptide/polypeptide linker domain, and $R_3$ may be a second polypeptide. Alternatively, $R_3$ may be all or part of one of the disclosed antibodies, antigen-binding fragments, or functional variants or fragments thereof, and $R_1$ may be the second polypeptide.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

E. Antibody Sequences 1. 4G9 and 5C2 Sequences

One embodiment of the present disclosure relates to affinity matured antibodies or antigen binding fragments thereof derived from a humanized antibody isolated from hybridoma 4G9. In particular, this embodiment provides antibodies and antigen-binding fragments comprising sequences found in or related to sequences from twenty antibodies designated 4G9-1 to 4G9-20. The heavy chain variable region (VH), CDR H1, CDR H2, and CDR H3 sequences of each of these antibodies are given in Table 1.

The antibodies 4G9-1, 4G9-2, 4G9-3, 4G9-4, 4G9-5, 4G9-6, 4G9-7, 4G9-8, 4G9-9 and 4G9-10 contain the same heavy chain and light chain CDRs as antibodies 4G9-11, 4G9-12, 4G9-13, 4G9-14, 4G9-15, 4G9-16, 4G9-17, 4G9-18, 4G9-19 and 4G9-20, respectively. Additionally, the light chain variable regions of 4G9-1, 4G9-2, 4G9-3, 4G9-4, 4G9-5, 4G9-6, 4G9-7, 4G9-8, 4G9-9 and 4G9-10 are the same as the light chain variable regions of 4G9-11, 4G9-12, 4G9-13, 4G9-14, 4G9-15, 4G9-16, 4G9-17, 4G9-18, 4G9-19 and 4G9-20, respectively. However, the heavy chain variable regions of 4G9-1, 4G9-2, 4G9-3, 4G9-4, 4G9-5, 4G9-6, 4G9-7, 4G9-8, 4G9-9 and 4G9-10 are not the same as the heavy chain variable regions of 4G9-11, 4G9-12, 4G9-13, 4G9-14, 4G9-15, 4G9-16, 4G9-17, 4G9-18, 4G9-19 and 4G9-20, respectively, and each of 4G9-11, 4G9-12, 4G9-13, 4G9-14, 4G9-15, 4G9-16, 4G9-17, 4G9-18, 4G9-19 and 4G9-20 include a N73D substitution.

TABLE 1

| Antibody | SEQ ID NO: | VH sequence | SEQ ID NO: | CDR H1 sequence | SEQ ID NO: | CDR H2 sequence | SEQ ID NO: | CDR H3 sequence |
|---|---|---|---|---|---|---|---|---|
| 4G9-1 | 1 | QVQLVQSGAEVKKP GASVKVSCKASGYT FTTYGINWVRQATG QGLEWMGWINTYS GVPGYAQKFQGRVT MTLNTSISTAYMELS SLRSEDTAVYYCAR GGRGIAYWGQGTLV TVSS | 21 | GYTFTT YG | 42 | INTYSG VP | 63 | ARGGR GIAY |
| 4G9-2 | 2 | QVQLVQSGAEVKKP GASVKVSCKASGYT FTTYGINWVRQATG QGLEWMGWINTYS GVPGYAQKFQGRVT MTLNTSISTAYMELS SLRSEDTAVYYCAR GSGGFAYWGQGTL VTVSS | 22 | GYTFTT YG | 43 | INTYSG VP | 64 | ARGSG GFAY |
| 4G9-3 | 3 | QVQLVQSGAEVKKP GASVKVSCKASGYT FTTYGINWVRQATG QGLEWMGWINTYS GVPGYAQKFQGRVT | 23 | GYTFTT YG | 44 | INTYSG VP | 65 | ARGGR ESAY |

TABLE 1-continued

VH, CDR H1, CDR H2, and CDR H3 sequences of antibodies 4G9-1 to 4G9-20

| Antibody | SEQ ID NO: | VH sequence | SEQ ID NO: | CDR H1 sequence | SEQ ID NO: | CDR H2 sequence | SEQ ID NO: | CDR H3 sequence |
|---|---|---|---|---|---|---|---|---|
| | | MTLNTSISTAYMELS SLRSEDTAVYYCAR GGRESAYWGQGTL VTVSS | | | | | | |
| 4G9-4 | 4 | QVQLVQSGAEVKKP GASVKVSCKASGYT FTTYGINWVRQATG QGLEWMGWINTYS GVPGYAQKFQGRVT MTLNTSISTAYMELS SLRSEDTAVYYCAR GLPSFGYWGQGTLV TVSS | 24 | GYTFTT YG | 45 | INTYSG VP | 66 | ARGLPS FGY |
| 4G9-5 | 5 | QVQLVQSGAEVKKP GASVKVSCKASGYT FTTYGINWVRQATG QGLEWMGWINTYS GVPGYAQKFQGRVT MTLNTSISTAYMELS SLRSEDTAVYYCAR GVRVFYHWGQGTL VTVSS | 25 | GYTFTT YG | 46 | INTYSG VP | 67 | ARGVR VFYH |
| 4G9-6 | 6 | QVQLVQSGAEVKKP GASVKVSCKASGYT FTTYGINWVRQATG QGLEWMGWINTYS GVPGYAQKFQGRVT MTLNTSISTAYMELS SLRSEDTAVYYCAR GGWWFADWGQGTL VTVSS | 26 | GYTFTT YG | 47 | INTYSG VP | 68 | ARGGW WFAD |
| 4G9-7 | 7 | QVQLVQSGAEVKKP GASVKVSCKASGYT FTTYGINWVRQATG QGLEWMGWINTYS GVPGYAQKFQGRVT MTLNTSISTAYMELS SLRSEDTAVYYCAR GISKGAYWGQGTLV TVSS | 27 | GYTFTT YG | 48 | INTYSG VP | 69 | ARGISK GAY |
| 4G9-8 | 8 | QVQLVQSGAEVKKP GASVKVSCKASGYT FTTYGINWVRQATG QGLEWMGWINTYS GVPGYAQKFQGRVT MTLNTSISTAYMELS SLRSEDTAVYYCAR VERGDAYWGQGTL VTVSS | 28 | GYTFTT YG | 49 | INTYSG VP | 70 | ARVER GDAY |
| 4G9-9 | 9 | QVQLVQSGAEVKKP GASVKVSCKASGYT FTTYGINWVRQATG QGLKWMGWINTYS GVPGYAQKFQGRVT MTLNTSISTAYMELS SLRSEDTAVYYCAR GVHGVSYWGQGTL VTVSS | 29 | GYTFTT YG | 50 | INTYSG VP | 71 | ARGVH GVSY |
| 4G9-10 | 10 | QVQLVQSGAEVKKP GASVKVSCKASGYT FTTYGINWVRQATG QGLEWMGWINTYS GVPGYAQKFQGRVT MTLNTSISTAYMELS SLRSEDTAVYYCAR GSKGDAYWGQGTL VTVSS | 30 | GYTFTT YG | 51 | INTYSG VP | 72 | ARGSK GDAY |

TABLE 1-continued

VH, CDR H1, CDR H2, and CDR H3 sequences of antibodies 4G9-1 to 4G9-20

| Antibody | SEQ ID NO: | VH sequence | SEQ ID NO: | CDR H1 sequence | SEQ ID NO: | CDR H2 sequence | SEQ ID NO: | CDR H3 sequence |
|---|---|---|---|---|---|---|---|---|
| 4G9-11 | 11 | QVQLVQSGAEVKKPGASVKVSCKASGYTFTTYGINWVRQATGQGLEWMGWINTYSGVPGYAQKFQGRVTMTLDTSISTAYMELSSLRSEDTAVYYCARGGRGIAYWGQGTLVTVSS | 31 | GYTFTTYG | 52 | INTYSGVP | 73 | ARGGRGIAY |
| 4G9-12 | 12 | QVQLVQSGAEVKKPGASVKVSCKASGYTFTTYGINWVRQATGQGLEWMGWINTYSGVPGYAQKFQGRVTMTLDTSISTAYMELSSLRSEDTAVYYCARGSGGFAYWGQGTLVTVSS | 32 | GYTFTTYG | 53 | INTYSGVP | 74 | ARGSGGFAY |
| 4G9-13 | 13 | QVQLVQSGAEVKKPGASVKVSCKASGYTFTTYGINWVRQATGQGLEWMGWINTYSGVPGYAQKFQGRVTMTLDTSISTAYMELSSLRSEDTAVYYCARGGRESAYWGQGTLVTVSS | 33 | GYTFTTYG | 54 | INTYSGVP | 75 | ARGGRESAY |
| 4G9-14 | 14 | QVQLVQSGAEVKKPGASVKVSCKASGYTFTTYGINWVRQATGQGLEWMGWINTYSGVPGYAQKFQGRVTMTLDTSISTAYMELSSLRSEDTAVYYCARGLPSFGYWGQGTLVTVSS | 34 | GYTFTTYG | 55 | INTYSGVP | 76 | ARGLPSFGY |
| 4G9-15 | 15 | QVQLVQSGAEVKKPGASVKVSCKASGYTFTTYGINWVRQATGQGLEWMGWINTYSGVPGYAQKFQGRVTMTLDTSISTAYMELSSLRSEDTAVYYCARGVRVFYHWGQGTLVTVSS | 35 | GYTFTTYG | 56 | INTYSGVP | 77 | ARGVRVFYH |
| 4G9-16 | 16 | QVQLVQSGAEVKKPGASVKVSCKASGYTFTTYGINWVRQATGQGLEWMGWINTYSGVPGYAQKFQGRVTMTLDTSISTAYMELSSLRSEDTAVYYCARGGWWFADWGQGTLVTVSS | 36 | GYTFTTYG | 57 | INTYSGVP | 78 | ARGGWWFAD |
| 4G9-17 | 17 | QVQLVQSGAEVKKPGASVKVSCKASGYTFTTYGINWVRQATGQGLEWMGWINTYSGVPGYAQKFQGRVTMTLDTSISTAYMELSSLRSEDTAVYYCARGISKGAYWGQGTLVTVSS | 37 | GYTFTTYG | 58 | INTYSGVP | 79 | ARGISKGAY |
| 4G9-18 | 18 | QVQLVQSGAEVKKPGASVKVSCKASGYTFTTYGINWVRQATGQGLEWMGWINTYSGVPGYAQKFQGRVT | 38 | GYTFTTYG | 59 | INTYSGVP | 80 | ARVERGDAY |

TABLE 1-continued

VH, CDR H1, CDR H2, and CDR H3 sequences of antibodies 4G9-1 to 4G9-20

| Antibody | SEQ ID NO: | VH sequence | SEQ ID NO: | CDR H1 sequence | SEQ ID NO: | CDR H2 sequence | SEQ ID NO: | CDR H3 sequence |
|---|---|---|---|---|---|---|---|---|
| | | MTLDTSISTAYMELS SLRSEDTAVYYCAR VERGDAYWGQGTL VTVSS | | | | | | |
| 4G9-19 | 19 | QVQLVQSGAEVKKP GASVKVSCKASGYT FTTYGINWVRQATG QGLKWMGWINTYS GVPGYAQKFQGRVT MTLDTSISTAYMELS SLRSEDTAVYYCAR GVHGVSYWGQGTL VTVSS | 39 | GYTFTT YG | 60 | INTYSG VP | 81 | ARGVH GVSY |
| 4G9-20 | 20 | QVQLVQSGAEVKKP GASVKVSCKASGYT FTTYGINWVRQATG QGLEWMGWINTYS GVPGYAQKFQGRVT MTLDTSISTAYMELS SLRSEDTAVYYCAR GSKGDAYWGQGTL VTVSS | 40 | GYTFTT YG | 61 | INTYSG VP | 82 | ARGSK GDAY |
| 4G9 HC CDR consensus sequences | n/a | n/a | 41 | GYTFTT YG | 62 | INTYSG VP | n/a | ARX$^1$X$^2$ X$^3$X$^4$X$^5$ X$^6$X$^7$ |

In ARX$^1$X$^2$X$^3$X$^4$X$^5$X$^6$X$^7$, X$^1$ is selected from the group consisting of G and V; X$^2$ is selected from the group consisting of G, S, L, V, I, and E; X$^3$ is selected from the group consisting of and R, G, P, W, S, H, and K; X$^4$ is selected from the group consisting of G, E, S, V, W, and K; X$^5$ is selected from the group consisting of I, F, S, G, D, and V; X$^6$ is selected from the group consisting of A, G, Y, and S; and X$^7$ is selected from the group consisting of Y, H, and D.

The light chain variable region (VK), CDR L1, CDR L2, and CDR L3 sequences of each of these antibodies are given in Table 2.

TABLE 2

VK, CDR L1, CDR L2, and CDR L3 sequences of antibodies 4G9-1 to 4G9-20

| Antibody | SEQ ID NO: | VK sequence | SEQ ID NO: | CDR L1 sequence | CDR L2 sequence | SEQ ID NO: | CDR L3 sequence |
|---|---|---|---|---|---|---|---|
| 4G9-1 | 83 | DIQLTQSPSSLSASV GDRVTITCRASQGI SNSLAWFQQKPGK VPKRLIYAASNLQS GVPSRFSGSGSGTE FTLTISSLQPEDFAT YYCQQSYSTPYTFG QGTKLEIK | 103 | QGISNS | AAS | 123 | QQSYS TPYT |
| 4G9-2 | 84 | DIVMTQSPLSLPVT LGQPASISCRSSQSL VYSDGNTYLNWFQ QRPGQSPRRLIYKV SNRDSGVPDRFSGS GSGTDFTLKISRVE AEDVGVYYCMQG THWPPFTFGPGTKV EIK | 104 | QSLVY SDGNT Y | KVS | 124 | MQGTH WPPFT |
| 4G9-3 | 85 | EIVMTQSPATLSVS PGERATLSCRASQS IGTSLHWYQQKPG GAPRLLIKYASESIT GIPARFSGSGSGTEF TLTISSLQSEDFAVY YCQQSNSWPYTFG QGTKLEIK | 105 | QSIGTS | YAS | 125 | QQSNS WPYT |

TABLE 2-continued

VK, CDR L1, CDR L2, and CDR L3 sequences of antibodies 4G9-1 to 4G9-20

| Antibody | SEQ ID NO: | VK sequence | SEQ ID NO: | CDR L1 sequence | CDR L2 sequence | SEQ ID NO: | CDR L3 sequence |
|---|---|---|---|---|---|---|---|
| 4G9-4 | 86 | AIQMTQSPSSLSAS VGDRVTITCRASQS ISSYLNWYQQKPG KAPKLLIYAASSLQ SGVPSRFSGSGSGT DFTLTISSLQPEDFA TYYCQQSYSTPYTF GQGTKLEIK | 106 | QSISSY | AAS | 126 | QQSYS TPYT |
| 4G9-5 | 87 | EIVMTQSPATLSVS PGERATLSCRASQS IGTSLHWYQQKPG GAPRLLIKYASESIT GIPARFSGSGSGTEF TLTISSLQSEDFAVY YCQQSNSWPYTFG QGTKLEIK | 107 | QSIGTS | YAS | 127 | QQSNS WPYT |
| 4G9-6 | 88 | AIRMTQSPSSLSAS VGDRVTITCRASQS ISSYLNWYQQKPG KAPKLLIYAASSLQ SGVPSRFSGSGSGT DFTLTISSLQPEDFA TYYCQQSYSTPRTF GQGTKVEIK | 108 | QSISSY | AAS | 128 | QQSYS TPRT |
| 4G9-7 | 89 | NIQMTQSPSSLSAS VGDRVTITCRASQS ISSYLNWYQQKPG KAPKLLIYAASSLQ SGVPSRFSGSGSGT DFTLTISSLQPEDFA TYYCQQSSSTPYTF GQGTKLEIK | 109 | QSISSY | AAS | 129 | QQSSST PYT |
| 4G9-8 | 90 | EIVLTQSPSSLSASV GDRVTITCRASQDI RRDFGWYQQKPGL APELLIYDASRLRS GVPSRFSGSGSGTL FTFTITNLQPEDFAT YYCLQDYDFPRTF GQGTKVDIK | 110 | QDIRRD | DAS | 130 | LQDYD FPRT |
| 4G9-9 | 91 | EIVMTQSPATLSVS PGERATLSCRASQS IGTSLHWYQQKPG GAPRLLIKYASESIT GIPARFSGSGSGTEF TLTISSLQSEDFAVY YCQQSNSWPYTFG QGTKLEIK | 111 | QSIGTS | YAS | 131 | QQSNS WPYT |
| 4G9-10 | 92 | DIVMTQSPSSLSAS VGDRVTITCRASQS ISTWLAWFQQKPG KAPKLLIYKASSLK SGVPSRFSGSGSGT EFTLTISSLQPDDFA TYYCQQSYSTPWT FGQGTKLEIK | 112 | QSISTW | KAS | 132 | QQSYS TPWT |
| 4G9-11 | 93 | DIQLTQSPSSLSASV GDRVTITCRASQGI SNSLAWFQQKPGK VPKRLIYAASNLQS GVPSRFSGSGSGTE FTLTISSLQPEDFAT YYCQQSYSTPYTFG QGTKLEIK | 113 | QGISNS | AAS | 133 | QQSYS TPYT |

TABLE 2-continued

VK, CDR L1, CDR L2, and CDR L3 sequences of antibodies 4G9-1 to 4G9-20

| Antibody | SEQ ID NO: | VK sequence | SEQ ID NO: | CDR L1 sequence | CDR L2 sequence | SEQ ID NO: | CDR L3 sequence |
|---|---|---|---|---|---|---|---|
| 4G9-12 | 94 | DIVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPPFTFGPGTKVEIK | 114 | QSLVYSDGNTY | KVS | 134 | MQGTHWPPFT |
| 4G9-13 | 95 | EIVMTQSPATLSVSPGERATLSCRASQSIGTSLHWYQQKPGGAPRLLIKYASESITGIPARFSGSGSGTEFTLTISSLQSEDFAVYYCQQSNSWPYTFGQGTKLEIK | 115 | QSIGTS | YAS | 135 | QQSNSWPYT |
| 4G9-14 | 96 | AIQMTQSPSSLSASVGDRVTITCRASQSISSYLNWYQQKPGKAPKLLIYAASSLQSGVPSRFSGSGSGTDFTLTISSLQPEDFATYYCQQSYSTPYTFGQGTKLEIK | 116 | QSISSY | AAS | 136 | QQSYSTPYT |
| 4G9-15 | 97 | EIVMTQSPATLSVSPGERATLSCRASQSIGTSLHWYQQKPGGAPRLLIKYASESITGIPARFSGSGSGTEFTLTISSLQSEDFAVYYCQQSNSWPYTFGQGTKLEIK | 117 | QSIGTS | YAS | 137 | QQSNSWPYT |
| 4G9-16 | 98 | AIRMTQSPSSLSASVGDRVTITCRASQSISSYLNWYQQKPGKAPKLLIYAASSLQSGVPSRFSGSGSGTDFTLTISSLQPEDFATYYCQQSYSTPRTFGQGTKVEIK | 118 | QSISSY | AAS | 138 | QQSYSTPRT |
| 4G9-17 | 99 | NIQMTQSPSSLSASVGDRVTITCRASQSISSYLNWYQQKPGKAPKLLIYAASSLQSGVPSRFSGSGSGTDFTLTISSLQPEDFATYYCQQSSTPYTFGQGTKLEIK | 119 | QSISSY | AAS | 139 | QQSSTPYT |
| 4G9-18 | 100 | EIVLTQSPSSLSASVGDRVTITCRASQDIRRDFGWYQQKPGLAPELLIYDASRLRSGVPSRFSGSGSGTLPFTFTITNLQPEDFATYYCLQDYDFPRTFGQGTKVDIK | 120 | QDIRRD | DAS | 140 | LQDYDFPRT |
| 4G9-19 | 101 | EIVMTQSPATLSVSPGERATLSCRASQSIGTSLHWYQQKPGGAPRLLIKYASESITGIPARFSGSGSGTEFTLTISSLQSEDFAVYYCQQSNSWPYTFGQGTKLEIK | 121 | QSIGTS | YAS | 141 | QQSNSWPYT |

TABLE 2-continued

VK, CDR L1, CDR L2, and CDR L3 sequences of antibodies 4G9-1 to 4G9-20

| Antibody | SEQ ID NO: | VK sequence | SEQ ID NO: | CDR L1 sequence | CDR L2 sequence | SEQ ID NO: | CDR L3 sequence |
|---|---|---|---|---|---|---|---|
| 4G9-20 | 102 | DIVMTQSPSSLSAS VGDRVTITCRASQS ISTWLAWFQQKPG KAPKLLIYKASSLK SGVPSRFSGSGSGT EFTLTISSLQPDDFA TYYCQQSYSTPWT FGQGTKLEIK | 122 | QSISTW | KAS | 142 | QQSYS TPWT |
| 4G9 LC CDR consensus sequences | n/a | n/a | n/a | $QX^8X^9X^{10}X^{11}X^{12}$ | $X^{13}X^{14}S$ | n/a | $X^{15}QX^{16}X^{17}X^{18}X^{19}PX^{20}X^{21}$ |

In $QX^8X^9X^{10}X^{11}X^{12}$, $X^{13}X^{14}S$ and $X^{15}QX^{16}X^{17}X^{18}X^{19}PX^{20}X^{21}$, $X^8$ is selected from the group consisting of G, S, and D; $X^9$ is selected from the group consisting of I and L; $X^{10}$ is selected from the group consisting of S, V, G, and R; $X^{11}$ is selected from the group consisting of N, Y, T, S, and R; $X^{12}$ is selected from the group consisting of S, Y, D, and W; $X^{13}$ is selected from the group consisting of A, K, Y, and D; $X^{14}$ is selected from the group consisting of A and V; $X^{15}$ is selected from the group consisting of Q, M, and L; $X^{16}$ is selected from the group consisting of S, G, and D; $X^{17}$ is selected from the group consisting of Y, T, N, and S; $X^{18}$ is selected from the group consisting of S, H, and D; $X^{19}$ is selected from the group consisting of T, W, and F; $X^{20}$ is selected from the group consisting of Y, P, R, and W; and $X^{21}$ is selected from the group consisting of T and F.

One embodiment of the present disclosure relates to affinity matured antibodies or antigen binding fragments thereof derived from a humanized antibody isolated from hybridoma 5C2. In particular, this embodiment provides antibodies and antigen-binding fragments comprising sequences found in or related to sequences from twenty antibodies designated 5C2-1 to 5C2-10. The heavy chain variable region (VH), CDR H1, CDR H2, and CDR H3 sequences of each of these antibodies are given in Table 3.

TABLE 3

VH, CDR H1, CDR H2, and CDR H3 sequences of antibodies 5C2-1 to 5C2-10

| Antibody | SEQ ID NO: | VH sequence | SEQ ID NO: | CDR H1 sequence | SEQ ID NO: | CDR H2 sequence | SEQ ID NO: | CDR H3 sequence |
|---|---|---|---|---|---|---|---|---|
| 5C2-1 | 143 | QVQLVQSGAEVKKP GASVKVSCKASGYT FNSYWMHWVRQAP GQGLEWMGRIHPRG IHTNYNQKFKGRVT LTVDTSTSTAYMEL SSLRSEDTAVYYCA PSSSYAWAFAHWG QGTLVTVSS | 153 | GYTFN SYW | 164 | IHPRGI HT | 174 | APSSSY AWAFA H |
| 5C2-2 | 144 | QVQLVQSGAEVKKP GASVKVSCKASGQT FTSYRMHWVRQAP GQGLEWMGRILPIRS DTNYNQKFKGRVTL TVDTSTSTAYMELSS LRSEDTAVYYCARD AGYGSLFAAWGQG TLVTVSS | 154 | GQTFTS YR | 165 | ILPIRSD T | 175 | ARDAG YGSLF AA |
| 5C2-3 | 145 | QVQLVQSGAEVKKP GASVKVSCKASGYT FTSYWMHWVRQAP GQGLEWMGRIHPSD SDTNYNQKFKGRVT LTVDTSTSTAYMEL SSLRSEDTAVYYCA PKGNYVVRFAYWG QGTLVTVSS | 155 | GYTFTS YW | 166 | IHPSDS DT | 176 | APKGN YVVRF AY |
| 5C2-4 | 146 | QVQLVQSGAEVKKP GASVKVSCKASGYT FTRYMHWVRQAP GQGLEWMGRIHPTD | 156 | GYTFTS YW | 167 | IHPTDS VT | 177 | APDVN YARAF AH |

TABLE 3-continued

VH, CDR H1, CDR H2, and CDR H3 sequences of antibodies 5C2-1 to 5C2-10

| Antibody | SEQ ID NO: | VH sequence | SEQ ID NO: | CDR H1 sequence | SEQ ID NO: | CDR H2 sequence | SEQ ID NO: | CDR H3 sequence |
|---|---|---|---|---|---|---|---|---|
| | | SVTNYNQKFKGRVT LTVDTSTSTAYMEL SSLRSEDTAVYYCA PDVNYARAFAHWG QGTLVTVSS | | | | | | |
| 5C2-5 | 147 | QVQLVQSGAEVKKP GASVKVSCKASGYT FGIYWMHWVRQAP GQGLEWMGRILPSN GYTNYNQKFKGRVT LTVDTSTSTAYMEL SSLRSEDTAVYYCA PYGIYTRDFSHWGQ GTLVTVSS | 157 | GYTFGI YW | 168 | ILPSNG YT | 178 | APYGIY TRDFSH |
| 5C2-6 | 148 | QVQLVQSGAEVKKP GASVKVSCKASGYT FTSYWMHWVRQAP GQGLEWMGRIHPSD SDTNYNQKFKGRVT LTVDTSTSTAYMEL SSLRSEDTAVYYCA PYVDLESGFAYWGQ GTLVTVSS | 158 | GYTFTS YW | 169 | IHPSDS DT | 179 | APYVD LESGFA Y |
| 5C2-7 | 149 | QVQLVQSGAEVKKP GASVKVSCKASGYT FTSYWMHWVRQAP GMGLEWMGRIHPIY RDTNYNQKFKGRVT LTVDTSTSTAYMEL SSLRSEDTAVYYCA PYVNYGDGFAYWG QGTLVTVSS | 159 | GYTFTS YW | 170 | IHPIYR DT | 180 | APYVN YGDGF AY |
| 5C2-8 | 150 | QVQLVQSGAEVKKP GASVKVSCKASGYT FNSYLMHWVRQAP GMGLEWMGRIRPN YSDTNYNQKFKGRV TLTVDTSTSTAYME LSSLRSEDTAVYYC APYGNNASGFSYWG QGTLVTVSS | 160 | GYTFN SYL | 171 | IRPNYS DT | 181 | APYGN NASGFS Y |
| 5C2-9 | 151 | QVQLVQSGAEVKKP GASVKVSCKASGQT FTNYLMHWVRQAP GQGLEWMGRIPLSD RDTNYNQKFKGRVT LTVDTSTSTAYMEL SSLRSEDTAVYYCA PYGRSASGFSSWGQ GTLVTVSS | 161 | GQTFT NYL | 172 | IPLSDR DT | 182 | APYGR SASGFS S |
| 5C2-10 | 152 | QVQLVQSGAEVKKP GASVKVSCKASGYT FTSYWMHWVRQAP GQGLEWMGRIHPSD SDTNYNQKFKGRVT LTVDTSTSTAYMEL SSLRSEDTAVYYCA PYFDHAGGFLHWG QGTLVTVSS | 162 | GYTFTS YW | 173 | IHPSDS DT | 183 | APYFD HAGGF LH |
| 5C2 HC CDR consensus sequences | n/a | n/a | 163 | $GX^{22}TFX^{23}X^{24}YX^{25}$ | n/a | $IX^{26}X^{27}X^{28}X^{29}X^{30}X^{31}T$ | n/a | $AX^{32}X^{33}X^{34}X^{35}X^{36}X^{37}X^{38}X^{39}FX^{40}X^{41}$ |

In $GX^{22}TFX^{23}X^{24}YX^{25}$ (SEQ ID NO: 163), $IX^{26}X^{27}X^{28}X^{29}X^{30}X^{31}T$, and $AX^{32}X^{33}X^{34}X^{35}X^{36}X^{37}X^{38}X^{39}FX^{40}X^{41}X^{22}$ is selected from the group consisting of Y and Q; $X^{23}$ is selected from the group consisting of N, T, and G; $X^{24}$ is selected from the group consisting of S, I, and N; $X^{25}$ is selected from the group consisting of W and L; $X^{26}$ is selected from the group consisting of H, L, R, and P; $X^{27}$ is selected from the group consisting of P and L; $X^{28}$ is selected from the group consisting of R, S, I, and N; $X^{29}$ is selected from the group consisting of G, D, N, and Y; $X^{30}$ is selected from the group consisting of I, S, G, and R; $X^{31}$ is selected from the group consisting of H, D, and Y; $X^{32}$ is selected from the group consisting of P and S; $X^{33}$ is selected from the group consisting of S, R, N, and Y; $X^{34}$ is selected from the group consisting of S, D, G, V, and F; $X^{35}$ is selected from the group consisting of S, N, G, I, D, and R; $X^{36}$ is selected from the group consisting of Y, N, C, L, S, and H; $X^{37}$ is selected from the group consisting of A, G, T, and E; $X^{38}$ is selected from the group consisting of W, C, S, R, D, and G; $X^{39}$ is selected from the group consisting of A, S, G, and D; $X^{40}$ is selected from the group consisting of A, S, and L; and $X^{41}$ is selected from the group consisting of H, Y, and S.

The light chain variable region (VK), CDR L1, CDR L2, and CDR L3 sequences of each of these antibodies are given in Table 4.

TABLE 4

VK, CDR L1, CDR L2, and CDR L3 sequences of antibodies 5C2-1 to 5C2-10

| Antibody | SEQ ID NO: | VK sequence | SEQ ID NO: | CDR L1 sequence | CDR L2 sequence | SEQ ID NO: | CDR L3 sequence |
|---|---|---|---|---|---|---|---|
| 5C2-1 | 184 | DIQMTQSPSSLSASVGDRVTITCRASQDVSTALAWYQQKPGKAPKLLIYWASTRHSGVPDRFSGSGSGTDFTLTISSLQPEDFATYYCQQHYRSPGTFGGGTKVEIK | 194 | QDVSTA | WAS | 204 | QQHYRSPGT |
| 5C2-2 | 185 | DIQMTQSPSSLSASVGDRVTITCRASQDVSTALAWYQQKPGKAPKLLIYWASTRHSGVPDRFSGSGSGTDFTLTISSLQPEDFATYYCQQHDSSPGTFGGGTKVEIK | 195 | QDVSTA | WAS | 205 | QQHDSSPGT |
| 5C2-3 | 186 | DIVMTQSPSSLSASVGDRVTITCRASQGIRNDLGWYQQKPGKAPKLLIYAASSLQSGVPSRFSGSGSDTDFTLTISSLQPEDFATYYCLQDYNYPWTFGQGTKVDIK | 196 | QGIRND | AAS | 206 | LQDYNYPWT |
| 5C2-4 | 187 | DIQMTQSPSSLSASVGDRVTITCRASQDVSTALAWYQQKPGKAPKLLIYWASTRHSGVPDRFSGSGSGTDFTLTISSLQPEDFATYYCQQHYGSPWTFGGGTKVEIK | 197 | QDVSTA | WAS | 207 | QQHYGSPWT |
| 5C2-5 | 188 | DIQMTQSPSSLSASVGDRVTITCRASQDVSTALAWYQQKPGKAPKLLIYWASTRHSGVPDRFSGSGSGTDFTLTISSLQPEDFATYYCQRDTTPRTFGGGTKVEIK | 198 | QDVSTA | WAS | 208 | QQRDTTPRT |
| 5C2-6 | 189 | DIAMTQTPSSLSASIGDRVTIACRASQGISSALAWYQQKPGRTPKLLIFDASTLQSGV | 199 | QGISSA | DAS | 209 | QQFNTYSSVT |

TABLE 4-continued

VK, CDR L1, CDR L2, and CDR L3 sequences of antibodies 5C2-1 to 5C2-10

| Antibody | SEQ ID NO: | VK sequence | SEQ ID NO: | CDR L1 sequence | CDR L2 sequence | SEQ ID NO: | CDR L3 sequence |
|---|---|---|---|---|---|---|---|
| | | PSRFSGSGSGT DFTLTISSLQPE DFATYYCQQFN TYSSVTFGQGT RLEIK | | | | | |
| 5C2-7 | 190 | DIQMTQSPSTLS ASVGDRVTITC RASQDVSTALA WYQQKPGKAP KLLIYWASTRH IGVPDRFSGSGS GTDFTLTISSLQ PEDFATYYCHQ DYITPRTFGGG TKVEIK | 200 | QDVSTA | WAS | 210 | HQDYIT PRT |
| 5C2-8 | 191 | DIQMTQSPSSLS ASVGDRVTITC RASQDVSTALA WYQQKPGKAP KLLIYWASTRH SGVPDRFSGSG SGTDFTLTISSL QPEDFATYYCQ QHYRSPWTFG GGTKVEIK | 201 | QDVSTA | WAS | 211 | QQHYR SPWT |
| 5C2-9 | 192 | DIQMTQSPSSLS ASVGDRVTITC RASQDVSTALA WYQQKPGKAP KLLIYWASTRH SGVPDRFSGSG SGTDFTLTISSL QPEDFATYYCQ QGSSTPLTFGG GTKVEIK | 202 | QDVSTA | WAS | 212 | QQGSS TPLT |
| 5C2-10 | 193 | DIVMTQSPGTL SLSPGERATLSC RASQSVSSSYL AWYQQKPGQA PRLLIYGASSRA TGIPDRFSGSGS GTDFTLTISRLE PEDFAVYYCQQ YGSWTFGQGT KLEIK | 203 | QSVSSSY | GAS | 213 | QQYGS WT |
| 5C2 LC CDR consensus sequences | n/a | n/a | n/a | $QX^{42}X^{43}X^{44}X^{45}X^{46}$ | $X^{47}AS$ | n/a | $X^{48}X^{49}X^{50}X^{51}X^{52}X^{53}X^{54}$ |

In $QX^{42}X^{43}X^{44}X^{45}X^{46}$, $X^{47}$ AS, and $X^{48}X^{49}X^{50}X^{51}X^{52}X^{53}X^{54}$, $X^{42}$ is selected from the group consisting of D, S, and G; $X^{43}$ is selected from the group consisting of V and I; $X^{44}$ is selected from the group consisting of S and G; $X^{45}$ is selected from the group consisting of T and 5; $X^{46}$ is selected from the group consisting of A, S, D, and W; $X^{47}$ is selected from the group consisting of W, G, and D; $X^{48}$ is selected from the group consisting of Q and H; $X^{49}$ is selected from the group consisting of Q, K, and H; $X^{50}$ is selected from the group consisting of H, Y, F, R, D, and G; $X^{51}$ is selected from the group consisting of Y, N, Y, D, S, and G; $X^{52}$ is selected from the group consisting of R, S, V, T, and I; $X^{53}$ is selected from the group consisting of S, A, F, T, Y, and W; and $X^{54}$ is selected from the group consisting of P, L, S, and T.

In embodiments, the antibody or antigen-binding fragment thereof having binding specificity for programmed cell death receptor protein 1 (PD-1) comprises a light chain variable region and a heavy chain variable region, wherein the light chain variable region contains any CDR L1 of Table 2 or Table 4, and any CDR L2 of Table 2 or Table 4, and any CDR L3 of Table 2 or Table 4, and the heavy chain variable region contains any CDR H1 of Table 1 or Table 3, any CDR H2 of Table 1 or Table 3, and any CDR H3 of Table 1 or Table 3.

In embodiments, the antibody or antigen-binding fragment thereof having binding specificity for programmed cell death receptor protein 1 (PD-1) comprises a light chain variable region and a heavy chain variable region, wherein the light chain variable region contains CDR L1, CDR L2, and CDR L3 of any one of antibodies 4G9-1 to 4G9-20 and 5C2-1 to 5C2-10, and the heavy chain variable region contains CDR H1, CDR H2, and CDR H3 of any one of the antibodies 4G9-1 to 4G9-20 and 5C2-1 to 5C2-10.

In embodiments, the antibody or antigen-binding fragment thereof comprises CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-1; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-2; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-3; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-4; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-5; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-6; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-7; CDR L1, CDR L2, CDR L3, CDR H1, CDR H2, and CDR H3 of 4G9-8; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-9; CDR L1, CDR L2, CDR L3, CDR H1, CDR H2, and CDR H3 of 4G9-10; CDR L1, CDR L2, CDR L3, CDR H1, CDR H2, and CDR H3 of 4G9-11; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-12; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-13; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-14; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-15; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-16; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-17; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-18; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-19; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 4G9-20; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-1; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-2; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-3; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-4; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-5; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-6; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-7; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-8; CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-9; or CDR L1, CDR L2, CDR L3, CDR H1, CDR H2, and CDR H3 that each have an amino acid sequence with at least about 90%, at least about 91%, at least about 92%, at least about 93%, at least about 94%, or at least about 95% identity to the amino acid sequence of the corresponding CDR of 5C2-10.

In embodiments, an antibody or antigen binding fragment thereof is defined by CDR L1, CDR L2, CDR L3, CDR H1, CDR H2, and CDR H3 each independently having at least 75% identity, such as at least 85% identity or at least 90% identity, with the corresponding CDR L1, CDR L2, CDR L3, CDR H1, CDR H2, and CDR H3 of any one of the antibodies 4G9-1 to 4G9-20 and 5C2-1 to 5C2-10.

In embodiments, the antibody or antigen-binding fragment thereof comprises CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-1; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-2; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-3; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-4; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-5; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-6; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-7; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-8; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-9; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-10; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-11; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-12; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-13; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-14; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-15; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-16; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-17; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-18; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-19; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 4G9-20; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-1; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-2; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-3; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-4; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-5; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-6; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-7; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-8; CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-9; or CDR L1, CDR L2, CDR L3, CDR H1, CDR H2, and CDR H3 that each independently have an amino acid sequence that is the same as, or contains one or two amino acid substitutions, insertions, or deletions compared to the sequence of the corresponding CDR of 5C2-10. In the foregoing embodiments, preferably each CDR independently has the same amino acid sequence as the reference CDR or contains one amino acid substitution, insertion or deletion with respect to the reference CDR. In the forgoing embodiments, preferably each of the one or two substitutions, insertions, or deletions are substitutions that are conservative substitutions.

In a particular embodiment, the antibody or antigen-binding fragment comprises CDR L1, CDR L2, CDR L3, CDR H1, CDR H2, and CDR H3 of 4G9-2. In another particular embodiment, the antibody or antigen-binding fragment comprises CDR L1, CDR L2, CDR L3, CDR H1, CDR H2, and CDR H3 of 4G9-12.

In some embodiments, an antibody or antigen binding fragment thereof comprises CDR L1, CDR L2, CDR L3, CDR H1, CDR H2, and CDR H3 each independently having at most one deletion, insertion or substitution compared to the comprises CDR L1, CDR L2, CDR L3, CDR H1, CDR H2, and CDR H3 of any one of antibodies 4G9-1 to 4G9-20 and 5C2-1 to 5C2-10.

In some embodiments, an antibody or antigen binding fragment thereof comprises CDR L1, CDR L2, CDR L3, CDR H1, CDR H2, and CDR H3 each independently having at most two deletions, insertions or substitutions compared to the comprises CDR L1, CDR L2, CDR L3, CDR H1, CDR H2, and CDR H3 of any one of antibodies 4G9-1 to 4G9-20 and 5C2-1 to 5C2-10.

Embodiments provide an antibody or antigen binding fragment thereof wherein CDR L1, CDR L2, CDR L3, CDR H1, CDR H2, and CDR H3 each independently has three or fewer amino acid substitutions, such as two amino acid substitutions or one amino acid substitution, relative to the corresponding CDR L1, CDR L2, CDR L3, CDR H1, CDR H2, and CDR H3 of any one of the antibodies 4G9-1 to 4G9-20 and 5C2-1 to 5C2-10.

In embodiments, the antibody or antigen-binding fragment comprises a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-1; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-2; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-3; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-4; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-5; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-6; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-7; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-8; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-9; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-10; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-11; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-12; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-13; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-14; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-15; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-16; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-17; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-18; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-19; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-20; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-1; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-2; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-3; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-4; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-5; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-6; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-7; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-8; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-9; or a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-10.

For example, a preferred antibody or antigen-binding fragment may comprise a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-2; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-4; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-8; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-9; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-12; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-14; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-18; a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 4G9-19; or a light chain variable region and a heavy chain variable region that each have at least about 85%, at least about 90%, at least about 91%, at least about 92%, at least about 93%, at least about 94%, at least about 95%, at least about 96%, at least about 97%, at least about 98%, or at least about 99% amino acid sequence identity with the corresponding light chain and heavy chain variable regions sequences of 5C2-8. Though not to be bound by theory, the exemplary antibodies or antigen-binding fragments of this paragraph have desirable PD-1 agonist activity.

In a particular embodiment, the antibody or antigen-binding fragment thereof comprises the light chain variable region and the heavy chain variable region of 4G9-2. In a particular, embodiment, the antibody or antigen-binding fragment thereof comprises or the light chain variable region and the heavy chain variable region of 4G9-12.

In embodiments, the antibody or antigen-binding fragment comprises a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-1; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-2; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-3; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-4; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-5; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-6; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-7; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-8; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-9; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-10; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-11; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-12; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-13; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-14; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-15; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-16; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-17; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-18; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-19; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 4G9-20; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-1; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-2; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-3; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-4; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-5; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-6; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-7; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-8; a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-9; or a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, or at most 24 deletions, insertions or substitutions compared to the corresponding light chain and heavy chain variable regions sequences of 5C2-10.

For example, a preferred antibody or antigen-binding fragment may comprise a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, or at most 18 deletions, insertions or substitutions compared to the corresponding light chain and heavy chain variable regions sequences of 4G9-2; or a light chain variable region and a heavy chain variable region that each have at most one, at most two, at most three, at most four, at most five, at most six, at most seven, at most eight, at most nine, at most ten, at most 11, at most 12, at most 13, at most 14, at most 15, at most 16, at most 17, or at most 18 deletions, insertions or substitutions compared to the corresponding light chain and heavy chain variable regions sequences of 4G9-12.

Embodiments provide an antibody or antigen binding fragment thereof wherein light chain variable region and the heavy chain variable region each independently has at least 75% identity, such as at least 85% identity, at least 90% identity, or at least 95% identity, with the corresponding light chain variable region and the heavy chain variable region of any one of the antibodies 4G9-1 to 4G9-20 and 5C2-1 to 5C2-10.

In some embodiments, an antibody or antigen binding fragment thereof is defined by a light chain variable region and a heavy chain variable region each independently having at most one, at most two, at most three, at most four, at most five, at most six, at most seven, at most eight, at most nine, at most ten, at most 11, at most 12, at most 13, at most 14, at most 15, at most 16, at most 17, or at most 18 deletions, insertions or substitutions compared to the corresponding light chain and heavy chain variable regions of any one of antibodies 4G9-1 to 4G9-20 and 5C2-1 to 5C2-10.

In embodiments, the antibody or antigen-binding fragment comprises a heavy chain amino acid sequence and a light chain amino acid sequence, or an antigen-binding portion of either sequence, of antibody 4G9-1, 4G9-2, 4G9-3, 4G9-4, 4G9-5, 4G9-6, 4G9-7, 4G9-8, 4G9-10, 5C2-1, 5C2-2, 5C2-3, 5C2-4, 5C2-5, 5C2-6, 5C2-7, 5C2-8, 5C2-9 or 5C2-10 comprising the sequences disclosed in Table 5 or Table 6. Tables 5 and 6 disclose the sequences of heavy and light chains of 4G9-1 to 4G9-20 and 5C2-1 to 5C2-10 with and without terminal lysine ("-K", heavy chains only) and with and without signal peptide ("-SP").

TABLE 5

| | 4G9 sequences | |
|---|---|---|
| SEQ ID NO: | Antibody Polypeptide Chain | Amino Acid Sequence |
| 214 | 4G9-1 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGGRGIAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 215 | 4G9-2 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGSGGFAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 216 | 4G9-3 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGGRESAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 217 | 4G9-4 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGLPSFGYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 218 | 4G9-5 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGVRVFYHWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 219 | 4G9-6 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGGWWFADWGQGTLVTVSSASTKGPSVF PLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKAL PAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPG |
| 220 | 4G9-7 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGISKGAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA |

TABLE 5-continued

4G9 sequences

| SEQ ID NO: | Antibody Polypeptide Chain | Amino Acid Sequence |
|---|---|---|
| | | PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 221 | 4G9-8 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARVERGDAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 222 | 4G9-9 HC | MDPKGSLSWRILLFLSLAFELSYGQVQLVQSGAEVKKPGASVKVSCKASG YTFTTYGINWVRQATGQGLKWMGWINTYSGVPGYAQKFQGRVTMTLNTS ISTAYMELSSLRSEDTAVYYCARGVHGVSYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 223 | 4G9-10 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGSKGDAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 224 | 4G9-11 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGGRGIAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 225 | 4G9-12 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGSGGFAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 226 | 4G9-13 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGGRESAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 227 | 4G9-14 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGLPSFGYWGQGTLVTVSSASTKGPSVFP LAPSSKSTSGGTAALGCLVKDYFPEPVTVSWNSGALTSGVHTFPAVLQSSG |

TABLE 5-continued

4G9 sequences

| SEQ ID NO: | Antibody Polypeptide Chain | Amino Acid Sequence |
|---|---|---|
| | | LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 228 | 4G9-15 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGVRVFYHWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 229 | 4G9-16 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGGWWFADWGQGTLVTVSSASTKGPSVF PLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKAL PAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPG |
| 230 | 4G9-17 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGISKGAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 231 | 4G9-18 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARVERGDAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 232 | 4G9-19 HC | MDPKGSLSWRILLFLSLAFELSYGQVQLVQSGAEVKKPGASVKVSCKASG YTFTTYGINWVRQATGQGLKWMGWINTYSGVPGYAQKFQGRVTMTLDTS ISTAYMELSSLRSEDTAVYYCARGVHGVSYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |
| 233 | 4G9-20 HC | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGSKGDAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPG |

TABLE 5-continued

4G9 sequences

| SEQ ID NO: | Antibody Polypeptide Chain | Amino Acid Sequence |
|---|---|---|
| 234 | 4G9-1 LC | METDTLLLWVLLLWVPGSTGDIQLTQSPSSLSASVGDRVTITCRASQGISNS LAWFQQKPGKVPKRLIYAASNLQSGVPSRFSGSGSGTEFTLTISSLQPEDFA TYYCQQSYSTPYTFGQGTKLEIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 235 | 4G9-2 LC | METDTLLLWVLLLWVPGSTGDIVMTQSPLSLPVTLGQPASISCRSSQSLVYS DGNTYLNWFQQRPGQSPRRLIYKVSNRDSGVPDRFSGSGSGTDFTLKISRV EAEDVGVYYCMQGTHWPPFTFGPGTKVEIKRTVAAPSVFIFPPSDEQLKSG TASVVCLLNNFYPREAKVQWKVDNALQSGNSQESVTEQDSKDSTYSLSST LTLSKADYEKHKVYACEVTHQGLSSPVTKSFNRGEC |
| 236 | 4G9-3 LC | METDTLLLWVLLLWVPGSTGEIVMTQSPATLSVSPGERATLSCRASQSIGTS LHWYQQKPGGAPRLLIKYASESITGIPARFSGSGSGTEFTLTISSLQSEDFAV YYCQQSNSWPYTFGQGTKLEIKRTVAAPSVFIFPPSDEQLKSGTASVVCLLN NFYPREAKVQWKVDNALQSGNSQESVTEQDSKDSTYSLSSTLTLSKADYE KHKVYACEVTHQGLSSPVTKSFNRGEC |
| 237 | 4G9-4 LC | METDTLLLWVLLLWVPGSTGAIQMTQSPSSLSASVGDRVTITCRASQSISSY LNWYQQKPGKAPKLLIYAASSLQSGVPSRFSGSGSGTDFTLTISSLQPEDFA TYYCQQSYSTPYTFGQGTKLEIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 238 | 4G9-5 LC | METDTLLLWVLLLWVPGSTGEIVMTQSPATLSVSPGERATLSCRASQSIGTS LHWYQQKPGGAPRLLIKYASESITGIPARFSGSGSGTEFTLTISSLQSEDFAV YYCQQSNSWPYTFGQGTKLEIKRTVAAPSVFIFPPSDEQLKSGTASVVCLLN NFYPREAKVQWKVDNALQSGNSQESVTEQDSKDSTYSLSSTLTLSKADYE KHKVYACEVTHQGLSSPVTKSFNRGEC |
| 239 | 4G9-6 LC | METDTLLLWVLLLWVPGSTGAIRMTQSPSSLSASVGDRVTITCRASQSISSY LNWYQQKPGKAPKLLIYAASSLQSGVPSRFSGSGSGTDFTLTISSLQPEDFA TYYCQQSYSTPRTFGQGTKVEIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 240 | 4G9-7 LC | METDTLLLWVLLLWVPGSTGNIQMTQSPSSLSASVGDRVTITCRASQSISSY LNWYQQKPGKAPKLLIYAASSLQSGVPSRFSGSGSGTDFTLTISSLQPEDFA TYYCQQSSSTPYTFGQGTKLEIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 241 | 4G9-8 LC | METDTLLLWVLLLWVPGSTGEIVLTQSPSSLSASVGDRVTITCRASQDIRRD FGWYQQKPGLAPELLIYDASRLRSGVPSRFSGSGSGTLFTFTITNLQPEDFA TYYCLQDYDFPRTFGQGTKVDIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 242 | 4G9-9 LC | METDTLLLWVLLLWVPGSTGEIVMTQSPATLSVSPGERATLSCRASQSIGTS LHWYQQKPGGAPRLLIKYASESITGIPARFSGSGSGTEFTLTISSLQSEDFAV YYCQQSNSWPYTFGQGTKLEIKRTVAAPSVFIFPPSDEQLKSGTASVVCLLN NFYPREAKVQWKVDNALQSGNSQESVTEQDSKDSTYSLSSTLTLSKADYE KHKVYACEVTHQGLSSPVTKSFNRGEC |
| 243 | 4G9-10 LC | METDTLLLWVLLLWVPGSTGDIVMTQSPSSLSASVGDRVTITCRASQSIST WLAWFQQKPGKAPKLLIYKASSLKSGVPSRFSGSGSGTEFTLTISSLQPDDF ATYYCQQSYSTPWTFGQGTKLEIKRTVAAPSVFIFPPSDEQLKSGTASVVCL LNNFYPREAKVQWKVDNALQSGNSQESVTEQDSKDSTYSLSSTLTLSKAD YEKHKVYACEVTHQGLSSPVTKSFNRGEC |
| 244 | 4G9-11 LC | METDTLLLWVLLLWVPGSTGDIQLTQSPSSLSASVGDRVTITCRASQGISNS LAWFQQKPGKVPKRLIYAASNLQSGVPSRFSGSGSGTEFTLTISSLQPEDFA TYYCQQSYSTPYTFGQGTKLEIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 245 | 4G9-12 LC | METDTLLLWVLLLWVPGSTGDIVMTQSPLSLPVTLGQPASISCRSSQSLVYS DGNTYLNWFQQRPGQSPRRLIYKVSNRDSGVPDRFSGSGSGTDFTLKISRV EAEDVGVYYCMQGTHWPPFTFGPGTKVEIKRTVAAPSVFIFPPSDEQLKSG TASVVCLLNNFYPREAKVQWKVDNALQSGNSQESVTEQDSKDSTYSLSST LTLSKADYEKHKVYACEVTHQGLSSPVTKSFNRGEC |

TABLE 5-continued

4G9 sequences

| SEQ ID NO: | Antibody Polypeptide Chain | Amino Acid Sequence |
|---|---|---|
| 246 | 4G9-13 LC | METDTLLLWVLLLWVPGSTGEIVMTQSPATLSVSPGERATLSCRASQSIGTS LHWYQQKPGGAPRLLIKYASESITGIPARFSGSGSGTEFTLTISSLQSEDFAV YYCQQSNSWPYTFGQGTKLEIKRTVAAPSVFIFPPSDEQLKSGTASVVCLLN NFYPREAKVQWKVDNALQSGNSQESVTEQDSKDSTYSLSSTLTLSKADYE KHKVYACEVTHQGLSSPVTKSFNRGEC |
| 247 | 4G9-14 LC | METDTLLLWVLLLWVPGSTGAIQMTQSPSSLSASVGDRVTITCRASQSISSY LNWYQQKPGKAPKLLIYAASSLQSGVPSRFSGSGSGTDFTLTISSLQPEDFA TYYCQQSYSTPYTFGQGTKLEIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 248 | 4G9-15 LC | METDTLLLWVLLLWVPGSTGEIVMTQSPATLSVSPGERATLSCRASQSIGTS LHWYQQKPGGAPRLLIKYASESITGIPARFSGSGSGTEFTLTISSLQSEDFAV YYCQQSNSWPYTFGQGTKLEIKRTVAAPSVFIFPPSDEQLKSGTASVVCLLN NFYPREAKVQWKVDNALQSGNSQESVTEQDSKDSTYSLSSTLTLSKADYE KHKVYACEVTHQGLSSPVTKSFNRGEC |
| 249 | 4G9-16 LC | METDTLLLWVLLLWVPGSTGAIRMTQSPSSLSASVGDRVTITCRASQSISSY LNWYQQKPGKAPKLLIYAASSLQSGVPSRFSGSGSGTDFTLTISSLQPEDFA TYYCQQSYSTPRTFGQGTKVEIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 250 | 4G9-17 LC | METDTLLLWVLLLWVPGSTGNIQMTQSPSSLSASVGDRVTITCRASQSISSY LNWYQQKPGKAPKLLIYAASSLQSGVPSRFSGSGSGTDFTLTISSLQPEDFA TYYCQQSSSTPYTFGQGTKLEIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 251 | 4G9-18 LC | METDTLLLWVLLLWVPGSTGEIVLTQSPSSLSASVGDRVTITCRASQDIRRD FGWYQQKPGLAPELLIYDASRLRSGVPSRFSGSGSGTLFTFTITNLQPEDFA TYYCLQDYDFPRTFGQGTKVDIKRTVAAPSVFIFPPSDEQLKSGTASVVCLL NNFYPREAKVQWKVDNALQSGNSQESVTEQDSKDSTYSLSSTLTLSKADY EKHKVYACEVTHQGLSSPVTKSFNRGEC |
| 252 | 4G9-19 LC | METDTLLLWVLLLWVPGSTGEIVMTQSPATLSVSPGERATLSCRASQSIGTS LHWYQQKPGGAPRLLIKYASESITGIPARFSGSGSGTEFTLTISSLQSEDFAV YYCQQSNSWPYTFGQGTKLEIKRTVAAPSVFIFPPSDEQLKSGTASVVCLLN NFYPREAKVQWKVDNALQSGNSQESVTEQDSKDSTYSLSSTLTLSKADYE KHKVYACEVTHQGLSSPVTKSFNRGEC |
| 253 | 4G9-20 LC | METDTLLLWVLLLWVPGSTGDIVMTQSPSSLSASVGDRVTITCRASQSIST WLAWFQQKPGKAPKLLIYKASSLKSGVPSRFSGSGSGTEFTLTISSLQPDDF ATYYCQQSYSTPWTFGQGTKLEIKRTVAAPSVFIFPPSDEQLKSGTASVVCL LNNFYPREAKVQWKVDNALQSGNSQESVTEQDSKDSTYSLSSTLTLSKAD YEKHKVYACEVTHQGLSSPVTKSFNRGEC |
| 254 | 4G9-1 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGGRGIAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 255 | 4G9-2 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGSGGFAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 256 | 4G9-3 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGGRESAYWGQGTLVTVSSASTKGPSVFP |

TABLE 5-continued

4G9 sequences

| SEQ ID NO: | Antibody Polypeptide Chain | Amino Acid Sequence |
|---|---|---|
| | | LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 257 | 4G9-4 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGLPSFGYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 258 | 4G9-5 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGVRVFYHWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 259 | 4G9-6 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGGWWFADWGQGTLVTVSSASTKGPSVF PLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKAL PAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPGK |
| 260 | 4G9-7 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGISKGAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 261 | 4G9-8 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARVERGDAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 262 | 4G9-9 HC + K | MDPKGSLSWRILLFLSLAFELSYGQVQLVQSGAEVKKPGASVKVSCKASG YTFTTYGINWVRQATGQGLKWMGWINTYSGVPGYAQKFQGRVTMTLNTS ISTAYMELSSLRSEDTAVYYCARGVHGVSYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |

TABLE 5-continued

4G9 sequences

| SEQ ID NO: | Antibody Polypeptide Chain | Amino Acid Sequence |
|---|---|---|
| 263 | 4G9-10 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLNTS ISTAYMELSSLRSEDTAVYYCARGSKGDAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 264 | 4G9-11 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGGRGIAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 265 | 4G9-12 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGSGGFAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 266 | 4G9-13 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGGRESAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 267 | 4G9-14 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGLPSFGYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 268 | 4G9-15 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGVRVFYHWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 269 | 4G9-16 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGGWWFADWGQGTLVTVSSASTKGPSVF PLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKAL |

TABLE 5-continued

| 4G9 sequences | | |
|---|---|---|
| SEQ ID NO: | Antibody Polypeptide Chain | Amino Acid Sequence |
| | | PAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPGK |
| 270 | 4G9-17 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGISKGAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 271 | 4G9-18 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARVERGDAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 272 | 4G9-19 HC + K | MDPKGSLSWRILLFLSLAFELSYGQVQLVQSGAEVKKPGASVKVSCKASG YTFTTYGINWVRQATGQGLKWMGWINTYSGVPGYAQKFQGRVTMTLDTS ISTAYMELSSLRSEDTAVYYCARGVHGVSYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 273 | 4G9-20 HC + K | MDPKGSLSWRILLFLSLAFELSYGQVQLVQSGAEVKKPGASVKVSCKASG YTFTTYGINWVRQATGQGLEWMGWINTYSGVPGYAQKFQGRVTMTLDTS ISTAYMELSSLRSEDTAVYYCARGSKGDAYWGQGTLVTVSSASTKGPSVFP LAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEAL HNHYTQKSLSLSPGK |
| 274 | 4G9-1 HC - SP | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GGRGIAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPG |
| 275 | 4G9-2 HC - SP | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GSGGFAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPG |
| 276 | 4G9-3 HC - SP | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GGRESAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV |

TABLE 5-continued

4G9 sequences

| SEQ ID NO: | Antibody Polypeptide Chain | Amino Acid Sequence |
|---|---|---|
| | | SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 277 | 4G9-4 HC - SP | QVQLVQSGAEVKKPGASVKVSCKASGYTFTTYGINWVRQATGQGLEWM<br>GWINTYSGVPGYAQKFQGRVTMTLNTSISTAYMELSSLRSEDTAVYYCAR<br>GLPSFGYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 278 | 4G9-5 HC - SP | QVQLVQSGAEVKKPGASVKVSCKASGYTFTTYGINWVRQATGQGLEWM<br>GWINTYSGVPGYAQKFQGRVTMTLNTSISTAYMELSSLRSEDTAVYYCAR<br>GVRVFYHWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPP<br>SREEMTKNQVSLTCLVKGFYPSDIAVEWESNGQPENNYKTTPPVLDSDGSF<br>FLYSKLTVDKSRWQQGNVFSCSVMHEALHNHYTQKSLSLSPG |
| 279 | 4G9-6 HC - SP | QVQLVQSGAEVKKPGASVKVSCKASGYTFTTYGINWVRQATGQGLEWM<br>GWINTYSGVPGYAQKFQGRVTMTLNTSISTAYMELSSLRSEDTAVYYCAR<br>GGWWFADWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPP<br>SREEMTKNQVSLTCLVKGFYPSDIAVEWESNGQPENNYKTTPPVLDSDGSF<br>FLYSKLTVDKSRWQQGNVFSCSVMHEALHNHYTQKSLSLSPG |
| 280 | 4G9-7 HC - SP | QVQLVQSGAEVKKPGASVKVSCKASGYTFTTYGINWVRQATGQGLEWM<br>GWINTYSGVPGYAQKFQGRVTMTLNTSISTAYMELSSLRSEDTAVYYCAR<br>GISKGAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 281 | 4G9-8 HC - SP | QVQLVQSGAEVKKPGASVKVSCKASGYTFTTYGINWVRQATGQGLEWM<br>GWINTYSGVPGYAQKFQGRVTMTLNTSISTAYMELSSLRSEDTAVYYCAR<br>VERGDAYWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPP<br>SREEMTKNQVSLTCLVKGFYPSDIAVEWESNGQPENNYKTTPPVLDSDGSF<br>FLYSKLTVDKSRWQQGNVFSCSVMHEALHNHYTQKSLSLSPG |
| 282 | 4G9-9 HC - SP | QVQLVQSGAEVKKPGASVKVSCKASGYTFTTYGINWVRQATGQGLKWM<br>GWINTYSGVPGYAQKFQGRVTMTLNTSISTAYMELSSLRSEDTAVYYCAR<br>GVHGVSYWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPP<br>SREEMTKNQVSLTCLVKGFYPSDIAVEWESNGQPENNYKTTPPVLDSDGSF<br>FLYSKLTVDKSRWQQGNVFSCSVMHEALHNHYTQKSLSLSPG |
| 283 | 4G9-10 HC - SP | QVQLVQSGAEVKKPGASVKVSCKASGYTFTTYGINWVRQATGQGLEWM<br>GWINTYSGVPGYAQKFQGRVTMTLNTSISTAYMELSSLRSEDTAVYYCAR<br>GSKGDAYWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPP<br>SREEMTKNQVSLTCLVKGFYPSDIAVEWESNGQPENNYKTTPPVLDSDGSF<br>FLYSKLTVDKSRWQQGNVFSCSVMHEALHNHYTQKSLSLSPG |

TABLE 5-continued

4G9 sequences

| SEQ ID NO: | Antibody Polypeptide Chain | Amino Acid Sequence |
|---|---|---|
| 284 | 4G9-11 HC - SP | QVQLVQSGAEVKKPGASVKVSCKASGYTFTTYGINWVRQATGQGLEWM<br>GWINTYSGVPGYAQKFQGRVTMTLDTSISTAYMELSSLRSEDTAVYYCAR<br>GGRGIAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 285 | 4G9-12 HC - SP | QVQLVQSGAEVKKPGASVKVSCKASGYTFTTYGINWVRQATGQGLEWM<br>GWINTYSGVPGYAQKFQGRVTMTLDTSISTAYMELSSLRSEDTAVYYCAR<br>GSGGFAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 286 | 4G9-13 HC - SP | QVQLVQSGAEVKKPGASVKVSCKASGYTFTTYGINWVRQATGQGLEWM<br>GWINTYSGVPGYAQKFQGRVTMTLDTSISTAYMELSSLRSEDTAVYYCAR<br>GGRESAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 287 | 4G9-14 HC - SP | QVQLVQSGAEVKKPGASVKVSCKASGYTFTTYGINWVRQATGQGLEWM<br>GWINTYSGVPGYAQKFQGRVTMTLDTSISTAYMELSSLRSEDTAVYYCAR<br>GLPSFGYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 288 | 4G9-15 HC - SP | QVQLVQSGAEVKKPGASVKVSCKASGYTFTTYGINWVRQATGQGLEWM<br>GWINTYSGVPGYAQKFQGRVTMTLDTSISTAYMELSSLRSEDTAVYYCAR<br>GVRVFYHWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYIC<br>VNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPP<br>SREEMTKNQVSLTCLVKGFYPSDIAVEWESNGQPENNYKTTPPVLDSDGSF<br>FLYSKLTVDKSRWQQGNVFSCSVMHEALHNHYTQKSLSLSPG |
| 289 | 4G9-16 HC - SP | QVQLVQSGAEVKKPGASVKVSCKASGYTFTTYGINWVRQATGQGLEWM<br>GWINTYSGVPGYAQKFQGRVTMTLDTSISTAYMELSSLRSEDTAVYYCAR<br>GGWWFADWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPP<br>SREEMTKNQVSLTCLVKGFYPSDIAVEWESNGQPENNYKTTPPVLDSDGSF<br>FLYSKLTVDKSRWQQGNVFSCSVMHEALHNHYTQKSLSLSPG |
| 290 | 4G9-17 HC - SP | QVQLVQSGAEVKKPGASVKVSCKASGYTFTTYGINWVRQATGQGLEWM<br>GWINTYSGVPGYAQKFQGRVTMTLDTSISTAYMELSSLRSEDTAVYYCAR<br>GISKGAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 291 | 4G9-18 HC - SP | QVQLVQSGAEVKKPGASVKVSCKASGYTFTTYGINWVRQATGQGLEWM<br>GWINTYSGVPGYAQKFQGRVTMTLDTSISTAYMELSSLRSEDTAVYYCAR<br>VERGDAYWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICN |

TABLE 5-continued

4G9 sequences

| SEQ ID NO: | Antibody Polypeptide Chain | Amino Acid Sequence |
|---|---|---|
| | | VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPG |
| 292 | 4G9-19 HC - SP | QVQLVQSGAEVKKPGASVKVSCKASGYTFTTYGINWVRQATGQGLKWM GWINTYSGVPGYAQKFQGRVTMTLDTSISTAYMELSSLRSEDTAVYYCAR GVHGVSYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPG |
| 293 | 4G9-20 HC - SP | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GSKGDAYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPG |
| 294 | 4G9-1 HC - SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GGRGIAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 295 | 4G9-2 HC - SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GSGGFAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 296 | 4G9-3 HC - SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GGRESAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 297 | 4G9-4 HC - SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GLPSFGYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 298 | 4G9-5 HC - SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GVRVFYHWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV |

TABLE 5-continued

4G9 sequences

| SEQ ID NO: | Antibody Polypeptide Chain | Amino Acid Sequence |
|---|---|---|
| | | VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 299 | 4G9-6 HC – SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GGWWFADWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 300 | 4G9-7 HC – SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GISKGAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 301 | 4G9-8 HC – SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR VERGDAYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 302 | 4G9-9 HC – SP + K | QVQLVQSGAEVKKPGASVKVSCKASGYTFTTYGINWVRQATGQGLKWM GWINTYSGVPGYAQKFQGRVTMTLNTSISTAYMELSSLRSEDTAVYYCAR GVHGVSYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 303 | 4G9-10 HC – SP + K | QVQLVQSGAEVKKPGASVKVSCKASGYTFTTYGINWVRQATGQGLEWM GWINTYSGVPGYAQKFQGRVTMTLNTSISTAYMELSSLRSEDTAVYYCAR GSKGDAYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 304 | 4G9-11 HC – SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GGRGIAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 305 | 4G9-12 HC – SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GSGGFAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |

TABLE 5-continued

4G9 sequences

| SEQ ID NO: | Antibody Polypeptide Chain | Amino Acid Sequence |
|---|---|---|
| 306 | 4G9-13 HC - SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GGRESAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 307 | 4G9-14 HC - SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GLPSFGYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 308 | 4G9-15 HC - SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GVRVFYHWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 309 | 4G9-16 HC - SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GGWWFADWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 310 | 4G9-17 HC - SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GISKGAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 311 | 4G9-18 HC - SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR VERGDAYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 312 | 4G9-19 HC - SP + K | QVQLVQSGAEVKKPGASVKVSCKASGYTFTTYGINWVRQATGQGLKWM GWINTYSGVPGYAQKFQGRVTMTLDTSISTAYMELSSLRSEDTAVYYCAR GVHGVSYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 313 | 4G9-20 HC - SP + K | QVQLVQSGAEVKKPGASVKVSCKASGYTFTTYGINWVRQATGQGLEWM GWINTYSGVPGYAQKFQGRVTMTLDTSISTAYMELSSLRSEDTAVYYCAR GSKGDAYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICN |

TABLE 5-continued

4G9 sequences

| SEQ ID NO: | Antibody Polypeptide Chain | Amino Acid Sequence |
|---|---|---|
| | | VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 314 | 4G9-1 LC - SP | DIQLTQSPSSLSASVGDRVTITCRASQGISNSLAWFQQKPGKVPKRLIYAAS NLQSGVPSRFSGSGSGTEFTLTISSLQPEDFATYYCQQSYSTPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 315 | 4G9-2 LC - SP | DIVMTQSPLSLPVTLGQPASISCRSSQSLVYSDGNTYLNWFQQRPGQSPRRL IYKVSNRDSGVPDRFSGSGSGTDFTLKISRVEAEDVGVYYCMQGTHWPPFT FGPGTKVEIKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC |
| 316 | 4G9-3 LC - SP | EIVMTQSPATLSVSPGERATLSCRASQSIGTSLHWYQQKPGGAPRLLIKYAS ESITGIPARFSGSGSGTEFTLTISSLQSEDFAVYYCQQSNSWPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 317 | 4G9-4 LC - SP | AIQMTQSPSSLSASVGDRVTITCRASQSISSYLNWYQQKPGKAPKLLIYAAS SLQSGVPSRFSGSGSGTDFTLTISSLQPEDFATYYCQQSYSTPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 318 | 4G9-5 LC - SP | EIVMTQSPATLSVSPGERATLSCRASQSIGTSLHWYQQKPGGAPRLLIKYAS ESITGIPARFSGSGSGTEFTLTISSLQSEDFAVYYCQQSNSWPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 319 | 4G9-6 LC - SP | AIRMTQSPSSLSASVGDRVTITCRASQSISSYLNWYQQKPGKAPKLLIYAAS SLQSGVPSRFSGSGSGTDFTLTISSLQPEDFATYYCQQSYSTPRTFGQGTKVE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 320 | 4G9-7 LC - SP | NIQMTQSPSSLSASVGDRVTITCRASQSISSYLNWYQQKPGKAPKLLIYAAS SLQSGVPSRFSGSGSGTDFTLTISSLQPEDFATYYCQQSSSTPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 321 | 4G9-8 LC - SP | EIVLTQSPSSLSASVGDRVTITCRASQDIRRDFGWYQQKPGLAPELLIYDAS RLRSGVPSRFSGSGSGTLFTFTITNLQPEDFATYYCLQDYDFPRTFGQGTKV DIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| 322 | 4G9-9 LC - SP | EIVMTQSPATLSVSPGERATLSCRASQSIGTSLHWYQQKPGGAPRLLIKYAS ESITGIPARFSGSGSGTEFTLTISSLQSEDFAVYYCQQSNSWPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 323 | 4G9-10 LC - SP | DIVMTQSPSSLSASVGDRVTITCRASQSISTWLAWFQQKPGKAPKLLIYKAS SLKSGVPSRFSGSGSGTEFTLTISSLQPDDFATYYCQQSYSTPWTFGQGTKL EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| 324 | 4G9-11 LC - SP | DIQLTQSPSSLSASVGDRVTITCRASQGISNSLAWFQQKPGKVPKRLIYAAS NLQSGVPSRFSGSGSGTEFTLTISSLQPEDFATYYCQQSYSTPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |

TABLE 5-continued

4G9 sequences

| SEQ ID NO: | Antibody Polypeptide Chain | Amino Acid Sequence |
|---|---|---|
| 325 | 4G9-12 LC - SP | DIVMTQSPLSLPVTLGQPASISCRSSQSLVYSDGNTYLNWFQQRPGQSPRRL IYKVSNRDSGVPDRFSGSGSGTDFTLKISRVEAEDVGVYYCMQGTHWPPFT FGPGTKVEIKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC |
| 326 | 4G9-13 LC - SP | EIVMTQSPATLSVSPGERATLSCRASQSIGTSLHWYQQKPGGAPRLLIKYAS ESITGIPARFSGSGSGTEFTLTISSLQSEDFAVYYCQQSNSWPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 327 | 4G9-14 LC - SP | AIQMTQSPSSLSASVGDRVTITCRASQSISSYLNWYQQKPGKAPKLLIYAAS SLQSGVPSRFSGSGSGTDFTLTISSLQPEDFATYYCQQSYSTPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 328 | 4G9-15 LC - SP | EIVMTQSPATLSVSPGERATLSCRASQSIGTSLHWYQQKPGGAPRLLIKYAS ESITGIPARFSGSGSGTEFTLTISSLQSEDFAVYYCQQSNSWPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 329 | 4G9-16 LC - SP | AIRMTQSPSSLSASVGDRVTITCRASQSISSYLNWYQQKPGKAPKLLIYAAS SLQSGVPSRFSGSGSGTDFTLTISSLQPEDFATYYCQQSYSTPRTFGQGTKVE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 330 | 4G9-17 LC - SP | NIQMTQSPSSLSASVGDRVTITCRASQSISSYLNWYQQKPGKAPKLLIYAAS SLQSGVPSRFSGSGSGTDFTLTISSLQPEDFATYYCQQSSSTPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 331 | 4G9-18 LC - SP | EIVLTQSPSSLSASVGDRVTITCRASQDIRRDFGWYQQKPGLAPELLIYDAS RLRSGVPSRFSGSGSGTLFTFTITNLQPEDFATYYCLQDYDFPRTFGQGTKV DIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| 332 | 4G9-19 LC - SP | EIVMTQSPATLSVSPGERATLSCRASQSIGTSLHWYQQKPGGAPRLLIKYAS ESITGIPARFSGSGSGTEFTLTISSLQSEDFAVYYCQQSNSWPYTFGQGTKLE IKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 333 | 4G9-20 LC - SP | DIVMTQSPSSLSASVGDRVTITCRASQSISTWLAWFQQKPGKAPKLLIYKAS SLKSGVPSRFSGSGSGTEFTLTISSLQPDDFATYYCQQSYSTPWTFGQGTKL EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |

TABLE 6

5C2 sequences

| SEQ ID NO: | Antibody Polypeptide Chain | Amino Acid Sequence |
|---|---|---|
| 334 | 5C2-1 HC | MDPKGSLSWRILLFLSLAFELSYGQVQLVQSGAEVKKPGASVKVSC KASGYTFNSYWMHWVRQAPGQGLEWMGRIHPRGIHTNYNQKFKG RVTLTVDTSTSTAYMELSSLRSEDTAVYYCAPSSSYAWAFAHWGQG TLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ |

TABLE 6-continued

5C2 sequences

| SEQ ID NO: | Antibody Polypeptide Chain | Amino Acid Sequence |
|---|---|---|
| | | PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 335 | 5C2-2 HC | MDPKGSLSWRILLFLSLAFELSYGQVQLVQSGAEVKKPGASVKVSC KASGQTFTSYRMHWVRQAPGQGLEWMGRILPIRSDTNYNQKFKGR VTLTVDTSTSTAYMELSSLRSEDTAVYYCARDAGYGSLFAAWGQGT LVTVSSASTKGPSVFPLAPSSKSTSGGTAALGCLVKDYFPEPVTVSW NSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMIS RTPEVTCVVVDVSHEDPEVKFNWYVDGVEVHNAKTKPREEQYNST YRVVSVLTVLHQDWLNGKEYKCKVSNKALPAPIEKTISKAKGQPRE PQVYTLPPSREEMTKNQVSLTCLVKGFYPSDIAVEWESNGQPENNY KTTPPVLDSDGSFFLYSKLTVDKSRWQQGNVFSCSVMHEALHNHYT QKSLSLSPG |
| 336 | 5C2-3 HC | MDPKGSLSWRILLFLSLAFELSYGQVQLVQSGAEVKKPGASVKVSC KASGYTFTSYWMHWVRQAPGQGLEWMGRIHPSDSDTNYNQKFKG RVTLTVDTSTSTAYMELSSLRSEDTAVYYCAPKGNYVVRFAYWGQ GTLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 337 | 5C2-4 HC | MDPKGSLSWRILLFLSLAFELSYGQVQLVQSGAEVKKPGASVKVSC KASGYTFTRYWMHWVRQAPGQGLEWMGRIHPTDSVTNYNQKFKG RVTLTVDTSTSTAYMELSSLRSEDTAVYYCAPDVNYARAFAHWGQ GTLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 338 | 5C2-5 HC | MDPKGSLSWRILLFLSLAFELSYGQVQLVQSGAEVKKPGASVKVSC KASGYTFGIYWMHWVRQAPGQGLEWMGRILPSNGYTNYNQKFKG RVTLTVDTSTSTAYMELSSLRSEDTAVYYCAPYGIYTRDFSHWGQG TLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 339 | 5C2-6 HC | MDPKGSLSWRILLFLSLAFELSYGQVQLVQSGAEVKKPGASVKVSC KASGYTFTSYWMHWVRQAPGQGLEWMGRIHPSDSDTNYNQKFKG RVTLTVDTSTSTAYMELSSLRSEDTAVYYCAPYVDLESGFAYWGQG TLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 340 | 5C2-7 HC | MDPKGSLSWRILLFLSLAFELSYGQVQLVQSGAEVKKPGASVKVSC KASGYTFTSYWMHWVRQAPGMGLEWMGRIHPIYRDTNYNQKFKG RVTLTVDTSTSTAYMELSSLRSEDTAVYYCAPYVNYGDFAYWGQ GTLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ |

TABLE 6-continued

| | 5C2 sequences | |
|---|---|---|
| SEQ ID NO: | Antibody Polypeptide Chain | Amino Acid Sequence |
| | | PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 341 | 5C2-8 HC | MDPKGSLSWRILLFLSLAFELSYGQVQLVQSGAEVKKPGASVKVSC KASGYTFNSYLMHWVRQAPGMGLEWMGIRPNYSDTNYNQKFKG RVTLTVDTSTSTAYMELSSLRSEDTAVYYCAPYGNNASGFSYWGQG TLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 342 | 5C2-9 HC | MDPKGSLSWRILLFLSLAFELSYGQVQLVQSGAEVKKPGASVKVSC KASGQTFTNYLMHWVRQAPGQGLEWMGRIPLSDRDTNYNQKFKG RVTLTVDTSTSTAYMELSSLRSEDTAVYYCAPYGRSASGFSSWGQG TLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 343 | 5C2-10 HC | MDPKGSLSWRILLFLSLAFELSYGQVQLVQSGAEVKKPGASVKVSC KASGYTFTSYWMHWVRQAPGQGLEWMGRIHPSDSDTNYNQKFKG RVTLTVDTSTSTAYMELSSLRSEDTAVYYCAPYFDHAGGFLHWGQG TLVTVSSASTKGPSVFPLAPSSKSTSGGTAALGCLVKDYFPEPVTVS WNSGALTSGVHTFPAVLQSSGLYSLSSVVTVPSSSLGTQTYICNVNH KPSNTKVDKKVEPKSCDKTHTCPPCPAPELLGGPSVFLFPPKPKDTL MISRTPEVTCVVVDVSHEDPEVKFNWYVDGVEVHNAKTKPREEQY NSTYRVVSVLTVLHQDWLNGKEYKCKVSNKALPAPIEKTISKAKGQ PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPG |
| 344 | 5C2-1 LC | METDTLLLWVLLLWVPGSTGDIQMTQSPSSLSASVGDRVTITCRASQ DVSTALAWYQQKPGKAPKLLIYWASTRHSGVPDRFSGSGSGTDFTL TISSLQPEDFATYYCQQHYRSPGTFGGGTKVEIKRTVAAPSVFIFPPSD EQLKSGTASVVCLLNNFYPREAKVQWKVDNALQSGNSQESVTEQD SKDSTYSLSSTLTLSKADYEKHKVYACEVTHQGLSSPVTKSFNRGEC |
| 345 | 5C2-2 LC | METDTLLLWVLLLWVPGSTGDIQMTQSPSSLSASVGDRVTITCRASQ DVSTALAWYQQKPGKAPKLLIYWASTRHSGVPDRFSGSGSGTDFTL TISSLQPEDFATYYCQQHDSSPGTFGGGTKVEIKRTVAAPSVFIFPPSD EQLKSGTASVVCLLNNFYPREAKVQWKVDNALQSGNSQESVTEQD SKDSTYSLSSTLTLSKADYEKHKVYACEVTHQGLSSPVTKSFNRGEC |
| 346 | 5C2-3 LC | METDTLLLWVLLLWVPGSTGDIVMTQSPSSLSASVGDRVTITCRASQ GIRNDLGWYQQKPGKAPKLLIYAASSLQSGVPSRFSGSGSGTDFTLTI SSLQPEDFATYYCLQDYNYPWTFGQGTKVDIKRTVAAPSVFIFPPSD EQLKSGTASVVCLLNNFYPREAKVQWKVDNALQSGNSQESVTEQD SKDSTYSLSSTLTLSKADYEKHKVYACEVTHQGLSSPVTKSFNRGEC |
| 347 | 5C2-4 LC | METDTLLLWVLLLWVPGSTGDIQMTQSPSSLSASVGDRVTITCRASQ DVSTALAWYQQKPGKAPKLLIYWASTRHSGVPDRFSGSGSGTDFTL TISSLQPEDFATYYCQQHYGSPWTFGGGTKVEIKRTVAAPSVFIFPPS DEQLKSGTASVVCLLNNFYPREAKVQWKVDNALQSGNSQESVTEQ DSKDSTYSLSSTLTLSKADYEKHKVYACEVTHQGLSSPVTKSFNRGE C |
| 348 | 5C2-5 LC | METDTLLLWVLLLWVPGSTGDIQMTQSPSSLSASVGDRVTITCRASQ DVSTALAWYQQKPGKAPKLLIYWASTRHSGVPDRFSGSGSGTDFTL TISSLQPEDFATYYCQQRDTTPRTFGGGTKVEIKRTVAAPSVFIFPPSD EQLKSGTASVVCLLNNFYPREAKVQWKVDNALQSGNSQESVTEQD SKDSTYSLSSTLTLSKADYEKHKVYACEVTHQGLSSPVTKSFNRGEC |
| 349 | 5C2-6 LC | METDTLLLWVLLLWVPGSTGDIAMTQTPSSLSASIGDRVTIACRASQ GISSALAWYQQKPGRTPKLLIFDASTLQSGVPSRFSGSGSGTDFTLTIS SLQPEDFATYYCQQFNTYSSVTFGQGTRLEIKRTVAAPSVFIFPPSDE |

TABLE 6-continued

5C2 sequences

| SEQ ID NO: | Antibody Polypeptide Chain | Amino Acid Sequence |
|---|---|---|
|  |  | QLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| 350 | 5C2-7 LC | METDTLLLWVLLLWVPGSTGDIQMTQSPSTLSASVGDRVTITCRASQ<br>DVSTALAWYQQKPGKAPKLLIYWASTRHIGVPDRFSGSGSGTDFTLT<br>ISSLQPEDFATYYCHQDYITPRTFGGGTKVEIKRTVAAPSVFIFPPSDE<br>QLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| 351 | 5C2-8 LC | METDTLLLWVLLLWVPGSTGDIQMTQSPSSLSASVGDRVTITCRASQ<br>DVSTALAWYQQKPGKAPKLLIYWASTRHSGVPDRFSGSGSGTDFTL<br>TISSLQPEDFATYYCQQHYRSPWTFGGGTKVEIKRTVAAPSVFIFPPS<br>DEQLKSGTASVVCLLNNFYPREAKVQWKVDNALQSGNSQESVTEQ<br>DSKDSTYSLSSTLTLSKADYEKHKVYACEVTHQGLSSPVTKSFNRGE<br>C |
| 352 | 5C2-9 LC | METDTLLLWVLLLWVPGSTGDIQMTQSPSSLSASVGDRVTITCRASQ<br>DVSTALAWYQQKPGKAPKLLIYWASTRHSGVPDRFSGSGSGTDFTL<br>TISSLQPEDFATYYCQQGSSTPLTFGGGTKVEIKRTVAAPSVFIFPPSD<br>EQLKSGTASVVCLLNNFYPREAKVQWKVDNALQSGNSQESVTEQD<br>SKDSTYSLSSTLTLSKADYEKHKVYACEVTHQGLSSPVTKSFNRGEC |
| 353 | 5C2-10 LC | METDTLLLWVLLLWVPGSTGDIVMTQSPGTLSLSPGERATLSCRASQ<br>SVSSSYLAWYQQKPGQAPRLLIYGASSRATGIPDRFSGSGSGTDFTLT<br>ISRLEPEDFAVYYCQQYGSWTFGQGTKLEIKRTVAAPSVFIFPPSDEQ<br>LKSGTASVVCLLNNFYPREAKVQWKVDNALQSGNSQESVTEQDSK<br>DSTYSLSSTLTLSKADYEKHKVYACEVTHQGLSSPVTKSFNRGEC |
| 354 | 5C2-1 HC + K | MDPKGSLSWRILLFLSLAFELSYGQVQLVQSGAEVKKPGASVKVSC<br>KASGYTFNSYWMHWVRQAPGQGLEWMGRIHPRGIHTNYNQKFKG<br>RVTLTVDTSTSTAYMELSSLRSEDTAVYYCAPSSSYAWAFAHWGQG<br>TLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ<br>PREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNH<br>YTQKSLSLSPGK |
| 355 | 5C2-2 HC + K | MDPKGSLSWRILLFLSLAFELSYGQVQLVQSGAEVKKPGASVKVSC<br>KASGQTFTSYRMHWVRQAPGQGLEWMGRILPIRSDTNYNQKFKGR<br>VTLTVDTSTSTAYMELSSLRSEDTAVYYCARDAGYGSLFAAWGQGT<br>LVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKP<br>SNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNST<br>YRVVSVLTVLHQDWLNGKEYKCKVSNKALPAPIEKTISKAKGQPRE<br>PQVYTLPPSREEMTKNQVSLTCLVKGFYPSDIAVEWESNGQPENNY<br>KTTPPVLDSDGSFFLYSKLTVDKSRWQQGNVFSCSVMHEALHNHYT<br>QKSLSLSPGK |
| 356 | 5C2-3 HC + K | MDPKGSLSWRILLFLSLAFELSYGQVQLVQSGAEVKKPGASVKVSC<br>KASGYTFTSYWMHWVRQAPGQGLEWMGRIHPSDSDTNYNQKFKG<br>RVTLTVDTSTSTAYMELSSLRSEDTAVYYCAPKGNYVRFAYWGQ<br>GTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ<br>PREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNH<br>YTQKSLSLSPGK |
| 357 | 5C2-4 HC + K | MDPKGSLSWRILLFLSLAFELSYGQVQLVQSGAEVKKPGASVKVSC<br>KASGYTFTRYWMHWVRQAPGQGLEWMGRIHPTDSVTNYNQKFKG<br>RVTLTVDTSTSTAYMELSSLRSEDTAVYYCAPDVNYARAFAHWGQ<br>GTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ |

TABLE 6-continued

5C2 sequences

| SEQ ID NO: | Antibody Polypeptide Chain | Amino Acid Sequence |
|---|---|---|
| | | PREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNH<br>YTQKSLSLSPGK |
| 358 | 5C2-5<br>HC + K | MDPKGSLSWRILLFLSLAFELSYGQVQLVQSGAEVKKPGASVKVSC<br>KASGYTFGIYWMHWVRQAPGQGLEWMGRILPSNGYTNYNQKFKG<br>RVTLTVDTSTSTAYMELSSLRSEDTAVYYCAPYGIYTRDFSHWGQG<br>TLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ<br>PREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNH<br>YTQKSLSLSPGK |
| 359 | 5C2-6<br>HC + K | MDPKGSLSWRILLFLSLAFELSYGQVQLVQSGAEVKKPGASVKVSC<br>KASGYTFTSYWMHWVRQAPGQGLEWMGRIHPSDSDTNYNQKFKG<br>RVTLTVDTSTSTAYMELSSLRSEDTAVYYCAPYVDLESGFAYWGQG<br>TLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ<br>PREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNH<br>YTQKSLSLSPGK |
| 360 | 5C2-7<br>HC + K | MDPKGSLSWRILLFLSLAFELSYGQVQLVQSGAEVKKPGASVKVSC<br>KASGYTFTSYWMHWVRQAPGMGLEWMGRIHPIYRDTNYNQKFKG<br>RVTLTVDTSTSTAYMELSSLRSEDTAVYYCAPYVNYGDGFAYWGQ<br>GTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ<br>PREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNH<br>YTQKSLSLSPGK |
| 361 | 5C2-8<br>HC + K | MDPKGSLSWRILLFLSLAFELSYGQVQLVQSGAEVKKPGASVKVSC<br>KASGYTFNSYLMHWVRQAPGMGLEWMGRIRPNYSDTNYNQKFKG<br>RVTLTVDTSTSTAYMELSSLRSEDTAVYYCAPYGNNASGFSYWGQG<br>TLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ<br>PREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNH<br>YTQKSLSLSPGK |
| 362 | 5C2-9<br>HC + K | MDPKGSLSWRILLFLSLAFELSYGQVQLVQSGAEVKKPGASVKVSC<br>KASGQTFTNYLMHWVRQAPGQGLEWMGRIPLSDRDTNYNQKFKG<br>RVTLTVDTSTSTAYMELSSLRSEDTAVYYCAPYGRSASGFSSWGQG<br>TLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ<br>PREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNH<br>YTQKSLSLSPGK |
| 363 | 5C2-10<br>HC + K | MDPKGSLSWRILLFLSLAFELSYGQVQLVQSGAEVKKPGASVKVSC<br>KASGYTFTSYWMHWVRQAPGQGLEWMGRIHPSDSDTNYNQKFKG<br>RVTLTVDTSTSTAYMELSSLRSEDTAVYYCAPYFDHAGGFLHWGQG<br>TLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQY<br>NSTYRVVSVLTVLHQDWLNGKEYKCKVSNKALPAPIEKTISKAKGQ |

TABLE 6-continued

| | 5C2 sequences | |
|---|---|---|
| SEQ ID NO: | Antibody Polypeptide Chain | Amino Acid Sequence |
| | | PREPQVYTLPPSREEMTKNQVSLTCLVKGFYPSDIAVEWESNGQPEN NYKTTPPVLDSDGSFFLYSKLTVDKSRWQQGNVFSCSVMHEALHNH YTQKSLSLSPGK |
| 364 | 5C2-1 HC - SP | QVQLVQSGAEVKKPGASVKVSCKASGYTFNSYWMHWVRQAPGQG LEWMGRIHPRGIHTNYNQKFKGRVTLTVDTSTSTAYMELSSLRSEDT AVYYCAPSSSYAWAFAHWGQGTLVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKKVEPKSCDKTHTCPPC PAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPG |
| 365 | 5C2-2 HC - SP | QVQLVQSGAEVKKPGASVKVSCKASGQTFTSYRMHWVRQAPGQGL EWMGRILPIRSDTNYNQKFKGRVTLTVDTSTSTAYMELSSLRSEDTA VYYCARDAGYGSLFAAWGQGTLVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKKVEPKSCDKTHTCPPC PAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPG |
| 366 | 5C2-3 HC - SP | QVQLVQSGAEVKKPGASVKVSCKASGYTFTSYWMHWVRQAPGQG LEWMGRIHPSDSDTNYNQKFKGRVTLTVDTSTSTAYMELSSLRSED TAVYYCAPKGNYVVRFAYWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTVD KSRWQQGNVFSCSVMHEALHNHYTQKSLSLSPG |
| 367 | 5C2-4 HC - SP | QVQLVQSGAEVKKPGASVKVSCKASGYTFTRYWMHWVRQAPGQG LEWMGRIHPTDVTNYNQKFKGRVTLTVDTSTSTAYMELSSLRSED TAVYYCAPDVNYARAFAHWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTVD KSRWQQGNVFSCSVMHEALHNHYTQKSLSLSPG |
| 368 | 5C2-5 HC - SP | QVQLVQSGAEVKKPGASVKVSCKASGYTFGIYWMHWVRQAPGQG LEWMGRILPSNGYTNYNQKFKGRVTLTVDTSTSTAYMELSSLRSED TAVYYCAPYGIYTRDFSHWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPG |
| 369 | 5C2-6 HC - SP | QVQLVQSGAEVKKPGASVKVSCKASGYTFTSYWMHWVRQAPGQG LEWMGRIHPSDSDTNYNQKFKGRVTLTVDTSTSTAYMELSSLRSED TAVYYCAPYVDLESGFAYWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPG |
| 370 | 5C2-7 HC - SP | QVQLVQSGAEVKKPGASVKVSCKASGYTFTSYWMHWVRQAPGMG LEWMGRIHPIYRDTNYNQKFKGRVTLTVDTSTSTAYMELSSLRSEDT AVYYCAPYVNYGDGFAYWGQGTLVTVSSASTKGPSVFPLAPSSKST SGGTAALGCLVKDYFPEPVTVSWNSGALTSGVHTFPAVLQSSGLYS |

TABLE 6-continued

5C2 sequences

| SEQ ID NO: | Antibody Polypeptide Chain | Amino Acid Sequence |
|---|---|---|
| | | LSSVVTVPSSSLGTQTYICNVNHKPSNTKVDKKVEPKSCDKTHTCPP<br>CPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPG |
| 371 | 5C2-8 HC – SP | QVQLVQSGAEVKKPGASVKVSCKASGYTFNSYLMHWVRQAPGMG<br>LEWMGRIRPNYSDTNYNQKFKGRVTLTVDTSTSTAYMELSSLRSED<br>TAVYYCAPYGNNASGFSYWGQGTLVTVSSASTKGPSVFPLAPSSKST<br>SGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPP<br>CPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPG |
| 372 | 5C2-9 HC – SP | QVQLVQSGAEVKKPGASVKVSCKASGQTFTNYLMHWVRQAPGQG<br>LEWMGRIPLSDRDTNYNQKFKGRVTLTVDTSTSTAYMELSSLRSED<br>TAVYYCAPYGRSASGFSSWGQGTLVTVSSASTKGPSVFPLAPSSKST<br>SGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPP<br>CPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPG |
| 373 | 5C2-10 HC – SP | QVQLVQSGAEVKKPGASVKVSCKASGYTFTSYWMHWVRQAPGQG<br>LEWMGRIHPSDSDTNYNQKFKGRVTLTVDTSTSTAYMELSSLRSED<br>TAVYYCAPYFDHAGGFLHWGQGTLVTVSSASTKGPSVFPLAPSSKS<br>TSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCP<br>PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSREEMTKNQVSLT<br>CLVKGFYPSDIAVEWESNGQPENNYKTTPPVLDSDGSFFLYSKLTVD<br>KSRWQQGNVFSCSVMHEALHNHYTQKSLSLSPG |
| 374 | 5C2-1 HC – SP + K | QVQLVQSGAEVKKPGASVKVSCKASGYTFNSYWMHWVRQAPGQG<br>LEWMGRIHPRGIHTNYNQKFKGRVTLTVDTSTSTAYMELSSLRSEDT<br>AVYYCAPSSSYAWAFAHWGQGTLVTVSSASTKGPSVFPLAPSSKSTS<br>GGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPC<br>PAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPGK |
| 375 | 5C2-2 HC – SP + K | QVQLVQSGAEVKKPGASVKVSCKASGQTFTSYRMHWVRQAPGQGL<br>EWMGRILPIRSDTNYNQKFKGRVTLTVDTSTSTAYMELSSLRSEDTA<br>VYYCARDAGYGSLFAAWGQGTLVTVSSASTKGPSVFPLAPSSKSTS<br>GGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPC<br>PAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPGK |
| 376 | 5C2-3 HC – SP + K | QVQLVQSGAEVKKPGASVKVSCKASGYTFTSYWMHWVRQAPGQG<br>LEWMGRIHPSDSDTNYNQKFKGRVTLTVDTSTSTAYMELSSLRSED<br>TAVYYCAPKGNYVVRFAYWGQGTLVTVSSASTKGPSVFPLAPSSKS<br>TSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCP<br>PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSREEMTKNQVSLT<br>CLVKGFYPSDIAVEWESNGQPENNYKTTPPVLDSDGSFFLYSKLTVD<br>KSRWQQGNVFSCSVMHEALHNHYTQKSLSLSPGK |

TABLE 6-continued

5C2 sequences

| SEQ ID NO: | Antibody Polypeptide Chain | Amino Acid Sequence |
|---|---|---|
| 377 | 5C2-4 HC - SP + K | QVQLVQSGAEVKKPGASVKVSCKASGYTFTRYWMHWVRQAPGQG LEWMGRIHPTDSVTNYNQKFKGRVTLTVDTSTSTAYMELSSLRSED TAVYYCAPDVNYARAFAHWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTVD KSRWQQGNVFSCSVMHEALHNHYTQKSLSLSPGK |
| 378 | 5C2-5 HC - SP + K | QVQLVQSGAEVKKPGASVKVSCKASGYTFGIYWMHWVRQAPGQG LEWMGRILPSNGYTNYNQKFKGRVTLTVDTSTSTAYMELSSLRSED TAVYYCAPYGIYTRDFSHWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPGK |
| 379 | 5C2-6 HC - SP + K | QVQLVQSGAEVKKPGASVKVSCKASGYTFTSYWMHWVRQAPGQG LEWMGRIHPSDSDTNYNQKFKGRVTLTVDTSTSTAYMELSSLRSED TAVYYCAPYVDLESGFAYWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPGK |
| 380 | 5C2-7 HC - SP + K | QVQLVQSGAEVKKPGASVKVSCKASGYTFTSYWMHWVRQAPGMG LEWMGRIHPIYRDTNYNQKFKGRVTLTVDTSTSTAYMELSSLRSEDT AVYYCAPYVNYGDGFAYWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPGK |
| 381 | 5C2-8 HC - SP + K | QVQLVQSGAEVKKPGASVKVSCKASGYTFNSYLMHWVRQAPGMG LEWMGRIRPNYSDTNYNQKFKGRVTLTVDTSTSTAYMELSSLRSED TAVYYCAPYGNNASGFSYWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPGK |
| 382 | 5C2-9 HC - SP + K | QVQLVQSGAEVKKPGASVKVSCKASGQTFTNYLMHWVRQAPGQG LEWMGRIPLSDRDTNYNQKFKGRVTLTVDTSTSTAYMELSSLRSED TAVYYCAPYGRSASGFSSWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPGK |
| 383 | 5C2-10 HC - SP + K | QVQLVQSGAEVKKPGASVKVSCKASGYTFTSYWMHWVRQAPGQG LEWMGRIHPSDSDTNYNQKFKGRVTLTVDTSTSTAYMELSSLRSED TAVYYCAPYFDHAGGFLHWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY |

TABLE 6-continued

5C2 sequences

| SEQ ID NO: | Antibody Polypeptide Chain | Amino Acid Sequence |
|---|---|---|
| | | KCKVSNKALPAPIEKTISKAKGQPREPQVYTLPPSREEMTKNQVSLT CLVKGFYPSDIAVEWESNGQPENNYKTTPPVLDSDGSFFLYSKLTVD KSRWQQGNVFSCSVMHEALHNHYTQKSLSLSPGK |
| 384 | 5C2-1 LC – SP | DIQMTQSPSSLSASVGDRVTITCRASQDVSTALAWYQQKPGKAPKLL IYWASTRHSGVPDRFSGSGSGTDFTLTISSLQPEDFATYYCQQHYRSP GTFGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 385 | 5C2-2 LC – SP | DIQMTQSPSSLSASVGDRVTITCRASQDVSTALAWYQQKPGKAPKLL IYWASTRHSGVPDRFSGSGSGTDFTLTISSLQPEDFATYYCQQHDSSP GTFGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 386 | 5C2-3 LC – SP | DIVMTQSPSSLSASVGDRVTITCRASQGIRNDLGWYQQKPGKAPKLL IYAASSLQSGVPSRFSGSGSDTDFTLTISSLQPEDFATYYCLQDYNYP WTFGQGTKVDIKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC |
| 387 | 5C2-4 LC – SP | DIQMTQSPSSLSASVGDRVTITCRASQDVSTALAWYQQKPGKAPKLL IYWASTRHSGVPDRFSGSGSGTDFTLTISSLQPEDFATYYCQQHYGSP WTFGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 388 | 5C2-5 LC – SP | DIQMTQSPSSLSASVGDRVTITCRASQDVSTALAWYQQKPGKAPKLL IYWASTRHSGVPDRFSGSGSGTDFTLTISSLQPEDFATYYCQQRDTTP RTFGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 389 | 5C2-6 LC – SP | DIAMTQTPSSLSASIGDRVTIACRASQGISSALAWYQQKPGRTPKLLI FDASTLQSGVPSRFSGSGSGTDFTLTISSLQPEDFATYYCQQFNTYSS VTFGQGTRLEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 390 | 5C2-7 LC – SP | DIQMTQSPSTLSASVGDRVTITCRASQDVSTALAWYQQKPGKAPKL LIYWASTRHIGVPDRFSGSGSGTDFTLTISSLQPEDFATYYCHQDYITP RTFGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 391 | 5C2-8 LC – SP | DIQMTQSPSSLSASVGDRVTITCRASQDVSTALAWYQQKPGKAPKLL IYWASTRHSGVPDRFSGSGSGTDFTLTISSLQPEDFATYYCQQHYRSP WTFGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 392 | 5C2-9 LC – SP | DIQMTQSPSSLSASVGDRVTITCRASQDVSTALAWYQQKPGKAPKLL IYWASTRHSGVPDRFSGSGSGTDFTLTISSLQPEDFATYYCQQGSSTP LTFGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 393 | 5C2-10 LC – SP | DIVMTQSPGTLSLSPGERATLSCRASQSVSSSYLAWYQQKPGQAPRL LIYGASSRATGIPDRFSGSGSGTDFTLTISRLEPEDFAVYYCQQYGSW TFGQGTKLEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGEC |

2. Polynucleotides Encoding 4G9 and 5C2 Sequences

In another aspect, the invention relates to an isolated nucleic acid molecule (e.g., a polynucleotide) encoding an antibody or antigen-binding fragment of an anti-PD1 agonist antibody disclosed herein. The present disclosure provides polynucleotides that encode an antibody or antigen-binding fragment comprising an amino acid sequence of antibodies 4G9-1 to 4G9-20 or 5C2-1 to 5C2-10 (e.g., SEQ ID NO: 1-393, Tables 1-6). The polynucleotides can encode the entire antibody or antigen binding fragments thereof or a light chain, heavy chain, combinations thereof or CDRs thereof. In embodiments, the polynucleotides can encode the heavy chain and/or light chain of an antibody or antigen-binding fragment selected from those presented in Tables 5 and 6 (e.g., SEQ ID NO: 214-393). In embodiments, the polynucleotides can encode a heavy chain variable region (e.g., VH) and/or a light chain variable region (e.g., VK) selected from those presented in Tables 1-4 (e.g., SEQ ID NO: 1-20, 83-102, 143-152, and 184-193). In embodiments, the polynucleotides can encode an antibody or antigen-binding fragment (e.g., the light and/or heavy chain variable regions/domains) comprising CDR sequences selected from those presented in Tables 1-4 (e.g., SEQ ID NO: 21-82, 103-142, 153-183, 194-213). In embodiments, the polynucleotide encodes the heavy chain and/or light chain variable regions of 4G9-12, e.g., SEQ ID NO: 12 and 94. In such embodiments, the polynucleotide optionally further encodes a heavy chain constant region and/or light chain constant region. In embodiments, the polynucleotide encodes the heavy chain and/or light chain variable regions of 4G9-2, e.g., SEQ ID NO: 2 and 84. In embodiments, the polynucleotide encodes an antibody or antigen-binding fragment comprising the CDR sequences of 4G9-12 (e.g., SEQ ID NO: 32, 53, and 74, and/or 114, KVS, and 134). In some embodiments the polynucleotide encodes an antibody or antigen-binding fragment comprising the heavy and light chain variable regions of 4G9-12 (e.g., SEQ ID NO: 12 and 94).

Isolated polynucleotide molecules can be produced by standard techniques, including, without limitation, common molecular cloning and chemical polynucleotide synthesis techniques. For example, polymerase chain reaction (PCR) techniques can be used to obtain an isolated polynucleotide encoding a variant polypeptide. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (CDNA) strand. Ligase chain reaction, strand displacement amplification, self-sustained sequence replication or polynucleotide sequence-based amplification also can be used to obtain isolated polynucleotides. See, for example, Lewis (0.1992) *Genetic Engineering News* 12:1; Guatelli et al. (1990) *Proc. Natl. Acad Sci. USA* 87:1874-1878; and Weiss (1991) *Science* 254:1292-1293.

Isolated polynucleotides can be chemically synthesized, either as a single polynucleotide molecule or as a series of oligonucleotides (e.g., using phosphoramidite technology for automated DNA. synthesis in the 3' to 5' direction), For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded polynucleotide molecule per oligonucleotide pair, which then can be heated into a vector. Isolated polynucleotides can also be obtained by mutagenesis. Protein-encoding polynucleotides can be mutated using standard techniques, including oligonucleotide-directed mutagenesis and/or site-directed mutagenesis through PER. See, Short Protocols in Molecular Biology, Chapter 8, Green Publishing Associates and John Wiley & Sons, edited by Ausubel et al, 1992.

The person of ordinary skill in the art will be aware that the redundancy of the genetic code allows any amino acid sequence to be encoded by a large number of polynucleotides. The person of ordinary skill in the art will also be aware that, depending on the organism in which a polynucleotide is to be maintained, duplicated, and/or transcribed, the polynucleotide sequence encoding a particular amino acid sequence may be selected in view of the organism's codon bias.

The polynucleotide can be in a vector, for example, an expression vector. The polynucleotide can be introduced into a suitable host cell for expression, e.g., can be extrachromosal or inserted into a chromosome, for example, a Chinese Hamster Ovary (CHO) cell or NSO cell. Preferably, the host cell is a mammalian host cell, such as a CHO or NSO cell, but bacterial, yeast, plant and other types of suitable cells can also be used.

In embodiments, the host cell may be part of a transgenic animal. Methods of making transgenic animals that produce antibodies are known in the art. See, for example, A. Jakobovits, Curt Opin Biotechnol., 6(5):5.61-6 (1995) and Brüggemann, M., et al., Arch Immunol Ther Exp (Warsz)., 63(2)101-108 (2015); Jakobovits, A., et al., "From XenoMouse technology to panitumumab, the first fully human antibody product from transgenic mice." Nat Biotechnol. 25(10):113.4-43 (2007); Lonberg N. (2005) "Human antibodies from transgenic animals." Nat Biotechnol. 23(9): 1117-25 and U.S. Pat. Nos. 9,708,635; 9,686,970; 9,499,838; 9,445,581; 9,388,446; 8,835,712; 8,703,485; 8,232,449; 7,795,494; and 5,939,598.

Techniques for the handling of polynucleotides, vectors, expression vectors, host cells, and transgenic animals are known in the art and need not be described in detail.

F. Pharmaceutical Compositions

Pharmaceutical compositions including the disclosed antibodies and antigen binding fragments thereof are provided. The pharmaceutical compositions typically include one or more pharmaceutically acceptable excipients.

The pharmaceutical compositions disclosed herein are administered to a subject in a therapeutically effective amount. An "effective amount" or "therapeutically effective amount" is typically an amount or a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being affected.

For the disclosed antibodies and antigen binding fragments thereof, the person of ordinary skill in the art, considering the therapeutic context, age, and general health of the recipient, will be able to ascertain proper dosing. The selected dosage depends upon the desired therapeutic effect, on the route of administration, and on the duration of the treatment desired. For the disclosed antibodies and antigen binding fragments thereof, generally dosage levels of 0.001 to 20 mg/kg of body weight daily may be administered to mammals. Generally, for intravenous injection or infusion, dosage may be lower.

In certain embodiments, the antibodies and antigen binding fragments thereof may be administered locally, for example by injection directly into a site to be treated. Typically, the injection may cause an increased localized concentration of the antibodies and/or antigen-binding fragments thereof which may be greater than that which can be achieved by systemic administration. The antibodies and antigen-binding fragments thereof disclosed herein can be combined with a matrix as described above to assist in creating an increased localized concentration of the polypeptide compositions by reducing the passive diffusion of the polypeptides out of the site to be treated.

1. Formulations for Parenteral Administration

In some embodiments, the compositions containing the disclosed antibodies and antigen binding fragments are administered in an aqueous solution, by parenteral injection. The formulation may also be in the form of a suspension or emulsion. In general, pharmaceutical compositions are provided including therapeutically effective amounts of an antibody or antigen binding fragment thereof, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HO, acetate, phosphate), pH, and ionic strength; and additives such as detergents and solubilizing agents (e.g., TWEEN 20 (polysorbate-20) TWEEN 80 (polysorbate-80), antioxidants (e.g., ascorbic acid, sodium metabisulfite), and preservatives (e.g., thiomersal, benzyl alcohol) and bulking substances (e.g., lactose, mannitol). Examples of non-aqueous solvents or vehicles include, but are not limited to, propylene glycol, polyethylene glycol, vegetable oils such as olive oil and corn oil, gelatin, and injectable organic esters such as ethyl oleate. The formulations may be lyophilized and redissolved/resuspended immediately before use. The formulation may be sterilized by, for example, filtration, by incorporating sterilizing agents into the compositions, by irradiating the compositions, or by heating the compositions.

2. Formulations for Oral Administration

In some embodiments the antibody compositions are formulated for oral delivery. The oral dosage forms of antibodies may resist proteolysis and deliver a greater fraction of immunoreactive antibody locally in the gastrointestinal tract for the treatment of infections or allow the absorption of antibodies for the treatment or prevention of systemic conditions (Reilly, R M, et al. Clin Pharmacokinet., 32(4):313.M (1997); Victoria. S Jasion and Bruce: P Burnett, Nutr J.; 14: 22 (2015); and. Philippart, M., et al., Drug. Res (Stuttg) 66(03):11.120 (2016)).

Oral solid dosage forms are described generally in Remington's Pharmaceutical Sciences, 18$^{th}$ Ed. 1990 (Mack Publishing Co. Easton Pa. 18042) at Chapter 89. Solid dosage forms include tablets, capsules, pills, troches or lozenges, cachets, pellets, powders; or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the antibodies or antigen-binding fragments. See, e.g., Remington's Pharmaceutical Sciences, 18$^{th}$ Ed. (1990, Mack Publishing. Co., Easton, Pa. 18042) pages 1435-1712 which are herein incorporated by reference.

The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the antibody or antigen-binding fragment (or chemically modified forms thereof) and inert ingredients which protect the antibody or antigen-binding fragment in the stomach environment, and release of the biologically active material in the intestine.

The antibodies and antigen binding fragments thereof can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-trioxocane [see, e.g., Abuchowski and Davis. (1981) "Soluble Polymer-Enzyme Adducts," in Enzymes as Drugs. Hocenberg and Roberts, OS. (Wiley-Interscience: New York, N.Y.) pp. 367383; and Newmark, et al. (1982) J. App, Biochem. 4:185-189.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

For oral formulations, the location of release may be the stomach, the small intestine (the duodenum, the jejunum, or the ileum), or the large intestine. In some embodiments., the release will avoid the deleterious effects of the stomach environment, either by protection of the agent (or derivative) or by release of the agent (or derivative) beyond the stomach environment, such as in the intestine. To ensure full gastric resistance, a coating impermeable to at least pH 5.0 is desirable. Examples of the more common inert ingredients that are used as enteric coatings are cellulose acetate trimellitate (CAT), hydroxypropylmethylcellulose phthalate (HPMCP), HPMCP 50, HPMCP-55, polyvinyl acetate-phthalate (PVAP), Eudragit L30D™, Aquateric™ cellulose acetate phthalate (CAP), Eudragit L™, Eudragit S™, and Shellac™. These coatings may be used as mixed films.

3. Controlled Delivery Polymeric Matrices

The antibodies and antigen binding fragments thereof disclosed herein can also be administered in controlled release formulations. The antibodies and antigen binding fragments thereof can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the antibody or antigen binding fragment thereof is enclosed in a semipermeable membrane which allows water to enter and push drug out through a single small opening due to osmotic effects.

Controlled release polymeric devices can be made for long term release systemically following implantation of a polymeric device (rod, cylinder, film disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to centimeters, a powder produced by grinding or other standard techniques, or a gel such as a hydrogel.

Either non-biodegradable or biodegradable matrices can be used for delivery of agonist anti-PD-1 antibodies, antigen-binding fragments or nucleic acids encoding the agonist anti-PD-1 antibodies or antigen-binding fragments, although in some embodiments biodegradable matrices are desired. These may be natural or synthetic polymers, although synthetic polymers are desired in some embodiments due to the better characterization of degradation and release profiles. The polymer is selected based on the period over which release is desired. In some cases, linear release may be most useful, although in others a pulse release or "bulk release" may provide more effective results. The polymer may be in the foot of a hydrogel (typically in absorbing up to about 90% by weight of water) and can optionally be cross-linked with multivalent ions or polymers.

The matrices can be formed by solvent evaporation, spray drying, solvent extraction and other methods known to those skilled in the art. Bio erodible microspheres can be prepared using any of the methods developed for making microspheres for drug delivery, for example, as described by Mathiowitz and Langer, *J. Controlled Release,* 5:13.22 (1987); Mathiowitz, et al., *Reclaim Polymers,* 6:275-283 (1987); and Mathiowitz, et al., *J Appl. Polymer Sci.,* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

G. Methods of Manufacture

1. Methods of Making Antibodies

The disclosed antibodies can be generated in cell culture, in phage, or in various animals, including but not limited to cows, rabbits, goats, mice, rats, hamsters, guinea pigs, sheep, dogs, cats, monkeys, chimpanzees, and apes. In embodiments, the various animals can be transgenic animals genetically engineered to produce human or humanized antibodies. In embodiments, the antibody is a mammalian antibody. Phage techniques can be used to isolate an initial antibody or to generate variants with altered specificity or avidity characteristics. Such techniques are routine and well known in the. Art. In embodiments, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993) *Current Protocols In Immunology* (John Wiley& Sons, most recent edition).

The disclosed antibodies and antigen-binding fragments can be modified by recombinant means to increase greater efficacy of the antibody in mediating the desired function. In other words, antibodies and antigen-binding fragments can be modified by substitutions using recombinant means. Typically, the substitutions will be conservative substitutions. For example, at least one amino acid in the constant region of the antibody or antigen-binding fragment can be replaced with a different residue. See, e.g., U.S. Pat. Nos. 5,624,821, 6,194,551, Application No. WO 9958572; and Angal, et al., *Mol Immunol.* 30:105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to proteins or polypeptides. See, e.g., Antibody Engineering: A Practical Approach (Oxford University Press, 1996).

For example, suitable antibodies with the desired biologic activities can be identified using in vitro assays including but not limited to proliferation, migration, adhesion, soft agar growth, angiogenesis, cell-cell communication, apoptosis, transport, signal transduction, and in vivo assays such as the inhibition of tumor growth. The antibodies provided herein can also be useful in diagnostic applications. As capture or non-neutralizing antibodies, they can be screened for the ability to bind to. The specific antigen without inhibiting the receptor-binding or biological activity of the antigen. As neutralizing antibodies, the antibodies can be useful in competitive binding assays.

Another embodiment provides a monoclonal antibody obtained from a substantially homogeneous population of antibodies, i.e., the individual antibodies. Within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The disclosed antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of minim antibodies). Libraries of antibodies or active antibody fragments (e.g., antigen-binding fragments) can also be generated and screened using phage display techniques.

Methods of making antibodies using protein chemistry are also known in the art. One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, CA). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allows relatively short peptide fragments to be joined to produce larger peptide fragments, polypeptides, or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

H. Methods of Use

The disclosed antibodies and antigen binding fragments thereof can be used to modulate an immune response in a subject in need thereof. One embodiment provides a method of activating immune cells expressing PD-1, for example, T cells, to proliferate or enhance the biological activity of the immune cells expressing PD-1 by administering the disclosed antibodies and antigen fragments thereof, optionally including a second therapeutic agent.

1. Immune Response Stimulation a. Therapeutic Strategies

Methods of inducing or enhancing an immune response in a subject are provided. Typically, the methods include administering a subject a therapeutically effective amount of one or more of the disclosed antibodies and antigen binding fragments thereof to immunospecifically bind to PD-1 and induce, promote, or enhance a stimulatory or activating signal through PD-1 to activate the immune cell. The immune response can be, for example inducing, promoting, or enhancing T cell activation, secretion of cytokines by immune cells, T cell proliferation. The disclosed antibodies or antigen binding fragments thereof can be administered to a subject in need thereof in a therapeutically effective amount to overcome T cell exhaustion and/or T cell energy. Overcoming I cell exhaustion or T cell anergy can be determined by measuring T cell function using known techniques.

The methods can be used in vivo or ex vivo to induce, promote, or enhance a stimulating immune response.

In some embodiments, the antibody or antigen binding fragment thereof is administered directly to the subject. It is also possible to administer a nucleic acid encoding the antibody or antigen binding fragment thereof, to the subject. Preferably, the nucleic acid can be expressed once administered to produce the antibody or antigen-binding fragment that binds PD-1. In some embodiments, antibody or antigen binding fragment thereof is contacted with cells (e.g., immune cells) ex vivo, and the treat cells are administered to the subject (e.g., adoptive transfer). The antibody or antigen binding fragment thereof can enable a more robust immune response to be possible. The disclosed compositions are useful to stimulate or enhance immune responses involving T cells causing an activating signal through PD-1 on immune cells.

2. Subjects to be Treated a. Treatment of Cancer

The disclosed antibodies and compositions thereof and methods can be used to treat cancer. Generally, the agents are used to stimulate or enhance an immune response to cancer in the subject by administering to the subject an amount of a disclosed antibody or antigen binding fragment thereof that induces, promotes, or enhances an activating signal through PD-1. The method can reduce one or more symptoms of the cancer. The methods can be used to reduce or inhibit tumor growth or to cause tumor regression. For example, as disclosed and exemplified herein, the antibodies or antigen-binding fragments of this disclosure have antitumor activity and can also induce central memory T cells (Tcm) and/or inhibit T cell exhaustion.

The immune cells activated by the disclosed antibodies or fragments thereof can kill cancer cells and reduce tumor burden in a subject. The tumor may be benign or malignant, and if malignant, at any stage of disease progression. In yet other embodiments, the cancer is associated with a specific cancer antigen (e.g., pan-carcinoma antigen (KS 1/4), ovarian carcinoma. antigen (CA125), prostate specific antigen (PSA), carcinoembryonic antigen (CEA), CD19, CD20, HER2/neu, etc.).

The methods and antibody compositions disclosed herein are useful in the treatment or prevention of a variety of cancers or other abnormal proliferative diseases, including (but not limited to) carcinoma, including that of the bladder, breast, colon, kidney, liver, lung, ovary, pancreas, stomach, cervix, thyroid and skin; including squamous cell carcinoma; hematopoietic tumors of lymphoid. lineage, including leukemia, acute lymphocytic leukemia, acute lymphoblastic leukemia, B-cell lymphoma, T-cell lymphoma, Burkett's lymphoma; hematopoietic tumors of myeloid lineage, including acute and chronic myelogenous leukemias, and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid. follicular cancer and teratocarcinoma.

Cancers caused by aberrations in apoptosis can also be treated by the disclosed methods and compositions. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's. disease or non-Hodgkin's disease lymphomas (e.g., diffuse anaplastic lymphoma kinase (ALK) negative, large B-cell lymphoma (DLBCL); diffuse anaplastic lymphoma kinase (ALX) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer; papillary breast cancer, Paget's disease, and inflammatory breast cancer; adrenal cancer, including but not limited to, pheochromocytoma and adrenocortical carcinoma; thyroid cancer such as but not limited to papillary or follicular thyroid cancer, medullary thyroid cancer and anaplastic thyroid cancer; pancreatic cancer, including but not limited to. insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipidus; eye cancers including, but not limited. to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not. limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid) ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penile cancers; oral cancers including, but not limited to, squamous cell. carcinoma; basal cancers; salivary gland cancers including, but not limited to, adenocarcinoma, mucoepidermoid carcinoma, and adenoid cystic carcinoma; pharynx cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterine); Wilms' tumor; bladder cancers including, but not limited to, transitional cell carcinoma, squamous cell cancer, adenocarcinoma, carcinosarcoma. In addition, cancers include myosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment and Recovery, Viking Penguin, Penguin Books U.S.A., Inc., United States of America). In a particular example, an agonist anti-PD-1 antibody or antigen-binding fragment (e.g., an antibody that has the heavy and light chain CDRs of 4G9-12) is used to treat non-small cell lung cancer in a patient in need thereof. For example, the invention relates to a method for treating non-small cell lung cancer comprising administering to a subject in need thereof a therapeutically effective amount of an agonist anti-PD-1 antibody or antigen-binding fragment (e.g., an antibody that has the heavy and light chain CDRs of 4G9-12).

The agonist anti-PD-1 antibody and antigen-binding fragments disclosed herein can be used to treat cancer that is or develops resistance to a checkpoint inhibition therapy. Resistance to checkpoint inhibition therapy can be primary resistance (e.g., the cancer is refractory to first and subsequent treatments with a checkpoint inhibition therapy) or can be secondary resistance (e.g., the cancer was responsive to first or initial treatments but refractory to subsequent treatments with a checkpoint inhibition therapy). Resistance to checkpoint inhibition therapy can develop, for example, by down regulation or lack of expression of PD-L1 in a tumor (e.g., PD-L1 negative cancer).

In some preferred embodiments, agonist anti-PD-1 antibodies and antigen-binding fragments disclosed herein can be used to treat a subject with cancer that has secondary resistance to checkpoint inhibition therapy, such as PD-1 checkpoint inhibition therapy. Accordingly, this disclosure relates to a method of treating cancer that has secondary resistance to checkpoint inhibition therapy (e.g., PD-1 checkpoint inhibition therapy) that includes administering to a subject in need thereof a therapeutically effective amount of a PD-1 agonist antibody or antigen-binding fragment as disclosed herein.

In some preferred embodiments, agonist anti-PD-1 antibodies and antigen-binding fragments disclosed herein can be used to treat a subject with cancer that has primary resistance to PD-1 checkpoint inhibition. Accordingly, this disclosure relates to a method of treating cancer that has primary resistance to checkpoint inhibition therapy (e.g., PD-1 checkpoint inhibition therapy) that includes administering to a subject in need thereof a therapeutically effective amount of a PD-1 agonist antibody or antigen-binding fragment as disclosed herein.

In some preferred embodiments, agonist anti-PD-1 antibody and antigen binding fragments disclosed herein can be used to treat a to a subject with a PD-L1 negative tumor (e.g., PD-L1 down regulated cancer). Accordingly, this disclosure relates to a method of treating cancer that is PD-L1 negative (e.g., PD-L1 down regulated cancer) that includes administering to a subject in need thereof a therapeutically effective amount of a PD-1 agonist antibody or antigen-binding fragment as disclosed herein.

b. Treatment of Infections

The disclosed antibody compositions and methods can be used to treat infections and infectious diseases. The agents are used to stimulate or enhance an immune response to an infection in the subject by administering to the subject amount of one or more of the disclosed antibodies or antigen binding fragments thereof that sends an activating or stimulating signal through PD-1. The method can reduce one or more symptoms of the infection.

The infection or disease can be caused by a bacterium, virus, protozoan, helminth, or other microbial pathogen that enters intracellularly and is attacked by cytotoxic T lymphocytes.

The infection or disease can be acute or chronic. An acute infection is typically an infection of short duration. During an acute microbial infection, immune cells begin expressing immunomodulatory receptors. Accordingly, in some embodiments, the method includes increasing an immune stimulatory response against an acute infection.

The infection can be caused by, for example, but not limited to *Candida albicans, Listeria monocytogenes, Streptococcus pyogenes, Streptococcus pneumoniae, Neisseria meningitidis, Staphylococcus aureus; Escherichia coli, Acinetobacter baumannii, Pseudomonas aeruginosa* or *Mycobacterium*.

In some embodiments, the disclosed antibody compositions are used to treat chronic infections, for example, infections in which T cell exhaustion has occurred causing the infection to remain with the host over a prolonged period of time.

Exemplary infections to be treated include chronic infections cause by a hepatitis virus, a human immunodeficiency virus (HIV), a human T-lymphotropic virus (HTLV), a herpes virus, an Epstein-Barr virus, or a human papilloma virus.

Because viral infections are cleared primarily by T cells, an increase in T-cell activity would be therapeutically useful in situations where more rapid or thorough clearance of an infective-viral agent would be beneficial to an animal or human subject. Thus, the disclosed compositions can be administered for the treatment of local or systemic viral infections, including, but not limited to, immunodeficiency (e.g., HIV, papilloma (e.g., HPV), herpes (e.g. HSV), encephalitis, influenza (e g., human influenza virus A), and common cold (e.g., human rhinovirus) and other viral infections, caused by, for example, HTLV, hepatitis virus, respiratory syncytial virus, vaccinia virus, rabies virus, and SARS-CoV2 virus. The molecules can be administered topically to treat viral skin diseases such as herpes lesions, shingles, or genital warts. The molecules can also be administered systemically to treat systemic viral diseases, including, but not limited to, AIDS influenza, the common cold, covid-19, or encephalitis.

Representative infections that can be treated, include but are not limited to infections caused by microorganisms including, but not limited to, *Actinomyces, Anabaena, Bacillus, Bacteroides, B. dellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium*; Heliobacter, Hemophilus, Hemophilus influenza type II⁻ (HIB), *Hyphomicrobium, Legionella, Leptospirosis, Listeria*, Meningococcus A, B and C, *Methanobacterium, Micrococcus, Myobacterium, Mycoplasma, Myxococcus, Neisseria, Nitrobacter, Oscillatoria*, Prochloron, *Proteus, Pseudomonas, Rhodospirillum, Rickettsia, Salmonella, Shigella, Spirillum, Spirochaete, Staphylococcus, Streptococcus, Streptomyces, Sulfolobus, Thermoplasma, Thiobacillus*, and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae*, Chlamydialpsittaci, Chlamydial *trachomatis, Plasmodium falciparum, Trypanosoma brucei, Entamoeba histolytica, Toxoplasma gondii, Trichomonas vaginalis*, and *Schistosoma mansoni*.

Other microorganisms that can be treated using the disclosed compositions and methods include bacteria such *Klebsiella, Serratia, Pasteurella*; pathogens associated with cholera, tetanus, botulism, anthrax, plague, and Lyme disease; or fungal or parasitic pathogens, such as *Candida* (*albicans, krusei, glabrata, tropicalis*, etc.), *Cryptococcus, Aspergillus* (*fumigatus, niger*, etc.), Genus Mucorales (*mucor, absidia*, rhizophus), *Sporothrix* (*schenkii*), *Blastomyces* (*dermatitidis*), *Paracoccidioides* (*brasiliensis*), *Coccidioides* (*immitis*) and *Histoplasma* (capsulatuma), *Entamoeba, histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi*, etc.), *Sporothrix, Blastomyces, Paracoccidioides, Coccidioides, Histoplasma, Entamoeba, Histolytica, Balanadium, Naegleria, Acanthamoeba, Giardia, Cryptosporidium, Pneumocystis, Plasmodium, Babesia*, or *Trypanosoma*, etc.

c. Combination Therapies for Increasing Immune Responses

The disclosed antibodies and antigen binding fragments thereof and compositions thereof can be administered to a subject in need thereof either alone or in combination with one or more additional therapeutic agents. In some embodiments, the antibodies and antigen binding fragments thereof and the additional therapeutic agent are administered separately but simultaneously. The antibodies and antigen binding fragments thereof and the additional therapeutic agent can also be administered as part of the same composition. In other embodiments, the antibodies and antigen binding fragments thereof and the second therapeutic agent are administered separately and at different times, but as part of the same treatment regimen. The additional therapeutic agents can be administered before, after, or in alternation with the administration of the disclosed antibodies and antigen binding fragments thereof.

The subject can be administered a first therapeutic agent 1, 2, 3, 4, 5, 6, or more hours, or 1., 2, 3, 4, 5, 6, 7, or more days before administration of a second therapeutic agent. In embodiments, the subject can be administered one or more doses of the first agent every 1, 2, 3, 4, 5, 6-7, 14, 21, 28, 35, or 48 days prior to a first administration of second agent. The antibodies and antigen binding fragments thereof can be the first or the second therapeutic agent.

The antibodies and antigen binding fragments thereof and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary additional therapeutic agents include, but are not limited to, cytokines (e.g., IL-2, IL-12), chemotherapeutic agents, radionuclides, other immunotherapeutics, enzymes, antibiotics, antivirals (especially protease inhibitors alone or in combination with nucleosides for treatment of HIV or Hepatitis B or C), anti-parasitics, growth factors, growth inhibitors, hormones, hormone antagonists, antibodies and bioactive-fragments thereof (including humanized, single chain, and chimeric antibodies), antigen and vaccine formulations (including adjuvants), peptide drugs, anti-inflammatories, ligands that bind to Toll-like Receptors (including but not limited to CpG oligonucleotides) to activate the innate immune system, molecules that mobilize and optimize the adaptive immune system (e.g., bispecific T cell engagers), other molecules that activate or up-regulate the action of cytotoxic T lymphocytes, natural killer cells and helper T-cells, and other molecules that deactivate or down-regulate suppressor or regulatory T-cells.

The additional therapeutic agents can be selected based on the condition, disorder, or disease to be treated. For example, an antibody or antigen-binding fragment disclosed herein can be co-administered with one or more additional agents that function to enhance or promote an immune response or reduce or inhibit an immune response. The selection of additional therapeutic agents, other than the antibodies or antigen-binding fragments disclosed herein, is a routine matter for the person of ordinary skill in the art having the benefit of the present disclosure.

Additional therapeutic agents suitable for combination with anti-PD-1 agonist antibodies or antigen-binding fragments described herein include cell therapies. Suitable cell therapies can include, for example, dendritic cells, B cells, T cells (e.g., alpha beta T cells, $CD3^+$ T cells, $CD4^+$ T cells, $CD8^+$ T cells, gamma delta T cells, etc.), macrophages, NK cells, NKT cells, and combinations thereof. Suitable cell therapies include, but are not limited to stem cell therapies, T cell therapies (e.g., tumor-infiltrating lymphocytes (TILs)), or engineered cell therapies (e.g., chimeric antigen receptor (CAR) therapies, engineered TCR therapies). In some preferred embodiments, an agonist anti-PD-1 antibody and/or antigen-binding fragment disclosed herein in combination with cell therapy can be used to treat a subject with cancer. According, this disclosure relates to a method of treating cancer that includes administration to a subject in need thereof a therapeutically effective amount of a PD-1 agonist antibody or antigen-binding fragment as disclosed herein and a cell therapy. In some preferred embodiments, an agonist anti-PD-1 antibody and/or antigen-binding fragment disclosed herein in combination with a T cell therapy can be used to treat a subject with cancer. According, this disclosure relates to a method of treating cancer that includes administration to a subject in need thereof a therapeutically effective amount of a PD-1 agonist antibody or antigen-binding fragment as disclosed herein and a T cell therapy. In some preferred embodiments, an agonist anti-PD-1 antibody and/or antigen-binding fragment disclosed herein in combination with tumor-infiltrating lymphocytes (TILs) can be used to treat a subject with cancer. According, this disclosure relates to a method of treating cancer that includes administration to a subject in need thereof a therapeutically effective amount of a PD-1 agonist antibody or antigen-binding fragment as disclosed herein and tumor-infiltrating lymphocytes (TILs). In some preferred embodiments, an agonist anti-PD-1 antibody and/or antigen-binding fragment disclosed herein in combination with an engineered cell therapy (e.g., engineered TCR therapy, a chimeric antigen receptor (CAR) therapy, or a combination thereof) can be used to treat a subject with cancer. According, this disclosure relates to a method of treating cancer that includes administration to a subject in need thereof a therapeutically effective amount of a PD-1 agonist antibody or antigen-binding fragment as disclosed herein and an engineered cell therapy (e.g., engineered TCR therapy, a chimeric antigen receptor (CAR) therapy, or a combination thereof).

One example of a suitable engineered cell therapy is chimeric antigen receptor therapy. Chimeric antigen receptor therapies can be CAR-T cells (e.g., axicabtagene ciloleucel, brexucabtagene autoleucel, ciltacabtagene autoleucel, idecabtagene vicleucel, lisocabtagene maraleucel, tisagenlecleucel), CAR-NK cells, CAR-macrophages, and combinations thereof. In some aspects, this disclosure relates to administration of agonist anti-PD-1 antibodies with CAR-T cells to a subject in need thereof. In some preferred embodiments, agonist anti-PD-1 antibodies and antigen-binding fragments disclosed herein in combination with CAR-T cells can be used to treat a cancer in a subject in need thereof. Accordingly, this disclosure relates to a method of treating cancer that includes administering to a subject in need thereof a therapeutically effective amount of agonist anti-PD-1 antibodies and antigen-binding fragment as disclosed herein in combination with CAR-T cells.

Another example of a suitable engineered cell therapy is engineered T cell receptor therapy. Engineered T cell receptor therapies can comprise an engineered TCR, TCR subunits, TCR fragments, and combinations thereof. Suitable engineered T cell receptor therapies include but are not limited to engineered TCR T cells (TCR-T cells), engineered TCR natural killer cells (TCR-NK), engineered TCR macrophages (TCR-macrophages), and combinations thereof. For example, the agonist anti-PD-1 antibody or antigen binding fragments thereof can be combined with $CD8^+$ T cells that express (e.g., transduced with) an engineered TCR. As another example, the agonist anti-PD-1 antibody or antigen binding fragments thereof can be combined with $CD4^+$ T cells that express (e.g., transduced with) an engineered TCR. In some preferred embodiments, agonist anti-PD-1 antibodies and antigen-binding fragments disclosed herein in combination with engineered TCR T cells (TCR-T cells) can be used to treat cancer in a subject in need thereof. Accordingly, this disclosure relates to a method of treating cancer that includes administering to a subject in need thereof a therapeutically effective amount of agonist anti-PD-1 antibody or antigen binding fragment as disclosed herein and engineered TCR T cells (TCR-T cells).

When an agonist anti-PD-1 antibody or antigen-binding fragment as disclosed herein is combined with a cell therapy, the two therapeutics can be administered to a subject in need thereof at substantially the same time (e.g., concurrently) or the cell therapy can be administered before or after the PD-1 antibody or antigen-binding fragment thereof. While the time of administration of each therapeutic can vary, typically they are administered so that there is an overlap of their respective pharmacological activity in the subject.

Engineered TCR or chimeric antigen receptors can be designed to bind to any antigen. For example, the TCR or chimeric antigen receptor can specifically bind to one of the following antigens: CD19, CD123, CD22, CD30, CD171, CS-1, CLL-1 (CLECL1), CD33, EGFRvIII, GD2, GD3, BCMA, Tn Ag, PSMA, ROR1, FLT3, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, FAP, IGF-1 receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, MAGE A1, ETV6-AML, sperm protein 17, XAGE1, Tie 2, MAD-CT-1, MAD-CT-2, Fos-related antigen 1, p53, $p^{53}$ mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, legumain, HPV E6, E7, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, fibronectin EDB (EDB-FN), 5T4 oncofetal antigen, and IGLL1.

Additional therapeutic agents suitable for combination with anti-PD-1 agonist antibodies include immunomodulators, which target and alter the patient's immune response, for example to provide an enhanced immune effector response against a tumor. Examples of suitable immunomodulators include immunostimulatory molecules such as cytokines (e.g., IL-2, IL-12, and the like), adjuvants, T cell engagers, and immunostimulatory antibodies (e.g., anti-CD3) and agents that block inhibitory immune pathways, such as immune checkpoint inhibitors (e.g., antibodies that bind immune checkpoint proteins). Immune checkpoint inhibitors include antibodies and antigen-binding fragments that bind to immune checkpoint proteins such as PD-L1 (B7-H1, CD274) and PD-L2 (B7-DC, CD273), CTLA-4 (CD152) which binds B7-1 (CD80) and B7-2 (CD86), LAG 3 (CD223) which binds Galectin3, LSECtin and FGL1; TIM3 (HAVCR2) which binds ligands Ceacam1 and Galectin9; TIGIT (VSTM3, WUCAM) which binds CD112 and CD155; BTLA (CD272) which binds HVEM (TNFRSF14), B7-H3 (CD276), B7-H4 (VTCN1), VISTA (B7-H5), KIR, CD44 (2B4), CD160 (BY55) which bind HVEM; CD134 (TNRFSR4, OX40) which binds CD252 (OX-40L), and the like. Many therapeutic agents, such as antibodies, that bind immune checkpoint proteins and inhibit their immunosuppressive activity have been developed as anti-tumor agents. Several such agents are now commercially available for cancer therapy, including the anti-PD1 antibodies pembrolizumab, dostarlimab, cemiplimab-rwlc, nivolumab, camrelizumab, tislelizumab, toripalimab, and sintilimab; the anti-PD-L1 antibodies avelumab, durvalumab, and atezolizumab; the anti-CTLA-4 antibody ipilimumab; and the anti-LAG-3 antibody relatlimab. In some aspects, this disclosure relates to combination of agonist anti-PD-1 antibody with an anti-CTLA4 antibody (e.g., ipilimumab). In some aspects, this disclosure relates to combination of an agonist anti-PD-1 antibody with an anti-LAG-3 antibody (e.g., relatlimab). In some preferred embodiments, an agonist anti-PD-1 antibody and/or antigen-binding fragment disclosed herein in combination with an immunomodulator can be used to treat a subject with cancer. According, this disclosure relates to a method of treating cancer that includes administration to a subject in need thereof a therapeutically effective amount of a PD-1 agonist antibody or antigen-binding fragment as disclosed herein and an immunomodulator. In some preferred embodiments, an agonist anti-PD-1 antibody and/or antigen-binding fragment disclosed herein in combination with an anti-CTLA4 antibody or antigen-binding fragment thereof can be used to treat a subject with cancer. According, this disclosure relates to a method of treating cancer that includes administration to a subject in need thereof a therapeutically effective amount of a PD-1 agonist antibody or antigen-binding fragment as disclosed herein and an anti-CTLA4 antibody or antigen-binding fragment thereof. In some preferred embodiments, an agonist anti-PD-1 antibody and/or antigen-binding fragment disclosed herein in combination with an anti-LAG-3 antibody or antigen-binding fragment thereof can be used to treat a subject with cancer. According, this disclosure relates to a method of treating cancer that includes administration to a subject in need thereof a therapeutically effective amount of a PD-1 agonist antibody or antigen-binding fragment as disclosed herein and an anti-LAG-3 antibody or antigen-binding fragment thereof.

In preferred embodiments, an agonist anti-PD1 antibody or antigen-binding fragment is administered with a checkpoint inhibitor that does not bind to PD-L1, PD-L2, and/or PD-1. For example, an agonist anti-PD1 antibody or antigen-binding fragment is administered with an antibody that binds any of the following: CTLA-4 (CD152) which binds B7-1 (CD80) and B7-2 (CD86), LAG 3 (CD223) which binds Galectin3, LSECtin and FGL1; TIM3 (HAVCR2) which binds ligands Ceacam1 and Galectin9; TIGIT (VSTM3, WUCAM) which binds CD112 and CD155; BTLA (CD272) which binds HVEM (TNFRSF14), B7-H3 (CD276), B7-H4 (VTCN1), VISTA (B7-H5), KIR, CD44 (2B4), CD160 (BY55) which bind HVEM; CD134 (TNRFSR4, OX40) which binds CD252 (OX-40L). In more specific examples, the checkpoint inhibitor is an anti-CTLA-4 antibody such as ipilimumab and/or an anti-LAG-3 antibody such as relatlimab. In some preferred embodiments, an agonist anti-PD-1 antibody and/or antigen-binding fragment disclosed herein in combination with a checkpoint inhibitor (e.g., a checkpoint inhibitor that does not inhibit the interaction of PD-1 with PD-L1 or PD-L2) can be used to treat a subject with cancer. According, this disclosure relates to a method of treating cancer that includes administration to a subject in need thereof a therapeutically effective amount of a PD-1 agonist antibody or antigen-binding fragment as disclosed herein and a checkpoint inhibitor (e.g., a checkpoint inhibitor that does not inhibit the interaction of PD-1 with PD-L1 or PD-L2).

In one particular embodiment, the antibodies and antigen binding fragments thereof may be co-administered with a PD-1 antagonist, by which is meant a molecule that inhibits suppression of PD-1 by PD-L1. In some embodiments, the PD-1 antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as 87-H1 or Er-DC) in close proximity to a peptide antigen presented by major histocompatibility complex (MHC) (see, for example, Freeman, *Proc. Nail. Acad. Sci*; KA, 105:10275-10276 (2008)). Therefore, proteins, antibodies or small molecules that prevent co-ligation of PD-1 and TCR on the cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind. to PD-1 or ligands of PD-1, and other antibodies.

Suitable anti-PD-1 antibodies include, but are not limited to, those described in the following U.S. Pat. Nos. 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540 all of which are incorporated by reference in their entireties. See also Berger et al., *Clin, Cancer Res.,* 14:30443051 (2008).

Exemplary anti-PD-L1 antibodies include, but are not limited to, those described in U.S. Pat. Nos. 8,383,796, 9,102,725, 9,273,135, 9,393,301, and 9,580,507, all of which are specifically incorporated by reference herein in their entirety.

Exemplary anti-PD-L2 antibodies include, but are not limited to, those described in U.S. Pat. Nos. 7,411,051, 7,052,694, 7,390,888, 8,188,238, and 9,255,147, all of which are specifically incorporated by reference herein in their entirety.

Other examples of suitable immunomodulators for combination with agonist anti-PD-1 antibodies or antigen-binding fragments described herein include T-cell engaging therapies (e.g., T cell engagers). T cell engagers are agents that direct T cell cytotoxic activity to a target tumor. Suitable T cell engagers include but are not limited to bispecific T cell engagers (BiTEs), bifunctional checkpoint-inhibitory T cell engagers (CiTEs), simultaneous multiple interaction T cell engagers (SMITEs), trispecific killer engagers (TriKEs), BiTE-expressing chimeric antigen receptor (CAR) T cells (CART.BiTE cells), or a combination thereof. This disclosure relates to compositions methods of use thereof comprising agonist anti-PD-1 antibodies and bispecific T cell engagers. In some preferred embodiments, an agonist anti-PD-1 antibody and/or antigen-binding fragment disclosed herein in combination with a T cell engager (e.g., bispecific T cell engagers (BiTEs), bifunctional checkpoint-inhibitory T cell engagers (CiTEs), simultaneous multiple interaction T cell engagers (SMITEs), trispecific killer engagers (TriKEs), BiTE-expressing chimeric antigen receptor (CAR) T cells (CART.BiTE cells), and combinations thereof) can be used to treat a subject with cancer. According, this disclosure relates to a method of treating cancer that includes administration to a subject in need thereof a therapeutically effective amount of a PD-1 agonist antibody or antigen-binding fragment as disclosed herein and a T cell engager (e.g., bispecific T cell engagers (BiTEs), bifunctional checkpoint-inhibitory T cell engagers (CiTEs), simultaneous multiple interaction T cell engagers (SMITEs), trispecific killer engagers (TriKEs), BiTE-expressing chimeric antigen receptor (CAR) T cells (CART.BiTE cells), and a combinations thereof).

The additional therapeutics that may be used in embodiments include those disclosed in U.S. Pat. No. 11,021,540.

III. Equivalents

It will be readily apparent to those skilled in the art that other suitable modifications and adaptions of the methods of the invention described herein are obvious and may be made using suitable equivalents without departing from the scope of the disclosure or the embodiments. Having now described certain compositions and methods in detail, the same will be more clearly understood by reference to the following examples, which are introduced for illustration only and not intended to be limiting.

IV. Examples

Example 1: hPD-1-HIS Binding of 4G9-1 Through 4G9-10

Antibodies 4G9-1 through 4G9-10 as set forth in Tables 1-2 and 5 underwent a HIS binding assay to human PD-1 (hPd-1). The assay involved the following procedure:

100 µl of 10 µg/ml PD1-Protein (Acro Biosystems catalog number HM5221) was coated overnight onto Maxisorpplate at 4° C. The following morning, wells were washed 1× with PBST and then blocked with 200 µl/well Superblock/4% BSA for 2 hours. Wells were washed 3× with 1×PBST. Then, 100 µl of 1-100 µg/ml of 4G9-12 in Superblock/4% BSA was added for 2 hours at RT or 4° C. overnight. Wells were washed 3× with 1×PBST. 100 µl of biotinylated anti-human IgG (ThermoFisher catalog number A18827) was added to wells and bound for 1 hour at RT according to manufacturer's suggestions. In some experiments anti-human IgG-HRP was used directly (signal is still detected).

Wells were washed 3× with 1×PBST. 100 µl of 1:5000 SA HRP was added to wells and bound for 1 hour at RT. Wells were washed 3× with 1×PBST and then 3× with 1×PBS. 100 µl TMB was added to the wells and development was stopped with 2N sulfuric acid. The optical density at 450 nm (OD 450) was determined.

The results are as set forth in Table 7.

TABLE 7 hPD-1-HIS binding of 4G9 series antibodies

| Antibody | hPD-1-HIS Binding (OD 450) |
|---|---|
| 4G9-1 | 0.874 |
| 4G9-2 | 0.453 |
| 4G9-3 | 0.451 |
| 4G9-4 | 0.386 |
| 4G9-5 | 0.383 |
| 4G9-6 | 0.377 |
| 4G9-7 | 0.361 |
| 4G9-8 | 0.346 |
| 4G9-9 | 0.31 |
| 4G9-10 | 0.287 |

Example 2: hPD-1-HIS Binding of 5C2-1 Through 5C2-10

Antibodies 5C2-1 through 5C2-10 as set forth in Tables 3-4 and 6 underwent a HIS binding assay to human PD-1

(hPd-1). The optical density at 450 nm (OD 450) was determined according to the protocol given in Example 1.

The results are as set forth in Table 8.

TABLE 8 hPD-1-HIS binding of 5C2 series antibodies

| Antibody | hPD-1-HIS Binding (OD 450) |
|---|---|
| 5C2-1 | 0.791 |
| 5C2-2 | 0.395 |
| 5C2-3 | 0.345 |
| 5C2-4 | 0.312 |
| 5C2-5 | 0.286 |
| 5C2-6 | 0.267 |
| 5C2-7 | 0.264 |
| 5C2-8 | 0.262 |
| 5C2-9 | 0.255 |
| 5C2-10 | 0.249 |

Example 3: Human T Cell Activation by 4G9-2 and 4G9-12

Antibodies 4G9-2 and 4G9-12 were assayed for PD-1 agonist activity according to the in vitro procedure below. To summarize, IFNγ levels in supernatant were attributed to T cell activation, and the T cell activation was attributed to PD-1 agonist activity by the antibodies. An antibody against human immunoglobulin GI (hIgG1) was used as a control.

Materials used were human CD4+/CD45+/CD25− naïve T cells (BioVit, Hicksville, NY); human IFNγ ELISA Kit (Invitrogen, Catalog No. KHC4021); LymphoOne T-Cell expansion Xeno-free medium (Takara, Catalog No. WK552S); fetal bovine serum, certified, Performance Plus (Gibco, Catalog No. 16000-044); Dynabeads human T-activator CD3/CD28 (Gibco, Catalog No. 11132D), interleukin-2 (IL-2; PeproTech, Catalog No. 200-02); round bottom sterile 96-well plates; and a plate reader for ELISA.

The following procedure was followed, with all procedures up to the ELISA determination of IFNγ concentrations being done under sterile conditions.

Human naïve CD4 T cells were thawed. The procedure was performed twice, each time with T cells from different donors. The cells were washed twice with PBS and LymphoOne cell culture medium was added. The cells were counted and their concentration adjusted to 1.5 million/mL in LymphoOne medium. IL-2 and anti-CD3/anti-CD28 coated Dynabeads were added according to manufacturer's suggestions. Cells (100 μL of cells per well) were added into a round-bottom 96-well plate, and then incubated for 48 hr at 5% C02, 37° C. Antibodies were added at a final concentrations of 10-50 μg/mL. An equivalent volume (20 μL) of medium was added to untreated (0 μg/mL antibody) wells, and the same amount and concentrations of the control antibody were used. The cells were then incubated for 24 hr at 5% C02, 37° C., after which supernatants were centrifuged and collected.

The collected supernatants were subjected to ELISA to detect IFNγ according to manufacturer's protocol with prior dilutions of supernatant from 1:1 to 1:50. The IFNγ concentrations determined by ELISA are shown in FIGS. 1A and 1B.

FIGS. 1A and 1B show that IFNγ production by T cells in the absence of antibody or at any tested concentration of control anti-hIgG1 antibody was essentially the same for each donor. Incubating the cells with 4G9-2 or a 4G9-12 at concentrations from 10-50 μg/mL led to ~75-125% increases in IFNγ production for Donor 1 and from ~25-65% increases in IFNγ production for Donor 2. The increases in IFNγ production for Donor 2 showed a dose-dependent response for both antibodies. The results show that 4G9-2 and 4G9-12 functioned as PD-1 agonists, leading to increased T cell activation compared to T cell activation in cells untreated with agonist anti-PD-1 antibody (dashed line in FIGS. 1A and 1B).

Example 4: Human T Cell Activation by Affinity Matured Antibodies 4G9-1 to 4G9-10

Figure 2:
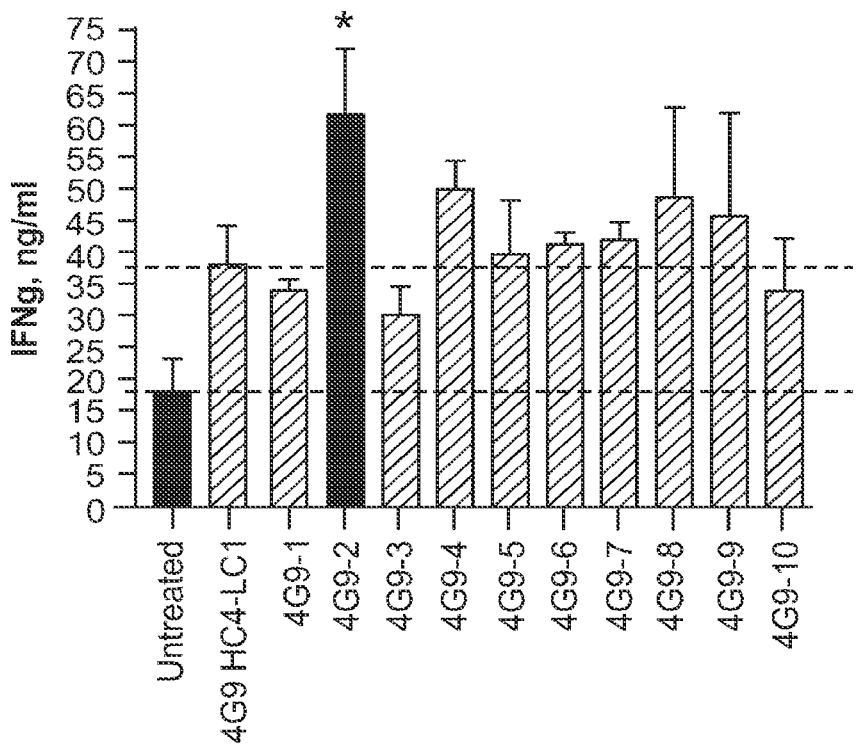
FIG. 2 is a graph showing human CD4+ T cell activation, as determined by interferon gamma (IFNγ) levels, by antibodies 4G9-1 to 4G9-10 according to Example 4 and also showing the 4G9-2 treatment significantly increased (*p<0.05) the IFNγ compared to antibody that was not affinity matured ('4G9 HC4-LC1'). The lower dotted line indicates the average IFNγ level in cells untreated with 4G9 lineage antibody ("Untreated"). The upper dotted line indicates the average IFNγ level in cells treated with an antibody that was not affinity matured ("4G9 HC4-L C1").

Affinity matured antibodies 4G9-1 to 4G9-10 were assayed for PD-1 agonist activity substantially as described in Example 3. Briefly, human CD4+ T cells were isolated from a donor and stimulated with anti-CD3/anti-CD28 coated beads and IL-2 for 24 hours. After 24 hours, the cells were treated with an antibody selected from 4G9-1 to 4G9-10, a control antibody for original 4G9 CDRs that was not affinity matured (4G9 HC4-LC1), or left untreated. Following another 48 hours of culture, supernatants were collected and tested for IFNγ production by ELISA. This experiment was performed with duplicate wells for each treatment. Data from one representative experiment is shown in FIG. 2. Production of IFNγ was significantly (*p<0.05) higher for the 4G9-2 antibody compared to the 4G9 control antibody that was not affinity matured (4G9 HC4-LC1, see FIG. 2, upper dashed line) and cells untreated with antibody ("Untreated", lower dashed line). Treatment with the 4G9-2 antibody resulted in the highest production of IFNγ compared to all other anti-PD1 agonist antibodies tested in the experiment.

Figure 3A:
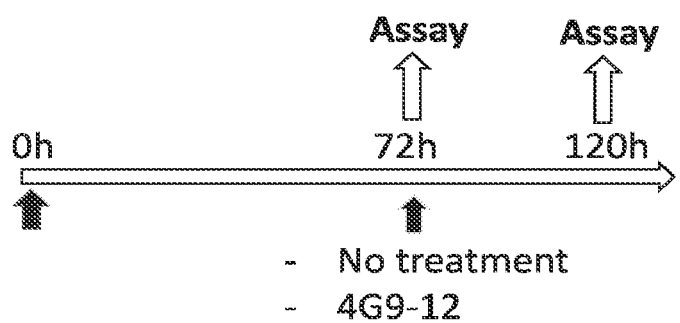
FIGS. 3A-3C are a schematic and graphs showing design and results of an experiment characterizing memory T cell and terminal effector T cell populations in response to agonist antibody (4G9-12) treatment of human CD4+ T cells.
Figures 3B, 3C:
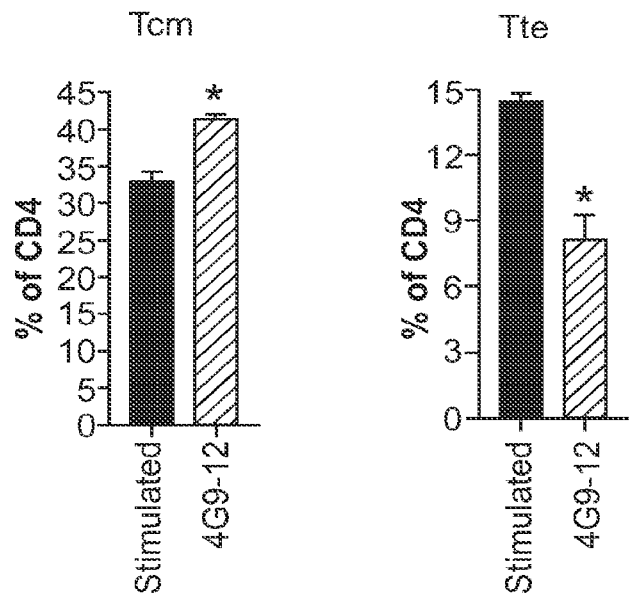

Example 5: Evaluation of T Memory Cell Induction and T Cell Exhaustion in Human T Cells with 4G9-12 Antibody Human CD4+ T cells (BIOIVT LLC) were stimulated with beads coated with anti-CD3 and anti-CD28 antibody (DYNABEADS™ GIBCO (THERMO FISHER SCIENTIFIC INC.) and IL-2 (100 U/mL—R&D SYSTEMS, INC.) substantially as described in Example 3. Following stimulation for 72 hours, cells were either treated with 4G9-12 anti-PD-1 agonist antibody (25 μg/mL) or left untreated (control). Following anti-PD-1 agonist antibody treatment for 48 hours, cells were collected, washed, and stained with fluorophore-labeled antibodies. Stained cells were analyzed by flow cytometery. FIG. 3A shows a schematic of the experiment. Central memory T cells (Tcm) were defined as $CD45RO^{high}/CD62L^{high}/CD45RA^{low}$. Exhausted T cells (e.g., terminal effector T cells (Tte)) were defined as $CD45RO^{low}/CD62L^{low}/CD45RA^{high}$. Treatment with 4G9-12 led to a significant increase in Tcm (*p<0.05) and significant decrease in Tte (*p<0.05) populations relative to total CD4+ T cells (see FIGS. 3B and 3C, respectively).

Figure 4A:
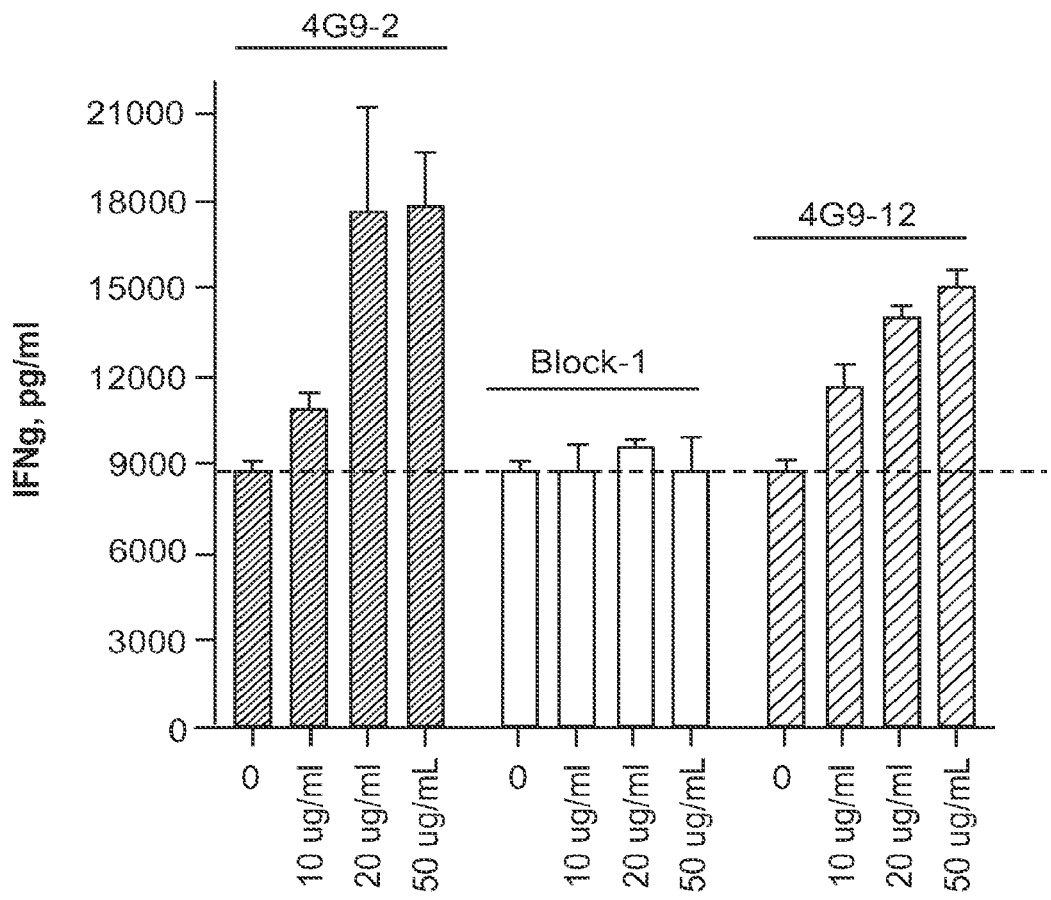
FIGS. 4A-4C are graphs showing stimulation of CD4+ T cells by anti-PD1 agonist antibodies but not by isotype control or PD-1 blocking antibodies in the studies described in Example 6.
Figure 4B:
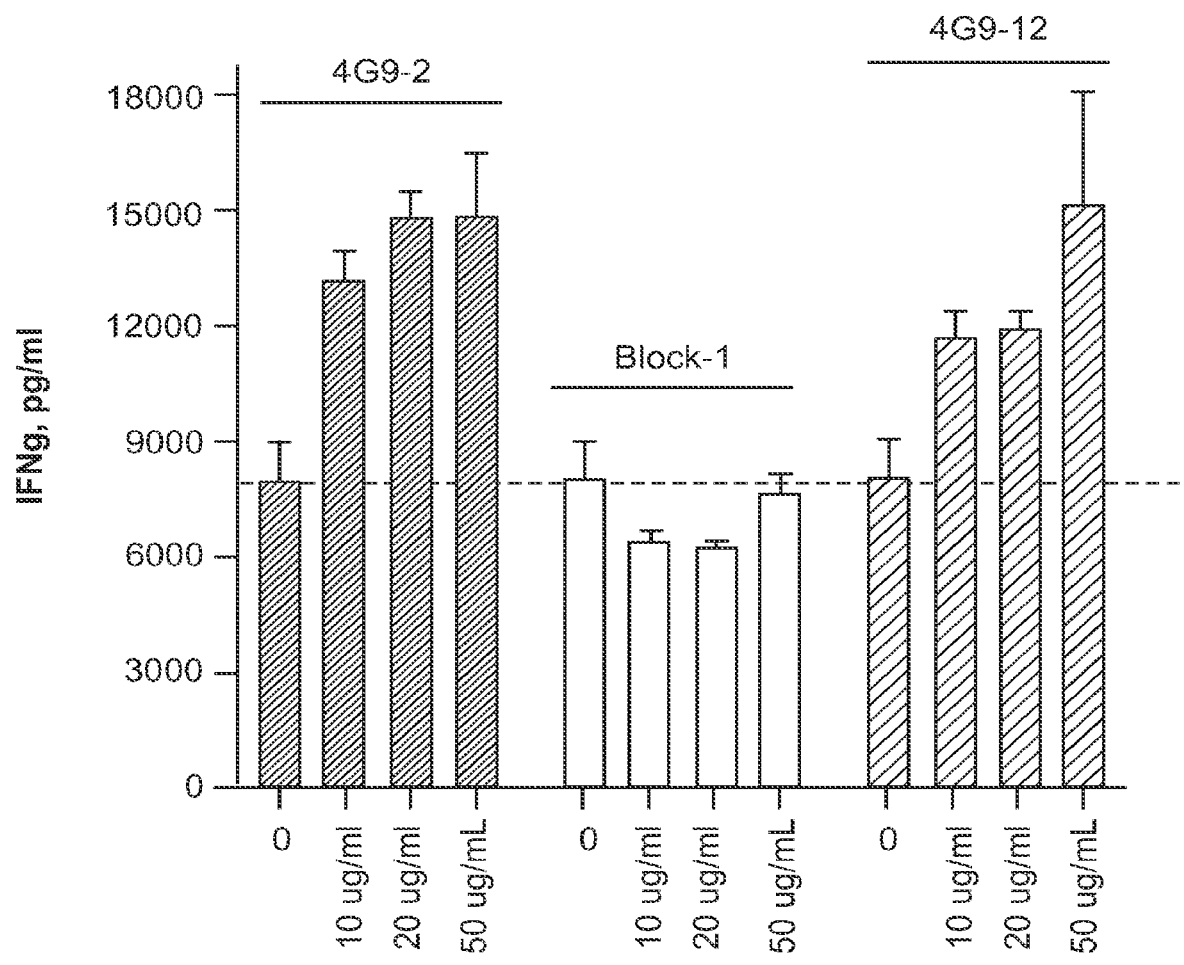
Figure 4C:
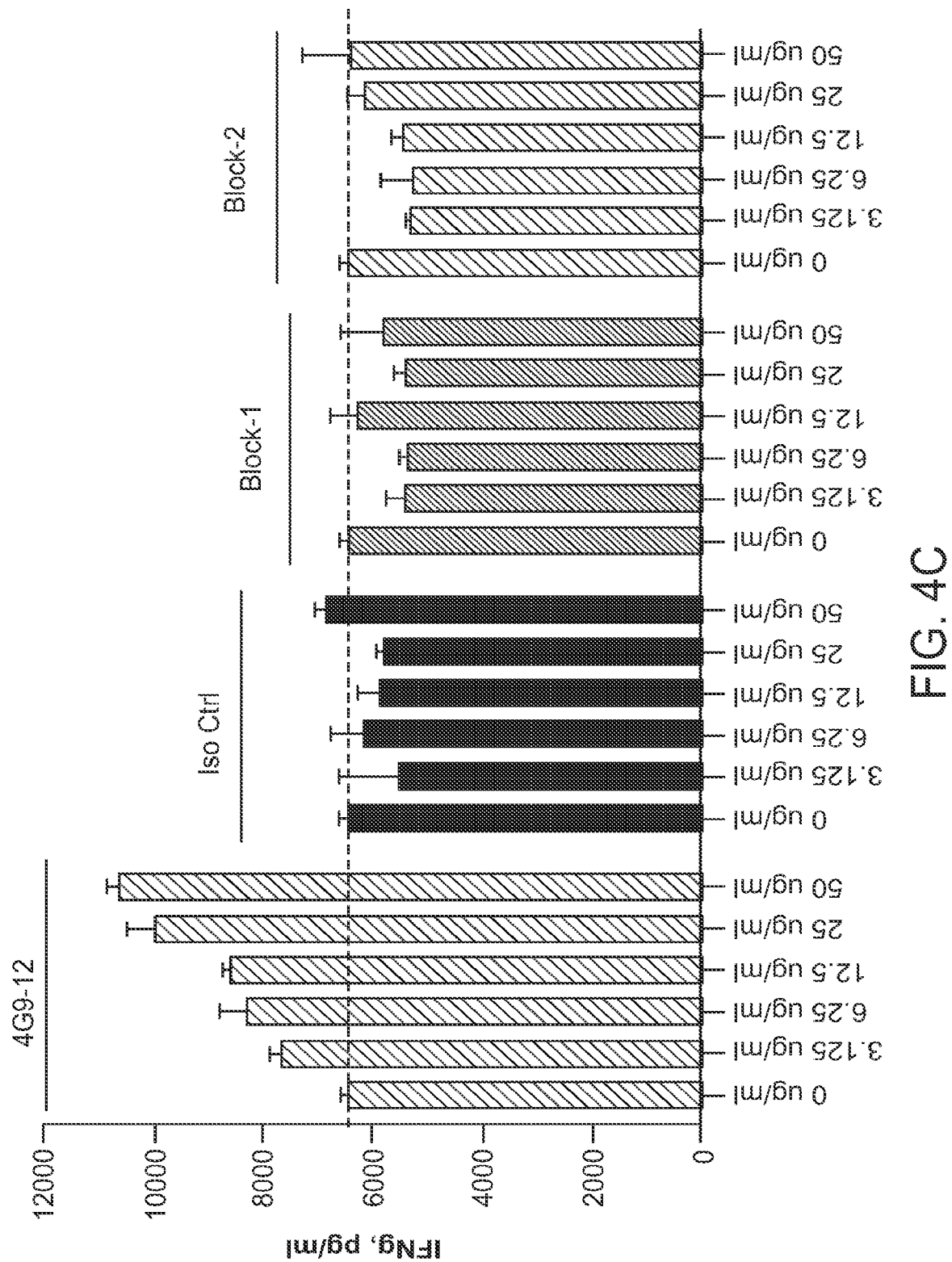

Example 6: Comparison of 4G9-12 and Blocking Anti-PD-1 Antibody in Human T Cells The objectives of this study were to test the activation of primary human CD4+ T cells after treatment with different concentrations of 4G9-12 and blocking anti-PD-1 antibody. The 4G9-12-mediated T cell stimulation was assessed in purified human CD4+ T cells from healthy donors. T cells were pre-stimulated with human anti-CD3/anti-CD28 Dynabeads and IL-2 for 24 hours at 37° C. substantially as described in Example 3. Following the priming step, the cells were exposed to either 4G9-12, 4G9-2, an isotype control (Iso Ctrl) or a blocking anti-PD-1 that is not a PD-1 agonist (PROMEGA Co., clone J1201 ("Block-1," FIGS. 4A, 4B and 4C) or pembrolizumab ("Block-2," FIG. 4C) antibody) for 48 hours at various concentrations, and the levels of IFN-γ were determined using ELISA (see FIGS. 4A-4C). While the blocking anti-PD-1 antibodies did not increase IFN-γ levels in supernatants from purified CD4 T cells when compared to levels observed in untreated cell supernatants (dashed line in FIGS. 4A-4C), 4G9-12 and 4G9-2 treatment resulted in comparable concentration-dependent increases in IFN-γ. The results show that T-cell stimulation as assessed by production of IFN-γ, is induced by the agonist anti-PD-1 antibodies disclosed herein, but not by antibodies that bind PD-1 and inhibit interaction with PD-L1, such as J1201 and pembrolizumab.

Figure 5:
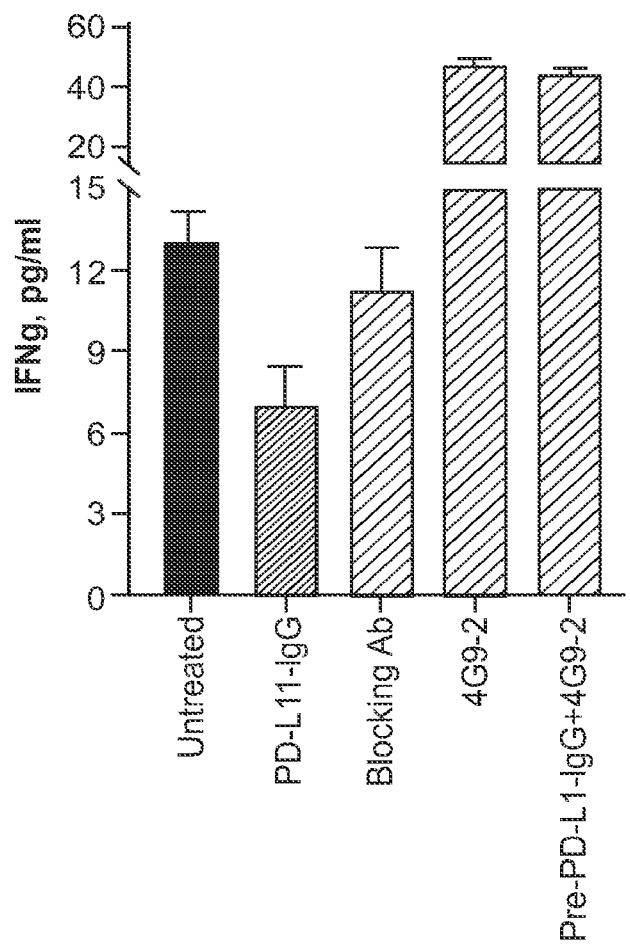
FIG. 5 is a graph showing that treatment of human CD4+ T cells with anti-PD-1 agonist antibody (4G9-2) and both PD-L1 (e.g., PD-L1-IgG) and 4G9-2, but not with PD-L1 (e.g., PD-L1-IgG) or blocking anti-PD-1 antibody, increased T cell activation as measured by IFNγ release compared to cells without antibody or ligand treatment ("Untreated"). The results show that anti-PD-1 agonist antibody dramatically increased T cell activation, as assessed by IFNγ release, even in the presence of PD-L1. Further experimental details are described in Example 7.

Example 7: Functional Evaluation of Agonist Antibody Activity in the Presence of PD-L1 or PD-1-Blocking Antibody 4G9-2 antibody was tested for its ability to activate human CD4 T cells that were pre-stimulated (for 24 hours) with CD3/CD28 coated Dynabeads and IL-2, substantially as described in Example 3, but in the absence or presence of plate-bound PD-L1 in the form of an Fc fusion protein (PD-L1-IgG). As shown in FIG. 5, following 72 hours of exposure to 4G9-2 at 25 µg/mL, there was a >3-fold increase in IFN-γ levels in the supernatants (measured using ELISA from THERMO FISHER SCIENTIFIC Inc.) compared to untreated T cells or T cells exposed to a blocking anti-PD-1 antibody (PROMEGA Co., clone J1201 "Blocking Ab", 25 µg/mL) confirming that 4G9-2 activated T cells. While pretreatment of the cells with plate-bound PD-L1 (PD-L1-IgG) inhibited IFN-γ production, addition of 4G9-2 treatment in presence of plate-bound PD-L1 (PD-L1-IgG) resulted in T cell activation comparable to 4G9-2 alone, suggesting agonist antibodies like 4G9-2 can activate T cells even in the presence of the natural ligand (PD-L1).

Example 8: Evaluation of Potential Anti-PD-1 Agonist Antibody Competition with PD-L1

Figures 6A, 6B, 6C:
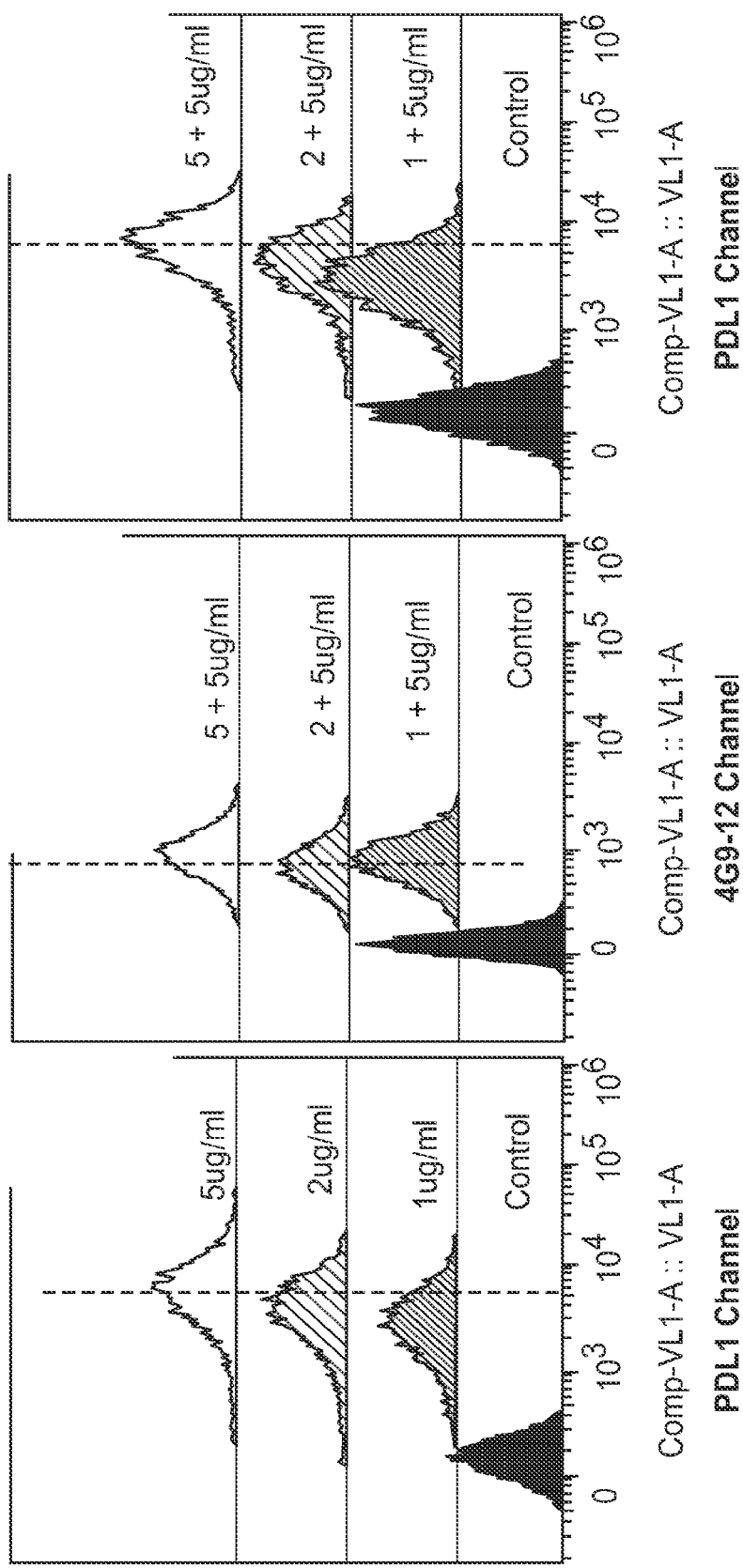
FIGS. 6A-6C are histograms showing flow cytometry results of competitive binding experiments between PD-L1 and an agonist anti-PD-1 antibody (4G9-12) as described in Example 8.

To evaluate if anti-PD-1 agonist antibodies compete with PD-L1 for binding to PD-1 or can bind to PD-1 simultaneously with PD-L1, APC-labeled 4G9-12 was evaluated at 5 µg/mL, for potential competitive binding with V450-labeled human PD-L1-IgG (at 1, 2, or 5 µg/mL) in Raji PD-1+ cells using flow cytometry. PD-L1 alone bound to PD-1 with higher binding seen at increasing concentrations of PD-L1 as shown in FIG. 6A (PDL1 fluorescence). As shown in FIG. 6B (4G9-12 fluorescence) and FIG. 6C (PD-L1 fluorescence), both 4G9-12 and the PD-L1-IgG were able to simultaneously bind the target, and the presence of increasing concentrations of PD-L1-IgG did not affect binding of 4G9-12. These data also demonstrate that the PD-L1-IgG maintains the same level of binding in presence of 4G9-12. These data confirm that PD-1 agonist antibodies like 4G9-12 do not compete with PD-L1 for binding to PD-1, and therefore their agonist activity is not due to inhibiting binding of PD-L1.

Figure 7:
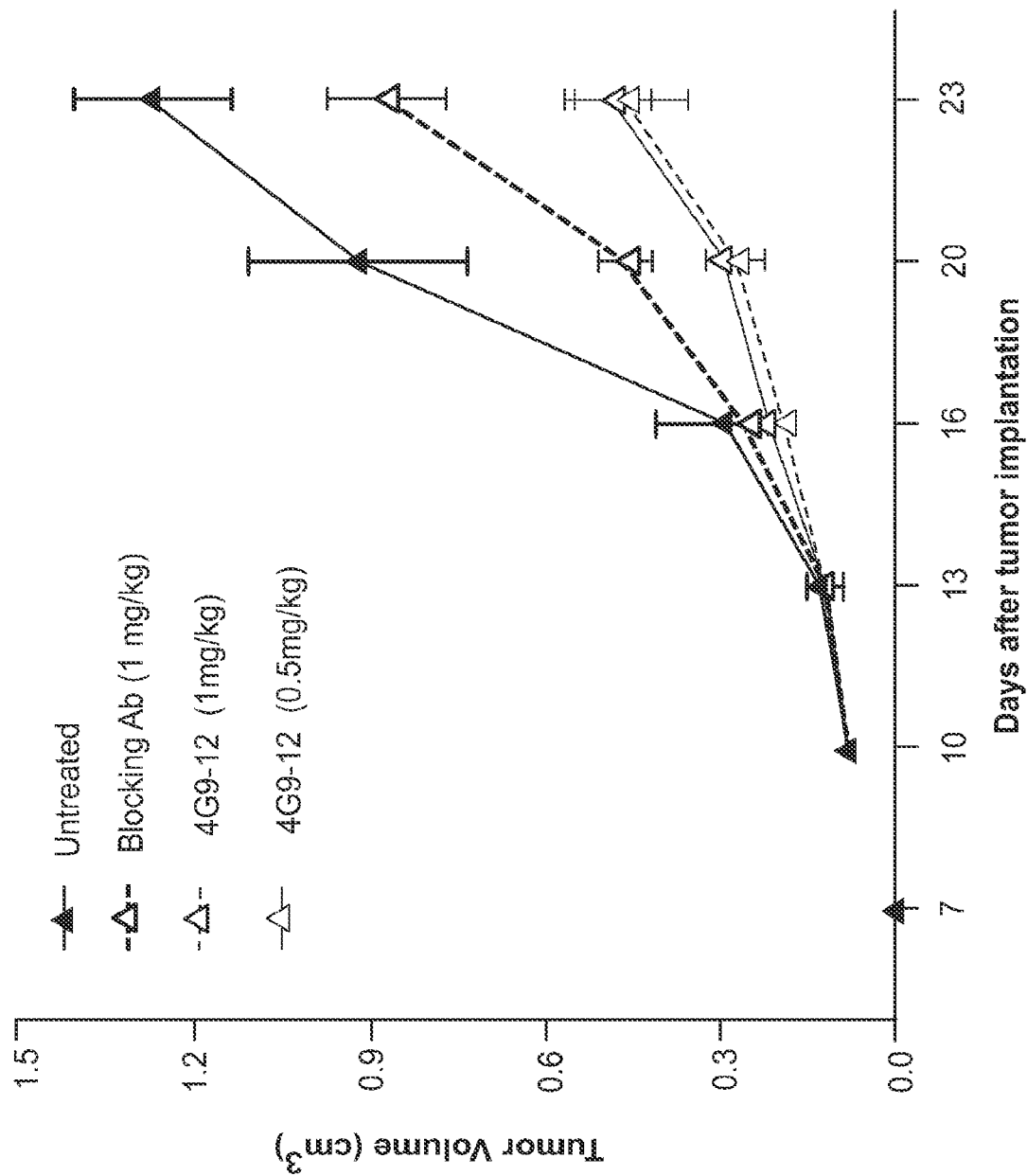
FIG. 7 is a graph showing that the average tumor volume in a syngeneic mouse model of colorectal carcinoma following intraperitoneal (i.p.) treatment with 4G9-12 (0.5 mg/kg or 1.0 mg/kg) and, to a lesser degree, blocking anti-PD-1 antibody (1.0 mg/kg, RMP1-14 clone), is reduced compared to untreated mice ("Untreated") in the studies described in Example 9.
Figure 8B:
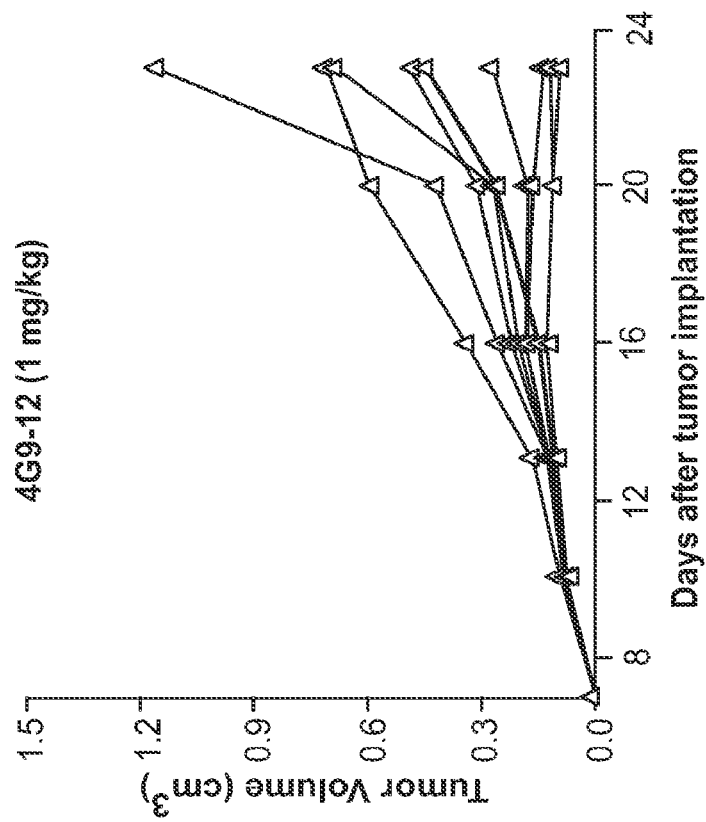
FIGS. 8A-8D are graphs showing the tumor volume of each mouse in the syngeneic mouse model of colorectal carcinoma of FIG. 7 and as further described in Example 9.
Figure 8A:
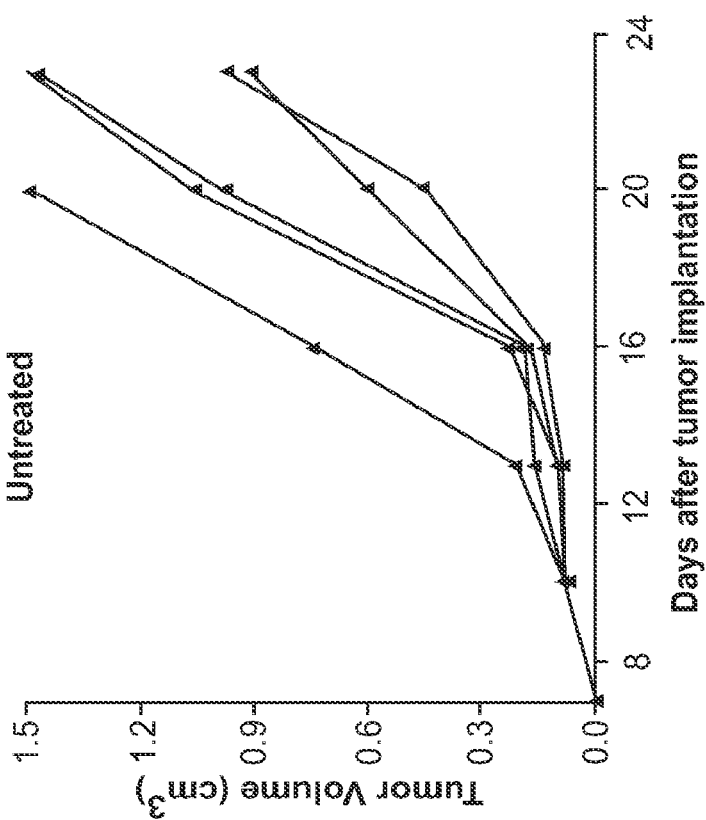
Figure 8C:
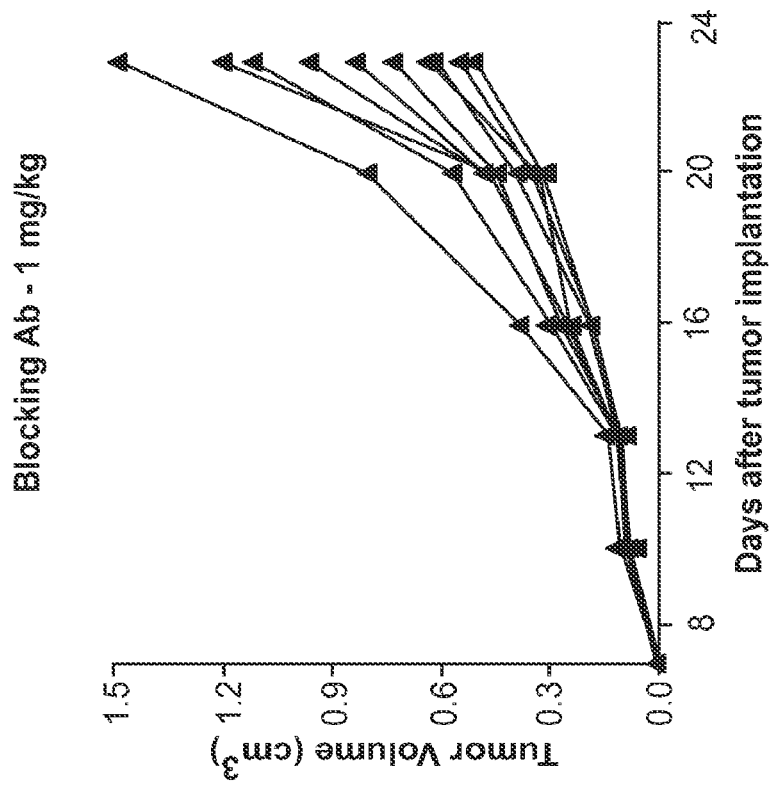
Figure 8D:
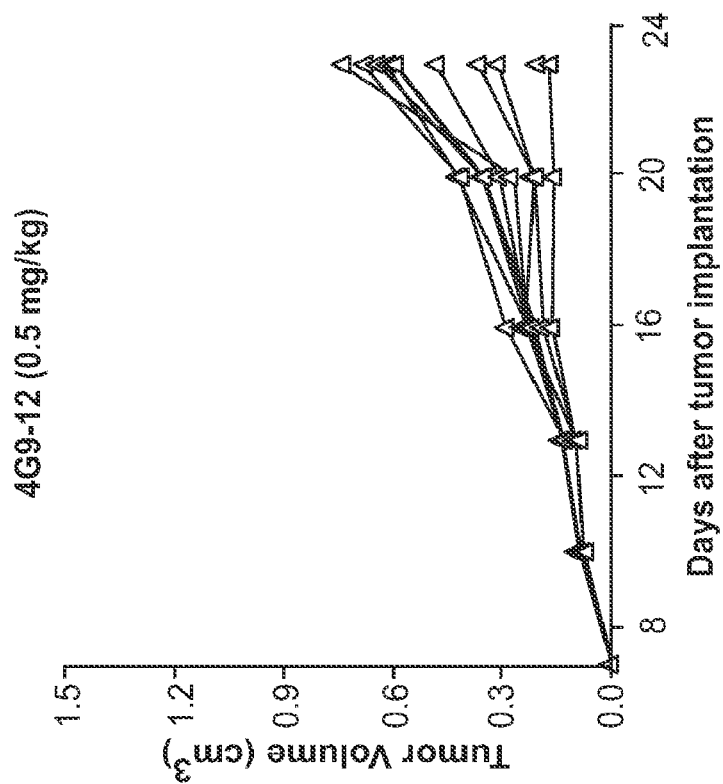

Example 9: Evaluation of Intraperitoneal Administration of 4G9-12 Antibody in a Syngeneic Colorectal Carcinoma Mouse Tumor Model The anti-tumor activity of 4G9-12 was evaluated in vivo using a syngeneic colorectal carcinoma (CRC) tumor model in BALB/c mice. On Day 0 mice were subcutaneously (SC) injected with CT26 tumor cells ($1 \times 10^5$ cells/mouse) and dosed via intraperitoneal (IP) injection with 4G9-12 (0.5 or 1 mg/kg) or a commercially available benchmark PD-1 blocking antibody that is not a PD-1 agonist (clone RMP1-14 (BioXCell, 1 mg/kg)) 10, 13, 16, and 20 days after tumor implantation (0, 3, 6, and 10 days post dose). A group of tumor-implanted mice that were not dosed with antibody were used as a negative control group. Tumor volume was monitored. Both doses of 4G9-12 resulted in significant anti-tumor activity compared to the untreated control and the 1 mg/kg PD-1 blocking antibody group. There were no significant differences between 0.5 and 1 mg/kg doses of 4G9-12 suggesting that, at those doses, the anti-tumor activity reaches a plateau response (see FIG. 7). Individual tumor volumes for each mouse are shown in FIG. 8A-8D. This study demonstrated the anti-tumor activity of 4G9-12 in a mouse model of colorectal cancer, and that the agonist antibodies have better antitumor activity in comparison to PD-1 blocking antibodies.

Figure 9:
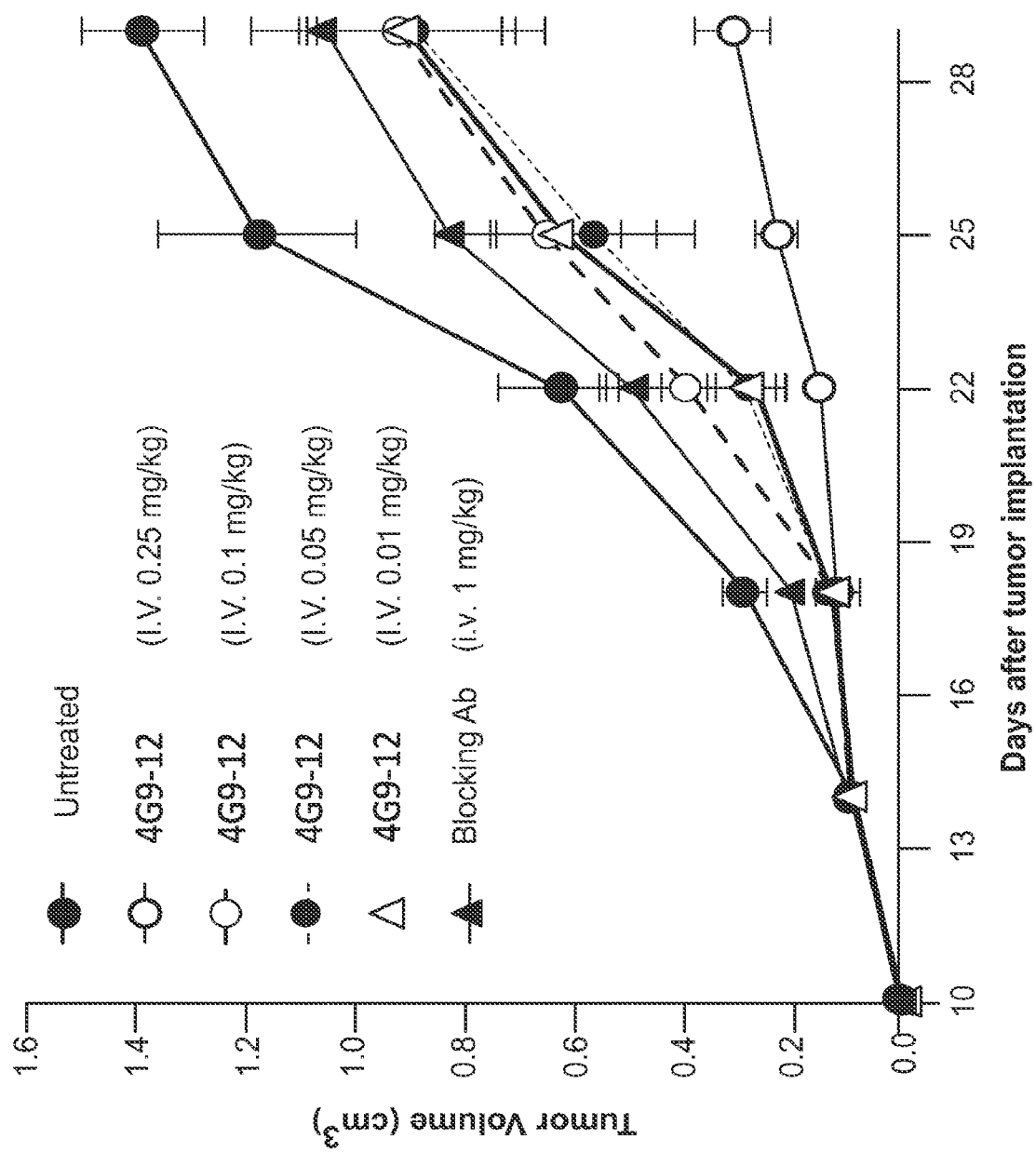
FIG. 9 is a graph showing that the average tumor volume in the CT26 mouse model of colorectal carcinoma following intravenous (i.v.) treatment with 4G9-12 (0.01 mg/kg, 0.05 mg/kg, 0.1 mg/kg, or 0.25 mg/kg), or blocking anti-PD-1 antibody (1.0 mg/kg, RMP1-14 clone), are reduced compared to untreated mice ("Untreated") as further described in Example 10.

Example 10: Evaluation of Intravenous Administration of 4G9-12 Antibody in a Syngeneic Colorectal Carcinoma Mouse Tumor Model The anti-tumor activity of 4G9-12 was evaluated in vivo using a syngeneic colorectal carcinoma (CRC) tumor model in BALB/c mice. On Day 0 mice were subcutaneously injected with CT26 tumor cells ($1 \times 10^5$ cells/mouse) and dosed via intravenous (IV) injection with 4G9-12 (0.01, 0.05, 0.1, or 0.25 mg/kg)) or a commercially available benchmark PD-1 blocking antibody (clone RMP1-14, BioX-Cell; 1 mg/kg, a non-agonist antibody) 14, 18, 22, and 25 days after tumor implantation (Day 0, 4, 8, and 11 postdose). A group of tumor implanted mice that were not dosed with antibody were used as a negative control group. Tumor volume was monitored for all mice. All doses of 4G9-12 resulted in statistically significant inhibition of tumor growth compared to the untreated control, with doses <0.1 mg/kg 4G9-12 having similar response to each other and to the 1 mg/kg anti-PD-1 blocking antibody (see FIG. 9). Individual tumor volumes for each mouse are shown in FIGS. 10A-10F. The benchmark PD-1 blocking antibody (4-fold higher concentration) had lower activity compared to 0.25 mg/kg 4G9-12. This study demonstrated the anti-tumor activity of IV administered agonist anti-PD-1 antibodies such as 4G9-12 in a mouse model of CRC. These data show agonist anti-PD-1 antibody 4G9-12 has enhanced inhibition of tumor growth in comparison to PD-1 blocking (e.g., non-agonist) antibodies.

Figure 11A:
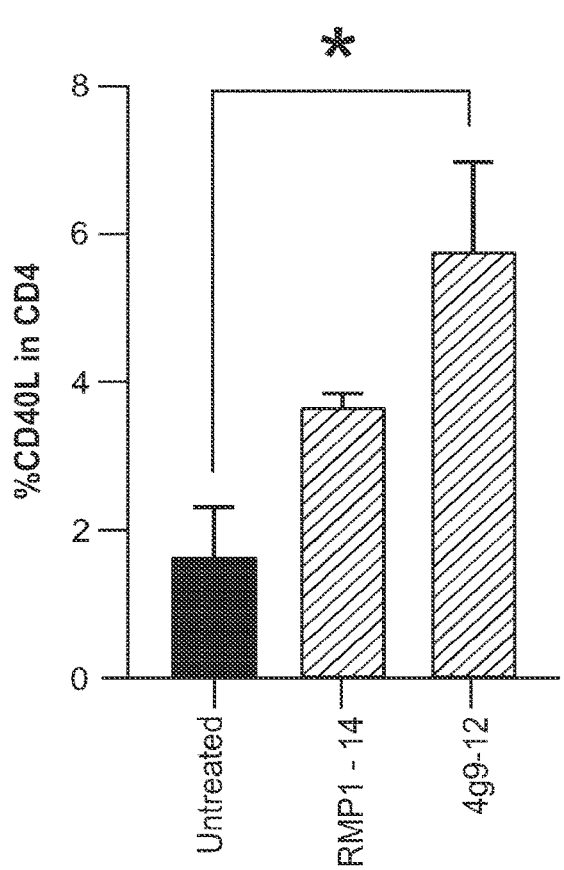
FIGS. 11A and 11B are graphs showing that in vivo treatment with 4G9-12 (anti-PD1 agonist antibody), but not blocking anti-PD-1 antibody (RMP1-14), significantly increases both CD4$^+$ T cell and CD8$^+$ T cell activation state by ex vivo analysis compared to mice not treated with antibody ("Untreated"), as further described in Example 11.
Figure 11B:
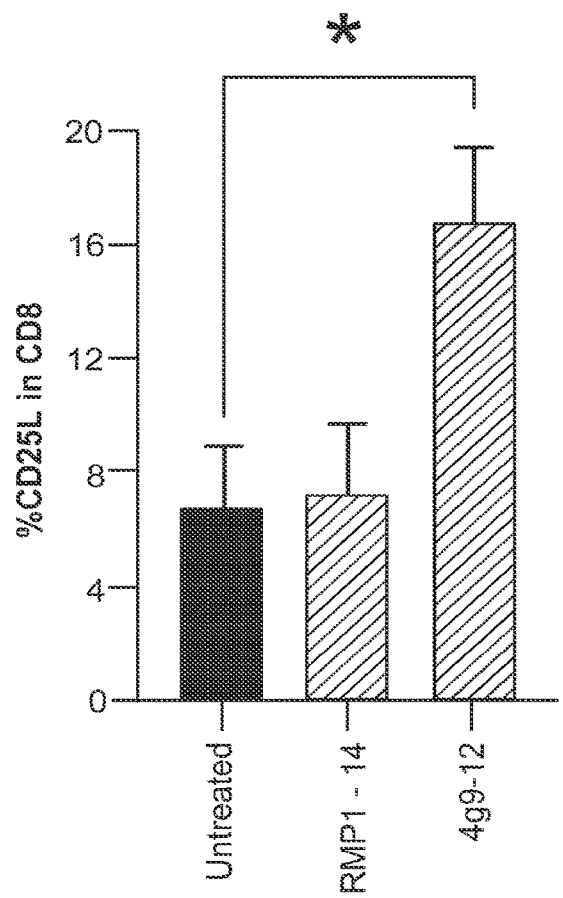

Example 11: Ex Vivo Assessment of T Cell Activation by Anti-PD-1 Agonist Antibody in a CT 26 Tumor Model The anti-tumor activity of 4G9-12 was evaluated in vivo using a CT26 tumor model in BALB/c mice. BALB/c mice were implanted with CT26 cells ($1 \times 10^5$) in the right flank. Ten days after tumor implantation, when tumors reached a diameter of 4-6 mm, mice were treated with single doses of 4G9-12 (1 mg/kg), PD-1 blocking antibody (RMP1-14 clone, 1 mg/kg, a non-agonist antibody), or were left untreated. Three days post treatment the mice were euthanized, and the tumors were isolated. Tumors were processed and activation status of CD4+ and $CD8^+$ T cells in the tumors was assessed using flow cytometry. CD40L was used as an activation marker for $CD4^+$ T cells and CD25 for $CD8^+$ T cells. These data show an agonist anti-PD-1 antibody such as 4G9-12, but not blocking anti-PD-1 antibody, induces activation of tumor infiltrating CD4+ and CD8+ T cells. In contrast to blocking anti-PD-1 antibody, 4G9-12 induces activation of tumor-infiltrated CD4+ and CD8+ T cells after a single dose treatment (see FIGS. 11A & 11B).

Example 12: Assessment of Cellular Signaling and T Cell Activation

Figure 12C:
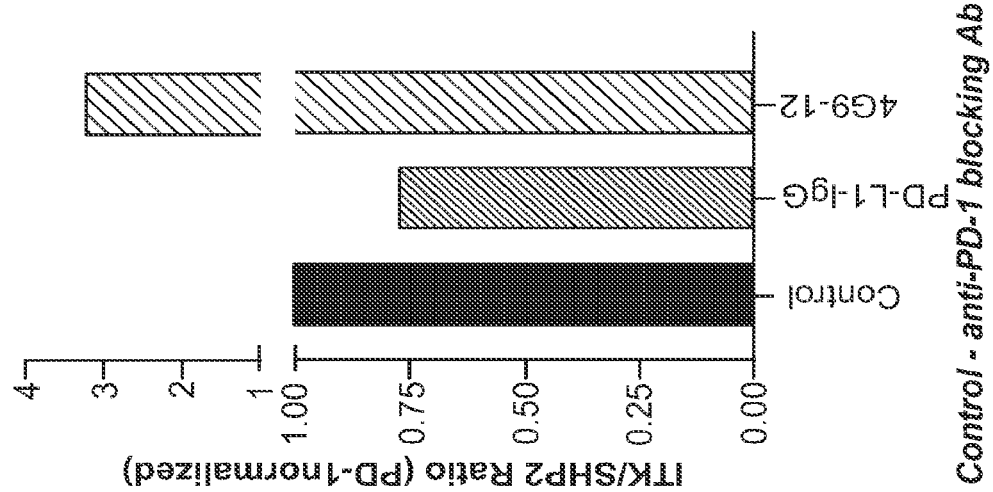
FIGS. 12A-12C are Western blots and a bar graph showing that the intracellular ratio of ITK to SHP2 is increased following treatment of human CD4$^+$ T cells with agonist anti-PD-1 antibody 4G9-12, but not blocking anti-PD-1 antibody (PROMEGA Co., "Control") or PD-L1 (e.g., PD-L1-IgG), as further described in Example 12.
Figure 12B:
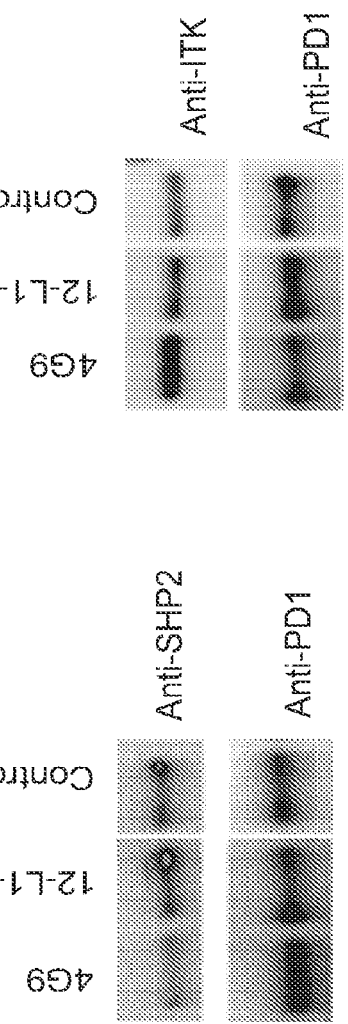
Figure 12A:
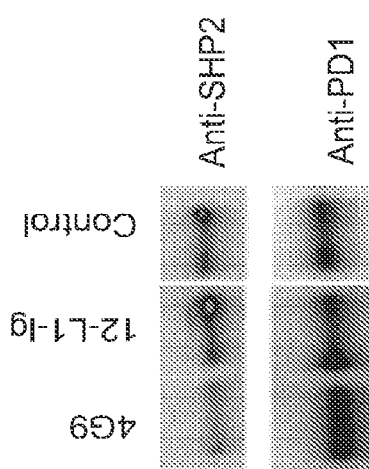

To determine whether the intracellular signal transduced via PD-1 differs when PD-1 is bound by an agonist antibody such as 4G9-12, PD-L1 ligand, and anti-PD-1 blocking antibodies, human CD4+ T cells were stimulated with anti-CD3/anti-CD28 Dynabeads and IL-2 substantially as described in Example 3. Following stimulation, cells were treated for 30 minutes with 25 µg/ml of either 4G9-12, PD-L1-IgG (R&D SYSTEMS, INC.), or anti-human PD-1 (clone J1201, PROMEGA Co., a non-agonist antibody). After 30 minutes of treatment the cells were washed and lysed, and Protein A was used for immunoprecipitation, followed by Western blot analysis of ITK, SHP2, and PD-1 (see FIGS. 12A and 12B). The ratio of ITK/SHP2 (normalized to levels of PD-1) was determined and showed that 4G9-12 results in a 3-fold increased ITK/SHP2 ratio when compared to anti-PD-1 blocking antibodies. As expected, PD-L1-IgG treatment resulted in a decrease ITK/SHP2 ratio (see FIG. 12C). Of particular note, 4G9-12 treatment increased the ITK/SHP2 ratio compared to control anti-human PD-1 blocking antibody, demonstrating that agonist antibodies like 4G9-12 induce signaling through PD-1 that is different from PD-L1-induced signaling.

Figure 13:
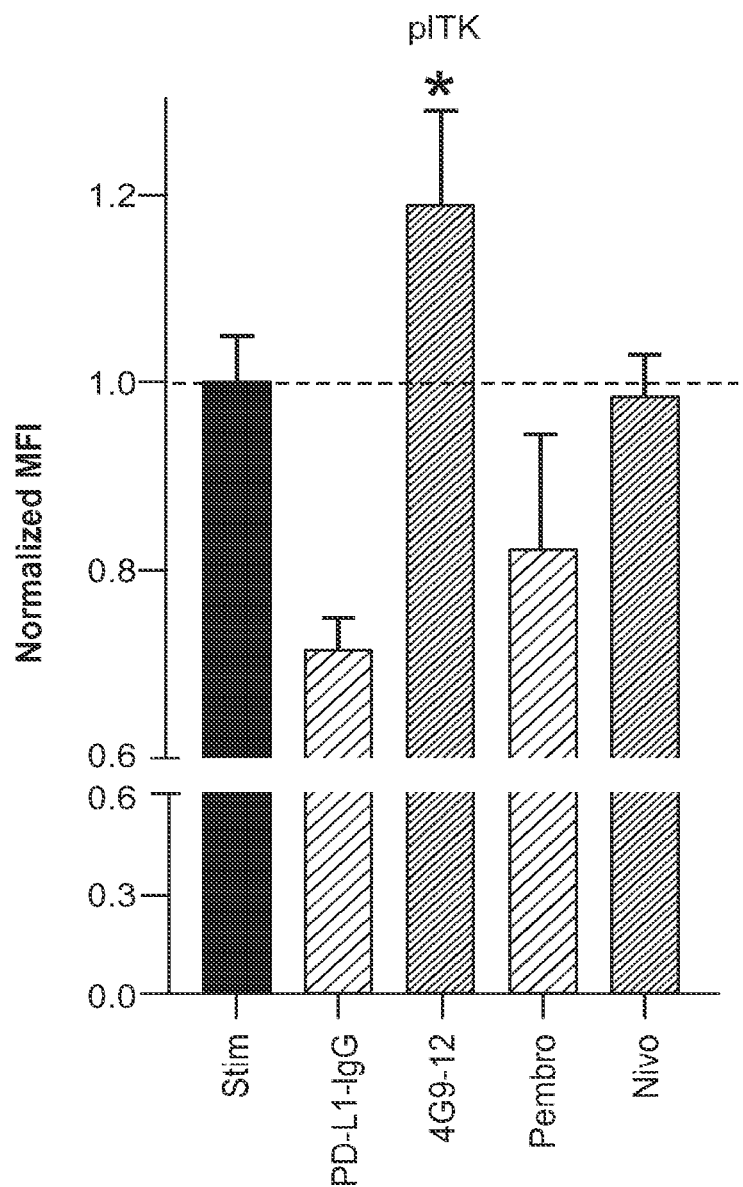
FIG. 13 is a graph showing that phosphorylated interleukin-2-inducible T cell kinase (pITK) in CD4$^+$ T cells, by normalized mean fluorescent intensity (MFI) obtained by flow cytometry, is increased by treatment with agonist anti-PD-1 antibody 4G9-12 (25 µg/mL), but not with PD-L1 (e.g., PD-LT-IgG), pembrolizumab ("Pembro"), or nivolumab ("Nivo") compared to cells only stimulated without additional treatment ("Stim"), as further described in Example 13. Data were normalized to only stimulated "Stim" group. The average of the stimulated group is shown with a dashed line. Statistical analysis consists of one-way ANOVA, with multiple comparison post-test.

Example 13: Flow Cytometric Analysis of Cell Signaling by Blocking and Agonist Anti-PD-1 Antibodies in Human CD4+ T Cells Since ITK is an important molecule in agonist PD-1 antibody mechanism of action, flow cytometry was used to evaluate the effect of 4G9-12 on phosphorylation of ITK when compared to blocking anti-PD-1 antibodies (e.g., non-agonist antibodies) pembrolizumab ("Pembro") and nivolumab ("Nivo"). Human CD4+ T cells were stimulated with anti-CD3/anti-CD28 Dynabeads and IL-2 for 24 hours substantially as described in Example 3, then treated with 25 µg/mL of either 4G9-12, PD-L1-IgG (R&D SYSTEMS, INC.), pembrolizumab, nivolumab, or left untreated ("Stim") for 24 hours. At the end of the treatment the cells were washed, fixed, permeabilized, and prepared for flow cytometry by staining with Live/Dead stain and PE-labeled anti-phospho-ITK antibody. PD-L1-IgG treatment decreased the phosphorylation of ITK. In contrast to the blocking PD-1 antibodies pembrolizumab and nivolumab, 4G9-12 significantly increased the level of phospho-ITK compared to untreated ("Stim") cells (see FIG. 13). These results provide a basis for how treatment with agonist antibodies such as 4G9-12 results in T cell activation, as ITK is an activating molecule within the T cell receptor signaling pathway.

What is claimed is:

1. An antibody or antigen-binding fragment thereof having binding specificity for programmed cell death receptor protein 1 (PD-1) comprising a light chain variable region and a heavy chain variable region, wherein the antibody or antigen-binding fragment comprises: CDR L1 comprising SEQ ID NO:114, CDR L2 comprising KVS, CDR L3 comprising SEQ ID NO:134, CDR H1 comprising SEQ ID NO:32, CDR H2 comprising SEQ ID NO:53, and CDR H3 comprising SEQ ID NO:74.

2. The antibody or antigen-binding fragment thereof of claim 1, wherein the antibody or antigen-binding fragment comprises:
   a light chain variable region comprising SEQ ID NO:84 or SEQ ID NO:94; and
   a heavy chain variable region comprising SEQ ID NO:2 or SEQ ID NO:12.

3. The antibody or antigen-binding fragment thereof of claim 2, wherein the antibody or antigen-binding fragment comprises a light chain variable region comprising SEQ ID NO:94 and a heavy chain variable region comprising SEQ ID NO:12.

4. The antibody or antigen-binding fragment thereof of claim 2, wherein the antibody or antigen-binding fragment comprises a light chain variable region comprising SEQ ID NO:84 and a heavy chain variable region comprising SEQ ID NO:2.

5. The antibody or antigen-binding fragment thereof of claim 1, further comprising a light chain constant region and a heavy chain constant region.

6. The antibody or antigen-binding fragment of claim 5, wherein the heavy chain constant region is an IgG constant region.

7. The antibody or antigen-binding fragment of claim 1, wherein the antibody or antigen-binding fragment is a PD-1 agonist.

8. The antibody or antigen-binding fragment of claim 1, wherein the antibody or antigen-binding fragment does not compete with PD-L1 for binding to PD-1.

9. The antibody or antigen-binding fragment of claim 1, wherein the antibody or antigen-binding fragment enhances pITK level, ITK/SHP2 ratio, or both pITK level and ITK/SHP2 ratio in cells upon binding to PD-1 on said cells.

10. The antibody or antigen-binding fragment of claim 1, wherein the antibody or antigen-binding fragment induces central memory T cells (Tcm).

11. The antibody or antigen-binding fragment of claim 1, wherein the antibody or antigen-binding fragment inhibits T cell exhaustion.

12. A pharmaceutical composition, comprising the antibody or antigen-binding fragment thereof of claim 1 and a pharmaceutically acceptable carrier.

13. A method for treating cancer, comprising administering to a subject in need thereof a therapeutically effective amount of the antibody or antigen-binding fragment of claim 1.

14. A method for inducing or enhancing central memory T cells, comprising administering to a subject in need thereof a therapeutically effective amount of the antibody or antigen-binding fragment of claim 1.

15. A method for inhibiting T cell exhaustion, comprising administering to a subject in need thereof a therapeutically effective amount of the antibody or antigen-binding fragment of claim 1.

16. An isolated polynucleotide encoding the antibody or antigen-binding fragment thereof of claim 1.

17. A host cell comprising the polynucleotide of claim 16.

18. The host cell of claim 17, wherein the host cell is a mammalian cell.

19. The antibody or antigen binding fragment thereof of claim 3, further comprising a light chain constant region or a heavy chain constant region.

20. The antibody or antigen binding fragment of claim 19, further comprising a heavy chain constant region, wherein the heavy chain constant region is an IgG constant region.

21. A pharmaceutical composition, comprising the antibody or antigen-binding fragment of claim 3 and a pharmaceutically acceptable carrier.

22. The antibody or antigen binding fragment thereof of claim 4, further comprising a light chain constant region or a heavy chain constant region.

23. The antibody or antigen binding fragment of claim 22, further comprising a heavy chain constant region, wherein the heavy chain constant region is an IgG constant region.

24. A pharmaceutical composition, comprising the antibody or antigen-binding fragment of claim 4 and a pharmaceutically acceptable carrier.

25. An isolated polynucleotide encoding the antibody or antigen-binding fragment thereof of claim 3.

26. A host cell comprising the polynucleotide of claim 23.

27. An isolated polynucleotide encoding the antibody or antigen-binding fragment thereof of claim 4.

28. A host cell comprising the polynucleotide of claim 27.

29. An isolated polynucleotide encoding the antibody or antigen-binding fragment thereof of claim 5.

30. A host cell comprising the polynucleotide of claim 29.

* * * * *

```
                        SEQUENCE LISTING

Sequence total quantity: 398
SEQ ID NO: 1            moltype = AA  length = 116
FEATURE                 Location/Qualifiers
source                  1..116
                        mol_type = protein
                        organism = synthetic construct
SEQUENCE: 1
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGG RGIAYWGQGT LVTVSS      116

SEQ ID NO: 2            moltype = AA  length = 116
FEATURE                 Location/Qualifiers
source                  1..116
                        mol_type = protein
                        organism = synthetic construct
SEQUENCE: 2
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGS GGFAYWGQGT LVTVSS      116

SEQ ID NO: 3            moltype = AA  length = 116
FEATURE                 Location/Qualifiers
source                  1..116
                        mol_type = protein
                        organism = synthetic construct
SEQUENCE: 3
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGG RESAYWGQGT LVTVSS      116

SEQ ID NO: 4            moltype = AA  length = 116
FEATURE                 Location/Qualifiers
source                  1..116
                        mol_type = protein
                        organism = synthetic construct
SEQUENCE: 4
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGL PSFGYWGQGT LVTVSS      116

SEQ ID NO: 5            moltype = AA  length = 116
FEATURE                 Location/Qualifiers
source                  1..116
```

```
                              mol_type = protein
                              organism = synthetic construct
SEQUENCE: 5
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARGV RVFYHWGQGT LVTVSS       116

SEQ ID NO: 6              moltype = AA  length = 116
FEATURE                   Location/Qualifiers
source                    1..116
                          mol_type = protein
                          organism = synthetic construct
SEQUENCE: 6
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARGG WWFADWGQGT LVTVSS       116

SEQ ID NO: 7              moltype = AA  length = 116
FEATURE                   Location/Qualifiers
source                    1..116
                          mol_type = protein
                          organism = synthetic construct
SEQUENCE: 7
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARGI SKGAYWGQGT LVTVSS       116

SEQ ID NO: 8              moltype = AA  length = 116
FEATURE                   Location/Qualifiers
source                    1..116
                          mol_type = protein
                          organism = synthetic construct
SEQUENCE: 8
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARVE RGDAYWGQGT LVTVSS       116

SEQ ID NO: 9              moltype = AA  length = 116
FEATURE                   Location/Qualifiers
source                    1..116
                          mol_type = protein
                          organism = synthetic construct
SEQUENCE: 9
QVQLVQSGAE VKKPGASVKV SCKASGYTFT TYGINWVRQA TGQGLKWMGW INTYSGVPGY    60
AQKFQGRVTM TLNTSISTAY MELSSLRSED TAVYYCARGV HGVSYWGQGT LVTVSS       116

SEQ ID NO: 10             moltype = AA  length = 116
FEATURE                   Location/Qualifiers
source                    1..116
                          mol_type = protein
                          organism = synthetic construct
SEQUENCE: 10
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARGS KGDAYWGQGT LVTVSS       116

SEQ ID NO: 11             moltype = AA  length = 116
FEATURE                   Location/Qualifiers
source                    1..116
                          mol_type = protein
                          organism = synthetic construct
SEQUENCE: 11
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGG RGIAYWGQGT LVTVSS       116

SEQ ID NO: 12             moltype = AA  length = 116
FEATURE                   Location/Qualifiers
source                    1..116
                          mol_type = protein
                          organism = synthetic construct
SEQUENCE: 12
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGS GGFAYWGQGT LVTVSS       116

SEQ ID NO: 13             moltype = AA  length = 116
FEATURE                   Location/Qualifiers
source                    1..116
                          mol_type = protein
                          organism = synthetic construct
SEQUENCE: 13
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGG RESAYWGQGT LVTVSS       116

SEQ ID NO: 14             moltype = AA  length = 116
```

```
FEATURE                 Location/Qualifiers
source                  1..116
                        mol_type = protein
                        organism = synthetic construct
SEQUENCE: 14
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGL PSFGYWGQGT LVTVSS       116

SEQ ID NO: 15           moltype = AA   length = 116
FEATURE                 Location/Qualifiers
source                  1..116
                        mol_type = protein
                        organism = synthetic construct
SEQUENCE: 15
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGV RVFYHWGQGT LVTVSS       116

SEQ ID NO: 16           moltype = AA   length = 116
FEATURE                 Location/Qualifiers
source                  1..116
                        mol_type = protein
                        organism = synthetic construct
SEQUENCE: 16
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGG WWFADWGQGT LVTVSS       116

SEQ ID NO: 17           moltype = AA   length = 116
FEATURE                 Location/Qualifiers
source                  1..116
                        mol_type = protein
                        organism = synthetic construct
SEQUENCE: 17
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGI SKGAYWGQGT LVTVSS       116

SEQ ID NO: 18           moltype = AA   length = 116
FEATURE                 Location/Qualifiers
source                  1..116
                        mol_type = protein
                        organism = synthetic construct
SEQUENCE: 18
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARVE RGDAYWGQGT LVTVSS       116

SEQ ID NO: 19           moltype = AA   length = 116
FEATURE                 Location/Qualifiers
source                  1..116
                        mol_type = protein
                        organism = synthetic construct
SEQUENCE: 19
QVQLVQSGAE VKKPGASVKV SCKASGYTFT TYGINWVRQA TGQGLKWMGW INTYSGVPGY    60
AQKFQGRVTM TLDTSISTAY MELSSLRSED TAVYYCARGV HGVSYWGQGT LVTVSS       116

SEQ ID NO: 20           moltype = AA   length = 116
FEATURE                 Location/Qualifiers
source                  1..116
                        mol_type = protein
                        organism = synthetic construct
SEQUENCE: 20
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGS KGDAYWGQGT LVTVSS       116

SEQ ID NO: 21           moltype = AA   length = 8
FEATURE                 Location/Qualifiers
source                  1..8
                        mol_type = protein
                        organism = synthetic construct
SEQUENCE: 21
GYTFTTYG                                                              8

SEQ ID NO: 22           moltype = AA   length = 8
FEATURE                 Location/Qualifiers
source                  1..8
                        mol_type = protein
                        organism = synthetic construct
SEQUENCE: 22
GYTFTTYG                                                              8

SEQ ID NO: 23           moltype = AA   length = 8
```

```
FEATURE              Location/Qualifiers
source               1..8
                     mol_type = protein
                     organism = synthetic construct
SEQUENCE: 23
GYTFTTYG                                                                    8

SEQ ID NO: 24        moltype = AA  length = 8
FEATURE              Location/Qualifiers
source               1..8
                     mol_type = protein
                     organism = synthetic construct
SEQUENCE: 24
GYTFTTYG                                                                    8

SEQ ID NO: 25        moltype = AA  length = 8
FEATURE              Location/Qualifiers
source               1..8
                     mol_type = protein
                     organism = synthetic construct
SEQUENCE: 25
GYTFTTYG                                                                    8

SEQ ID NO: 26        moltype = AA  length = 8
FEATURE              Location/Qualifiers
source               1..8
                     mol_type = protein
                     organism = synthetic construct
SEQUENCE: 26
GYTFTTYG                                                                    8

SEQ ID NO: 27        moltype = AA  length = 8
FEATURE              Location/Qualifiers
source               1..8
                     mol_type = protein
                     organism = synthetic construct
SEQUENCE: 27
GYTFTTYG                                                                    8

SEQ ID NO: 28        moltype = AA  length = 8
FEATURE              Location/Qualifiers
source               1..8
                     mol_type = protein
                     organism = synthetic construct
SEQUENCE: 28
GYTFTTYG                                                                    8

SEQ ID NO: 29        moltype = AA  length = 8
FEATURE              Location/Qualifiers
source               1..8
                     mol_type = protein
                     organism = synthetic construct
SEQUENCE: 29
GYTFTTYG                                                                    8

SEQ ID NO: 30        moltype = AA  length = 8
FEATURE              Location/Qualifiers
source               1..8
                     mol_type = protein
                     organism = synthetic construct
SEQUENCE: 30
GYTFTTYG                                                                    8

SEQ ID NO: 31        moltype = AA  length = 8
FEATURE              Location/Qualifiers
source               1..8
                     mol_type = protein
                     organism = synthetic construct
SEQUENCE: 31
GYTFTTYG                                                                    8

SEQ ID NO: 32        moltype = AA  length = 8
FEATURE              Location/Qualifiers
source               1..8
                     mol_type = protein
                     organism = synthetic construct
SEQUENCE: 32
GYTFTTYG                                                                    8
```

```
SEQ ID NO: 33           moltype = AA   length = 8
FEATURE                 Location/Qualifiers
source                  1..8
                        mol_type = protein
                        organism = synthetic construct
SEQUENCE: 33
GYTFTTYG                                                                  8

SEQ ID NO: 34           moltype = AA   length = 8
FEATURE                 Location/Qualifiers
source                  1..8
                        mol_type = protein
                        organism = synthetic construct
SEQUENCE: 34
GYTFTTYG                                                                  8

SEQ ID NO: 35           moltype = AA   length = 8
FEATURE                 Location/Qualifiers
source                  1..8
                        mol_type = protein
                        organism = synthetic construct
SEQUENCE: 35
GYTFTTYG                                                                  8

SEQ ID NO: 36           moltype = AA   length = 8
FEATURE                 Location/Qualifiers
source                  1..8
                        mol_type = protein
                        organism = synthetic construct
SEQUENCE: 36
GYTFTTYG                                                                  8

SEQ ID NO: 37           moltype = AA   length = 8
FEATURE                 Location/Qualifiers
source                  1..8
                        mol_type = protein
                        organism = synthetic construct
SEQUENCE: 37
GYTFTTYG                                                                  8

SEQ ID NO: 38           moltype = AA   length = 8
FEATURE                 Location/Qualifiers
source                  1..8
                        mol_type = protein
                        organism = synthetic construct
SEQUENCE: 38
GYTFTTYG                                                                  8

SEQ ID NO: 39           moltype = AA   length = 8
FEATURE                 Location/Qualifiers
source                  1..8
                        mol_type = protein
                        organism = synthetic construct
SEQUENCE: 39
GYTFTTYG                                                                  8

SEQ ID NO: 40           moltype = AA   length = 8
FEATURE                 Location/Qualifiers
source                  1..8
                        mol_type = protein
                        organism = synthetic construct
SEQUENCE: 40
GYTFTTYG                                                                  8

SEQ ID NO: 41           moltype = AA   length = 8
FEATURE                 Location/Qualifiers
source                  1..8
                        mol_type = protein
                        organism = synthetic construct
SEQUENCE: 41
GYTFTTYG                                                                  8

SEQ ID NO: 42           moltype = AA   length = 8
FEATURE                 Location/Qualifiers
source                  1..8
                        mol_type = protein
                        organism = synthetic construct
SEQUENCE: 42
INTYSGVP                                                                  8
```

| SEQ ID NO: 43 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 43 | | |
| INTYSGVP | | 8 |

| SEQ ID NO: 44 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 44 | | |
| INTYSGVP | | 8 |

| SEQ ID NO: 45 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 45 | | |
| INTYSGVP | | 8 |

| SEQ ID NO: 46 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 46 | | |
| INTYSGVP | | 8 |

| SEQ ID NO: 47 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 47 | | |
| INTYSGVP | | 8 |

| SEQ ID NO: 48 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 48 | | |
| INTYSGVP | | 8 |

| SEQ ID NO: 49 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 49 | | |
| INTYSGVP | | 8 |

| SEQ ID NO: 50 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 50 | | |
| INTYSGVP | | 8 |

| SEQ ID NO: 51 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 51 | | |
| INTYSGVP | | 8 |

| SEQ ID NO: 52 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 52 | | |

-continued

| | | |
|---|---|---|
| INTYSGVP | | 8 |
| SEQ ID NO: 53<br>FEATURE<br>source | moltype = AA   length = 8<br>Location/Qualifiers<br>1..8<br>mol_type = protein<br>organism = synthetic construct | |
| SEQUENCE: 53<br>INTYSGVP | | 8 |
| SEQ ID NO: 54<br>FEATURE<br>source | moltype = AA   length = 8<br>Location/Qualifiers<br>1..8<br>mol_type = protein<br>organism = synthetic construct | |
| SEQUENCE: 54<br>INTYSGVP | | 8 |
| SEQ ID NO: 55<br>FEATURE<br>source | moltype = AA   length = 8<br>Location/Qualifiers<br>1..8<br>mol_type = protein<br>organism = synthetic construct | |
| SEQUENCE: 55<br>INTYSGVP | | 8 |
| SEQ ID NO: 56<br>FEATURE<br>source | moltype = AA   length = 8<br>Location/Qualifiers<br>1..8<br>mol_type = protein<br>organism = synthetic construct | |
| SEQUENCE: 56<br>INTYSGVP | | 8 |
| SEQ ID NO: 57<br>FEATURE<br>source | moltype = AA   length = 8<br>Location/Qualifiers<br>1..8<br>mol_type = protein<br>organism = synthetic construct | |
| SEQUENCE: 57<br>INTYSGVP | | 8 |
| SEQ ID NO: 58<br>FEATURE<br>source | moltype = AA   length = 8<br>Location/Qualifiers<br>1..8<br>mol_type = protein<br>organism = synthetic construct | |
| SEQUENCE: 58<br>INTYSGVP | | 8 |
| SEQ ID NO: 59<br>FEATURE<br>source | moltype = AA   length = 8<br>Location/Qualifiers<br>1..8<br>mol_type = protein<br>organism = synthetic construct | |
| SEQUENCE: 59<br>INTYSGVP | | 8 |
| SEQ ID NO: 60<br>FEATURE<br>source | moltype = AA   length = 8<br>Location/Qualifiers<br>1..8<br>mol_type = protein<br>organism = synthetic construct | |
| SEQUENCE: 60<br>INTYSGVP | | 8 |
| SEQ ID NO: 61<br>FEATURE<br>source | moltype = AA   length = 8<br>Location/Qualifiers<br>1..8<br>mol_type = protein<br>organism = synthetic construct | |
| SEQUENCE: 61<br>INTYSGVP | | 8 |
| SEQ ID NO: 62<br>FEATURE<br>source | moltype = AA   length = 8<br>Location/Qualifiers<br>1..8<br>mol_type = protein<br>organism = synthetic construct | |

-continued

```
SEQUENCE: 62
INTYSGVP                                                                        8

SEQ ID NO: 63          moltype = AA  length = 9
FEATURE                Location/Qualifiers
source                 1..9
                       mol_type = protein
                       organism = synthetic construct
SEQUENCE: 63
ARGGRGIAY                                                                       9

SEQ ID NO: 64          moltype = AA  length = 9
FEATURE                Location/Qualifiers
source                 1..9
                       mol_type = protein
                       organism = synthetic construct
SEQUENCE: 64
ARGSGGFAY                                                                       9

SEQ ID NO: 65          moltype = AA  length = 9
FEATURE                Location/Qualifiers
source                 1..9
                       mol_type = protein
                       organism = synthetic construct
SEQUENCE: 65
ARGGRESAY                                                                       9

SEQ ID NO: 66          moltype = AA  length = 9
FEATURE                Location/Qualifiers
source                 1..9
                       mol_type = protein
                       organism = synthetic construct
SEQUENCE: 66
ARGLPSFGY                                                                       9

SEQ ID NO: 67          moltype = AA  length = 9
FEATURE                Location/Qualifiers
source                 1..9
                       mol_type = protein
                       organism = synthetic construct
SEQUENCE: 67
ARGVRVFYH                                                                       9

SEQ ID NO: 68          moltype = AA  length = 9
FEATURE                Location/Qualifiers
source                 1..9
                       mol_type = protein
                       organism = synthetic construct
SEQUENCE: 68
ARGGWWFAD                                                                       9

SEQ ID NO: 69          moltype = AA  length = 9
FEATURE                Location/Qualifiers
source                 1..9
                       mol_type = protein
                       organism = synthetic construct
SEQUENCE: 69
ARGISKGAY                                                                       9

SEQ ID NO: 70          moltype = AA  length = 9
FEATURE                Location/Qualifiers
source                 1..9
                       mol_type = protein
                       organism = synthetic construct
SEQUENCE: 70
ARVERGDAY                                                                       9

SEQ ID NO: 71          moltype = AA  length = 9
FEATURE                Location/Qualifiers
source                 1..9
                       mol_type = protein
                       organism = synthetic construct
SEQUENCE: 71
ARGVHGVSY                                                                       9

SEQ ID NO: 72          moltype = AA  length = 9
FEATURE                Location/Qualifiers
source                 1..9
                       mol_type = protein
```

```
                                        -continued organism = synthetic construct
SEQUENCE: 72
ARGSKGDAY                                                                       9

SEQ ID NO: 73               moltype = AA   length = 9
FEATURE                     Location/Qualifiers
source                      1..9
                            mol_type = protein
                            organism = synthetic construct
SEQUENCE: 73
ARGGRGIAY                                                                       9

SEQ ID NO: 74               moltype = AA   length = 9
FEATURE                     Location/Qualifiers
source                      1..9
                            mol_type = protein
                            organism = synthetic construct
SEQUENCE: 74
ARGSGGFAY                                                                       9

SEQ ID NO: 75               moltype = AA   length = 9
FEATURE                     Location/Qualifiers
source                      1..9
                            mol_type = protein
                            organism = synthetic construct
SEQUENCE: 75
ARGGRESAY                                                                       9

SEQ ID NO: 76               moltype = AA   length = 9
FEATURE                     Location/Qualifiers
source                      1..9
                            mol_type = protein
                            organism = synthetic construct
SEQUENCE: 76
ARGLPSFGY                                                                       9

SEQ ID NO: 77               moltype = AA   length = 9
FEATURE                     Location/Qualifiers
source                      1..9
                            mol_type = protein
                            organism = synthetic construct
SEQUENCE: 77
ARGVRVFYH                                                                       9

SEQ ID NO: 78               moltype = AA   length = 9
FEATURE                     Location/Qualifiers
source                      1..9
                            mol_type = protein
                            organism = synthetic construct
SEQUENCE: 78
ARGGWWFAD                                                                       9

SEQ ID NO: 79               moltype = AA   length = 9
FEATURE                     Location/Qualifiers
source                      1..9
                            mol_type = protein
                            organism = synthetic construct
SEQUENCE: 79
ARGISKGAY                                                                       9

SEQ ID NO: 80               moltype = AA   length = 9
FEATURE                     Location/Qualifiers
source                      1..9
                            mol_type = protein
                            organism = synthetic construct
SEQUENCE: 80
ARVERGDAY                                                                       9

SEQ ID NO: 81               moltype = AA   length = 9
FEATURE                     Location/Qualifiers
source                      1..9
                            mol_type = protein
                            organism = synthetic construct
SEQUENCE: 81
ARGVHGVSY                                                                       9

SEQ ID NO: 82               moltype = AA   length = 9
FEATURE                     Location/Qualifiers
source                      1..9
```

```
                            mol_type = protein
                            organism = synthetic construct
SEQUENCE: 82
ARGSKGDAY                                                                 9

SEQ ID NO: 83           moltype = AA   length = 107
FEATURE                 Location/Qualifiers
source                  1..107
                        mol_type = protein
                        organism = synthetic construct
SEQUENCE: 83
DIQLTQSPSS LSASVGDRVT ITCRASQGIS NSLAWFQQKP GKVPKRLIYA ASNLQSGVPS         60
RFSGSGSGTE FTLTISSLQP EDFATYYCQQ SYSTPYTFGQ GTKLEIK                      107

SEQ ID NO: 84           moltype = AA   length = 113
FEATURE                 Location/Qualifiers
source                  1..113
                        mol_type = protein
                        organism = synthetic construct
SEQUENCE: 84
DIVMTQSPLS LPVTLGQPAS ISCRSSQSLV YSDGNTYLNW FQQRPGQSPR RLIYKVSNRD         60
SGVPDRFSGS GSGTDFTLKI SRVEAEDVGV YYCMQGTHWP PFTFGPGTKV EIK                113

SEQ ID NO: 85           moltype = AA   length = 107
FEATURE                 Location/Qualifiers
source                  1..107
                        mol_type = protein
                        organism = synthetic construct
SEQUENCE: 85
EIVMTQSPAT LSVSPGERAT LSCRASQSIG TSLHWYQQKP GGAPRLLIKY ASESITGIPA         60
RFSGSGSGTE FTLTISSLQS EDFAVYYCQQ SNSWPYTFGQ GTKLEIK                      107

SEQ ID NO: 86           moltype = AA   length = 107
FEATURE                 Location/Qualifiers
source                  1..107
                        mol_type = protein
                        organism = synthetic construct
SEQUENCE: 86
AIQMTQSPSS LSASVGDRVT ITCRASQSIS SYLNWYQQKP GKAPKLLIYA ASSLQSGVPS         60
RFSGSGSGTD FTLTISSLQP EDFATYYCQQ SYSTPYTFGQ GTKLEIK                      107

SEQ ID NO: 87           moltype = AA   length = 107
FEATURE                 Location/Qualifiers
source                  1..107
                        mol_type = protein
                        organism = synthetic construct
SEQUENCE: 87
EIVMTQSPAT LSVSPGERAT LSCRASQSIG TSLHWYQQKP GGAPRLLIKY ASESITGIPA         60
RFSGSGSGTE FTLTISSLQS EDFAVYYCQQ SNSWPYTFGQ GTKLEIK                      107

SEQ ID NO: 88           moltype = AA   length = 107
FEATURE                 Location/Qualifiers
source                  1..107
                        mol_type = protein
                        organism = synthetic construct
SEQUENCE: 88
AIRMTQSPSS LSASVGDRVT ITCRASQSIS SYLNWYQQKP GKAPKLLIYA ASSLQSGVPS         60
RFSGSGSGTD FTLTISSLQP EDFATYYCQQ SYSTPRTFGQ GTKVEIK                      107

SEQ ID NO: 89           moltype = AA   length = 107
FEATURE                 Location/Qualifiers
source                  1..107
                        mol_type = protein
                        organism = synthetic construct
SEQUENCE: 89
NIQMTQSPSS LSASVGDRVT ITCRASQSIS SYLNWYQQKP GKAPKLLIYA ASSLQSGVPS         60
RFSGSGSGTD FTLTISSLQP EDFATYYCQQ SSSTPYTFGQ GTKLEIK                      107

SEQ ID NO: 90           moltype = AA   length = 107
FEATURE                 Location/Qualifiers
source                  1..107
                        mol_type = protein
                        organism = synthetic construct
SEQUENCE: 90
EIVLTQSPSS LSASVGDRVT ITCRASQDIR RDFGWYQQKP GLAPELLIYD ASRLRSGVPS         60
RFSGSGSGTL FTFTITNLQP EDFATYYCLQ DYDFPRTFGQ GTKVDIK                      107

SEQ ID NO: 91           moltype = AA   length = 107
FEATURE                 Location/Qualifiers
```

```
source                  1..107
                        mol_type = protein
                        organism = synthetic construct
SEQUENCE: 91
EIVMTQSPAT LSVSPGERAT LSCRASQSIG TSLHWYQQKP GGAPRLLIKY ASESITGIPA    60
RFSGSGSGTE FTLTISSLQS EDFAVYYCQQ SNSWPYTFGQ GTKLEIK                 107

SEQ ID NO: 92           moltype = AA   length = 107
FEATURE                 Location/Qualifiers
source                  1..107
                        mol_type = protein
                        organism = synthetic construct
SEQUENCE: 92
DIVMTQSPSS LSASVGDRVT ITCRASQSIS TWLAWFQQKP GKAPKLLIYK ASSLKSGVPS    60
RFSGSGSGTE FTLTISSLQP DDFATYYCQQ SYSTPWTFGQ GTKLEIK                 107

SEQ ID NO: 93           moltype = AA   length = 107
FEATURE                 Location/Qualifiers
source                  1..107
                        mol_type = protein
                        organism = synthetic construct
SEQUENCE: 93
DIQLTQSPSS LSASVGDRVT ITCRASQGIS NSLAWFQQKP GKVPKRLIYA ASNLQSGVPS    60
RFSGSGSGTE FTLTISSLQP EDFATYYCQQ SYSTPYTFGQ GTKLEIK                 107

SEQ ID NO: 94           moltype = AA   length = 113
FEATURE                 Location/Qualifiers
source                  1..113
                        mol_type = protein
                        organism = synthetic construct
SEQUENCE: 94
DIVMTQSPLS LPVTLGQPAS ISCRSSQSLV YSDGNTYLNW FQQRPGQSPR RLIYKVSNRD    60
SGVPDRFSGS GSGTDFTLKI SRVEAEDVGV YYCMQGTHWP PFTFGPGTKV EIK          113

SEQ ID NO: 95           moltype = AA   length = 107
FEATURE                 Location/Qualifiers
source                  1..107
                        mol_type = protein
                        organism = synthetic construct
SEQUENCE: 95
EIVMTQSPAT LSVSPGERAT LSCRASQSIG TSLHWYQQKP GGAPRLLIKY ASESITGIPA    60
RFSGSGSGTE FTLTISSLQS EDFAVYYCQQ SNSWPYTFGQ GTKLEIK                 107

SEQ ID NO: 96           moltype = AA   length = 107
FEATURE                 Location/Qualifiers
source                  1..107
                        mol_type = protein
                        organism = synthetic construct
SEQUENCE: 96
AIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPYTFGQ GTKLEIK                 107

SEQ ID NO: 97           moltype = AA   length = 107
FEATURE                 Location/Qualifiers
source                  1..107
                        mol_type = protein
                        organism = synthetic construct
SEQUENCE: 97
EIVMTQSPAT LSVSPGERAT LSCRASQSIG TSLHWYQQKP GGAPRLLIKY ASESITGIPA    60
RFSGSGSGTE FTLTISSLQS EDFAVYYCQQ SNSWPYTFGQ GTKLEIK                 107

SEQ ID NO: 98           moltype = AA   length = 107
FEATURE                 Location/Qualifiers
source                  1..107
                        mol_type = protein
                        organism = synthetic construct
SEQUENCE: 98
AIRMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPRTFGQ GTKVEIK                 107

SEQ ID NO: 99           moltype = AA   length = 107
FEATURE                 Location/Qualifiers
source                  1..107
                        mol_type = protein
                        organism = synthetic construct
SEQUENCE: 99
NIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SSSTPYTFGQ GTKLEIK                 107
```

```
SEQ ID NO: 100          moltype = AA   length = 107
FEATURE                 Location/Qualifiers
source                  1..107
                        mol_type = protein
                        organism = synthetic construct
SEQUENCE: 100
EIVLTQSPSS LSASVGDRVT ITCRASQDIR RDFGWYQQKP GLAPELLIYD ASRLRSGVPS    60
RFSGSGSGTL FTFTITNLQP EDFATYYCLQ DYDFPRTFGQ GTKVDIK                 107

SEQ ID NO: 101          moltype = AA   length = 107
FEATURE                 Location/Qualifiers
source                  1..107
                        mol_type = protein
                        organism = synthetic construct
SEQUENCE: 101
EIVMTQSPAT LSVSPGERAT LSCRASQSIG TSLHWYQQKP GGAPRLLIKY ASESITGIPA    60
RFSGSGSGTE FTLTISSLQS EDFAVYYCQQ SNSWPYTFGQ GTKLEIK                 107

SEQ ID NO: 102          moltype = AA   length = 107
FEATURE                 Location/Qualifiers
source                  1..107
                        mol_type = protein
                        organism = synthetic construct
SEQUENCE: 102
DIVMTQSPSS LSASVGDRVT ITCRASQSIS TWLAWFQQKP GKAPKLLIYK ASSLKSGVPS    60
RFSGSGSGTE FTLTISSLQP DDFATYYCQQ SYSTPWTFGQ GTKLEIK                 107

SEQ ID NO: 103          moltype = AA   length = 6
FEATURE                 Location/Qualifiers
source                  1..6
                        mol_type = protein
                        organism = synthetic construct
SEQUENCE: 103
QGISNS                                                                6

SEQ ID NO: 104          moltype = AA   length = 11
FEATURE                 Location/Qualifiers
source                  1..11
                        mol_type = protein
                        organism = synthetic construct
SEQUENCE: 104
QSLVYSDGNT Y                                                         11

SEQ ID NO: 105          moltype = AA   length = 6
FEATURE                 Location/Qualifiers
source                  1..6
                        mol_type = protein
                        organism = synthetic construct
SEQUENCE: 105
QSIGTS                                                                6

SEQ ID NO: 106          moltype = AA   length = 6
FEATURE                 Location/Qualifiers
source                  1..6
                        mol_type = protein
                        organism = synthetic construct
SEQUENCE: 106
QSISSY                                                                6

SEQ ID NO: 107          moltype = AA   length = 6
FEATURE                 Location/Qualifiers
source                  1..6
                        mol_type = protein
                        organism = synthetic construct
SEQUENCE: 107
QSIGTS                                                                6

SEQ ID NO: 108          moltype = AA   length = 6
FEATURE                 Location/Qualifiers
source                  1..6
                        mol_type = protein
                        organism = synthetic construct
SEQUENCE: 108
QSISSY                                                                6

SEQ ID NO: 109          moltype = AA   length = 6
FEATURE                 Location/Qualifiers
source                  1..6
                        mol_type = protein
```

```
                       organism = synthetic construct
SEQUENCE: 109
QSISSY                                                                      6

SEQ ID NO: 110         moltype = AA   length = 6
FEATURE                Location/Qualifiers
source                 1..6
                       mol_type = protein
                       organism = synthetic construct
SEQUENCE: 110
QDIRRD                                                                      6

SEQ ID NO: 111         moltype = AA   length = 6
FEATURE                Location/Qualifiers
source                 1..6
                       mol_type = protein
                       organism = synthetic construct
SEQUENCE: 111
QSIGTS                                                                      6

SEQ ID NO: 112         moltype = AA   length = 6
FEATURE                Location/Qualifiers
source                 1..6
                       mol_type = protein
                       organism = synthetic construct
SEQUENCE: 112
QSISTW                                                                      6

SEQ ID NO: 113         moltype = AA   length = 6
FEATURE                Location/Qualifiers
source                 1..6
                       mol_type = protein
                       organism = synthetic construct
SEQUENCE: 113
QGISNS                                                                      6

SEQ ID NO: 114         moltype = AA   length = 11
FEATURE                Location/Qualifiers
source                 1..11
                       mol_type = protein
                       organism = synthetic construct
SEQUENCE: 114
QSLVYSDGNT Y                                                               11

SEQ ID NO: 115         moltype = AA   length = 6
FEATURE                Location/Qualifiers
source                 1..6
                       mol_type = protein
                       organism = synthetic construct
SEQUENCE: 115
QSIGTS                                                                      6

SEQ ID NO: 116         moltype = AA   length = 6
FEATURE                Location/Qualifiers
source                 1..6
                       mol_type = protein
                       organism = synthetic construct
SEQUENCE: 116
QSISSY                                                                      6

SEQ ID NO: 117         moltype = AA   length = 6
FEATURE                Location/Qualifiers
source                 1..6
                       mol_type = protein
                       organism = synthetic construct
SEQUENCE: 117
QSIGTS                                                                      6

SEQ ID NO: 118         moltype = AA   length = 6
FEATURE                Location/Qualifiers
source                 1..6
                       mol_type = protein
                       organism = synthetic construct
SEQUENCE: 118
QSISSY                                                                      6

SEQ ID NO: 119         moltype = AA   length = 6
FEATURE                Location/Qualifiers
source                 1..6
```

```
                            mol_type = protein
                            organism = synthetic construct
SEQUENCE: 119
QSISSY                                                                        6

SEQ ID NO: 120              moltype = AA  length = 6
FEATURE                     Location/Qualifiers
source                      1..6
                            mol_type = protein
                            organism = synthetic construct
SEQUENCE: 120
QDIRRD                                                                        6

SEQ ID NO: 121              moltype = AA  length = 6
FEATURE                     Location/Qualifiers
source                      1..6
                            mol_type = protein
                            organism = synthetic construct
SEQUENCE: 121
QSIGTS                                                                        6

SEQ ID NO: 122              moltype = AA  length = 6
FEATURE                     Location/Qualifiers
source                      1..6
                            mol_type = protein
                            organism = synthetic construct
SEQUENCE: 122
QSISTW                                                                        6

SEQ ID NO: 123              moltype = AA  length = 9
FEATURE                     Location/Qualifiers
source                      1..9
                            mol_type = protein
                            organism = synthetic construct
SEQUENCE: 123
QQSYSTPYT                                                                     9

SEQ ID NO: 124              moltype = AA  length = 10
FEATURE                     Location/Qualifiers
source                      1..10
                            mol_type = protein
                            organism = synthetic construct
SEQUENCE: 124
MQGTHWPPFT                                                                   10

SEQ ID NO: 125              moltype = AA  length = 9
FEATURE                     Location/Qualifiers
source                      1..9
                            mol_type = protein
                            organism = synthetic construct
SEQUENCE: 125
QQSNSWPYT                                                                     9

SEQ ID NO: 126              moltype = AA  length = 9
FEATURE                     Location/Qualifiers
source                      1..9
                            mol_type = protein
                            organism = synthetic construct
SEQUENCE: 126
QQSYSTPYT                                                                     9

SEQ ID NO: 127              moltype = AA  length = 9
FEATURE                     Location/Qualifiers
source                      1..9
                            mol_type = protein
                            organism = synthetic construct
SEQUENCE: 127
QQSNSWPYT                                                                     9

SEQ ID NO: 128              moltype = AA  length = 9
FEATURE                     Location/Qualifiers
source                      1..9
                            mol_type = protein
                            organism = synthetic construct
SEQUENCE: 128
QQSYSTPRT                                                                     9

SEQ ID NO: 129              moltype = AA  length = 9
FEATURE                     Location/Qualifiers
```

```
source                      1..9
                            mol_type = protein
                            organism = synthetic construct
SEQUENCE: 129
QQSSSTPYT                                                                      9

SEQ ID NO: 130              moltype = AA   length = 9
FEATURE                     Location/Qualifiers
source                      1..9
                            mol_type = protein
                            organism = synthetic construct
SEQUENCE: 130
LQDYDFPRT                                                                      9

SEQ ID NO: 131              moltype = AA   length = 9
FEATURE                     Location/Qualifiers
source                      1..9
                            mol_type = protein
                            organism = synthetic construct
SEQUENCE: 131
QQSNSWPYT                                                                      9

SEQ ID NO: 132              moltype = AA   length = 9
FEATURE                     Location/Qualifiers
source                      1..9
                            mol_type = protein
                            organism = synthetic construct
SEQUENCE: 132
QQSYSTPWT                                                                      9

SEQ ID NO: 133              moltype = AA   length = 9
FEATURE                     Location/Qualifiers
source                      1..9
                            mol_type = protein
                            organism = synthetic construct
SEQUENCE: 133
QQSYSTPYT                                                                      9

SEQ ID NO: 134              moltype = AA   length = 10
FEATURE                     Location/Qualifiers
source                      1..10
                            mol_type = protein
                            organism = synthetic construct
SEQUENCE: 134
MQGTHWPPFT                                                                    10

SEQ ID NO: 135              moltype = AA   length = 9
FEATURE                     Location/Qualifiers
source                      1..9
                            mol_type = protein
                            organism = synthetic construct
SEQUENCE: 135
QQSNSWPYT                                                                      9

SEQ ID NO: 136              moltype = AA   length = 9
FEATURE                     Location/Qualifiers
source                      1..9
                            mol_type = protein
                            organism = synthetic construct
SEQUENCE: 136
QQSYSTPYT                                                                      9

SEQ ID NO: 137              moltype = AA   length = 9
FEATURE                     Location/Qualifiers
source                      1..9
                            mol_type = protein
                            organism = synthetic construct
SEQUENCE: 137
QQSNSWPYT                                                                      9

SEQ ID NO: 138              moltype = AA   length = 9
FEATURE                     Location/Qualifiers
source                      1..9
                            mol_type = protein
                            organism = synthetic construct
SEQUENCE: 138
QQSYSTPRT                                                                      9

SEQ ID NO: 139              moltype = AA   length = 9
```

```
FEATURE                 Location/Qualifiers
source                  1..9
                        mol_type = protein
                        organism = synthetic construct
SEQUENCE: 139
QQSSSTPYT                                                                       9

SEQ ID NO: 140          moltype = AA  length = 9
FEATURE                 Location/Qualifiers
source                  1..9
                        mol_type = protein
                        organism = synthetic construct
SEQUENCE: 140
LQDYDFPRT                                                                       9

SEQ ID NO: 141          moltype = AA  length = 9
FEATURE                 Location/Qualifiers
source                  1..9
                        mol_type = protein
                        organism = synthetic construct
SEQUENCE: 141
QQSNSWPYT                                                                       9

SEQ ID NO: 142          moltype = AA  length = 9
FEATURE                 Location/Qualifiers
source                  1..9
                        mol_type = protein
                        organism = synthetic construct
SEQUENCE: 142
QQSYSTPWT                                                                       9

SEQ ID NO: 143          moltype = AA  length = 119
FEATURE                 Location/Qualifiers
source                  1..119
                        mol_type = protein
                        organism = synthetic construct
SEQUENCE: 143
QVQLVQSGAE VKKPGASVKV SCKASGYTFN SYWMHWVRQA PGQGLEWMGR IHPRGIHTNY               60
NQKFKGRVTL TVDTSTSTAY MELSSLRSED TAVYYCAPSS SYAWAFAHWG QGTLVTVSS               119

SEQ ID NO: 144          moltype = AA  length = 119
FEATURE                 Location/Qualifiers
source                  1..119
                        mol_type = protein
                        organism = synthetic construct
SEQUENCE: 144
QVQLVQSGAE VKKPGASVKV SCKASGQTFT SYRMHWVRQA PGQGLEWMGR ILPIRSDTNY               60
NQKFKGRVTL TVDTSTSTAY MELSSLRSED TAVYYCARDA GYGSLFAAWG QGTLVTVSS               119

SEQ ID NO: 145          moltype = AA  length = 119
FEATURE                 Location/Qualifiers
source                  1..119
                        mol_type = protein
                        organism = synthetic construct
SEQUENCE: 145
QVQLVQSGAE VKKPGASVKV SCKASGYTFT SYWMHWVRQA PGQGLEWMGR IHPSDSDTNY               60
NQKFKGRVTL TVDTSTSTAY MELSSLRSED TAVYYCAPKG NYVVRFAYWG QGTLVTVSS               119

SEQ ID NO: 146          moltype = AA  length = 119
FEATURE                 Location/Qualifiers
source                  1..119
                        mol_type = protein
                        organism = synthetic construct
SEQUENCE: 146
QVQLVQSGAE VKKPGASVKV SCKASGYTFT RYWMHWVRQA PGQGLEWMGR IHPTDSVTNY               60
NQKFKGRVTL TVDTSTSTAY MELSSLRSED TAVYYCAPDV NYARAFAHWG QGTLVTVSS               119

SEQ ID NO: 147          moltype = AA  length = 119
FEATURE                 Location/Qualifiers
source                  1..119
                        mol_type = protein
                        organism = synthetic construct
SEQUENCE: 147
QVQLVQSGAE VKKPGASVKV SCKASGYTFG IYWMHWVRQA PGQGLEWMGR ILPSNGYTNY               60
NQKFKGRVTL TVDTSTSTAY MELSSLRSED TAVYYCAPYG IYTRDFSHWG QGTLVTVSS               119

SEQ ID NO: 148          moltype = AA  length = 119
FEATURE                 Location/Qualifiers
source                  1..119
```

```
                          mol_type = protein
                          organism = synthetic construct
SEQUENCE: 148
QVQLVQSGAE VKKPGASVKV SCKASGYTFT SYWMHWVRQA PGQGLEWMGR IHPSDSDTNY    60
NQKFKGRVTL TVDTSTSTAY MELSSLRSED TAVYYCAPYV DLESGFAYWG QGTLVTVSS    119

SEQ ID NO: 149            moltype = AA   length = 119
FEATURE                   Location/Qualifiers
source                    1..119
                          mol_type = protein
                          organism = synthetic construct
SEQUENCE: 149
QVQLVQSGAE VKKPGASVKV SCKASGYTFT SYWMHWVRQA PGMGLEWMGR IHPIYRDTNY    60
NQKFKGRVTL TVDTSTSTAY MELSSLRSED TAVYYCAPYV NYGDGFAYWG QGTLVTVSS    119

SEQ ID NO: 150            moltype = AA   length = 119
FEATURE                   Location/Qualifiers
source                    1..119
                          mol_type = protein
                          organism = synthetic construct
SEQUENCE: 150
QVQLVQSGAE VKKPGASVKV SCKASGYTFN SYLMHWVRQA PGMGLEWMGR IRPNYSDTNY    60
NQKFKGRVTL TVDTSTSTAY MELSSLRSED TAVYYCAPYG NNASGFSYWG QGTLVTVSS    119

SEQ ID NO: 151            moltype = AA   length = 119
FEATURE                   Location/Qualifiers
source                    1..119
                          mol_type = protein
                          organism = synthetic construct
SEQUENCE: 151
QVQLVQSGAE VKKPGASVKV SCKASGQTFT NYLMHWVRQA PGQGLEWMGR IPLSDRDTNY    60
NQKFKGRVTL TVDTSTSTAY MELSSLRSED TAVYYCAPYG RSASGFSSWG QGTLVTVSS    119

SEQ ID NO: 152            moltype = AA   length = 119
FEATURE                   Location/Qualifiers
source                    1..119
                          mol_type = protein
                          organism = synthetic construct
SEQUENCE: 152
QVQLVQSGAE VKKPGASVKV SCKASGYTFT SYWMHWVRQA PGQGLEWMGR IHPSDSDTNY    60
NQKFKGRVTL TVDTSTSTAY MELSSLRSED TAVYYCAPYF DHAGGFLHWG QGTLVTVSS    119

SEQ ID NO: 153            moltype = AA   length = 8
FEATURE                   Location/Qualifiers
source                    1..8
                          mol_type = protein
                          organism = synthetic construct
SEQUENCE: 153
GYTFNSYW                                                              8

SEQ ID NO: 154            moltype = AA   length = 8
FEATURE                   Location/Qualifiers
source                    1..8
                          mol_type = protein
                          organism = synthetic construct
SEQUENCE: 154
GQTFTSYR                                                              8

SEQ ID NO: 155            moltype = AA   length = 8
FEATURE                   Location/Qualifiers
source                    1..8
                          mol_type = protein
                          organism = synthetic construct
SEQUENCE: 155
GYTFTSYW                                                              8

SEQ ID NO: 156            moltype = AA   length = 8
FEATURE                   Location/Qualifiers
source                    1..8
                          mol_type = protein
                          organism = synthetic construct
SEQUENCE: 156
GYTFTSYW                                                              8

SEQ ID NO: 157            moltype = AA   length = 8
FEATURE                   Location/Qualifiers
source                    1..8
                          mol_type = protein
                          organism = synthetic construct
```

```
SEQUENCE: 157
GYTFGIYW                                                                        8

SEQ ID NO: 158           moltype = AA  length = 8
FEATURE                  Location/Qualifiers
source                   1..8
                         mol_type = protein
                         organism = synthetic construct
SEQUENCE: 158
GYTFTSYW                                                                        8

SEQ ID NO: 159           moltype = AA  length = 8
FEATURE                  Location/Qualifiers
source                   1..8
                         mol_type = protein
                         organism = synthetic construct
SEQUENCE: 159
GYTFTSYW                                                                        8

SEQ ID NO: 160           moltype = AA  length = 8
FEATURE                  Location/Qualifiers
source                   1..8
                         mol_type = protein
                         organism = synthetic construct
SEQUENCE: 160
GYTFNSYL                                                                        8

SEQ ID NO: 161           moltype = AA  length = 8
FEATURE                  Location/Qualifiers
source                   1..8
                         mol_type = protein
                         organism = synthetic construct
SEQUENCE: 161
GQTFTNYL                                                                        8

SEQ ID NO: 162           moltype = AA  length = 8
FEATURE                  Location/Qualifiers
source                   1..8
                         mol_type = protein
                         organism = synthetic construct
SEQUENCE: 162
GYTFTSYW                                                                        8

SEQ ID NO: 163           moltype = AA  length = 8
FEATURE                  Location/Qualifiers
source                   1..8
                         mol_type = protein
                         organism = synthetic construct
VARIANT                  2
                         note = Y or Q
VARIANT                  5
                         note = N, T or G
VARIANT                  6
                         note = S, I or N
VARIANT                  8
                         note = W or L
SEQUENCE: 163
GXTFXXYX                                                                        8

SEQ ID NO: 164           moltype = AA  length = 8
FEATURE                  Location/Qualifiers
source                   1..8
                         mol_type = protein
                         organism = synthetic construct
SEQUENCE: 164
IHPRGIHT                                                                        8

SEQ ID NO: 165           moltype = AA  length = 8
FEATURE                  Location/Qualifiers
source                   1..8
                         mol_type = protein
                         organism = synthetic construct
SEQUENCE: 165
ILPIRSDT                                                                        8

SEQ ID NO: 166           moltype = AA  length = 8
FEATURE                  Location/Qualifiers
source                   1..8
                         mol_type = protein
```

```
                                -continued

SEQUENCE: 166
IHPSDSDT                                                                     8

SEQ ID NO: 167          moltype = AA   length = 8
FEATURE                 Location/Qualifiers
source                  1..8
                        mol_type = protein
                        organism = synthetic construct
SEQUENCE: 167
IHPTDSVT                                                                     8

SEQ ID NO: 168          moltype = AA   length = 8
FEATURE                 Location/Qualifiers
source                  1..8
                        mol_type = protein
                        organism = synthetic construct
SEQUENCE: 168
ILPSNGYT                                                                     8

SEQ ID NO: 169          moltype = AA   length = 8
FEATURE                 Location/Qualifiers
source                  1..8
                        mol_type = protein
                        organism = synthetic construct
SEQUENCE: 169
IHPSDSDT                                                                     8

SEQ ID NO: 170          moltype = AA   length = 8
FEATURE                 Location/Qualifiers
source                  1..8
                        mol_type = protein
                        organism = synthetic construct
SEQUENCE: 170
IHPIYRDT                                                                     8

SEQ ID NO: 171          moltype = AA   length = 8
FEATURE                 Location/Qualifiers
source                  1..8
                        mol_type = protein
                        organism = synthetic construct
SEQUENCE: 171
IRPNYSDT                                                                     8

SEQ ID NO: 172          moltype = AA   length = 8
FEATURE                 Location/Qualifiers
source                  1..8
                        mol_type = protein
                        organism = synthetic construct
SEQUENCE: 172
IPLSDRDT                                                                     8

SEQ ID NO: 173          moltype = AA   length = 8
FEATURE                 Location/Qualifiers
source                  1..8
                        mol_type = protein
                        organism = synthetic construct
SEQUENCE: 173
IHPSDSDT                                                                     8

SEQ ID NO: 174          moltype = AA   length = 12
FEATURE                 Location/Qualifiers
source                  1..12
                        mol_type = protein
                        organism = synthetic construct
SEQUENCE: 174
APSSSYAWAF AH                                                               12

SEQ ID NO: 175          moltype = AA   length = 12
FEATURE                 Location/Qualifiers
source                  1..12
                        mol_type = protein
                        organism = synthetic construct
SEQUENCE: 175
ARDAGYGSLF AA                                                               12

SEQ ID NO: 176          moltype = AA   length = 12
FEATURE                 Location/Qualifiers
source                  1..12
```

```
                              mol_type = protein
                              organism = synthetic construct
SEQUENCE: 176
APKGNYVVRF AY                                                              12

SEQ ID NO: 177            moltype = AA   length = 12
FEATURE                   Location/Qualifiers
source                    1..12
                          mol_type = protein
                          organism = synthetic construct
SEQUENCE: 177
APDVNYARAF AH                                                              12

SEQ ID NO: 178            moltype = AA   length = 12
FEATURE                   Location/Qualifiers
source                    1..12
                          mol_type = protein
                          organism = synthetic construct
SEQUENCE: 178
APYGIYTRDF SH                                                              12

SEQ ID NO: 179            moltype = AA   length = 12
FEATURE                   Location/Qualifiers
source                    1..12
                          mol_type = protein
                          organism = synthetic construct
SEQUENCE: 179
APYVDLESGF AY                                                              12

SEQ ID NO: 180            moltype = AA   length = 12
FEATURE                   Location/Qualifiers
source                    1..12
                          mol_type = protein
                          organism = synthetic construct
SEQUENCE: 180
APYVNYGDGF AY                                                              12

SEQ ID NO: 181            moltype = AA   length = 12
FEATURE                   Location/Qualifiers
source                    1..12
                          mol_type = protein
                          organism = synthetic construct
SEQUENCE: 181
APYGNNASGF SY                                                              12

SEQ ID NO: 182            moltype = AA   length = 12
FEATURE                   Location/Qualifiers
source                    1..12
                          mol_type = protein
                          organism = synthetic construct
SEQUENCE: 182
APYGRSASGF SS                                                              12

SEQ ID NO: 183            moltype = AA   length = 12
FEATURE                   Location/Qualifiers
source                    1..12
                          mol_type = protein
                          organism = synthetic construct
SEQUENCE: 183
APYFDHAGGF LH                                                              12

SEQ ID NO: 184            moltype = AA   length = 107
FEATURE                   Location/Qualifiers
source                    1..107
                          mol_type = protein
                          organism = synthetic construct
SEQUENCE: 184
DIQMTQSPSS LSASVGDRVT ITCRASQDVS TALAWYQQKP GKAPKLLIYW ASTRHSGVPD           60
RFSGSGSGTD FTLTISSLQP EDFATYYCQQ HYRSPGTFGG GTKVEIK                       107

SEQ ID NO: 185            moltype = AA   length = 107
FEATURE                   Location/Qualifiers
source                    1..107
                          mol_type = protein
                          organism = synthetic construct
SEQUENCE: 185
DIQMTQSPSS LSASVGDRVT ITCRASQDVS TALAWYQQKP GKAPKLLIYW ASTRHSGVPD           60
RFSGSGSGTD FTLTISSLQP EDFATYYCQQ HDSSPGTFGG GTKVEIK                       107
```

```
SEQ ID NO: 186           moltype = AA   length = 107
FEATURE                  Location/Qualifiers
source                   1..107
                         mol_type = protein
                         organism = synthetic construct
SEQUENCE: 186
DIVMTQSPSS LSASVGDRVT ITCRASQGIR NDLGWYQQKP GKAPKLLIYA ASSLQSGVPS    60
RFSGSGSDTD FTLTISSLQP EDFATYYCLQ DYNYPWTFGQ GTKVDIK                 107

SEQ ID NO: 187           moltype = AA   length = 107
FEATURE                  Location/Qualifiers
source                   1..107
                         mol_type = protein
                         organism = synthetic construct
SEQUENCE: 187
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ HYGSPWTFGG GTKVEIK                 107

SEQ ID NO: 188           moltype = AA   length = 107
FEATURE                  Location/Qualifiers
source                   1..107
                         mol_type = protein
                         organism = synthetic construct
SEQUENCE: 188
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ RDTTPRTFGG GTKVEIK                 107

SEQ ID NO: 189           moltype = AA   length = 108
FEATURE                  Location/Qualifiers
source                   1..108
                         mol_type = protein
                         organism = synthetic construct
SEQUENCE: 189
DIAMTQTPSS LSASIGDRVT IACRASQGIS SALAWYQQKP GRTPKLLIFD ASTLQSGVPS    60
RFSGSGSGTD FTLTISSLQP EDFATYYCQQ FNTYSSVTFG QGTRLEIK                108

SEQ ID NO: 190           moltype = AA   length = 107
FEATURE                  Location/Qualifiers
source                   1..107
                         mol_type = protein
                         organism = synthetic construct
SEQUENCE: 190
DIQMTQSPST LSASVGDRVT ITCRASQDVS TALAWYQQKP GKAPKLLIYW ASTRHIGVPD    60
RFSGSGSGTD FTLTISSLQP EDFATYYCHQ DYITPRTFGG GTKVEIK                 107

SEQ ID NO: 191           moltype = AA   length = 107
FEATURE                  Location/Qualifiers
source                   1..107
                         mol_type = protein
                         organism = synthetic construct
SEQUENCE: 191
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ HYRSPWTFGG GTKVEIK                 107

SEQ ID NO: 192           moltype = AA   length = 107
FEATURE                  Location/Qualifiers
source                   1..107
                         mol_type = protein
                         organism = synthetic construct
SEQUENCE: 192
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ GSSTPLTFGG GTKVEIK                 107

SEQ ID NO: 193           moltype = AA   length = 106
FEATURE                  Location/Qualifiers
source                   1..106
                         mol_type = protein
                         organism = synthetic construct
SEQUENCE: 193
DIVMTQSPGT LSLSPGERAT LSCRASQSVS SSYLAWYQQK PGQAPRLLIY GASSRATGIP    60
DRFSGSGSGT DFTLTISRLE PEDFAVYYCQ QYGSWTFGQG TKLEIK                  106

SEQ ID NO: 194           moltype = AA   length = 6
FEATURE                  Location/Qualifiers
source                   1..6
                         mol_type = protein
                         organism = synthetic construct
SEQUENCE: 194
QDVSTA                                                                6
```

| | | |
|---|---|---|
| SEQ ID NO: 195<br>FEATURE<br>source | moltype = AA  length = 6<br>Location/Qualifiers<br>1..6<br>mol_type = protein<br>organism = synthetic construct | |
| SEQUENCE: 195<br>QDVSTA | | 6 |
| SEQ ID NO: 196<br>FEATURE<br>source | moltype = AA  length = 6<br>Location/Qualifiers<br>1..6<br>mol_type = protein<br>organism = synthetic construct | |
| SEQUENCE: 196<br>QGIRND | | 6 |
| SEQ ID NO: 197<br>FEATURE<br>source | moltype = AA  length = 6<br>Location/Qualifiers<br>1..6<br>mol_type = protein<br>organism = synthetic construct | |
| SEQUENCE: 197<br>QDVSTA | | 6 |
| SEQ ID NO: 198<br>FEATURE<br>source | moltype = AA  length = 6<br>Location/Qualifiers<br>1..6<br>mol_type = protein<br>organism = synthetic construct | |
| SEQUENCE: 198<br>QDVSTA | | 6 |
| SEQ ID NO: 199<br>FEATURE<br>source | moltype = AA  length = 6<br>Location/Qualifiers<br>1..6<br>mol_type = protein<br>organism = synthetic construct | |
| SEQUENCE: 199<br>QGISSA | | 6 |
| SEQ ID NO: 200<br>FEATURE<br>source | moltype = AA  length = 6<br>Location/Qualifiers<br>1..6<br>mol_type = protein<br>organism = synthetic construct | |
| SEQUENCE: 200<br>QDVSTA | | 6 |
| SEQ ID NO: 201<br>FEATURE<br>source | moltype = AA  length = 6<br>Location/Qualifiers<br>1..6<br>mol_type = protein<br>organism = synthetic construct | |
| SEQUENCE: 201<br>QDVSTA | | 6 |
| SEQ ID NO: 202<br>FEATURE<br>source | moltype = AA  length = 6<br>Location/Qualifiers<br>1..6<br>mol_type = protein<br>organism = synthetic construct | |
| SEQUENCE: 202<br>QDVSTA | | 6 |
| SEQ ID NO: 203<br>FEATURE<br>source | moltype = AA  length = 7<br>Location/Qualifiers<br>1..7<br>mol_type = protein<br>organism = synthetic construct | |
| SEQUENCE: 203<br>QSVSSSY | | 7 |
| SEQ ID NO: 204<br>FEATURE<br>source | moltype = AA  length = 9<br>Location/Qualifiers<br>1..9<br>mol_type = protein<br>organism = synthetic construct | |
| SEQUENCE: 204 | | |

QQHYRSPGT 9

SEQ ID NO: 205                  moltype = AA  length = 9
FEATURE                         Location/Qualifiers
source                          1..9
                                mol_type = protein
                                organism = synthetic construct

SEQUENCE: 205
QQHDSSPGT 9

SEQ ID NO: 206                  moltype = AA  length = 9
FEATURE                         Location/Qualifiers
source                          1..9
                                mol_type = protein
                                organism = synthetic construct

SEQUENCE: 206
LQDYNYPWT 9

SEQ ID NO: 207                  moltype = AA  length = 9
FEATURE                         Location/Qualifiers
source                          1..9
                                mol_type = protein
                                organism = synthetic construct

SEQUENCE: 207
QQHYGSPWT 9

SEQ ID NO: 208                  moltype = AA  length = 9
FEATURE                         Location/Qualifiers
source                          1..9
                                mol_type = protein
                                organism = synthetic construct

SEQUENCE: 208
QQRDTTPRT 9

SEQ ID NO: 209                  moltype = AA  length = 10
FEATURE                         Location/Qualifiers
source                          1..10
                                mol_type = protein
                                organism = synthetic construct

SEQUENCE: 209
QQFNTYSSVT 10

SEQ ID NO: 210                  moltype = AA  length = 9
FEATURE                         Location/Qualifiers
source                          1..9
                                mol_type = protein
                                organism = synthetic construct

SEQUENCE: 210
HQDYITPRT 9

SEQ ID NO: 211                  moltype = AA  length = 9
FEATURE                         Location/Qualifiers
source                          1..9
                                mol_type = protein
                                organism = synthetic construct

SEQUENCE: 211
QQHYRSPWT 9

SEQ ID NO: 212                  moltype = AA  length = 9
FEATURE                         Location/Qualifiers
source                          1..9
                                mol_type = protein
                                organism = synthetic construct

SEQUENCE: 212
QQGSSTPLT 9

SEQ ID NO: 213                  moltype = AA  length = 7
FEATURE                         Location/Qualifiers
source                          1..7
                                mol_type = protein
                                organism = synthetic construct

SEQUENCE: 213
QQYGSWT 7

SEQ ID NO: 214                  moltype = AA  length = 469
FEATURE                         Location/Qualifiers
source                          1..469
                                mol_type = protein
                                organism = synthetic construct

```
SEQUENCE: 214
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
ARGGRGIAYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPG              469

SEQ ID NO: 215           moltype = AA  length = 469
FEATURE                  Location/Qualifiers
source                   1..469
                         mol_type = protein
                         organism = synthetic construct
SEQUENCE: 215
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
ARGSGGFAYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPG              469

SEQ ID NO: 216           moltype = AA  length = 469
FEATURE                  Location/Qualifiers
source                   1..469
                         mol_type = protein
                         organism = synthetic construct
SEQUENCE: 216
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
ARGGRESAYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPG              469

SEQ ID NO: 217           moltype = AA  length = 469
FEATURE                  Location/Qualifiers
source                   1..469
                         mol_type = protein
                         organism = synthetic construct
SEQUENCE: 217
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
ARGLPSFGYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPG              469

SEQ ID NO: 218           moltype = AA  length = 469
FEATURE                  Location/Qualifiers
source                   1..469
                         mol_type = protein
                         organism = synthetic construct
SEQUENCE: 218
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
ARGVRVFYHW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPG              469

SEQ ID NO: 219           moltype = AA  length = 469
FEATURE                  Location/Qualifiers
source                   1..469
                         mol_type = protein
                         organism = synthetic construct
SEQUENCE: 219
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
ARGWWFADW GQGTLVTVSS ASTKGPSVFP LAPSSKSTSG GTAALGCLVK DYFPEPVTVS    180
```

```
WNSGALTSGV HTFPAVLQSS GLYSLSSVVT VPSSSLGTQT YICNVNHKPS NTKVDKKVEP    240
KSCDKTHTCP PCPAPELLGG PSVFLFPPKP KDTLMISRTP EVTCVVVDVS HEDPEVKFNW    300
YVDGVEVHNA KTKPREEQYN STYRVVSVLT VLHQDWLNGK EYKCKVSNKA LPAPIEKTIS    360
KAKGQPREPQ VYTLPPSREE MTKNQVSLTC LVKGFYPSDI AVEWESNGQP ENNYKTTPPV    420
LDSDGSFFLY SKLTVDKSRW QQGNVFSCSV MHEALHNHYT QKSLSLSPG                469

SEQ ID NO: 220         moltype = AA   length = 469
FEATURE                Location/Qualifiers
source                 1..469
                       mol_type = protein
                       organism = synthetic construct
SEQUENCE: 220
MDPKGSLSWR ILLFLSLAFE LSYGQVQLVQ SGAEVKKPGA SVKVSCKASG YTFTTYGINW     60
VRQATGQGLE WMGWINTYSG VPGYAQKFQG RVTMTLNTSI STAYMELSSL RSEDTAVYYC    120
ARGISKGAYW GQGTLVTVSS ASTKGPSVFP LAPSSKSTSG GTAALGCLVK DYFPEPVTVS    180
WNSGALTSGV HTFPAVLQSS GLYSLSSVVT VPSSSLGTQT YICNVNHKPS NTKVDKKVEP    240
KSCDKTHTCP PCPAPELLGG PSVFLFPPKP KDTLMISRTP EVTCVVVDVS HEDPEVKFNW    300
YVDGVEVHNA KTKPREEQYN STYRVVSVLT VLHQDWLNGK EYKCKVSNKA LPAPIEKTIS    360
KAKGQPREPQ VYTLPPSREE MTKNQVSLTC LVKGFYPSDI AVEWESNGQP ENNYKTTPPV    420
LDSDGSFFLY SKLTVDKSRW QQGNVFSCSV MHEALHNHYT QKSLSLSPG                469

SEQ ID NO: 221         moltype = AA   length = 469
FEATURE                Location/Qualifiers
source                 1..469
                       mol_type = protein
                       organism = synthetic construct
SEQUENCE: 221
MDPKGSLSWR ILLFLSLAFE LSYGQVQLVQ SGAEVKKPGA SVKVSCKASG YTFTTYGINW     60
VRQATGQGLE WMGWINTYSG VPGYAQKFQG RVTMTLNTSI STAYMELSSL RSEDTAVYYC    120
ARVERGDAYW GQGTLVTVSS ASTKGPSVFP LAPSSKSTSG GTAALGCLVK DYFPEPVTVS    180
WNSGALTSGV HTFPAVLQSS GLYSLSSVVT VPSSSLGTQT YICNVNHKPS NTKVDKKVEP    240
KSCDKTHTCP PCPAPELLGG PSVFLFPPKP KDTLMISRTP EVTCVVVDVS HEDPEVKFNW    300
YVDGVEVHNA KTKPREEQYN STYRVVSVLT VLHQDWLNGK EYKCKVSNKA LPAPIEKTIS    360
KAKGQPREPQ VYTLPPSREE MTKNQVSLTC LVKGFYPSDI AVEWESNGQP ENNYKTTPPV    420
LDSDGSFFLY SKLTVDKSRW QQGNVFSCSV MHEALHNHYT QKSLSLSPG                469

SEQ ID NO: 222         moltype = AA   length = 469
FEATURE                Location/Qualifiers
source                 1..469
                       mol_type = protein
                       organism = synthetic construct
SEQUENCE: 222
MDPKGSLSWR ILLFLSLAFE LSYGQVQLVQ SGAEVKKPGA SVKVSCKASG YTFTTYGINW     60
VRQATGQGLK WMGWINTYSG VPGYAQKFQG RVTMTLNTSI STAYMELSSL RSEDTAVYYC    120
ARGVHGVSYW GQGTLVTVSS ASTKGPSVFP LAPSSKSTSG GTAALGCLVK DYFPEPVTVS    180
WNSGALTSGV HTFPAVLQSS GLYSLSSVVT VPSSSLGTQT YICNVNHKPS NTKVDKKVEP    240
KSCDKTHTCP PCPAPELLGG PSVFLFPPKP KDTLMISRTP EVTCVVVDVS HEDPEVKFNW    300
YVDGVEVHNA KTKPREEQYN STYRVVSVLT VLHQDWLNGK EYKCKVSNKA LPAPIEKTIS    360
KAKGQPREPQ VYTLPPSREE MTKNQVSLTC LVKGFYPSDI AVEWESNGQP ENNYKTTPPV    420
LDSDGSFFLY SKLTVDKSRW QQGNVFSCSV MHEALHNHYT QKSLSLSPG                469

SEQ ID NO: 223         moltype = AA   length = 469
FEATURE                Location/Qualifiers
source                 1..469
                       mol_type = protein
                       organism = synthetic construct
SEQUENCE: 223
MDPKGSLSWR ILLFLSLAFE LSYGQVQLVQ SGAEVKKPGA SVKVSCKASG YTFTTYGINW     60
VRQATGQGLE WMGWINTYSG VPGYAQKFQG RVTMTLNTSI STAYMELSSL RSEDTAVYYC    120
ARGSKGDAYW GQGTLVTVSS ASTKGPSVFP LAPSSKSTSG GTAALGCLVK DYFPEPVTVS    180
WNSGALTSGV HTFPAVLQSS GLYSLSSVVT VPSSSLGTQT YICNVNHKPS NTKVDKKVEP    240
KSCDKTHTCP PCPAPELLGG PSVFLFPPKP KDTLMISRTP EVTCVVVDVS HEDPEVKFNW    300
YVDGVEVHNA KTKPREEQYN STYRVVSVLT VLHQDWLNGK EYKCKVSNKA LPAPIEKTIS    360
KAKGQPREPQ VYTLPPSREE MTKNQVSLTC LVKGFYPSDI AVEWESNGQP ENNYKTTPPV    420
LDSDGSFFLY SKLTVDKSRW QQGNVFSCSV MHEALHNHYT QKSLSLSPG                469

SEQ ID NO: 224         moltype = AA   length = 469
FEATURE                Location/Qualifiers
source                 1..469
                       mol_type = protein
                       organism = synthetic construct
SEQUENCE: 224
MDPKGSLSWR ILLFLSLAFE LSYGQVQLVQ SGAEVKKPGA SVKVSCKASG YTFTTYGINW     60
VRQATGQGLE WMGWINTYSG VPGYAQKFQG RVTMTLDTSI STAYMELSSL RSEDTAVYYC    120
ARGGRGIAYW GQGTLVTVSS ASTKGPSVFP LAPSSKSTSG GTAALGCLVK DYFPEPVTVS    180
WNSGALTSGV HTFPAVLQSS GLYSLSSVVT VPSSSLGTQT YICNVNHKPS NTKVDKKVEP    240
KSCDKTHTCP PCPAPELLGG PSVFLFPPKP KDTLMISRTP EVTCVVVDVS HEDPEVKFNW    300
YVDGVEVHNA KTKPREEQYN STYRVVSVLT VLHQDWLNGK EYKCKVSNKA LPAPIEKTIS    360
KAKGQPREPQ VYTLPPSREE MTKNQVSLTC LVKGFYPSDI AVEWESNGQP ENNYKTTPPV    420
```

```
LDSDGSFFLY SKLTVDKSRW QQGNVFSCSV MHEALHNHYT QKSLSLSPG          469

SEQ ID NO: 225          moltype = AA  length = 469
FEATURE                 Location/Qualifiers
source                  1..469
                        mol_type = protein
                        organism = synthetic construct
SEQUENCE: 225
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLDTSI STAYMELSSL RSEDTAVYYC 120
ARGSGGFAYW GQGTLVTVSS ASTKGPSVFP LAPSSKSTSG GTAALGCLVK DYFPEPVTVS 180
WNSGALTSGV HTFPAVLQSS GLYSLSSVVT VPSSSLGTQT YICNVNHKPS NTKVDKKVEP 240
KSCDKTHTCP PCPAPELLGG PSVFLFPPKP KDTLMISRTP EVTCVVVDVS HEDPEVKFNW 300
YVDGVEVHNA KTKPREEQYN STYRVVSVLT VLHQDWLNGK EYKCKVSNKA LPAPIEKTIS 360
KAKGQPREPQ VYTLPPSREE MTKNQVSLTC LVKGFYPSDI AVEWESNGQP ENNYKTTPPV 420
LDSDGSFFLY SKLTVDKSRW QQGNVFSCSV MHEALHNHYT QKSLSLSPG          469

SEQ ID NO: 226          moltype = AA  length = 469
FEATURE                 Location/Qualifiers
source                  1..469
                        mol_type = protein
                        organism = synthetic construct
SEQUENCE: 226
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLDTSI STAYMELSSL RSEDTAVYYC 120
ARGGRESAYW GQGTLVTVSS ASTKGPSVFP LAPSSKSTSG GTAALGCLVK DYFPEPVTVS 180
WNSGALTSGV HTFPAVLQSS GLYSLSSVVT VPSSSLGTQT YICNVNHKPS NTKVDKKVEP 240
KSCDKTHTCP PCPAPELLGG PSVFLFPPKP KDTLMISRTP EVTCVVVDVS HEDPEVKFNW 300
YVDGVEVHNA KTKPREEQYN STYRVVSVLT VLHQDWLNGK EYKCKVSNKA LPAPIEKTIS 360
KAKGQPREPQ VYTLPPSREE MTKNQVSLTC LVKGFYPSDI AVEWESNGQP ENNYKTTPPV 420
LDSDGSFFLY SKLTVDKSRW QQGNVFSCSV MHEALHNHYT QKSLSLSPG          469

SEQ ID NO: 227          moltype = AA  length = 469
FEATURE                 Location/Qualifiers
source                  1..469
                        mol_type = protein
                        organism = synthetic construct
SEQUENCE: 227
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLDTSI STAYMELSSL RSEDTAVYYC 120
ARGLPSFGYW GQGTLVTVSS ASTKGPSVFP LAPSSKSTSG GTAALGCLVK DYFPEPVTVS 180
WNSGALTSGV HTFPAVLQSS GLYSLSSVVT VPSSSLGTQT YICNVNHKPS NTKVDKKVEP 240
KSCDKTHTCP PCPAPELLGG PSVFLFPPKP KDTLMISRTP EVTCVVVDVS HEDPEVKFNW 300
YVDGVEVHNA KTKPREEQYN STYRVVSVLT VLHQDWLNGK EYKCKVSNKA LPAPIEKTIS 360
KAKGQPREPQ VYTLPPSREE MTKNQVSLTC LVKGFYPSDI AVEWESNGQP ENNYKTTPPV 420
LDSDGSFFLY SKLTVDKSRW QQGNVFSCSV MHEALHNHYT QKSLSLSPG          469

SEQ ID NO: 228          moltype = AA  length = 469
FEATURE                 Location/Qualifiers
source                  1..469
                        mol_type = protein
                        organism = synthetic construct
SEQUENCE: 228
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLDTSI STAYMELSSL RSEDTAVYYC 120
ARGVRVFYHW GQGTLVTVSS ASTKGPSVFP LAPSSKSTSG GTAALGCLVK DYFPEPVTVS 180
WNSGALTSGV HTFPAVLQSS GLYSLSSVVT VPSSSLGTQT YICNVNHKPS NTKVDKKVEP 240
KSCDKTHTCP PCPAPELLGG PSVFLFPPKP KDTLMISRTP EVTCVVVDVS HEDPEVKFNW 300
YVDGVEVHNA KTKPREEQYN STYRVVSVLT VLHQDWLNGK EYKCKVSNKA LPAPIEKTIS 360
KAKGQPREPQ VYTLPPSREE MTKNQVSLTC LVKGFYPSDI AVEWESNGQP ENNYKTTPPV 420
LDSDGSFFLY SKLTVDKSRW QQGNVFSCSV MHEALHNHYT QKSLSLSPG          469

SEQ ID NO: 229          moltype = AA  length = 469
FEATURE                 Location/Qualifiers
source                  1..469
                        mol_type = protein
                        organism = synthetic construct
SEQUENCE: 229
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLDTSI STAYMELSSL RSEDTAVYYC 120
ARGGWWFADW GQGTLVTVSS ASTKGPSVFP LAPSSKSTSG GTAALGCLVK DYFPEPVTVS 180
WNSGALTSGV HTFPAVLQSS GLYSLSSVVT VPSSSLGTQT YICNVNHKPS NTKVDKKVEP 240
KSCDKTHTCP PCPAPELLGG PSVFLFPPKP KDTLMISRTP EVTCVVVDVS HEDPEVKFNW 300
YVDGVEVHNA KTKPREEQYN STYRVVSVLT VLHQDWLNGK EYKCKVSNKA LPAPIEKTIS 360
KAKGQPREPQ VYTLPPSREE MTKNQVSLTC LVKGFYPSDI AVEWESNGQP ENNYKTTPPV 420
LDSDGSFFLY SKLTVDKSRW QQGNVFSCSV MHEALHNHYT QKSLSLSPG          469

SEQ ID NO: 230          moltype = AA  length = 469
FEATURE                 Location/Qualifiers
```

```
source                      1..469
                            mol_type = protein
                            organism = synthetic construct
SEQUENCE: 230
MDPKGSLSWR ILLFLSLAFE LSYGQVQLVQ SGAEVKKPGA SVKVSCKASG YTFTTYGINW   60
VRQATGQGLE WMGWINTYSG VPGYAQKFQG RVTMTLDTSI STAYMELSSL RSEDTAVYYC  120
ARGISKGAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPG             469

SEQ ID NO: 231             moltype = AA   length = 469
FEATURE                    Location/Qualifiers
source                      1..469
                            mol_type = protein
                            organism = synthetic construct
SEQUENCE: 231
MDPKGSLSWR ILLFLSLAFE LSYGQVQLVQ SGAEVKKPGA SVKVSCKASG YTFTTYGINW   60
VRQATGQGLE WMGWINTYSG VPGYAQKFQG RVTMTLDTSI STAYMELSSL RSEDTAVYYC  120
ARVERGDAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPG             469

SEQ ID NO: 232             moltype = AA   length = 469
FEATURE                    Location/Qualifiers
source                      1..469
                            mol_type = protein
                            organism = synthetic construct
SEQUENCE: 232
MDPKGSLSWR ILLFLSLAFE LSYGQVQLVQ SGAEVKKPGA SVKVSCKASG YTFTTYGINW   60
VRQATGQGLK WMGWINTYSG VPGYAQKFQG RVTMTLDTSI STAYMELSSL RSEDTAVYYC  120
ARGVHGVSYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPG             469

SEQ ID NO: 233             moltype = AA   length = 469
FEATURE                    Location/Qualifiers
source                      1..469
                            mol_type = protein
                            organism = synthetic construct
SEQUENCE: 233
MDPKGSLSWR ILLFLSLAFE LSYGQVQLVQ SGAEVKKPGA SVKVSCKASG YTFTTYGINW   60
VRQATGQGLE WMGWINTYSG VPGYAQKFQG RVTMTLDTSI STAYMELSSL RSEDTAVYYC  120
ARGSKGDAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPG             469

SEQ ID NO: 234             moltype = AA   length = 234
FEATURE                    Location/Qualifiers
source                      1..234
                            mol_type = protein
                            organism = synthetic construct
SEQUENCE: 234
METDTLLLWV LLLWVPGSTG DIQLTQSPSS LSASVGDRVT ITCRASQGIS NSLAWFQQKP   60
GKVPKRLIYA ASNLQSGVPS RFSGSGSGTE FTLTISSLQP EDFATYYCQQ SYSTPYTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 235             moltype = AA   length = 240
FEATURE                    Location/Qualifiers
source                      1..240
                            mol_type = protein
                            organism = synthetic construct
SEQUENCE: 235
METDTLLLWV LLLWVPGSTG DIVMTQSPLS LPVTLGQPAS ISCRSSQSLV YSDGNTYLNW   60
FQQRPGQSPR RLIYKVSNRD SGVPDRFSGS GSGTDFTLKI SRVEAEDVGV YYCMQGTHWP  120
PFTFGPGTKV EIKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240
```

```
SEQ ID NO: 236          moltype = AA   length = 234
FEATURE                 Location/Qualifiers
source                  1..234
                        mol_type = protein
                        organism = synthetic construct
SEQUENCE: 236
METDTLLLWV LLLWVPGSTG EIVMTQSPAT LSVSPGERAT LSCRASQSIG TSLHWYQQKP   60
GGAPRLLIKY ASESITGIPA RFSGSGSGTE FTLTISSLQS EDFAVYYCQQ SNSWPYTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 237          moltype = AA   length = 234
FEATURE                 Location/Qualifiers
source                  1..234
                        mol_type = protein
                        organism = synthetic construct
SEQUENCE: 237
METDTLLLWV LLLWVPGSTG AIQMTQSPSS LSASVGDRVT ITCRASQSIS SYLNWYQQKP   60
GKAPKLLIYA ASSLQSGVPS RFSGSGSGTD FTLTISSLQP EDFATYYCQQ SYSTPYTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 238          moltype = AA   length = 234
FEATURE                 Location/Qualifiers
source                  1..234
                        mol_type = protein
                        organism = synthetic construct
SEQUENCE: 238
METDTLLLWV LLLWVPGSTG EIVMTQSPAT LSVSPGERAT LSCRASQSIG TSLHWYQQKP   60
GGAPRLLIKY ASESITGIPA RFSGSGSGTE FTLTISSLQS EDFAVYYCQQ SNSWPYTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 239          moltype = AA   length = 234
FEATURE                 Location/Qualifiers
source                  1..234
                        mol_type = protein
                        organism = synthetic construct
SEQUENCE: 239
METDTLLLWV LLLWVPGSTG AIRMTQSPSS LSASVGDRVT ITCRASQSIS SYLNWYQQKP   60
GKAPKLLIYA ASSLQSGVPS RFSGSGSGTD FTLTISSLQP EDFATYYCQQ SYSTPRTFGQ  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 240          moltype = AA   length = 234
FEATURE                 Location/Qualifiers
source                  1..234
                        mol_type = protein
                        organism = synthetic construct
SEQUENCE: 240
METDTLLLWV LLLWVPGSTG NIQMTQSPSS LSASVGDRVT ITCRASQSIS SYLNWYQQKP   60
GKAPKLLIYA ASSLQSGVPS RFSGSGSGTD FTLTISSLQP EDFATYYCQQ SSSTPYTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 241          moltype = AA   length = 234
FEATURE                 Location/Qualifiers
source                  1..234
                        mol_type = protein
                        organism = synthetic construct
SEQUENCE: 241
METDTLLLWV LLLWVPGSTG EIVLTQSPSS LSASVGDRVT ITCRASQDIR RDFGWYQQKP   60
GLAPELLIYD ASRLRSGVPS RFSGSGSGTL FTFTITNLQP EDFATYYCLQ DYDFPRTFGQ  120
GTKVDIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 242          moltype = AA   length = 234
FEATURE                 Location/Qualifiers
source                  1..234
                        mol_type = protein
                        organism = synthetic construct
SEQUENCE: 242
METDTLLLWV LLLWVPGSTG EIVMTQSPAT LSVSPGERAT LSCRASQSIG TSLHWYQQKP   60
GGAPRLLIKY ASESITGIPA RFSGSGSGTE FTLTISSLQS EDFAVYYCQQ SNSWPYTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 243          moltype = AA   length = 234
```

```
FEATURE            Location/Qualifiers
source             1..234
                   mol_type = protein
                   organism = synthetic construct
SEQUENCE: 243
METDTLLLWV LLLWVPGSTG DIVMTQSPSS LSASVGDRVT ITCRASQSIS TWLAWFQQKP    60
GKAPKLLIYK ASSLKSGVPS RFSGSGSGTE FTLTISSLQP DDFATYYCQQ SYSTPWTFGQ   120
GTKLEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 244     moltype = AA  length = 234
FEATURE            Location/Qualifiers
source             1..234
                   mol_type = protein
                   organism = synthetic construct
SEQUENCE: 244
METDTLLLWV LLLWVPGSTG DIQLTQSPSS LSASVGDRVT ITCRASQGIS NSLAWFQQKP    60
GKVPKRLIYA ASNLQSGVPS RFSGSGSGTE FTLTISSLQP EDFATYYCQQ SYSTPYTFGQ   120
GTKLEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 245     moltype = AA  length = 240
FEATURE            Location/Qualifiers
source             1..240
                   mol_type = protein
                   organism = synthetic construct
SEQUENCE: 245
METDTLLLWV LLLWVPGSTG DIVMTQSPLS LPVTLGQPAS ISCRSSQSLV YSDGNTYLNW    60
FQQRPGQSPR RLIYKVSNRD SGVPDRFSGS GSGTDFTLKI SRVEAEDVGV YYCMQGTHWP   120
PFTFGPGTKV EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 246     moltype = AA  length = 234
FEATURE            Location/Qualifiers
source             1..234
                   mol_type = protein
                   organism = synthetic construct
SEQUENCE: 246
METDTLLLWV LLLWVPGSTG EIVMTQSPAT LSVSPGERAT LSCRASQSIG TSLHWYQQKP    60
GGAPRLLIKY ASESITGIPA RFSGSGSGTE FTLTISSLQS EDFAVYYCQQ SNSWPYTFGQ   120
GTKLEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 247     moltype = AA  length = 234
FEATURE            Location/Qualifiers
source             1..234
                   mol_type = protein
                   organism = synthetic construct
SEQUENCE: 247
METDTLLLWV LLLWVPGSTG AIQMTQSPSS LSASVGDRVT ITCRASQSIS SYLNWYQQKP    60
GKAPKLLIYA ASSLQSGVPS RFSGSGSGTD FTLTISSLQP EDFATYYCQQ SYSTPYTFGQ   120
GTKLEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 248     moltype = AA  length = 234
FEATURE            Location/Qualifiers
source             1..234
                   mol_type = protein
                   organism = synthetic construct
SEQUENCE: 248
METDTLLLWV LLLWVPGSTG EIVMTQSPAT LSVSPGERAT LSCRASQSIG TSLHWYQQKP    60
GGAPRLLIKY ASESITGIPA RFSGSGSGTE FTLTISSLQS EDFAVYYCQQ SNSWPYTFGQ   120
GTKLEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 249     moltype = AA  length = 234
FEATURE            Location/Qualifiers
source             1..234
                   mol_type = protein
                   organism = synthetic construct
SEQUENCE: 249
METDTLLLWV LLLWVPGSTG AIRMTQSPSS LSASVGDRVT ITCRASQSIS SYLNWYQQKP    60
GKAPKLLIYA ASSLQSGVPS RFSGSGSGTD FTLTISSLQP EDFATYYCQQ SYSTPRTFGQ   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 250     moltype = AA  length = 234
FEATURE            Location/Qualifiers
source             1..234
```

```
                          mol_type = protein
                          organism = synthetic construct
SEQUENCE: 250
METDTLLLWV LLLWVPGSTG NIQMTQSPSS LSASVGDRVT ITCRASQSIS SYLNWYQQKP    60
GKAPKLLIYA ASSLQSGVPS RFSGSGSGTD FTLTISSLQP EDFATYYCQQ SSSTPYTFGQ   120
GTKLEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 251             moltype = AA   length = 234
FEATURE                    Location/Qualifiers
source                     1..234
                          mol_type = protein
                          organism = synthetic construct
SEQUENCE: 251
METDTLLLWV LLLWVPGSTG EIVLTQSPSS LSASVGDRVT ITCRASQDIR RDFGWYQQKP    60
GLAPELLIYD ASRLRSGVPS RFSGSGSGTL FTFTITNLQP EDFATYYCLQ DYDFPRTFGQ   120
GTKVDIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 252             moltype = AA   length = 234
FEATURE                    Location/Qualifiers
source                     1..234
                          mol_type = protein
                          organism = synthetic construct
SEQUENCE: 252
METDTLLLWV LLLWVPGSTG EIVMTQSPAT LSVSPGERAT LSCRASQSIG TSLHWYQQKP    60
GGAPRLLIKY ASESITGIPA RFSGSGSGTE FTLTISSLQS EDFAVYYCQQ SNSWPYTFGQ   120
GTKLEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 253             moltype = AA   length = 234
FEATURE                    Location/Qualifiers
source                     1..234
                          mol_type = protein
                          organism = synthetic construct
SEQUENCE: 253
METDTLLLWV LLLWVPGSTG DIVMTQSPSS LSASVGDRVT ITCRASQSIS TWLAWFQQKP    60
GKAPKLLIYK ASSLKSGVPS RFSGSGSGTE FTLTISSLQP DDFATYYCQQ SYSTPWTFGQ   120
GTKLEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 254             moltype = AA   length = 470
FEATURE                    Location/Qualifiers
source                     1..470
                          mol_type = protein
                          organism = synthetic construct
SEQUENCE: 254
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
ARGGRGIAYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK              470

SEQ ID NO: 255             moltype = AA   length = 470
FEATURE                    Location/Qualifiers
source                     1..470
                          mol_type = protein
                          organism = synthetic construct
SEQUENCE: 255
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
ARGSGGFAYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK              470

SEQ ID NO: 256             moltype = AA   length = 470
FEATURE                    Location/Qualifiers
source                     1..470
                          mol_type = protein
                          organism = synthetic construct
SEQUENCE: 256
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLNTSI STAYMELSSL RSEDTAVYYC   120
```

```
ARGGRESAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 257          moltype = AA  length = 470
FEATURE                 Location/Qualifiers
source                  1..470
                        mol_type = protein
                        organism = synthetic construct
SEQUENCE: 257
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLNTSI STAYMELSSL RSEDTAVYYC  120
ARGLPSFGYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 258          moltype = AA  length = 470
FEATURE                 Location/Qualifiers
source                  1..470
                        mol_type = protein
                        organism = synthetic construct
SEQUENCE: 258
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLNTSI STAYMELSSL RSEDTAVYYC  120
ARGVRVFYHW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 259          moltype = AA  length = 470
FEATURE                 Location/Qualifiers
source                  1..470
                        mol_type = protein
                        organism = synthetic construct
SEQUENCE: 259
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLNTSI STAYMELSSL RSEDTAVYYC  120
ARGGWWFADW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 260          moltype = AA  length = 470
FEATURE                 Location/Qualifiers
source                  1..470
                        mol_type = protein
                        organism = synthetic construct
SEQUENCE: 260
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLNTSI STAYMELSSL RSEDTAVYYC  120
ARGISKGAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 261          moltype = AA  length = 470
FEATURE                 Location/Qualifiers
source                  1..470
                        mol_type = protein
                        organism = synthetic construct
SEQUENCE: 261
MDPKGSLSWR ILLFLSLAFE LSYGQVQLVQ SGAEVKKPGA SVKVSCKASG YTFTTYGINW  60
VRQATGQGLE WMGWINTYSG VPGYAQKFQG RVTMTLNTSI STAYMELSSL RSEDTAVYYC  120
ARVERGDAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
```

```
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 262          moltype = AA  length = 470
FEATURE                 Location/Qualifiers
source                  1..470
                        mol_type = protein
                        organism = synthetic construct
SEQUENCE: 262
MDPKGSLSWR ILLFLSLAFE LSYGQVQLVQ SGAEVKKPGA SVKVSCKASG YTFTTYGINW   60
VRQATGQGLK WMGWINTYSG VPGYAQKFQG RVTMTLNTSI STAYMELSSL RSEDTAVYYC  120
ARGVHGVSYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 263          moltype = AA  length = 470
FEATURE                 Location/Qualifiers
source                  1..470
                        mol_type = protein
                        organism = synthetic construct
SEQUENCE: 263
MDPKGSLSWR ILLFLSLAFE LSYGQVQLVQ SGAEVKKPGA SVKVSCKASG YTFTTYGINW   60
VRQATGQGLE WMGWINTYSG VPGYAQKFQG RVTMTLNTSI STAYMELSSL RSEDTAVYYC  120
ARGSKGDAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 264          moltype = AA  length = 470
FEATURE                 Location/Qualifiers
source                  1..470
                        mol_type = protein
                        organism = synthetic construct
SEQUENCE: 264
MDPKGSLSWR ILLFLSLAFE LSYGQVQLVQ SGAEVKKPGA SVKVSCKASG YTFTTYGINW   60
VRQATGQGLE WMGWINTYSG VPGYAQKFQG RVTMTLDTSI STAYMELSSL RSEDTAVYYC  120
ARGGRGIAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 265          moltype = AA  length = 470
FEATURE                 Location/Qualifiers
source                  1..470
                        mol_type = protein
                        organism = synthetic construct
SEQUENCE: 265
MDPKGSLSWR ILLFLSLAFE LSYGQVQLVQ SGAEVKKPGA SVKVSCKASG YTFTTYGINW   60
VRQATGQGLE WMGWINTYSG VPGYAQKFQG RVTMTLDTSI STAYMELSSL RSEDTAVYYC  120
ARGSGGFAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 266          moltype = AA  length = 470
FEATURE                 Location/Qualifiers
source                  1..470
                        mol_type = protein
                        organism = synthetic construct
SEQUENCE: 266
MDPKGSLSWR ILLFLSLAFE LSYGQVQLVQ SGAEVKKPGA SVKVSCKASG YTFTTYGINW   60
VRQATGQGLE WMGWINTYSG VPGYAQKFQG RVTMTLDTSI STAYMELSSL RSEDTAVYYC  120
ARGGRESAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 267          moltype = AA  length = 470
```

```
FEATURE                 Location/Qualifiers
source                  1..470
                        mol_type = protein
                        organism = synthetic construct
SEQUENCE: 267
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLDTSI STAYMELSSL RSEDTAVYYC   120
ARGLPSFGYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK             470

SEQ ID NO: 268          moltype = AA  length = 470
FEATURE                 Location/Qualifiers
source                  1..470
                        mol_type = protein
                        organism = synthetic construct
SEQUENCE: 268
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLDTSI STAYMELSSL RSEDTAVYYC   120
ARGVRVFYHW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK             470

SEQ ID NO: 269          moltype = AA  length = 470
FEATURE                 Location/Qualifiers
source                  1..470
                        mol_type = protein
                        organism = synthetic construct
SEQUENCE: 269
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLDTSI STAYMELSSL RSEDTAVYYC   120
ARGGWWFADW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK             470

SEQ ID NO: 270          moltype = AA  length = 470
FEATURE                 Location/Qualifiers
source                  1..470
                        mol_type = protein
                        organism = synthetic construct
SEQUENCE: 270
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLDTSI STAYMELSSL RSEDTAVYYC   120
ARGISKGAYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK             470

SEQ ID NO: 271          moltype = AA  length = 470
FEATURE                 Location/Qualifiers
source                  1..470
                        mol_type = protein
                        organism = synthetic construct
SEQUENCE: 271
MDPKGSLSWR ILLFLSLAFE LSYGQVQLVQ SGAEVKKPGA SVKVSCKASG YTFTTYGINW    60
VRQATGQGLE WMGWINTYSG VPGYAQKFQG RVTMTLDTSI STAYMELSSL RSEDTAVYYC   120
ARVERGDAYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK             470

SEQ ID NO: 272          moltype = AA  length = 470
FEATURE                 Location/Qualifiers
source                  1..470
                        mol_type = protein
                        organism = synthetic construct
```

```
SEQUENCE: 272
MDPKGSLSWR ILLFLSLAFE LSYGQVQLVQ SGAEVKKPGA SVKVSCKASG YTFTTYGINW   60
VRQATGQGLK WMGWINTYSG VPGYAQKFQG RVTMTLDTSI STAYMELSSL RSEDTAVYYC  120
ARGVHGVSYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK            470

SEQ ID NO: 273           moltype = AA  length = 470
FEATURE                  Location/Qualifiers
source                   1..470
                         mol_type = protein
                         organism = synthetic construct
SEQUENCE: 273
MDPKGSLSWR ILLFLSLAFE LSYGQVQLVQ SGAEVKKPGA SVKVSCKASG YTFTTYGINW   60
VRQATGQGLE WMGWINTYSG VPGYAQKFQG RVTMTLDTSI STAYMELSSL RSEDTAVYYC  120
ARGSKGDAYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK            470

SEQ ID NO: 274           moltype = AA  length = 445
FEATURE                  Location/Qualifiers
source                   1..445
                         mol_type = protein
                         organism = synthetic construct
SEQUENCE: 274
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGG RGIAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 275           moltype = AA  length = 445
FEATURE                  Location/Qualifiers
source                   1..445
                         mol_type = protein
                         organism = synthetic construct
SEQUENCE: 275
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGS GGFAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 276           moltype = AA  length = 445
FEATURE                  Location/Qualifiers
source                   1..445
                         mol_type = protein
                         organism = synthetic construct
SEQUENCE: 276
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGG RESAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 277           moltype = AA  length = 445
FEATURE                  Location/Qualifiers
source                   1..445
                         mol_type = protein
                         organism = synthetic construct
SEQUENCE: 277
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGL PSFGYWGQGT LVTVSSASTK  120
GPSVFPLAPS SKSTSGGTAA LGCLVKDYFP EPVTVSWNSG ALTSGVHTFP AVLQSSGLYS  180
```

```
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 278          moltype = AA  length = 445
FEATURE                 Location/Qualifiers
source                  1..445
                        mol_type = protein
                        organism = synthetic construct
SEQUENCE: 278
QVQLVQSGAE VKKPGASVKV SCKASGYTFT TYGINWVRQA TGQGLEWMGW INTYSGVPGY     60
AQKFQGRVTM TLNTSISTAY MELSSLRSED TAVYYCARGV RVFYHWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 279          moltype = AA  length = 445
FEATURE                 Location/Qualifiers
source                  1..445
                        mol_type = protein
                        organism = synthetic construct
SEQUENCE: 279
QVQLVQSGAE VKKPGASVKV SCKASGYTFT TYGINWVRQA TGQGLEWMGW INTYSGVPGY     60
AQKFQGRVTM TLNTSISTAY MELSSLRSED TAVYYCARGG WWFADWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 280          moltype = AA  length = 445
FEATURE                 Location/Qualifiers
source                  1..445
                        mol_type = protein
                        organism = synthetic construct
SEQUENCE: 280
QVQLVQSGAE VKKPGASVKV SCKASGYTFT TYGINWVRQA TGQGLEWMGW INTYSGVPGY     60
AQKFQGRVTM TLNTSISTAY MELSSLRSED TAVYYCARGI SKGAYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 281          moltype = AA  length = 445
FEATURE                 Location/Qualifiers
source                  1..445
                        mol_type = protein
                        organism = synthetic construct
SEQUENCE: 281
QVQLVQSGAE VKKPGASVKV SCKASGYTFT TYGINWVRQA TGQGLEWMGW INTYSGVPGY     60
AQKFQGRVTM TLNTSISTAY MELSSLRSED TAVYYCARVE RGDAYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 282          moltype = AA  length = 445
FEATURE                 Location/Qualifiers
source                  1..445
                        mol_type = protein
                        organism = synthetic construct
SEQUENCE: 282
QVQLVQSGAE VKKPGASVKV SCKASGYTFT TYGINWVRQA TGQGLKWMGW INTYSGVPGY     60
AQKFQGRVTM TLNTSISTAY MELSSLRSED TAVYYCARGV HGVSYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
```

```
VFSCSVMHEA LHNHYTQKSL SLSPG                                              445

SEQ ID NO: 283            moltype = AA  length = 445
FEATURE                   Location/Qualifiers
source                    1..445
                          mol_type = protein
                          organism = synthetic construct
SEQUENCE: 283
QVQLVQSGAE VKKPGASVKV SCKASGYTFT TYGINWVRQA TGQGLEWMGW INTYSGVPGY          60
AQKFQGRVTM TLNTSISTAY MELSSLRSED TAVYYCARGS KGDAYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKKVEPKSCD KTHTCPPCPA PELLGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 284            moltype = AA  length = 445
FEATURE                   Location/Qualifiers
source                    1..445
                          mol_type = protein
                          organism = synthetic construct
SEQUENCE: 284
QVQLVQSGAE VKKPGASVKV SCKASGYTFT TYGINWVRQA TGQGLEWMGW INTYSGVPGY          60
AQKFQGRVTM TLDTSISTAY MELSSLRSED TAVYYCARGG RGIAYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKKVEPKSCD KTHTCPPCPA PELLGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 285            moltype = AA  length = 445
FEATURE                   Location/Qualifiers
source                    1..445
                          mol_type = protein
                          organism = synthetic construct
SEQUENCE: 285
QVQLVQSGAE VKKPGASVKV SCKASGYTFT TYGINWVRQA TGQGLEWMGW INTYSGVPGY          60
AQKFQGRVTM TLDTSISTAY MELSSLRSED TAVYYCARGS GGFAYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKKVEPKSCD KTHTCPPCPA PELLGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 286            moltype = AA  length = 445
FEATURE                   Location/Qualifiers
source                    1..445
                          mol_type = protein
                          organism = synthetic construct
SEQUENCE: 286
QVQLVQSGAE VKKPGASVKV SCKASGYTFT TYGINWVRQA TGQGLEWMGW INTYSGVPGY          60
AQKFQGRVTM TLDTSISTAY MELSSLRSED TAVYYCARGG RESAYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKKVEPKSCD KTHTCPPCPA PELLGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 287            moltype = AA  length = 445
FEATURE                   Location/Qualifiers
source                    1..445
                          mol_type = protein
                          organism = synthetic construct
SEQUENCE: 287
QVQLVQSGAE VKKPGASVKV SCKASGYTFT TYGINWVRQA TGQGLEWMGW INTYSGVPGY          60
AQKFQGRVTM TLDTSISTAY MELSSLRSED TAVYYCARGL PSFGYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKKVEPKSCD KTHTCPPCPA PELLGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 288            moltype = AA  length = 445
FEATURE                   Location/Qualifiers
```

```
source                  1..445
                        mol_type = protein
                        organism = synthetic construct
SEQUENCE: 288
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGV RVFYHWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 289          moltype = AA   length = 445
FEATURE                 Location/Qualifiers
source                  1..445
                        mol_type = protein
                        organism = synthetic construct
SEQUENCE: 289
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGG WWFADWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 290          moltype = AA   length = 445
FEATURE                 Location/Qualifiers
source                  1..445
                        mol_type = protein
                        organism = synthetic construct
SEQUENCE: 290
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGI SKGAYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 291          moltype = AA   length = 445
FEATURE                 Location/Qualifiers
source                  1..445
                        mol_type = protein
                        organism = synthetic construct
SEQUENCE: 291
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARVE RGDAYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 292          moltype = AA   length = 445
FEATURE                 Location/Qualifiers
source                  1..445
                        mol_type = protein
                        organism = synthetic construct
SEQUENCE: 292
QVQLVQSGAE VKKPGASVKV SCKASGYTFT TYGINWVRQA TGQGLKWMGW INTYSGVPGY    60
AQKFQGRVTM TLDTSISTAY MELSSLRSED TAVYYCARGV HGVSYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 293          moltype = AA   length = 445
FEATURE                 Location/Qualifiers
source                  1..445
                        mol_type = protein
                        organism = synthetic construct
SEQUENCE: 293
```

```
QVQLVQSGAE VKKPGASVKV SCKASGYTFT TYGINWVRQA TGQGLEWMGW INTYSGVPGY   60
AQKFQGRVTM TLDTSISTAY MELSSLRSED TAVYYCARGS KGDAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 294          moltype = AA  length = 446
FEATURE                 Location/Qualifiers
source                  1..446
                        mol_type = protein
                        organism = synthetic construct
SEQUENCE: 294
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGG RGIAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 295          moltype = AA  length = 446
FEATURE                 Location/Qualifiers
source                  1..446
                        mol_type = protein
                        organism = synthetic construct
SEQUENCE: 295
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGS GGFAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 296          moltype = AA  length = 446
FEATURE                 Location/Qualifiers
source                  1..446
                        mol_type = protein
                        organism = synthetic construct
SEQUENCE: 296
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGG RESAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 297          moltype = AA  length = 446
FEATURE                 Location/Qualifiers
source                  1..446
                        mol_type = protein
                        organism = synthetic construct
SEQUENCE: 297
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGL PSFGYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 298          moltype = AA  length = 446
FEATURE                 Location/Qualifiers
source                  1..446
                        mol_type = protein
                        organism = synthetic construct
SEQUENCE: 298
QVQLVQSGAE VKKPGASVKV SCKASGYTFT TYGINWVRQA TGQGLEWMGW INTYSGVPGY   60
AQKFQGRVTM TLNTSISTAY MELSSLRSED TAVYYCARGV RVFYHWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
```

```
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 299          moltype = AA   length = 446
FEATURE                 Location/Qualifiers
source                  1..446
                        mol_type = protein
                        organism = synthetic construct
SEQUENCE: 299
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARGG WWFADWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 300          moltype = AA   length = 446
FEATURE                 Location/Qualifiers
source                  1..446
                        mol_type = protein
                        organism = synthetic construct
SEQUENCE: 300
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARGI SKGAYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 301          moltype = AA   length = 446
FEATURE                 Location/Qualifiers
source                  1..446
                        mol_type = protein
                        organism = synthetic construct
SEQUENCE: 301
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARVE RGDAYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 302          moltype = AA   length = 446
FEATURE                 Location/Qualifiers
source                  1..446
                        mol_type = protein
                        organism = synthetic construct
SEQUENCE: 302
QVQLVQSGAE VKKPGASVKV SCKASGYTFT TYGINWVRQA TGQGLKWMGW INTYSGVPGY    60
AQKFQGRVTM TLNTSISTAY MELSSLRSED TAVYYCARGV HGVSYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 303          moltype = AA   length = 446
FEATURE                 Location/Qualifiers
source                  1..446
                        mol_type = protein
                        organism = synthetic construct
SEQUENCE: 303
QVQLVQSGAE VKKPGASVKV SCKASGYTFT TYGINWVRQA TGQGLEWMGW INTYSGVPGY    60
AQKFQGRVTM TLNTSISTAY MELSSLRSED TAVYYCARGS KGDAYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446
```

```
SEQ ID NO: 304          moltype = AA  length = 446
FEATURE                 Location/Qualifiers
source                  1..446
                        mol_type = protein
                        organism = synthetic construct
SEQUENCE: 304
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGG RGIAYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 305          moltype = AA  length = 446
FEATURE                 Location/Qualifiers
source                  1..446
                        mol_type = protein
                        organism = synthetic construct
SEQUENCE: 305
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGS GGFAYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 306          moltype = AA  length = 446
FEATURE                 Location/Qualifiers
source                  1..446
                        mol_type = protein
                        organism = synthetic construct
SEQUENCE: 306
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGG RESAYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 307          moltype = AA  length = 446
FEATURE                 Location/Qualifiers
source                  1..446
                        mol_type = protein
                        organism = synthetic construct
SEQUENCE: 307
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGL PSFGYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 308          moltype = AA  length = 446
FEATURE                 Location/Qualifiers
source                  1..446
                        mol_type = protein
                        organism = synthetic construct
SEQUENCE: 308
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGV RVFYHWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 309          moltype = AA  length = 446
FEATURE                 Location/Qualifiers
source                  1..446
```

```
                        mol_type = protein
                        organism = synthetic construct
SEQUENCE: 309
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGG WWFADWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 310          moltype = AA  length = 446
FEATURE                 Location/Qualifiers
source                  1..446
                        mol_type = protein
                        organism = synthetic construct
SEQUENCE: 310
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGI SKGAYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 311          moltype = AA  length = 446
FEATURE                 Location/Qualifiers
source                  1..446
                        mol_type = protein
                        organism = synthetic construct
SEQUENCE: 311
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARVE RGDAYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 312          moltype = AA  length = 446
FEATURE                 Location/Qualifiers
source                  1..446
                        mol_type = protein
                        organism = synthetic construct
SEQUENCE: 312
QVQLVQSGAE VKKPGASVKV SCKASGYTFT TYGINWVRQA TGQGLKWMGW INTYSGVPGY    60
AQKFQGRVTM TLDTSISTAY MELSSLRSED TAVYYCARGV HGVSYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 313          moltype = AA  length = 446
FEATURE                 Location/Qualifiers
source                  1..446
                        mol_type = protein
                        organism = synthetic construct
SEQUENCE: 313
QVQLVQSGAE VKKPGASVKV SCKASGYTFT TYGINWVRQA TGQGLEWMGW INTYSGVPGY    60
AQKFQGRVTM TLDTSISTAY MELSSLRSED TAVYYCARGS KGDAYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 314          moltype = AA  length = 214
FEATURE                 Location/Qualifiers
source                  1..214
                        mol_type = protein
                        organism = synthetic construct
SEQUENCE: 314
DIQLTQSPSS LSASVGDRVT ITCRASQGIS NSLAWFQQKP GKVPKRLIYA ASNLQSGVPS    60
```

```
RFSGSGSGTE FTLTISSLQP EDFATYYCQQ SYSTPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 315           moltype = AA   length = 220
FEATURE                  Location/Qualifiers
source                   1..220
                         mol_type = protein
                         organism = synthetic construct
SEQUENCE: 315
DIVMTQSPLS LPVTLGQPAS ISCRSSQSLV YSDGNTYLNW FQQRPGQSPR RLIYKVSNRD    60
SGVPDRFSGS GSGTDFTLKI SRVEAEDVGV YYCMQGTHWP PFTFGPGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 316           moltype = AA   length = 214
FEATURE                  Location/Qualifiers
source                   1..214
                         mol_type = protein
                         organism = synthetic construct
SEQUENCE: 316
EIVMTQSPAT LSVSPGERAT LSCRASQSIG TSLHWYQQKP GGAPRLLIKY ASESITGIPA    60
RFSGSGSGTE FTLTISSLQS EDFAVYYCQQ SNSWPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 317           moltype = AA   length = 214
FEATURE                  Location/Qualifiers
source                   1..214
                         mol_type = protein
                         organism = synthetic construct
SEQUENCE: 317
AIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 318           moltype = AA   length = 214
FEATURE                  Location/Qualifiers
source                   1..214
                         mol_type = protein
                         organism = synthetic construct
SEQUENCE: 318
EIVMTQSPAT LSVSPGERAT LSCRASQSIG TSLHWYQQKP GGAPRLLIKY ASESITGIPA    60
RFSGSGSGTE FTLTISSLQS EDFAVYYCQQ SNSWPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 319           moltype = AA   length = 214
FEATURE                  Location/Qualifiers
source                   1..214
                         mol_type = protein
                         organism = synthetic construct
SEQUENCE: 319
AIRMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 320           moltype = AA   length = 214
FEATURE                  Location/Qualifiers
source                   1..214
                         mol_type = protein
                         organism = synthetic construct
SEQUENCE: 320
NIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SSSTPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 321           moltype = AA   length = 214
FEATURE                  Location/Qualifiers
source                   1..214
                         mol_type = protein
                         organism = synthetic construct
SEQUENCE: 321
EIVLTQSPSS LSASVGDRVT ITCRASQDIR RDFGWYQQKP GLAPELLIYD ASRLRSGVPS    60
RFSGSGSGTL FTFTITNLQP EDFATYYCLQ DYDFPRTFGQ GTKVDIKRTV AAPSVFIFPP   120
SDEQLKSGTA SVVCLLNNFY PREAKVQWKV DNALQSGNSQ ESVTEQDSKD STYSLSSTLT   180
```

```
LSKADYEKHK VYACEVTHQG LSSPVTKSFN RGEC                                  214

SEQ ID NO: 322         moltype = AA   length = 214
FEATURE                Location/Qualifiers
source                 1..214
                       mol_type = protein
                       organism = synthetic construct
SEQUENCE: 322
EIVMTQSPAT LSVSPGERAT LSCRASQSIG TSLHWYQQKP GGAPRLLIKY ASESITGIPA       60
RFSGSGSGTE FTLTISSLQS EDFAVYYCQQ SNSWPYTFGQ GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                  214

SEQ ID NO: 323         moltype = AA   length = 214
FEATURE                Location/Qualifiers
source                 1..214
                       mol_type = protein
                       organism = synthetic construct
SEQUENCE: 323
DIVMTQSPSS LSASVGDRVT ITCRASQSIS TWLAWFQQKP GKAPKLLIYK ASSLKSGVPS       60
RFSGSGSGTE FTLTISSLQP DDFATYYCQQ SYSTPWTFGQ GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                  214

SEQ ID NO: 324         moltype = AA   length = 214
FEATURE                Location/Qualifiers
source                 1..214
                       mol_type = protein
                       organism = synthetic construct
SEQUENCE: 324
DIQLTQSPSS LSASVGDRVT ITCRASQGIS NSLAWFQQKP GKVPKRLIYA ASNLQSGVPS       60
RFSGSGSGTE FTLTISSLQP EDFATYYCQQ SYSTPYTFGQ GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                  214

SEQ ID NO: 325         moltype = AA   length = 220
FEATURE                Location/Qualifiers
source                 1..220
                       mol_type = protein
                       organism = synthetic construct
SEQUENCE: 325
DIVMTQSPLS LPVTLGQPAS ISCRSSQSLV YSDGNTYLNW FQQRPGQSPR RLIYKVSNRD       60
SGVPDRFSGS GSGTDFTLKI SRVEAEDVGV YYCMQGTHWP PFTFGPGTKV EIKRTVAAPS      120
VFIFPPSDEQ LKSGTASVVC LLNNFYPREA KVQWKVDNAL QSGNSQESVT EQDSKDSTYS      180
LSSTLTLSKA DYEKHKVYAC EVTHQGLSSP VTKSFNRGEC                            220

SEQ ID NO: 326         moltype = AA   length = 214
FEATURE                Location/Qualifiers
source                 1..214
                       mol_type = protein
                       organism = synthetic construct
SEQUENCE: 326
EIVMTQSPAT LSVSPGERAT LSCRASQSIG TSLHWYQQKP GGAPRLLIKY ASESITGIPA       60
RFSGSGSGTE FTLTISSLQS EDFAVYYCQQ SNSWPYTFGQ GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                  214

SEQ ID NO: 327         moltype = AA   length = 214
FEATURE                Location/Qualifiers
source                 1..214
                       mol_type = protein
                       organism = synthetic construct
SEQUENCE: 327
AIQMTQSPSS LSASVGDRVT ITCRASQSIS SYLNWYQQKP GKAPKLLIYA ASSLQSGVPS       60
RFSGSGSGTD FTLTISSLQP EDFATYYCQQ SYSTPYTFGQ GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                  214

SEQ ID NO: 328         moltype = AA   length = 214
FEATURE                Location/Qualifiers
source                 1..214
                       mol_type = protein
                       organism = synthetic construct
SEQUENCE: 328
EIVMTQSPAT LSVSPGERAT LSCRASQSIG TSLHWYQQKP GGAPRLLIKY ASESITGIPA       60
RFSGSGSGTE FTLTISSLQS EDFAVYYCQQ SNSWPYTFGQ GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                  214
```

```
SEQ ID NO: 329            moltype = AA   length = 214
FEATURE                   Location/Qualifiers
source                    1..214
                          mol_type = protein
                          organism = synthetic construct
SEQUENCE: 329
AIRMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 330            moltype = AA   length = 214
FEATURE                   Location/Qualifiers
source                    1..214
                          mol_type = protein
                          organism = synthetic construct
SEQUENCE: 330
NIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SSSTPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 331            moltype = AA   length = 214
FEATURE                   Location/Qualifiers
source                    1..214
                          mol_type = protein
                          organism = synthetic construct
SEQUENCE: 331
EIVLTQSPSS LSASVGDRVT ITCRASQDIR RDFGWYQQKP GLAPELLIYD ASRLRSGVPS   60
RFSGSGSGTL FTFTITNLQP EDFATYYCLQ DYDFPRTFGQ GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 332            moltype = AA   length = 214
FEATURE                   Location/Qualifiers
source                    1..214
                          mol_type = protein
                          organism = synthetic construct
SEQUENCE: 332
EIVMTQSPAT LSVSPGERAT LSCRASQSIG TSLHWYQQKP GGAPRLLIKY ASESITGIPA   60
RFSGSGSGTE FTLTISSLQS EDFAVYYCQQ SNSWPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 333            moltype = AA   length = 214
FEATURE                   Location/Qualifiers
source                    1..214
                          mol_type = protein
                          organism = synthetic construct
SEQUENCE: 333
DIVMTQSPSS LSASVGDRVT ITCRASQSIS TWLAWFQQKP GKAPKLLIYK ASSLKSGVPS   60
RFSGSGSGTE FTLTISSLQP DDFATYYCQQ SYSTPWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 334            moltype = AA   length = 472
FEATURE                   Location/Qualifiers
source                    1..472
                          mol_type = protein
                          organism = synthetic construct
SEQUENCE: 334
MDPKGSLSWR ILLFLSLAFE LSYGQVQLVQ SGAEVKKPGA SVKVSCKASG YTFNSYWMHW   60
VRQAPGQGLE WMGRIHPRGI HTNYNQKFKG RVTLTVDTST STAYMELSSL RSEDTAVYYC  120
APSSSYAWAF AHWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PG          472

SEQ ID NO: 335            moltype = AA   length = 472
FEATURE                   Location/Qualifiers
source                    1..472
                          mol_type = protein
                          organism = synthetic construct
SEQUENCE: 335
MDPKGSLSWR ILLFLSLAFE LSYGQVQLVQ SGAEVKKPGA SVKVSCKASG QTFTSYRMHW   60
VRQAPGQGLE WMGRILPIRS DTNYNQKFKG RVTLTVDTST STAYMELSSL RSEDTAVYYC  120
ARDAGYGSLF AAWGQGTLVT VSSASTKGPS VFPLAPSSKS TSGGTAALGC LVKDYFPEPV  180
```

```
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PG           472

SEQ ID NO: 336             moltype = AA  length = 472
FEATURE                    Location/Qualifiers
source                     1..472
                           mol_type = protein
                           organism = synthetic construct
SEQUENCE: 336
MDPKGSLSWR ILLFLSLAFE LSYGQVQLVQ SGAEVKKPGA SVKVSCKASG YTFTSYWMHW   60
VRQAPGQGLE WMGRIHPSDS DTNYNQKFKG RVTLTVDTST STAYMELSSL RSEDTAVYYC   120
APKGNYVVRF AYWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PG           472

SEQ ID NO: 337             moltype = AA  length = 472
FEATURE                    Location/Qualifiers
source                     1..472
                           mol_type = protein
                           organism = synthetic construct
SEQUENCE: 337
MDPKGSLSWR ILLFLSLAFE LSYGQVQLVQ SGAEVKKPGA SVKVSCKASG YTFTRYWMHW   60
VRQAPGQGLE WMGRIHPTDS VTNYNQKFKG RVTLTVDTST STAYMELSSL RSEDTAVYYC   120
APDVNYARAF AHWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PG           472

SEQ ID NO: 338             moltype = AA  length = 472
FEATURE                    Location/Qualifiers
source                     1..472
                           mol_type = protein
                           organism = synthetic construct
SEQUENCE: 338
MDPKGSLSWR ILLFLSLAFE LSYGQVQLVQ SGAEVKKPGA SVKVSCKASG YTFGIYWMHW   60
VRQAPGQGLE WMGRILPSNG YTNYNQKFKG RVTLTVDTST STAYMELSSL RSEDTAVYYC   120
APYGIYTRDF SHWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PG           472

SEQ ID NO: 339             moltype = AA  length = 472
FEATURE                    Location/Qualifiers
source                     1..472
                           mol_type = protein
                           organism = synthetic construct
SEQUENCE: 339
MDPKGSLSWR ILLFLSLAFE LSYGQVQLVQ SGAEVKKPGA SVKVSCKASG YTFTSYWMHW   60
VRQAPGQGLE WMGRIHPSDS DTNYNQKFKG RVTLTVDTST STAYMELSSL RSEDTAVYYC   120
APYVDLESGF AYWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PG           472

SEQ ID NO: 340             moltype = AA  length = 472
FEATURE                    Location/Qualifiers
source                     1..472
                           mol_type = protein
                           organism = synthetic construct
SEQUENCE: 340
MDPKGSLSWR ILLFLSLAFE LSYGQVQLVQ SGAEVKKPGA SVKVSCKASG YTFTSYWMHW   60
VRQAPGMGLE WMGRIHPIYR DTNYNQKFKG RVTLTVDTST STAYMELSSL RSEDTAVYYC   120
APYVNYGDGF AYWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
```

```
PPVLDSDGSF FLYSKLTVDK SRWQQGNVFS CSVMHEALHN HYTQKSLSLS PG          472

SEQ ID NO: 341              moltype = AA  length = 472
FEATURE                     Location/Qualifiers
source                      1..472
                            mol_type = protein
                            organism = synthetic construct
SEQUENCE: 341
MDPKGSLSWR ILLFLSLAFE LSYGQVQLVQ SGAEVKKPGA SVKVSCKASG YTFNSYLMHW   60
VRQAPGMGLE WMGRIRPNYS DTNYNQKFKG RVTLTVDTST STAYMELSSL RSEDTAVYYC  120
APYGNNASGF SYWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PG          472

SEQ ID NO: 342              moltype = AA  length = 472
FEATURE                     Location/Qualifiers
source                      1..472
                            mol_type = protein
                            organism = synthetic construct
SEQUENCE: 342
MDPKGSLSWR ILLFLSLAFE LSYGQVQLVQ SGAEVKKPGA SVKVSCKASG QTFTNYLMHW   60
VRQAPGQGLE WMGRIPLSDR DTNYNQKFKG RVTLTVDTST STAYMELSSL RSEDTAVYYC  120
APYGRSASGF SSWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PG          472

SEQ ID NO: 343              moltype = AA  length = 472
FEATURE                     Location/Qualifiers
source                      1..472
                            mol_type = protein
                            organism = synthetic construct
SEQUENCE: 343
MDPKGSLSWR ILLFLSLAFE LSYGQVQLVQ SGAEVKKPGA SVKVSCKASG YTFTSYWMHW   60
VRQAPGQGLE WMGRIHPSDS DTNYNQKFKG RVTLTVDTST STAYMELSSL RSEDTAVYYC  120
APYFDHAGGF LHWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PG          472

SEQ ID NO: 344              moltype = AA  length = 234
FEATURE                     Location/Qualifiers
source                      1..234
                            mol_type = protein
                            organism = synthetic construct
SEQUENCE: 344
METDTLLLWV LLLWVPGSTG DIQMTQSPSS LSASVGDRVT ITCRASQDVS TALAWYQQKP   60
GKAPKLLIYW ASTRHSGVPD RFSGSGSGTD FTLTISSLQP EDFATYYCQQ HYRSPGTFGG  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 345              moltype = AA  length = 234
FEATURE                     Location/Qualifiers
source                      1..234
                            mol_type = protein
                            organism = synthetic construct
SEQUENCE: 345
METDTLLLWV LLLWVPGSTG DIQMTQSPSS LSASVGDRVT ITCRASQDVS TALAWYQQKP   60
GKAPKLLIYW ASTRHSGVPD RFSGSGSGTD FTLTISSLQP EDFATYYCQQ HDSSPGTFGG  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 346              moltype = AA  length = 234
FEATURE                     Location/Qualifiers
source                      1..234
                            mol_type = protein
                            organism = synthetic construct
SEQUENCE: 346
METDTLLLWV LLLWVPGSTG DIVMTQSPSS LSASVGDRVT ITCRASQGIR NDLGWYQQKP   60
GKAPKLLIYA ASSLQSGVPS RFSGSGSGTD FTLTISSLQP EDFATYYCLQ DYNYPWTFGQ  120
GTKVDIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234
```

```
SEQ ID NO: 347          moltype = AA  length = 234
FEATURE                 Location/Qualifiers
source                  1..234
                        mol_type = protein
                        organism = synthetic construct
SEQUENCE: 347
METDTLLLWV LLLWVPGSTG DIQMTQSPSS LSASVGDRVT ITCRASQDVS TALAWYQQKP    60
GKAPKLLIYW ASTRHSGVPD RFSGSGSGTD FTLTISSLQP EDFATYYCQQ HYGSPWTFGG   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 348          moltype = AA  length = 234
FEATURE                 Location/Qualifiers
source                  1..234
                        mol_type = protein
                        organism = synthetic construct
SEQUENCE: 348
METDTLLLWV LLLWVPGSTG DIQMTQSPSS LSASVGDRVT ITCRASQDVS TALAWYQQKP    60
GKAPKLLIYW ASTRHSGVPD RFSGSGSGTD FTLTISSLQP EDFATYYCQQ RDTTPRTFGG   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 349          moltype = AA  length = 235
FEATURE                 Location/Qualifiers
source                  1..235
                        mol_type = protein
                        organism = synthetic construct
SEQUENCE: 349
METDTLLLWV LLLWVPGSTG DIAMTQTPSS LSASIGDRVT IACRASQGIS SALAWYQQKP    60
GRTPKLLIFD ASTLQSGVPS RFSGSGSGTD FTLTISSLQP EDFATYYCQQ FNTYSSVTFG   120
QGTRLEIKRT VAAPSVFIFP PSDEQLKSGT ASVVCLLNNF YPREAKVQWK VDNALQSGNS   180
QESVTEQDSK DSTYSLSSTL TLSKADYEKH KVYACEVTHQ GLSSPVTKSF NRGEC        235

SEQ ID NO: 350          moltype = AA  length = 234
FEATURE                 Location/Qualifiers
source                  1..234
                        mol_type = protein
                        organism = synthetic construct
SEQUENCE: 350
METDTLLLWV LLLWVPGSTG DIQMTQSPST LSASVGDRVT ITCRASQDVS TALAWYQQKP    60
GKAPKLLIYW ASTRHIGVPD RFSGSGSGTD FTLTISSLQP EDFATYYCHQ DYITPRTFGG   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 351          moltype = AA  length = 234
FEATURE                 Location/Qualifiers
source                  1..234
                        mol_type = protein
                        organism = synthetic construct
SEQUENCE: 351
METDTLLLWV LLLWVPGSTG DIQMTQSPSS LSASVGDRVT ITCRASQDVS TALAWYQQKP    60
GKAPKLLIYW ASTRHSGVPD RFSGSGSGTD FTLTISSLQP EDFATYYCQQ HYRSPWTFGG   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 352          moltype = AA  length = 234
FEATURE                 Location/Qualifiers
source                  1..234
                        mol_type = protein
                        organism = synthetic construct
SEQUENCE: 352
METDTLLLWV LLLWVPGSTG DIQMTQSPSS LSASVGDRVT ITCRASQDVS TALAWYQQKP    60
GKAPKLLIYW ASTRHSGVPD RFSGSGSGTD FTLTISSLQP EDFATYYCQQ GSSTPLTFGG   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 353          moltype = AA  length = 233
FEATURE                 Location/Qualifiers
source                  1..233
                        mol_type = protein
                        organism = synthetic construct
SEQUENCE: 353
METDTLLLWV LLLWVPGSTG DIVMTQSPGT LSLSPGERAT LSCRASQSVS SSYLAWYQQK    60
PGQAPRLLIY GASSRATGIP DRFSGSGSGT DFTLTISRLE PEDFAVYYCQ QYGSWTFGQG   120
TKLEIKRTVA APSVFIFPPS DEQLKSGTAS VVCLLNNFYP REAKVQWKVD NALQSGNSQE   180
SVTEQDSKDS TYSLSSTLTL SKADYEKHKV YACEVTHQGL SSPVTKSFNR GEC          233

SEQ ID NO: 354          moltype = AA  length = 473
```

```
FEATURE                 Location/Qualifiers
source                  1..473
                        mol_type = protein
                        organism = synthetic construct
SEQUENCE: 354
MDPKGSLSWR ILLFLSLAFE LSYGQVQLVQ SGAEVKKPGA SVKVSCKASG YTFNSYWMHW   60
VRQAPGQGLE WMGRIHPRGI HTNYNQKFKG RVTLTVDTST STAYMELSSL RSEDTAVYYC  120
APSSSYAWAF AHWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 355          moltype = AA  length = 473
FEATURE                 Location/Qualifiers
source                  1..473
                        mol_type = protein
                        organism = synthetic construct
SEQUENCE: 355
MDPKGSLSWR ILLFLSLAFE LSYGQVQLVQ SGAEVKKPGA SVKVSCKASG QTFTSYRMHW   60
VRQAPGQGLE WMGRILPIRS DTNYNQKFKG RVTLTVDTST STAYMELSSL RSEDTAVYYC  120
ARDAGYGSLF AAWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 356          moltype = AA  length = 473
FEATURE                 Location/Qualifiers
source                  1..473
                        mol_type = protein
                        organism = synthetic construct
SEQUENCE: 356
MDPKGSLSWR ILLFLSLAFE LSYGQVQLVQ SGAEVKKPGA SVKVSCKASG YTFTSYWMHW   60
VRQAPGQGLE WMGRIHPSDS DTNYNQKFKG RVTLTVDTST STAYMELSSL RSEDTAVYYC  120
APKGNYVVRF AYWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 357          moltype = AA  length = 473
FEATURE                 Location/Qualifiers
source                  1..473
                        mol_type = protein
                        organism = synthetic construct
SEQUENCE: 357
MDPKGSLSWR ILLFLSLAFE LSYGQVQLVQ SGAEVKKPGA SVKVSCKASG YTFTRYWMHW   60
VRQAPGQGLE WMGRIHPTDS VTNYNQKFKG RVTLTVDTST STAYMELSSL RSEDTAVYYC  120
APDVNYARAF AHWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 358          moltype = AA  length = 473
FEATURE                 Location/Qualifiers
source                  1..473
                        mol_type = protein
                        organism = synthetic construct
SEQUENCE: 358
MDPKGSLSWR ILLFLSLAFE LSYGQVQLVQ SGAEVKKPGA SVKVSCKASG YTFGIYWMHW   60
VRQAPGQGLE WMGRILPSNG YTNYNQKFKG RVTLTVDTST STAYMELSSL RSEDTAVYYC  120
APYGIYTRDF SHWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 359          moltype = AA  length = 473
FEATURE                 Location/Qualifiers
source                  1..473
                        mol_type = protein
                        organism = synthetic construct
```

```
SEQUENCE: 359
MDPKGSLSWR ILLFLSLAFE LSYGQVQLVQ SGAEVKKPGA SVKVSCKASG YTFTSYWMHW    60
VRQAPGQGLE WMGRIHPSDS DTNYNQKFKG RVTLTVDTST STAYMELSSL RSEDTAVYYC   120
APYVDLESGS AYWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 360         moltype = AA  length = 473
FEATURE                Location/Qualifiers
source                 1..473
                       mol_type = protein
                       organism = synthetic construct
SEQUENCE: 360
MDPKGSLSWR ILLFLSLAFE LSYGQVQLVQ SGAEVKKPGA SVKVSCKASG YTFTSYWMHW    60
VRQAPGMGLE WMGRIHPIYR DTNYNQKFKG RVTLTVDTST STAYMELSSL RSEDTAVYYC   120
APYVNYGDGF AYWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 361         moltype = AA  length = 473
FEATURE                Location/Qualifiers
source                 1..473
                       mol_type = protein
                       organism = synthetic construct
SEQUENCE: 361
MDPKGSLSWR ILLFLSLAFE LSYGQVQLVQ SGAEVKKPGA SVKVSCKASG YTFNSYLMHW    60
VRQAPGMGLE WMGRIRPNYS DTNYNQKFKG RVTLTVDTST STAYMELSSL RSEDTAVYYC   120
APYGNNASGF SYWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 362         moltype = AA  length = 473
FEATURE                Location/Qualifiers
source                 1..473
                       mol_type = protein
                       organism = synthetic construct
SEQUENCE: 362
MDPKGSLSWR ILLFLSLAFE LSYGQVQLVQ SGAEVKKPGA SVKVSCKASG QTFTNYLMHW    60
VRQAPGQGLE WMGRIPLSDR DTNYNQKFKG RVTLTVDTST STAYMELSSL RSEDTAVYYC   120
APYGRSASGF SSWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 363         moltype = AA  length = 473
FEATURE                Location/Qualifiers
source                 1..473
                       mol_type = protein
                       organism = synthetic construct
SEQUENCE: 363
MDPKGSLSWR ILLFLSLAFE LSYGQVQLVQ SGAEVKKPGA SVKVSCKASG YTFTSYWMHW    60
VRQAPGQGLE WMGRIHPSDS DTNYNQKFKG RVTLTVDTST STAYMELSSL RSEDTAVYYC   120
APYFDHAGGF LHWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 364         moltype = AA  length = 448
FEATURE                Location/Qualifiers
source                 1..448
                       mol_type = protein
                       organism = synthetic construct
SEQUENCE: 364
QVQLVQSGAE VKKPGASVKV SCKASGYTFN SYWMHWVRQA PGQGLEWMGR IHPRGIHTNY    60
NQKFKGRVTL TVDTSTSTAY MELSSLRSED TAVYYCAPSS SYAWAFAHWG QGTLVTVSSA   120
STKGPSVFPL APSSKSTSGG TAALGCLVKD YFPEPVTVSW NSGALTSGVH TFPAVLQSSG   180
```

```
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 365          moltype = AA  length = 448
FEATURE                 Location/Qualifiers
source                  1..448
                        mol_type = protein
                        organism = synthetic construct
SEQUENCE: 365
QVQLVQSGAE VKKPGASVKV SCKASGQTFT SYRMHWVRQA PGQGLEWMGR ILPIRSDTNY     60
NQKFKGRVTL TVDTSTSTAY MELSSLRSED TAVYYCARDA GYGSLFAAWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 366          moltype = AA  length = 448
FEATURE                 Location/Qualifiers
source                  1..448
                        mol_type = protein
                        organism = synthetic construct
SEQUENCE: 366
QVQLVQSGAE VKKPGASVKV SCKASGYTFT SYWMHWVRQA PGQGLEWMGR IHPSDSDTNY     60
NQKFKGRVTL TVDTSTSTAY MELSSLRSED TAVYYCAPKG NYVVRFAYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 367          moltype = AA  length = 448
FEATURE                 Location/Qualifiers
source                  1..448
                        mol_type = protein
                        organism = synthetic construct
SEQUENCE: 367
QVQLVQSGAE VKKPGASVKV SCKASGYTFT RYWMHWVRQA PGQGLEWMGR IHPTDSVTNY     60
NQKFKGRVTL TVDTSTSTAY MELSSLRSED TAVYYCAPDV NYARAFAHWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 368          moltype = AA  length = 448
FEATURE                 Location/Qualifiers
source                  1..448
                        mol_type = protein
                        organism = synthetic construct
SEQUENCE: 368
QVQLVQSGAE VKKPGASVKV SCKASGYTFG IYWMHWVRQA PGQGLEWMGR ILPSNGYTNY     60
NQKFKGRVTL TVDTSTSTAY MELSSLRSED TAVYYCAPYG IYTRDFSHWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 369          moltype = AA  length = 448
FEATURE                 Location/Qualifiers
source                  1..448
                        mol_type = protein
                        organism = synthetic construct
SEQUENCE: 369
QVQLVQSGAE VKKPGASVKV SCKASGYTFT SYWMHWVRQA PGQGLEWMGR IHPSDSDTNY     60
NQKFKGRVTL TVDTSTSTAY MELSSLRSED TAVYYCAPYV DLESGFAYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
```

```
QGNVFSCSVM HEALHNHYTQ KSLSLSPG                                          448

SEQ ID NO: 370           moltype = AA  length = 448
FEATURE                  Location/Qualifiers
source                   1..448
                         mol_type = protein
                         organism = synthetic construct
SEQUENCE: 370
QVQLVQSGAE VKKPGASVKV SCKASGYTFT SYWMHWVRQA PGMGLEWMGR IHPIYRDTNY        60
NQKFKGRVTL TVDTSTSTAY MELSSLRSED TAVYYCAPYV NYGDGFAYWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYNS       300
TYRVVSVLTV LHQDWLNGKE YKCKVSNKAL PAPIEKTISK AKGQPREPQV YTLPPSREEM       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPG                                          448

SEQ ID NO: 371           moltype = AA  length = 448
FEATURE                  Location/Qualifiers
source                   1..448
                         mol_type = protein
                         organism = synthetic construct
SEQUENCE: 371
QVQLVQSGAE VKKPGASVKV SCKASGYTFN SYLMHWVRQA PGMGLEWMGR IRPNYSDTNY        60
NQKFKGRVTL TVDTSTSTAY MELSSLRSED TAVYYCAPYG NNASGFSYWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYNS       300
TYRVVSVLTV LHQDWLNGKE YKCKVSNKAL PAPIEKTISK AKGQPREPQV YTLPPSREEM       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPG                                          448

SEQ ID NO: 372           moltype = AA  length = 448
FEATURE                  Location/Qualifiers
source                   1..448
                         mol_type = protein
                         organism = synthetic construct
SEQUENCE: 372
QVQLVQSGAE VKKPGASVKV SCKASGQTFT NYLMHWVRQA PGQGLEWMGR IPLSDRDTNY        60
NQKFKGRVTL TVDTSTSTAY MELSSLRSED TAVYYCAPYG RSASGFSSWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYNS       300
TYRVVSVLTV LHQDWLNGKE YKCKVSNKAL PAPIEKTISK AKGQPREPQV YTLPPSREEM       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPG                                          448

SEQ ID NO: 373           moltype = AA  length = 448
FEATURE                  Location/Qualifiers
source                   1..448
                         mol_type = protein
                         organism = synthetic construct
SEQUENCE: 373
QVQLVQSGAE VKKPGASVKV SCKASGYTFT SYWMHWVRQA PGQGLEWMGR IHPSDSDTNY        60
NQKFKGRVTL TVDTSTSTAY MELSSLRSED TAVYYCAPYF DHAGGFLHWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYNS       300
TYRVVSVLTV LHQDWLNGKE YKCKVSNKAL PAPIEKTISK AKGQPREPQV YTLPPSREEM       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPG                                          448

SEQ ID NO: 374           moltype = AA  length = 449
FEATURE                  Location/Qualifiers
source                   1..449
                         mol_type = protein
                         organism = synthetic construct
SEQUENCE: 374
QVQLVQSGAE VKKPGASVKV SCKASGYTFN SYWMHWVRQA PGQGLEWMGR IHPRGIHTNY        60
NQKFKGRVTL TVDTSTSTAY MELSSLRSED TAVYYCAPSS SYAWAFAHWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYNS       300
TYRVVSVLTV LHQDWLNGKE YKCKVSNKAL PAPIEKTISK AKGQPREPQV YTLPPSREEM       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPGK                                         449

SEQ ID NO: 375           moltype = AA  length = 449
FEATURE                  Location/Qualifiers
```

```
source                      1..449
                            mol_type = protein
                            organism = synthetic construct
SEQUENCE: 375
QVQLVQSGAE VKKPGASVKV SCKASGQTFT SYRMHWVRQA PGQGLEWMGR ILPIRSDTNY      60
NQKFKGRVTL TVDTSTSTAY MELSSLRSED TAVYYCARDA GYGSLFAAWG QGTLVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHTCPP CPAPELLGGP     240
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSREEM     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPGK                                      449

SEQ ID NO: 376              moltype = AA   length = 449
FEATURE                     Location/Qualifiers
source                      1..449
                            mol_type = protein
                            organism = synthetic construct
SEQUENCE: 376
QVQLVQSGAE VKKPGASVKV SCKASGYTFT SYWMHWVRQA PGQGLEWMGR IHPSDSDTNY      60
NQKFKGRVTL TVDTSTSTAY MELSSLRSED TAVYYCAPKG NYVVRFAYWG QGTLVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHTCPP CPAPELLGGP     240
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSREEM     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPGK                                      449

SEQ ID NO: 377              moltype = AA   length = 449
FEATURE                     Location/Qualifiers
source                      1..449
                            mol_type = protein
                            organism = synthetic construct
SEQUENCE: 377
QVQLVQSGAE VKKPGASVKV SCKASGYTFT RYWMHWVRQA PGQGLEWMGR IHPTDSVTNY      60
NQKFKGRVTL TVDTSTSTAY MELSSLRSED TAVYYCAPDV NYARAFAHWG QGTLVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHTCPP CPAPELLGGP     240
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSREEM     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPGK                                      449

SEQ ID NO: 378              moltype = AA   length = 449
FEATURE                     Location/Qualifiers
source                      1..449
                            mol_type = protein
                            organism = synthetic construct
SEQUENCE: 378
QVQLVQSGAE VKKPGASVKV SCKASGYTFG IYWMHWVRQA PGQGLEWMGR ILPSNGYTNY      60
NQKFKGRVTL TVDTSTSTAY MELSSLRSED TAVYYCAPYG IYTRDFSHWG QGTLVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHTCPP CPAPELLGGP     240
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSREEM     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPGK                                      449

SEQ ID NO: 379              moltype = AA   length = 449
FEATURE                     Location/Qualifiers
source                      1..449
                            mol_type = protein
                            organism = synthetic construct
SEQUENCE: 379
QVQLVQSGAE VKKPGASVKV SCKASGYTFT SYWMHWVRQA PGQGLEWMGR IHPSDSDTNY      60
NQKFKGRVTL TVDTSTSTAY MELSSLRSED TAVYYCAPYV DLESGFAYWG QGTLVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHTCPP CPAPELLGGP     240
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSREEM     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPGK                                      449

SEQ ID NO: 380              moltype = AA   length = 449
FEATURE                     Location/Qualifiers
source                      1..449
                            mol_type = protein
                            organism = synthetic construct
SEQUENCE: 380
```

```
QVQLVQSGAE VKKPGASVKV SCKASGYTFT SYWMHWVRQA PGMGLEWMGR IHPIYRDTNY    60
NQKFKGRVTL TVDTSTSTAY MELSSLRSED TAVYYCAPYV NYGDGFAYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 381          moltype = AA  length = 449
FEATURE                 Location/Qualifiers
source                  1..449
                        mol_type = protein
                        organism = synthetic construct
SEQUENCE: 381
QVQLVQSGAE VKKPGASVKV SCKASGYTFN SYLMHWVRQA PGMGLEWMGR IRPNYSDTNY    60
NQKFKGRVTL TVDTSTSTAY MELSSLRSED TAVYYCAPYG NNASGFSYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 382          moltype = AA  length = 449
FEATURE                 Location/Qualifiers
source                  1..449
                        mol_type = protein
                        organism = synthetic construct
SEQUENCE: 382
QVQLVQSGAE VKKPGASVKV SCKASGQTFT NYLMHWVRQA PGQGLEWMGR IPLSDRDTNY    60
NQKFKGRVTL TVDTSTSTAY MELSSLRSED TAVYYCAPYG RSASGFSSWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 383          moltype = AA  length = 449
FEATURE                 Location/Qualifiers
source                  1..449
                        mol_type = protein
                        organism = synthetic construct
SEQUENCE: 383
QVQLVQSGAE VKKPGASVKV SCKASGYTFT SYWMHWVRQA PGQGLEWMGR IHPSDSDTNY    60
NQKFKGRVTL TVDTSTSTAY MELSSLRSED TAVYYCAPYF DHAGGFLHWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 384          moltype = AA  length = 214
FEATURE                 Location/Qualifiers
source                  1..214
                        mol_type = protein
                        organism = synthetic construct
SEQUENCE: 384
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ HYRSPGTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 385          moltype = AA  length = 214
FEATURE                 Location/Qualifiers
source                  1..214
                        mol_type = protein
                        organism = synthetic construct
SEQUENCE: 385
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ HDSSPGTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 386          moltype = AA  length = 214
FEATURE                 Location/Qualifiers
source                  1..214
```

```
                              mol_type = protein
                              organism = synthetic construct
SEQUENCE: 386
DIVMTQSPSS LSASVGDRVT ITCRASQGIR NDLGWYQQKP GKAPKLLIYA ASSLQSGVPS    60
RFSGSGSDTD FTLTISSLQP EDFATYYCLQ DYNYPWTFGQ GTKVDIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 387            moltype = AA   length = 214
FEATURE                   Location/Qualifiers
source                    1..214
                          mol_type = protein
                          organism = synthetic construct
SEQUENCE: 387
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ HYGSPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 388            moltype = AA   length = 214
FEATURE                   Location/Qualifiers
source                    1..214
                          mol_type = protein
                          organism = synthetic construct
SEQUENCE: 388
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ RDTTPRTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 389            moltype = AA   length = 215
FEATURE                   Location/Qualifiers
source                    1..215
                          mol_type = protein
                          organism = synthetic construct
SEQUENCE: 389
DIAMTQTPSS LSASIGDRVT IACRASQGIS SALAWYQQKP GRTPKLLIFD ASTLQSGVPS    60
RFSGSGSGTD FTLTISSLQP EDFATYYCQQ FNTYSSVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 390            moltype = AA   length = 214
FEATURE                   Location/Qualifiers
source                    1..214
                          mol_type = protein
                          organism = synthetic construct
SEQUENCE: 390
DIQMTQSPST LSASVGDRVT ITCRASQDVS TALAWYQQKP GKAPKLLIYW ASTRHIGVPD    60
RFSGSGSGTD FTLTISSLQP EDFATYYCHQ DYITPRTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 391            moltype = AA   length = 214
FEATURE                   Location/Qualifiers
source                    1..214
                          mol_type = protein
                          organism = synthetic construct
SEQUENCE: 391
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ HYRSPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 392            moltype = AA   length = 214
FEATURE                   Location/Qualifiers
source                    1..214
                          mol_type = protein
                          organism = synthetic construct
SEQUENCE: 392
DIQMTQSPSS LSASVGDRVT ITCRASQDVS TALAWYQQKP GKAPKLLIYW ASTRHSGVPD    60
RFSGSGSGTD FTLTISSLQP EDFATYYCQQ GSSTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 393            moltype = AA   length = 213
FEATURE                   Location/Qualifiers
source                    1..213
                          mol_type = protein
                          organism = synthetic construct
```

```
SEQUENCE: 393
DIVMTQSPGT LSLSPGERAT LSCRASQSVS SSYLAWYQQK PGQAPRLLIY GASSRATGIP    60
DRFSGSGSGT DFTLTISRLE PEDFAVYYCQ QYGSWTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 394          moltype = AA  length = 8
FEATURE                 Location/Qualifiers
source                  1..8
                        mol_type = protein
                        organism = synthetic construct
SEQUENCE: 394
GYTFTTYG                                                              8

SEQ ID NO: 395          moltype = AA  length = 8
FEATURE                 Location/Qualifiers
source                  1..8
                        mol_type = protein
                        organism = synthetic construct
SEQUENCE: 395
INTYSGVP                                                              8

SEQ ID NO: 396          moltype = AA  length = 288
FEATURE                 Location/Qualifiers
source                  1..288
                        mol_type = protein
                        organism = Homo sapiens
SEQUENCE: 396
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHSPSPS RPAGQFQTLV VGVVGGLLGS   180
LVLLVWVLAV ICSRAARGTI GARRTGQPLK EDPSAVPVFS VDYGELDFQW REKTPEPPVP   240
CVPEQTEYAT IVFPSGMGTS SPARRGSADG PRSAQPLRPE DGHCSWPL                288

SEQ ID NO: 397          moltype = AA  length = 288
FEATURE                 Location/Qualifiers
source                  1..288
                        mol_type = protein
                        organism = Mus musculus
SEQUENCE: 397
MWVRQVPWSF TWAVLQLSWQ SGWLLEVPNG PWRSLTFYPA WLTVSEGANA TFTCSLSNWS    60
EDLMLNWNRL SPSNQTEKQA AFCNGLSQPV QDARFQIIQL PNRHDFHMNI LDTRRNDSGI   120
YLCGAISLHP KAKIEESPGA ELVVTERILE TSTRYPSPSP KPEGRFQGMV IGIMSALVGI   180
PVLLLLAWAL AVFCSTSMSE ARGAGSKDDT LKEEPSAAPV PSVAYEELDF QGREKTPELP   240
TACVHTEYAT IVFTEGLGAS AMGRRGSADG LQGPRPPRHE DGHCSWPL                288

SEQ ID NO: 398          moltype = AA  length = 15
FEATURE                 Location/Qualifiers
source                  1..15
                        mol_type = protein
                        organism = Homo sapiens
SEQUENCE: 398
TYLCGAISLA PKAQI                                                     15
```